(12) United States Patent
Pasternak et al.

(10) Patent No.: US 9,573,961 B2
(45) Date of Patent: Feb. 21, 2017

(54) INHIBITORS OF THE RENAL OUTER MEDULLARY POTASSIUM CHANNEL

(71) Applicant: Merck Sharp & Dohme Corp., Rahway, NJ (US)

(72) Inventors: Alexander Pasternak, Princeton, NJ (US); Reynalda Keh DeJesus, East Brunswick, NJ (US); Jessica L. Frie, Harleysville, PA (US); Barbara Pio, West Orange, NJ (US); Haifeng Tang, Bridgewater, NJ (US); Shawn P. Walsh, Bridgewater, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/651,296

(22) PCT Filed: Dec. 13, 2013

(86) PCT No.: PCT/US2013/074846
§ 371 (c)(1),
(2) Date: Jun. 11, 2015

(87) PCT Pub. No.: WO2014/099633
PCT Pub. Date: Jun. 26, 2014

(65) Prior Publication Data
US 2015/0329557 A1 Nov. 19, 2015

Related U.S. Application Data

(60) Provisional application No. 61/739,571, filed on Dec. 19, 2012, provisional application No. 61/762,079, filed on Feb. 7, 2013.

(51) Int. Cl.
| | |
|---|---|
| *A61K 31/5383* | (2006.01) |
| *C07D 498/04* | (2006.01) |
| *A61K 31/551* | (2006.01) |
| *A61K 45/06* | (2006.01) |
| *A61K 31/4985* | (2006.01) |
| *C07D 487/04* | (2006.01) |

(52) U.S. Cl.
CPC ......... *C07D 498/04* (2013.01); *A61K 31/4985* (2013.01); *A61K 31/5383* (2013.01); *A61K 31/551* (2013.01); *A61K 45/06* (2013.01); *C07D 487/04* (2013.01)

(58) Field of Classification Search
USPC ...................... 514/91, 221, 223.5, 230.5, 249
See application file for complete search history.

(56) References Cited

U.S. PATENT DOCUMENTS

| | | |
|---|---|---|
| 2,988,551 A | 6/1961 | Morren |
| 3,435,002 A | 3/1969 | Holub |
| 3,632,608 A | 1/1972 | Holub |
| 3,749,722 A | 7/1973 | Holub |
| 4,579,863 A | 4/1986 | Horwell et al. |
| 4,806,536 A | 2/1989 | Cross et al. |
| 4,992,547 A | 2/1991 | Berner et al. |
| 5,145,885 A | 9/1992 | Berner et al. |
| 5,215,989 A | 6/1993 | Baldwin et al. |
| 5,614,526 A | 3/1997 | Godel et al. |
| 5,736,546 A | 4/1998 | Kawashima et al. |
| 6,258,813 B1 | 7/2001 | Arlt et al. |
| 6,787,543 B2 | 9/2004 | Take et al. |
| 8,673,920 B2 | 3/2014 | Pasternak et al. |
| 8,952,166 B2 | 2/2015 | Ding et al. |
| 9,206,199 B2 * | 12/2015 | Pio .................. A61K 31/4178 |
| 2004/0110793 A1 | 6/2004 | Lloyd et al. |
| 2004/0204404 A1 | 10/2004 | Zelle et al. |
| 2005/0215526 A1 | 9/2005 | Hulme et al. |
| 2005/0267121 A1 | 12/2005 | Li et al. |
| 2006/0183739 A1 | 8/2006 | Tsaklakidis et al. |
| 2006/0183742 A1 | 8/2006 | Mederski et al. |
| 2006/0211692 A1 | 9/2006 | Mederski et al. |
| 2007/0004750 A1 | 1/2007 | Lorsbach et al. |
| 2007/0072695 A1 | 3/2007 | Fukatsu et al. |
| 2007/0093472 A1 | 4/2007 | Mederski et al. |
| 2008/0003214 A1 | 1/2008 | Cezanne et al. |
| 2008/0090794 A1 | 4/2008 | Dinsmore et al. |
| 2010/0286123 A1 | 11/2010 | Pasternak et al. |

FOREIGN PATENT DOCUMENTS

| | | |
|---|---|---|
| EP | 0099148 B1 | 2/1988 |
| EP | 0175376 B1 | 4/1991 |
| EP | 1094063 A1 | 4/2001 |
| EP | 1939175 A1 | 7/2009 |
| FR | 2673182 | 8/1992 |

(Continued)

OTHER PUBLICATIONS

ACCF/AHA Practice Guideline, 2009 Focused update incorporated into the ACC/AHA 2005 guidelines . . . , Circulation, 2009, e391-e436, 119.

(Continued)

*Primary Examiner* — Pancham Bakshi
(74) *Attorney, Agent, or Firm* — Baerbel R. Brown; Catherine D. Fitch

(57) ABSTRACT

The present invention provides compounds of Formula I

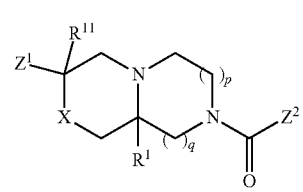

and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and conditions associated with excessive salt and water retention.

12 Claims, No Drawings

(56) References Cited

FOREIGN PATENT DOCUMENTS

| | | |
|---|---|---|
| FR | 2673182 A1 | 8/1992 |
| GB | 949088 A | 2/1964 |
| GB | 1575310 A | 9/1980 |
| GB | 2116967 | 7/1986 |
| JP | 10203986 | 8/1998 |
| WO | 9744329 | 11/1997 |
| WO | 0051611 A1 | 9/2000 |
| WO | 0204314 A1 | 6/2002 |
| WO | 0250061 A1 | 6/2002 |
| WO | 02032874 | 11/2003 |
| WO | 2004020422 A1 | 3/2004 |
| WO | 2004037817 A1 | 5/2004 |
| WO | 2004046110 | 6/2004 |
| WO | 2005037843 | 4/2005 |
| WO | 2005044797 | 5/2005 |
| WO | 2006034341 A2 | 3/2006 |
| WO | 2006034769 A1 | 4/2006 |
| WO | 2006098342 A1 | 9/2006 |
| WO | 2007075629 A2 | 7/2007 |
| WO | 2008147864 | 12/2008 |
| WO | 2008147864 A2 | 12/2008 |
| WO | 2009149508 | 11/2009 |
| WO | 2010129379 A1 | 11/2010 |
| WO | 2012058116 A1 | 5/2012 |
| WO | 2012058134 A1 | 5/2012 |
| WO | 2006129199 A1 | 12/2012 |
| WO | 2013028474 A1 | 2/2013 |
| WO | 2013039802 A1 | 3/2013 |
| WO | 2013062892 A1 | 5/2013 |
| WO | 2013062900 A1 | 5/2013 |
| WO | 2013066714 A1 | 5/2013 |
| WO | 2013066717 A1 | 5/2013 |
| WO | 2013066718 A2 | 5/2013 |
| WO | 2013090271 A1 | 6/2013 |
| WO | 2014018764 A1 | 1/2014 |
| WO | WO2014085210 A1 | 6/2014 |
| WO | WO2014099633 A2 | 6/2014 |
| WO | WO2014126944 A2 | 8/2014 |
| WO | WO2014150132 A1 | 9/2014 |
| WO | WO2015017305 A1 | 2/2015 |
| WO | WO2015065866 A1 | 5/2015 |

OTHER PUBLICATIONS

Baltzly, R., The preparation of N-mono-substituted and unsymmetrically disubstituted piperazines, J. Am. Chemoc., 1944, 263-266, 66.

Bhave, G., Small-molecule modulators of inward rectifier K+ channels: recent advances and future possibilities, Future Med Chem, 2010, 757-774, 2(5).

Bhave, G., Development of a selective small-molecule inhibitor Kir1.1, the renal outer medullary potassium channel, Mol. Pharmacol., 2011, 42-50, 79.

Brater et al., Diuretic Therapy, Drug Therapy, 1998, 387-395, 339.

Brewster et al., Antihypertensive 1,4-bis (2-indol-3-ylethyl)piperazines, Chimie Ther., 1973, 169-172 (English trans.), 2.

Cerkvenik-Flajs V, Determination of residues of azaperone in the kidneys by liquid chromatography with fluorescence, Anal. Chim. Acta., 2007, 374-382, 586.

Chemical Abstracts (2004), Abstract No. 697771-49-6, "1,3-Isobenzofurandione 5-[[4-[(5-chloro-2-methoxyphenyl) sulfonyl]-1- . . . ".

Cheymol et al., Increase in the effects of epinephrine and acetylcholine . . . , Comptes Rendus des seances de la Societe de Biologie, 1951, 496-499 (English trans.), 145.

Dorwald, Side reactions in Organic Synthesis: A Guide to Successful Synthesis Design, 2005, Chapter 1.

Fallen, K., The Kir channel immunoglobuling domain is essential for Kir1.1 (ROMK) thermodynamic stability, trafficking and gating, Channels, 2009, 57-66, 3.

Felker et al, Diuretic strategies in patients with acute decompensated heart failure, New Eng. J. Med., 2011, 797-805, 364.

Frank, Managing hypertension using combination therapy, Am. Fam. Physician, 2008, 1279-1286, 77.

International Search Report for PCT/US 13/74846, mailed Aug. 15, 2014, 8 pages.

Kulkarni, YD, Possible antifertility agents, part III. Synthesis of 4-(substituted aminomethyl)-5,6,7-trimethoxy phthalid . . . (abstract)), Biol. Mem., 1987, 141-144, 13.

Lanyi et al., Piperazine-Derivatives II, Res. Lab. of Chinoin-Fabrik Chemisch-Pharma. Prod., 1968, 1431-1435 (English trans.), 18.

Lewis, L. M., High-throughput screening reveals a small-molecule inhibitor of the Renal Outer Medullary Potassium Channel and Kir7.1, Mol. Pharncol., 2009, 1094-1103, 76.

Lutz, R. E., Antimalarials. Some Piperazine Derivatives, J. Org. Chem., 1947, 771-775, 12, BO.

Miyake et al., Synthesis of 1-substituted isochroman . . . , Takeda Res. Lab., 1982, 24-40 (English trans.), 41.

Sica, D. A., Diuretic use in renal disease, Nature, 2012, 100-109, 8.

Zejc et al., Piperazine derivative of dimethylxanthines, Polish J. Pharmacol. & Pharm., 1975, 311-316 (English trans.), 27.

\* cited by examiner

INHIBITORS OF THE RENAL OUTER MEDULLARY POTASSIUM CHANNEL

CROSS REFERENCE TO RELATED APPLICATIONS

This application is a U.S. National Phase application under 35 U.S.C. §371 of PCT Application No. PCT/US13/74846 filed Dec. 13, 2013, which claims priority from U.S. Provisional Application Ser. Nos. 61/739,571, filed Dec. 19, 2012, and 61/762,079, filed Feb. 7, 2013.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

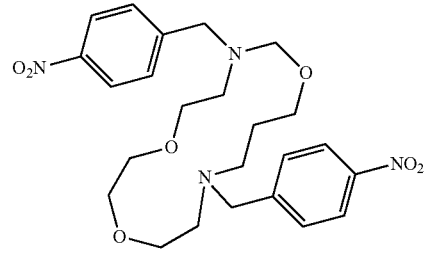

VU590

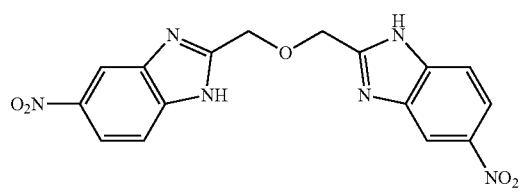

VU591

Patent application publication number WO2010/129379, published Nov. 11, 2010 having common representative Merck Sharp & Dohme Corp., (also published as US2010/0286123 on same date), describes ROMK inhibitors having the generic formula:

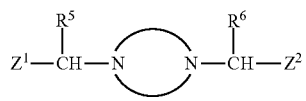

and, e.g., an embodiment

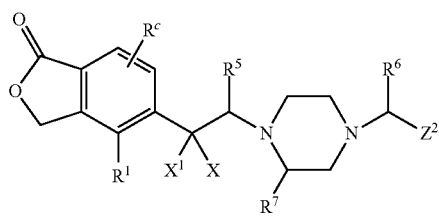

wherein $R^5$ and $R^6$ are independently —H, —$C_{1-6}$ alkyl, —$C_{3-6}$ cycloalkyl, —$CF_3$, —$CHF_2$, —$CH_2F$ or —$CH_2OH$; X is —H, —OH, —$OC_{1-3}$alkyl, —F, oxo, $NH_2$ or —$CH_3$; and $X^1$ is —H or —$CH_3$.

Patent application publication number WO2012/058134, published May 3, 2012, having common representative Merck Sharp & Dohme Corp., describes ROMK inhibitors having the generic formula:

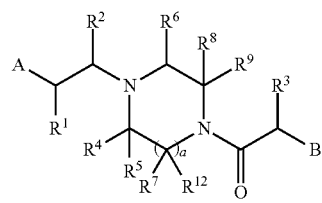

wherein A and B are mono and/or bicyclic aromatic groups; $R^2$ is —H, —$C_{1-6}$ alkyl, —$C_{3-6}$ cycloalkyl, $CF_3$, —$CH_2OH$, or —$CO_2R$, or $R^2$ can be joined to $R^1$ or $R^{10a}$ to form a ring; $R^3$ is —H, —$C_{1-6}$ alkyl, —$C_{3-6}$ cycloalkyl, —OH, —F, —$OC_{1-3}$ alkyl, or —$CH_2OH$, or $R^3$ can be joined to $R^{10b}$ to form a ring.

Patent application publication number WO2012/058116, published May 3, 2012, having common representative Merck Sharp & Dohme Corp., describes ROMK inhibitors having the generic formula:

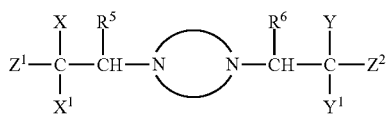

and, e.g., an embodiment

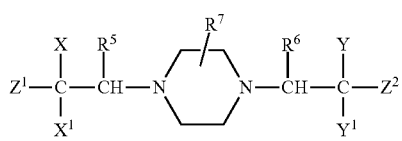

wherein $R^5$ and $R^6$ are independently —H, —$C_{1-6}$ alkyl or —$C(O)OC_{1-3}$alkyl; and X, $X^1$, Y and $Y^1$ are independently —H or —$C_{1-6}$alkyl; or $Y^1$ can be joined together with $Z^2$ to form a fused ring system.

However, continuing discovery of selective small molecule inhibitors of ROMK is still needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I

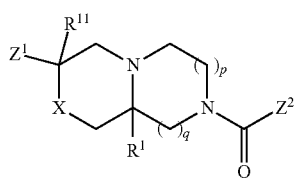

and the pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure, and conditions associated with excessive salt and water retention. The compounds of this invention could further be used in combination with other therapeutically effective agents, including but not limited to, other drugs which are useful for the treatment of hypertension, heart failure as well as chronic kidney disease, and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention is directed to compounds having structural Formula I:

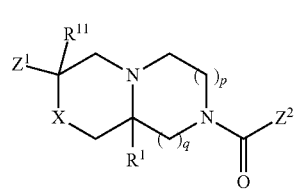

and the pharmaceutically acceptable salts thereof wherein:

X is O, NH, S or $SO_2$;

p is an integer selected from 1 (one) or 2 (two), and q is an integer selected from 1 (one) or 2 (two), provided that only one of p and q can be 2;

$Z^1$ is

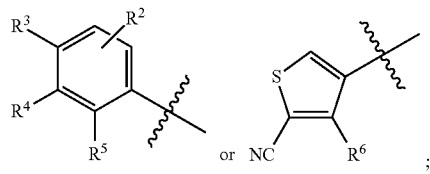

$R^1$ is —H or —$C_{1-4}$alkyl;

$R^2$ is —H, —F, —Cl, —$C_{1-6}$alkyl, —$C_{3-6}$cycloalkyl or —$OC_{1-4}$alkyl;

$R^3$ is —H, —F, —Cl, —CN, —$C_{1-6}$alkyl, —$C_{3-6}$cycloalkyl, —$OC_{1-4}$alkyl or N-tetrazolyl optionally substituted with —$CH_3$;

$R^4$ is —H, —F, —Cl, —CN, —$C_{1-6}$alkyl, —$C_{3-6}$cycloalkyl, —$OC_{1-4}$alkyl or N-tetrazolyl optionally substituted with —$CH_3$;

or $R^3$ and $R^4$ are joined together with the phenyl ring to which they are attached to form a bicyclic ring system that is:

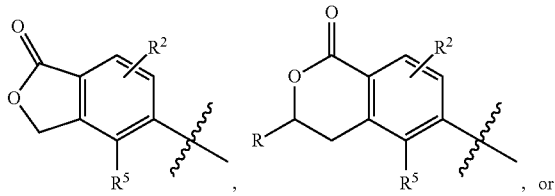

-continued

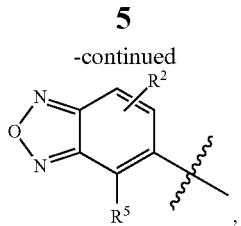

wherein R is —H or —$C_{1-4}$alkyl;
$R^5$ is —H, —F, —Cl, —CN, —$C_{1-4}$alkyl, —$C_{3-6}$cycloalkyl or —$OC_{1-4}$alkyl; provided that when $R^3$ and $R^4$ are not joined together, then either
 (a) one of $R^3$, $R^4$ or $R^5$ is —CN and the others are not —CN, or
 (b) one of $R^3$ or $R^4$ is N-tetrazolyl optionally substituted with —$CH_3$ and the other is not N-tetrazolyl optionally substituted with —$CH_3$;
$R^6$ is —H or —$C_{1-6}$alkyl;
$Z^2$ is

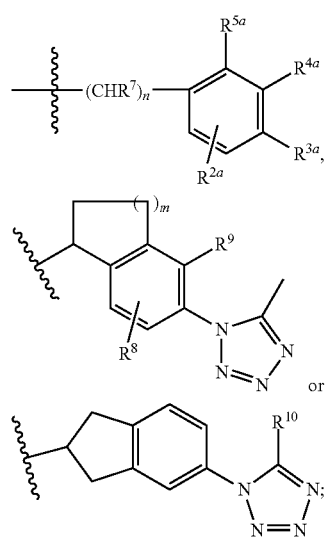

n is an integer selected from 1 (one) or 2 (two);
m is an integer selected from 1 (one) or 2 (two);
$R^{2a}$ is —H, —F, —Cl, —$C_{1-6}$alkyl, —$C_{3-6}$cycloalkyl or —$OC_{1-4}$alkyl;
$R^{3a}$ is —H, —F, —Cl, —CN, —$C_{1-6}$alkyl, —$C_{3-6}$cycloalkyl, —$OC_{1-4}$alkyl or N-tetrazolyl optionally substituted with —$CH_3$;
$R^{4a}$ is —H, —F, —Cl, —CN, —$C_{1-6}$alkyl, —$C_{3-6}$cycloalkyl, —$OC_{1-4}$alkyl or N-tetrazolyl optionally substituted with —$CH_3$;
or $R^{3a}$ and $R^{4a}$ are joined together with the phenyl ring to which they are attached to form:

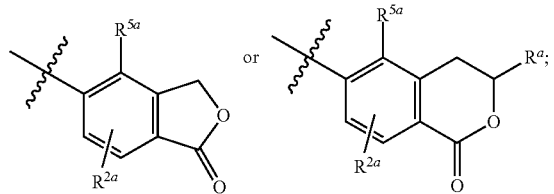

wherein $R^a$ is —H or —$C_{1-4}$alkyl;
$R^{5a}$ is —H, —F, —Cl, —CN, —$C_{1-4}$alkyl, —$C_{3-6}$cycloalkyl or —$OC_{1-4}$alkyl; provided that when $R^{3a}$ and $R^{4a}$ are not joined together, then either
 (a) only one of $R^{3a}$, $R^{4a}$ or $R^{5a}$ is —CN and the others are not —CN, or
 (b) only one of $R^{3a}$ or $R^{4a}$ is N-tetrazolyl optionally substituted with —$CH_3$ and the other is not N-tetrazolyl optionally substituted with —$CH_3$;
$R^7$ is independently at each occurrence —H or —$C_{1-3}$alkyl;
$R^8$ is —H, —F, —Cl, —$C_{1-6}$alkyl, —$C_{3-6}$cycloalkyl or —$OC_{1-4}$alkyl;
$R^9$ is —H, —F, —Cl, —CN, —$C_{1-6}$alkyl, —$C_{3-6}$cycloalkyl or —$OC_{1-4}$alkyl;
$R^{10}$ is —H or —$CH_3$; and
$R^{11}$ is —H or —$CH_3$.

In an embodiment of this invention are compounds of Formula I wherein p and q are both 1.

In an embodiment of this invention are compounds of Formula I wherein $R^1$ is —H or —$CH_3$, and particularly it is —H.

In an embodiment of this invention are compounds of Formula I wherein each $R^7$ is independently —H or —$CH_3$, and more particularly $R^7$ is —H when n is 1, or $R^7$ is —H at both occurrences when n is 2.

In an embodiment of this invention are compounds of Formula I wherein $R^{11}$ is —H.

In an embodiment of this invention are compounds of Formula I wherein n is one.

In four embodiments of this invention are compounds of Formula I having structural Formula II, III, IV or IV as follows:

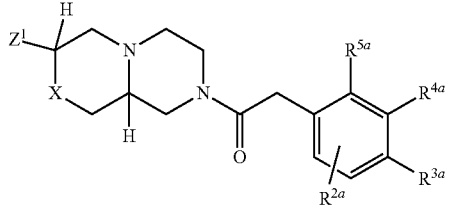

II wherein one of $R^{3a}$ or $R^{4a}$ is N-tetrazolyl optionally substituted with —$CH_3$ and the other is not N-tetrazolyl optionally substituted with —$CH_3$;

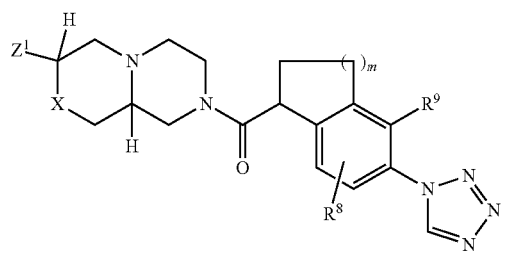

III wherein $R^9$ is not tetrazolyl optionally substituted with —$CH_3$;

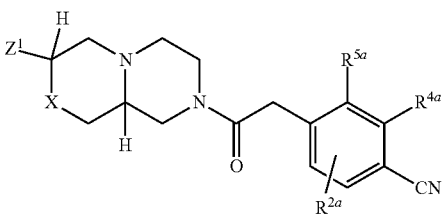

IV wherein $R^{4a}$ and $R^{5a}$ are not —CN; or

-continued

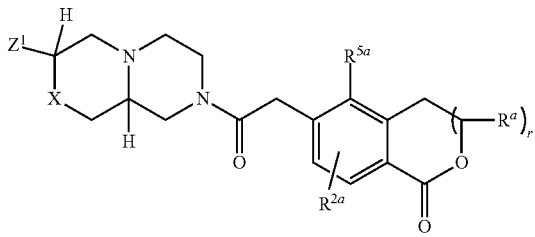

wherein r is an integer selected from 0 or 1.

In an embodiment of this invention are compounds of Formula I, II, III, IV or V wherein X is O or N, and more particularly it is O.

In further embodiments of this invention are compounds of Formula I, II, IV or V wherein $Z^2$ is

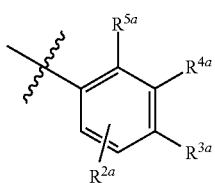

and
(a) one of $R^{3a}$ or $R^{4a}$ is N-tetrazolyl optionally substituted with —$CH_3$ and the other is not N-tetrazolyl optionally substituted with —$CH_3$; and more particularly $R^{3a}$ is N-tetrazolyl optionally substituted with —$CH_3$; or
(b) one of $R^{3a}$ or $R^{4a}$ is —CN and the other is not —CN; and more particularly, $R^{3a}$ is —CN; or
(c) $R^{3a}$ and $R^{4a}$ are joined together with the phenyl ring to which they are attached to form a bicyclic ring system that is:

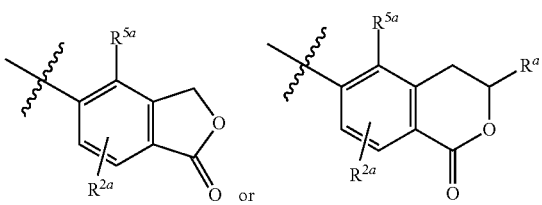

wherein $R^a$ is —H or —$CH_3$.

In an embodiment of this invention are compounds of Formula I, II or IV, wherein in $Z^2$, $R^{2a}$ is —H or —F.

In an embodiment of this invention are compounds of Formula I, II or IV, wherein in $Z^2$, one of $R^{3a}$ or $R^{4a}$ is —H, —F or —$OCH_3$, and the other is —CN or N-tetrazolyl optionally substituted with —$CH_3$. In another embodiment, are compounds of Formula IV wherein $R^{4a}$ is —F, —Cl, —$C_{1-4}$alkyl, —$OC_{1-4}$alkyl, or N-tetrazolyl optionally substituted with —$CH_3$.

In an embodiment of this invention are compounds of Formula I or II, wherein in $Z^2$, $R^{5a}$ is —H, —F, —Cl, —CN or —$CH_3$.

In an embodiment of this invention are compounds of Formula I or III, wherein in $Z^2$, $R^8$ is —H, —F, —Cl or —$CH_3$, and $R^9$ is —H. In a class of this embodiment, $R^8$ and $R^9$ are both —H.

In an embodiment of this invention are compounds of Formula I and each of the embodiments thereof described above, and Formula II, III, IV or V, wherein in $Z^1$, $R^3$ and $R^4$ are joined together to form a bicyclic ring system, and $R^5$ is —H, —Cl, —F, —$C_{1-4}$alkyl or —$OC_{1-4}$alkyl, with the latter two moieties more particularly being —$CH_3$ or —$OCH_3$.

In an embodiment of this invention are compounds of Formula I, II, III, IV or V, wherein in $Z^1$, $R^3$ and $R^4$ are not joined together and $R^2$ is —H, —$C_{1-3}$alkyl (particularly —$CH_3$), —F or —Cl;

In an embodiment of this invention are compounds of Formula I, II, III, IV or V, wherein in $Z^1$, $R^3$ and $R^4$ are not joined together, and one of $R^3$ and $R^4$ is —CN and the other is —H, —Cl, —F, —$C_{1-4}$alkyl or —$OC_{1-3}$alkyl, and $R^5$ is not —CN. In a particular embodiment, one of $R^3$ and $R^4$ is —CN and the other is —F or —$OC_{1-3}$alkyl; and more particularly, $R^3$ is —F, $R^4$ is —CN and $R^5$ is —$CH_3$.

In an embodiment of this invention are compounds of Formula I, II, III, IV or V, wherein in $Z^1$, $R^3$ and $R^4$ are not joined together, and one of $R^3$ and $R^4$ is N-tetrazolyl optionally substituted with —$CH_3$, and the other is —H, —Cl, —F, —$C_{1-4}$alkyl or —$OC_{1-3}$alkyl.

In an embodiment of this invention are compounds of Formula I, II, III, IV or V, wherein in $Z^1$, $R^3$ and $R^4$ are not joined together and $R^5$ is —H, —Cl, —F, —$C_{1-4}$alkyl or —$OC_{1-3}$alkyl.

In an embodiment of this invention are compounds of Formula I, II, III, IV or V wherein $R^6$ is —H or —$C_{1-3}$alkyl, and more particularly it is —H or —$CH_3$.

In an embodiment of this invention are compounds of Formula II wherein one of $R^{3a}$ or $R^{4a}$ is N-tetrazolyl optionally substituted with —$CH_3$, and the other is —H; $R^{2a}$ is —H, —F, Cl or —$CH_3$; and $R^{5a}$ is —H, —F, Cl, —CN or —$CH_3$. In a class of this embodiment, $R^{3a}$ is N-tetrazolyl and $R^{4a}$ is —H.

In an embodiment of this invention are compounds of Formula IV wherein $R^{2a}$ is —H, —F, Cl or —$CH_3$; one of $R^{3a}$ or $R^{4a}$ is —F, —Cl or —$OC_{1-4}$alkyl and the other is —CN. In a class of this embodiment, $R^{3a}$ is —CN, and; $R^{4a}$ is —F or —$OCH_3$.

In an embodiment of this invention are compounds of Formula V wherein $R^{2a}$ is —H, —F, —Cl or —$CH_3$; and $R^{5a}$ is —H, —F, —Cl, —CN or —$CH_3$.

All structural Formulas and embodiments thereof described herein include the pharmaceutically acceptable salts of the compounds defined therein.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me).

"Cycloalkyl" is a cyclized alkyl ring having the indicated number of carbon atoms. Examples of cycloalkyl include cyclopropyl, cyclobutyl, cyclopentyl and cyclohexyl.

"Halo" means —F, —Cl, —Br, or —I.

Unless expressly depicted or described otherwise, variables depicted in a structural formula with a "floating" bond, such as $R^2$, are permitted on any available carbon atom in the ring to which the variable is attached.

The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof.

The compounds of the instant invention have at least two chiral (i.e., asymmetric) centers from the central fused bicyclic ring of Formula I, as indicated by the asterisk at each chiral center in example A. Also, when $Z^2$ contains a non-aromatic carbon ring fused to a phenyl ring, the carbon in the non-aromatic ring that is the point of attachment to the rest of the structure in Formula I is a chiral center and is referred to herein for brevity as an indane chiral center or tetrahydronaphthalene chiral center, or a similar-meaning variation thereof. An illustrative example of an indane chiral center (when m is 1) or tetrahydronaphthalene chiral center (when m is 2) is indicated by the asterisk in example B:

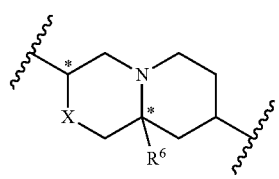

A)

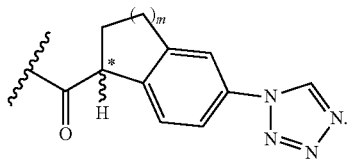

B)

Additional chiral centers may be present depending upon the nature of the various substituents on a molecule. In some of the chemical structures shown in the examples an asterisk is used to identify one or more chiral centers.

Reference to the compounds of Formula I herein encompasses the compounds of Formulas I, II, III, IV and IV and all embodiments thereof. Reference to the compounds of this invention as those of a specific formula or embodiment, e.g., Formula I, II, III, IV and IV and embodiments thereof, or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding pharmaceutically acceptable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. The inhibition of ROMK by the compounds of Formula I can be examined, for example, in the Thallium Flux Assay and/or Electrophysiology Assay described below. Moreover, this invention also relates to the use of the compounds of Formula I or salts thereof to validate in vitro assays, for example but not limited to the Thallium Flux and Electrophysiology Assays described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (both acute and chronic, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment in patients with medical conditions such as heart failure or chronic kidney disease. Furthermore, the compounds of Formula I could be used in methods for treatment of, prevention of or reduction of risk for developing one or more disorders such as pulmonary hypertension, particularly pulmonary arterial hypertension (PAH), cardiovascular disease, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascitis, pre-eclampsia, cerebral edema, nephropathy, glomerulonephritis, nephrotic syndrome, acute and chronic kidney insufficiency (also referred to as chronic kidney disease, or more generally as renal impairment), acute tubular necrosis, hypercalcemia, idiopathic edema, Dent's disease, Meniere's disease, edematous states, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 µM or less, preferably 1 µM or less, and more preferably 0.25 µM or less, in at least one of the following assays: 1) Thallium Flux Assay, 2) Electrophysiology Assay. These assays are described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prohylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, eplerenone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)-N-(2-carbamoyl-2-methylpropyl)-5-amino-4-hydroxy-2,7-diisopropyl-8-[4-methoxy-3-(3-methoxy-propoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholytics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a prostaglandin D2 receptor 1 antagonist (DP antagonist) such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products.

The "R" substituents in the Schemes correspond to the substituents defined in Formula I at the equivalent positions on the Scheme structures.

Compounds of the formula I may be prepared as shown in Scheme 1 by coupling of appropriately substituted piperazines 1 with carboxylic acids of the structure 2 to form amides. This can be accomplished in many ways well-known to the chemist, including by using EDC in the presence or absence of HOBt and a base such as triethylamine, or by using a variety of other amide coupling reagents such as HATU.

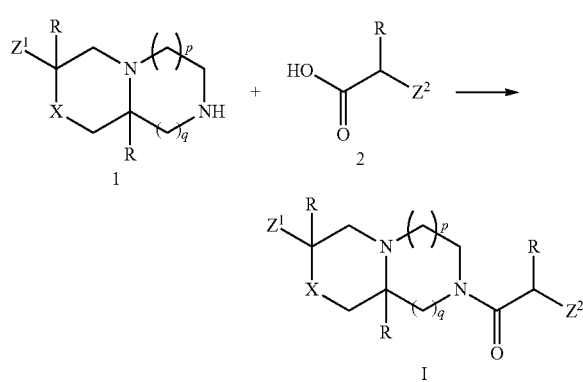

SCHEME 1

Piperazines 1 can be prepared according to Scheme 2. Epoxides 4 can be coupled with appropriately protected hydroxyalkylpiperazines 5 by heating in a solvent such as ethanol, DMSO, or toluene to afford the diols 6 (Nomura, Y. et al. Chemical & Pharmaceutical Bulletin, 1995, 43(2), 241-6). Heating can be by conventional thermal bath or by microwave irradiation. The diols 6 can be cyclized to afford 6 or 7-membered rings 7 by a variety of ways, including by heating with the reagent cyanomethylene tri-n-butylphosphorane in a suitable solvent such as benzene or toluene. Heating can be by conventional thermal bath or by microwave irradiation. The resulting compounds 7 are generally mixtures of cis and trans isomers. The protective group (Greene, T.; Wuts, P. G. M. *Protective Groups in Organic Synthesis*, John Wiley and Sons, Inc., New York, N.Y. 1991) can then be removed. For example when the protective group is Boc as shown in Scheme 2, removal can be achieved by treatment with an acid such as TFA or HCl to afford piperazines 1A. Alternatively compounds 7 can be separated by means of silica chromatography or preparative high pressure liquid chromatography employing a chiral column to afford the separated cis 7 (cis) and trans 7 (trans) isomers. The protective group of the pure cis and trans isomers can be removed by treatment with an acid such as TFA or HCl, in the case of a Boc group, to afford piperazines 1A as pure cis and trans isomers 1A (cis) and 1A (trans). If a single enantiomer of the hydroxyalkylpiperazines 5 is employed, then single enantiomer cis and trans isomers 1A (cis), and 1A (trans) can be obtained.

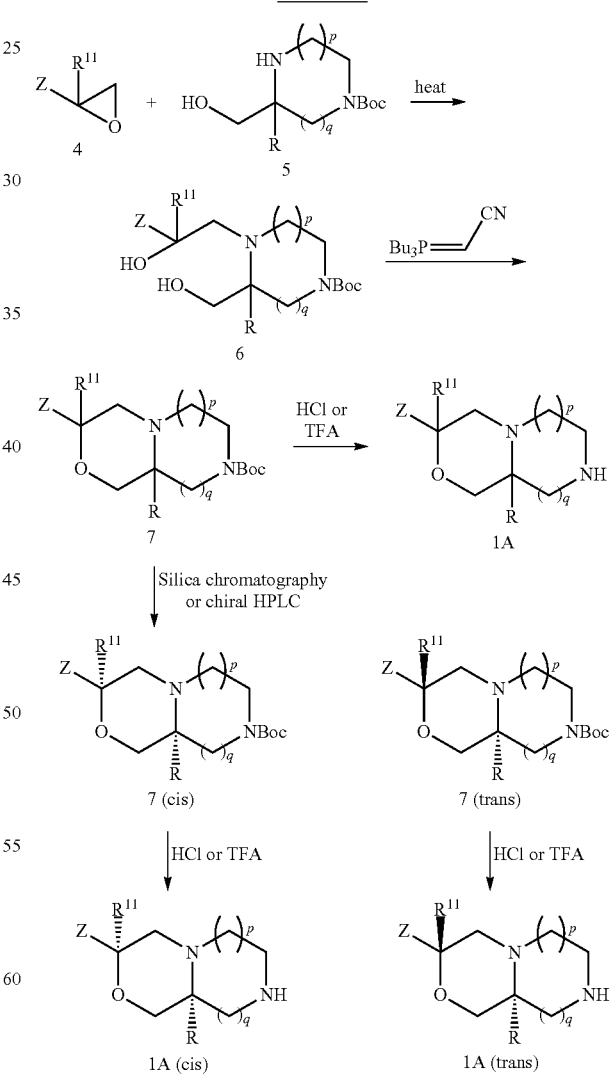

SCHEME 2

Protected piperazines 7 can also be prepared according to Scheme 3 by initially coupling hydroxyalkylpiperazines 5 with bromomethylketones (or chloromethyl ketones) 8 to afford hemiketals 9. This is typically accomplished in the presence of a base such as triethylamine or diethylisopropylamine. The resulting hemiketals 9 can be converted directly to piperazines 1A by reduction using, for example, triethylsilane in the presence of an acid catalyst such as trifluoroacetic acid. If separation of the cis and trans isomers is desired, a protective group such as Boc may be installed using, for example, Boc$_2$O, to give intermediates 7A which can be separated into cis and trans isomers as described in Scheme 2. Alternatively, the hemiketals 9 may be reduced by a three step sequence involving formation of a mesylate with mesyl chloride and a base such as triethylamine, followed by elimination in the presence of base to give enol ethers 10. Enol ethers 10 can then be reduced by hydrogenation in the presence of a catalyst such as palladium on carbon to afford protected piperazines 7A which can be separated into cis and trans isomers as described in Scheme 2. These may then be converted to piperazine intermediates 1A (cis) and 1A (trans) as described in Scheme 3.

afford the allyl substituted fused piperazines 11. The allyl groups may be removed in several ways, including by warming with 1,3-dimethylpyrimidine-2,4,6(1H,3H,5H)-trione in the presence of a catalyst such as palladium tetrakis triphenylphosphine. The revealed amines are then re-protected with tert-butoxycarbamate groups by treatment with Boc$_2$O in the presence of an amine such as triethylamine to provide intermediates 7B, generally as mixtures of cis and trans isomers. The cis and trans isomers can be separated as described in Scheme 2 by silica chromatography or by chiral preparative HPLC. If intermediates 6 are single enantiomers, then the resulting intermediates 7B (cis) and 7B (trans) are also single isomers. Alternatively, separation of the cis and trans isomers can be performed at an earlier stage by separation of the cis/trans isomers of intermediates 11. The Cbz protective groups of intermediates 7B (cis) and 7B (trans) can be removed, for example, by hydrogenolysis in the presence of a catalyst such as palladium on carbon to afford intermediates 1B (cis) and 1B (trans).

SCHEME 3

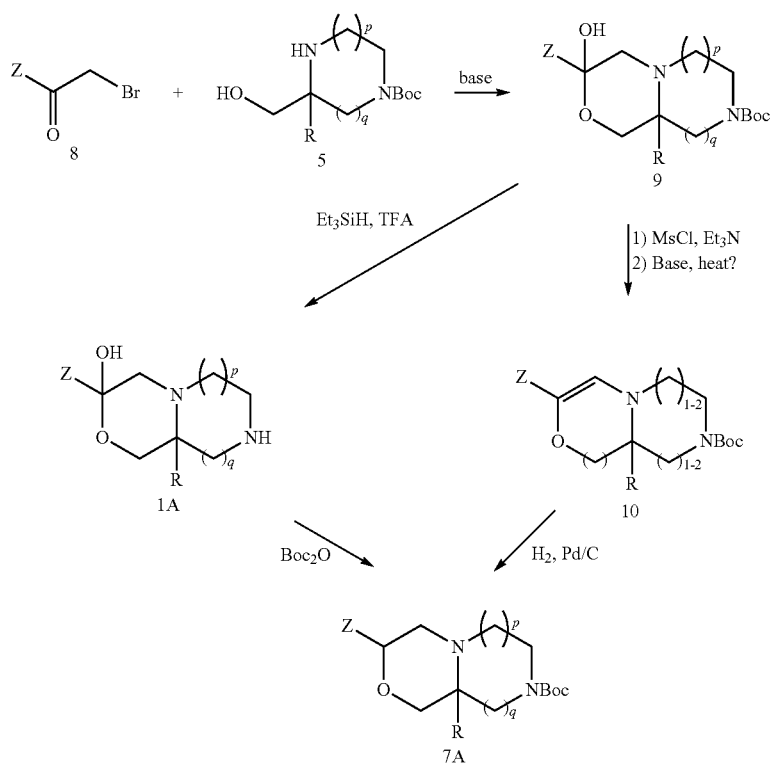

Alternatively, a subclass of intermediates 1, piperazines 1B, can be prepared as described in Scheme 4. The Boc protective group of intermediates 6 (prepared as described in Scheme 2) are switched to benzyl carbamate (Cbz) groups by initial treatment with an acid such as TFA or HCl, followed by coupling with benzyl chloroformate in the presence of a base such as triethylamine. The resulting Cbz-piperazine diols 6A are converted to the corresponding dichloro intermediates by heating with thionyl chloride, then heated with allylamine in the presence of sodium iodide to

SCHEME 4

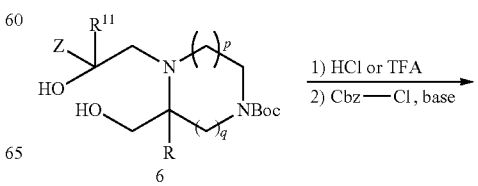

-continued

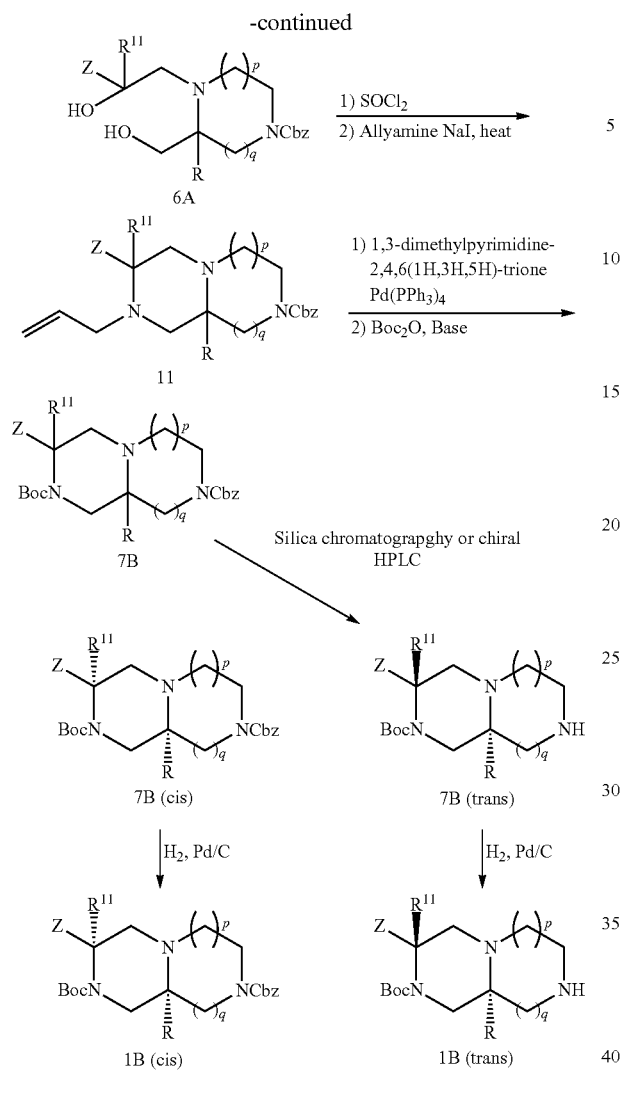

SCHEME 5

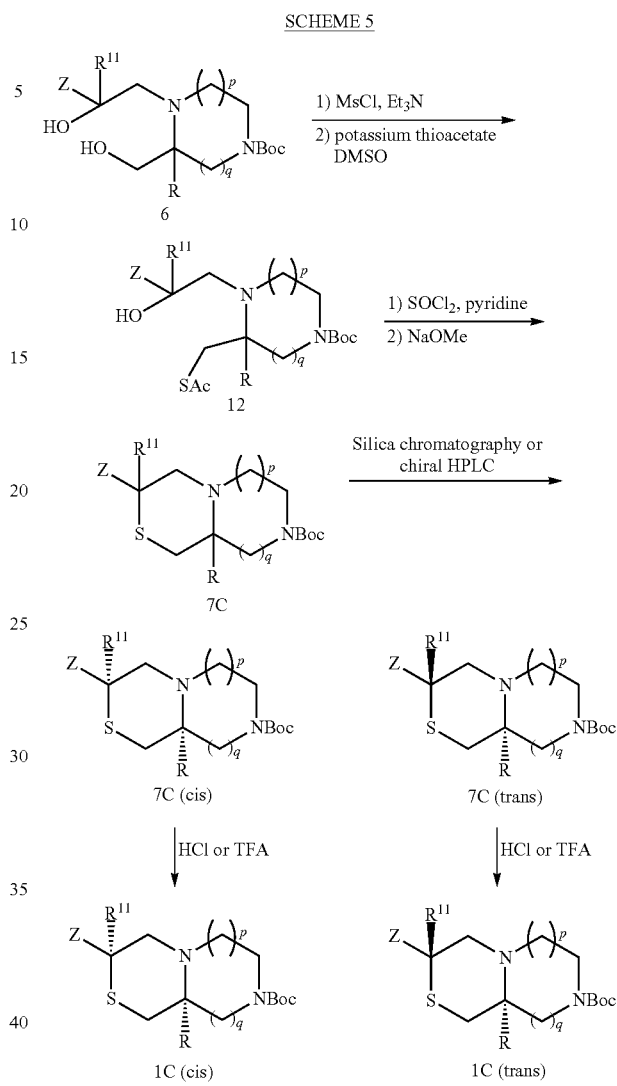

Alternatively, a sub-class of intermediates 1 (1C) may be prepared according to Scheme 5. Diols 6 are initially converted to their corresponding mono-mesylates by treatment with methanesulfonyl chloride, a base such as triethyl amine, and a catalyst such as 4-dimethylaminopyridine. Subsequent reaction with potassium thiocetate in a solvent such as dimethyl sulfoxide (DMSO) provides intermediates 12. The remaining hydroxyl group of 12 is then converted to the corresponding chloro intermediate by treatment with, for example, thionyl chloride, followed by addition of a base such as pyridine. The resulting chloro intermediate is then treated with sodium methoxide to afford the cyclized sulfides 7C. When the starting diols 6 used are single isomers (starting from enantiomerically pure epoxides 4 and enantiomerically pure hydroxyalkylpiperazines 5 (Scheme 3), the resulting intermediates 7C may be obtained as single isomers. Alternatively, when racemic epoxides 4, and single enantiomer hydroxyalkylpiperazines 5 are employed, the resulting intermediates 7C are obtained as a mixture of two isomers (cis and trans), which can then be separated to single isomers 7C (cis) and 7C (trans) by silica chromatography or by chiral preparative HPLC. Removal of the tert-butyl carbamate protective group can then be achieved by treatment with an acid such as TFA or HCl to provide the piperazines 1C (cis) and 1C (trans).

The floating bond "—R" on the phenylene ring in Schemes 6-10 represents the one or more substituents that may be present on this ring as defined in Formula I.

Intermediates 2 may be prepared in a variety of ways. A sub-class (2A) of carboxylic acids of the structure 2 may be prepared according to Scheme 6. By this route malonates 13 are reacted in the presence of a base such as sodium hydride with nitro-substituted aromatic groups bearing a halogen leaving group such as a fluoro or chloro (14 shown). The resulting coupled products 15 are decarboxylated with hydrolysis of the remaining ester to afford carboxylic acids 16. Reduction of the nitro group can be achieved in a variety of ways. One approach is to reduce with hydrogen gas in the presence of a catalyst such as Pd on carbon. The anilines 17 may then be cyclized to the tetrazoles (2A) by a number of different methods, including reaction (often with heating) with sodium azide and triethylorthoformate in a solvent such as acetic acid. Alternatively, the tetrazoles 2A may be formed by reaction with trimethylsilyl azide, trimethylsilyl trifluoroacetate, and triethyl orthoformate.

SCHEME 6

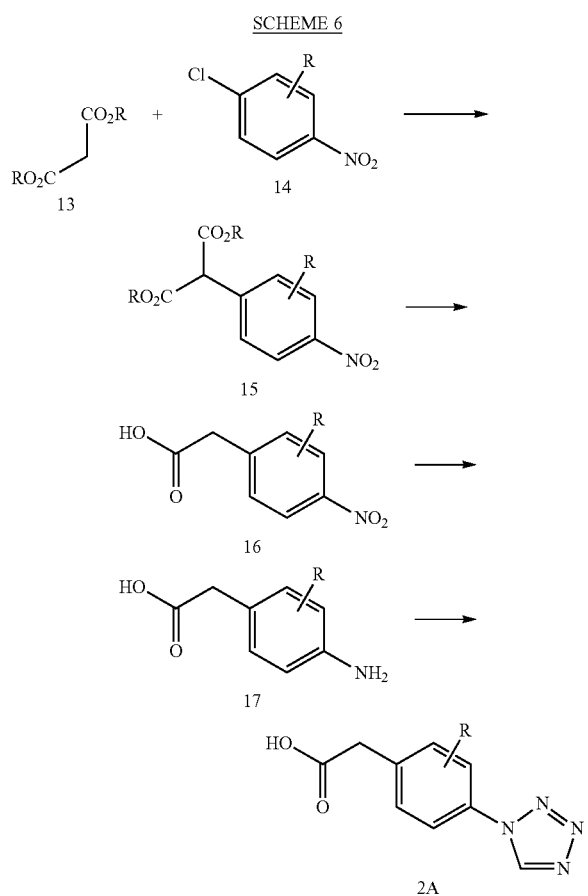

Alternatively, intermediates of the sub-class 2A may be prepared according to Scheme 7. In this case, a mixed malonate 13a is used to afford compounds 15A in a similar fashion as described in Scheme 6. Decarboxylation under acidic conditions with, for example TFA, provides the esters 18. Reduction, under conditions described for Scheme 6, provides amines 19. Cyclization to afford the tetrazoles 20 again could be accomplished as described above for Scheme 6. Finally ester hydrolysis using a base such as lithium hydroxide or sodium hydroxide with water and an organic solvent such as THF or dioxane affords the intermediates 2A.

SCHEME 7

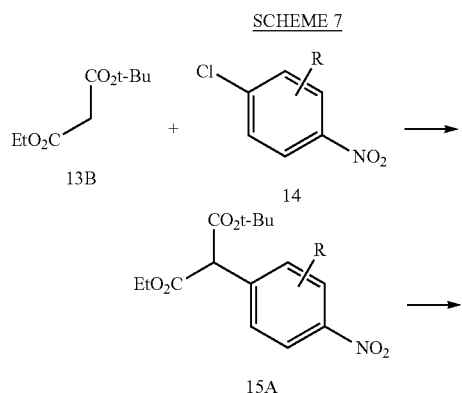

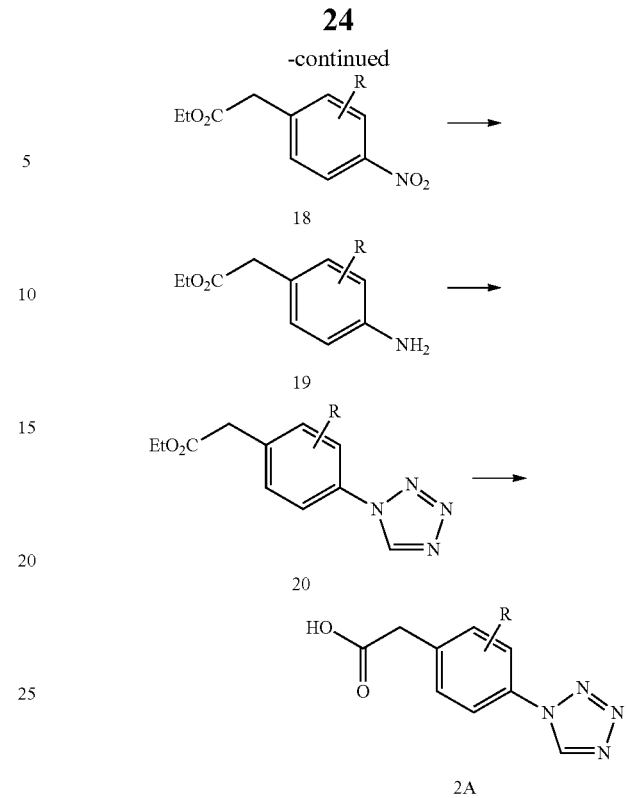

Another sub-class of acids 2B can be prepared in a variety of ways. One approach is depicted in Scheme 8. Malonate 12B, in the presence of a base such as sodium hydride can be coupled to cyano aryl or heterocycle compounds bearing a halogen leaving group such as a chloride, bromide, or fluoride (for example 21). Hydrolysis and decarboxylation of intermediates 22 can be achieved under acidic conditions (for example TFA) to provide the acids 2b.

SCHEME 8

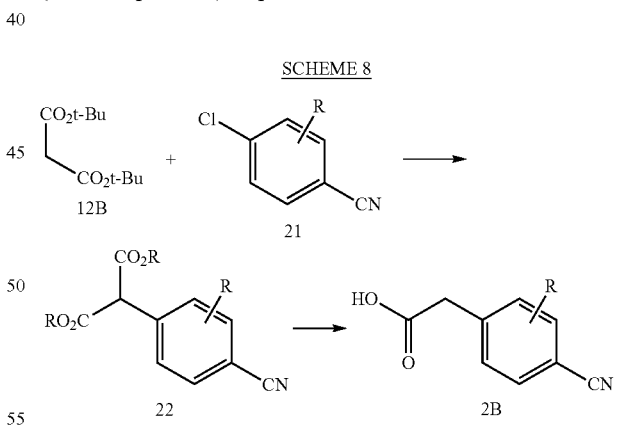

Alternatively, acids 2B can be prepared according to Scheme 9. Commercially available cyano phenols (23) can be converted to their triflates 24 using, for example triflic anhydride. Heating 24 with (2-tert-butoxy-2-oxoethyl)(chloro)zinc (25) in the presence of a palladium catalyst such as palladium Tetrakis triphenylphoshine can provide the coupled products 26. Hydrolysis is then achieved under acidic conditions with, for example, TFA to afford the acids 2B. In place of triflates 24, cyanophenyl halides or cyano-heterocyclic halides may be employed in a similar fashion.

SCHEME 9

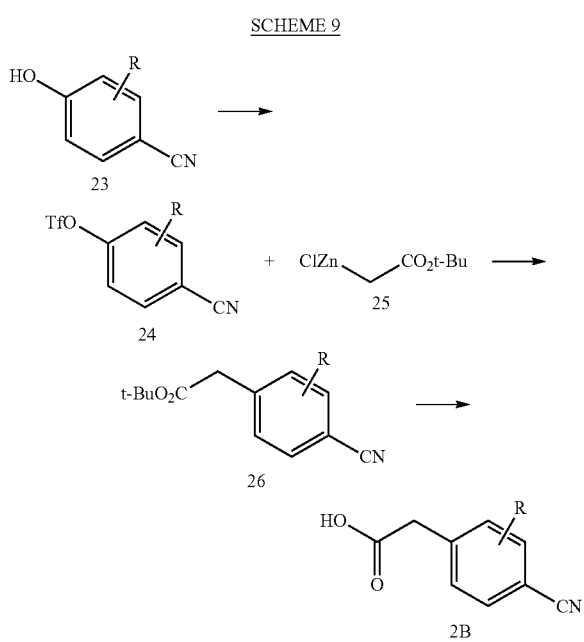

Similarly, acids 2A may be prepared according to Scheme 10. In this case, haloanilines (bromoanilines shown) are coupled to (2-tert-butoxy-2-oxoethyl)(chloro)zinc (25) in the presence of a palladium catalyst such as palladium tetrakis triphenylphoshine to provide the coupled products 28. Cyclization to afford the tetrazoles 29 again could be accomplished as described above for Scheme 6. Hydrolysis is then achieved under acidic conditions with, for example, TFA to afford the acids 2A.

SCHEME 10

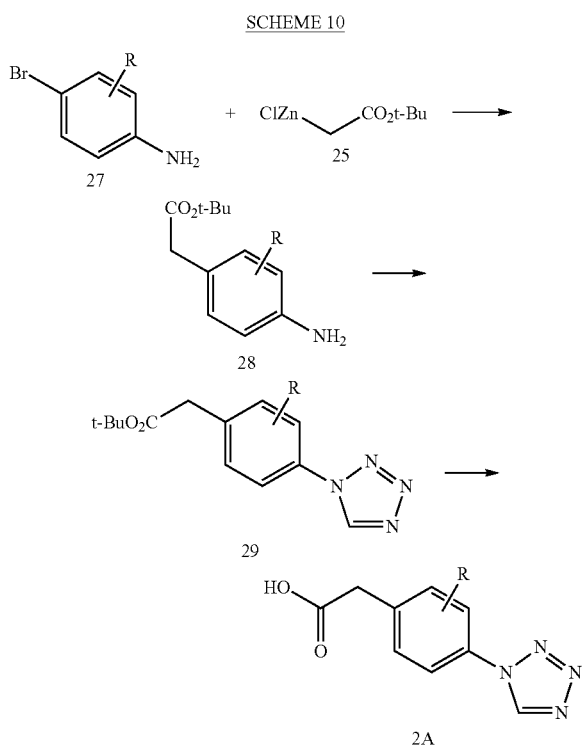

Epoxides 4 may be prepared by a variety of methods. One approach is described by Scheme 11. Aryl or heterocyclic halides (bromide 30 shown) may be coupled to form alkene products 31 in a number of ways, for example by Heck reaction or by reaction with vinyl tetrafluoroborate (Molander, G.; Luciana, A. Journal of Organic Chemistry, 2005, 70(10), 3950-3956) under palladium catalyzed coupling conditions with an appropriate phosphine ligand (Molander, G.; Brown, A. Journal of Organic Chemistry, 2006, 71(26), 9681-9686). The alkenes 28 can then be converted to the corresponding epoxides 6 by several ways, including treatment with meta-chloroperoxybenzoic acid (Fringuelli, F. et al. Organic Preparations and Procedures International, 1989, 21(6), 757-761).

SCHEME 11

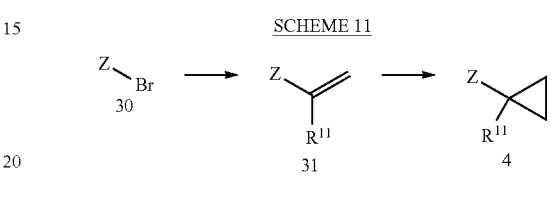

Bromomethylketones 8 may be prepared in a variety of ways; one route is depicted in Scheme 12. According to the Scheme, aryl or heterocyclic halides (bromide shown) can be reacted with tributyl(1-ethoxyvinyl)tin in the presence of a metal catalyst such as $PdCl_2(PPh_3)_2$ to provide an intermediate ethylenolether. This is subsequently treated in the same reaction vessel with N-bromosuccinimide (NBS) with added tetrahydrofuran and water to provide bromomethylketones 8. Chloromethyl ketones can similarly be prepared by employing N-chlorosuccinimide in place of N-bromosuccinimide.

SCHEME 12

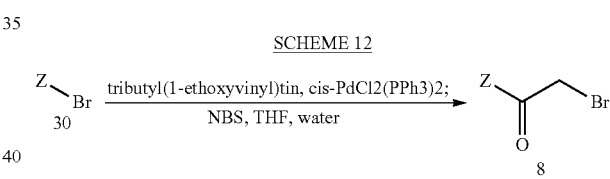

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

The subject compounds may be prepared by modification of the procedures disclosed in the Examples as appropriate. Starting materials are commercially available or made by known procedures or as illustrated. The following examples are provided for the purpose of further illustration only and are not intended to be limitations on the disclosed invention.

Reactions sensitive to moisture or air were performed under nitrogen or argon using anhydrous solvents and reagents. The progress of reactions was determined by either analytical thin layer chromatography (TLC) usually performed with E. Merck precoated TLC plates, silica gel 60F-254, layer thickness 0.25 mm or liquid chromatography-mass spectrometry (LC-MS). Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 µm. The flow rate was 1 mL/min, and the injection volume was 10 µL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detetor, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage. Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz).

Chiral analytical chromatography was usually performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography. Alternatively, chiral preparative chromatography was by supercritical fluid (SFC) conditions using one of Chiralpak AS, Chiralpak AD-H, Chiralcel OD-H, Chiralpak IC, or Chiralcel OJ-H columns (250×21.2 mm) (Daicel Chemical Industries, Ltd.). Where retention times are provided, they are not intended to be a definitive characteristic of a particular compound, since retention times will vary depending on the chromatographic conditions and equipment used.

Concentration of solutions was generally carried out on a rotary evaporator under reduced pressure. Flash chromatography was carried out on silica gel (230-400 mesh). NMR spectra were obtained in CDCl$_3$ solution unless otherwise noted. Coupling constants (J) are in hertz (Hz).

Abbreviations and acronyms used herein include: acetonitrile (ACN); acetic acid (AcOH; HOAc); t-butyloxycarbonyl (Boc or BOC); di-t-butyl dicarbonate (BOC$_2$O, Boc$_2$O); benzyl carbamate (Cbz); Carbonyldiimidazole (CDI); Cyclopentyl methyl ether (CPME); 1,8-diazabicyclo[5.4.0] undec-7-ene (DBU) 1,2-dichloroethane (DCE); dichloromethane (DCM), diisopropylamine (DIPA); N,N-diisopropylethylamine (DIEA, Hunig's base, DIPEA); dimethylacetamide (DMA; DMAC); 4-dimethylaminopyridine (DMAP); dimethoxyethane (DME); N;N-dimethylformamide (DMF); dimethylsulfoxide (DMSO); 1,3-Bis(diphenylphosphino)propane (DPPP); 1-ethyl-3-(3-dimethylaminopropyl)carbodiimide (EDC, EDAC, or EDCI); diethyl ether (ether); ethyl acetate (EtOAc or AcOEt, or EA), 2-(7-Aza-1H-benzotriazole-1-yl)-1,1,3,3-tetramethyluronium hexafluorophosphate (HATU); hexamethylphosphoramide (HMPA); 1-Hydroxybenzotriazole hydrate (HOBt); isopropanol (IPA); isopropyl acetate (IPAc); lithium aluminum hydride (LAH); lithium diisopropylamide (LDA); 3-chloroperoxybenzoic acid (mCPBA); CH$_3$SO$_2$— (mesyl or Ms); methane sulfonyl chloride or mesyl chloride (Ms-Cl); methanesulfonic acid (MsOH); methyl tert-butyl ether (MTBE); nicotinamide adenine dinucleotide phosphate (NADP); N-bromo succinimide (NBS); N-iodosuccinimide (NIS); N-methyl morpholine (NMP); Tris(dibenzylideneacetone)dipalladium(0) ((Pd$_2$(dba)$_3$); petroleum ether (petrol ether or PE); triethylamine (TEA); trifluoroacetic acid (TFA); —SO$_2$CF$_3$ (Tf); trifluoromethanesulfonic anhydride (triflic anhydride, Tf$_2$O); triflic acid or trifluoromethanesulfonic acid (TfOH); tetrahydrofuran (THF); Toluenesulfonylmethyl isocyanide (TosMIC); p-toluenesulfonic acid (TsOH); p-toluene-SO$_2$— (tosyl or Ts); Pd(dppf)Cl$_2$ or PdCl$_2$(dppf) is 1,1'-Bis(diphenylphosphino)ferrocene)dichloropalladium(II) which may be complexed with CH$_2$Cl$_2$; 2-Dicyclohexylphosphino-2',4',6'-triisopropylbiphenyl (X-Phos); Additional abbreviations and acronyms are: starting material (SM), round-bottom flask (RB or RBF); aqueous (aq); saturated aqueous (sat'd); saturated aqueous sodium chloride solution (brine); medium pressure liquid chromatography (MPLC); high pressure liquid chromatography (HPLC); preparative HPLC (prep-HPLC); flash chromatography (FC); liquid chromatography (LC); supercritical fluid chromatography (SFC); thin layer chromatography (TLC); preparative TLC (prep-TLC); mass spectrum (ms or MS); liquid chromatography-mass spectrometry (LC-MS, LCMS or LC/MS); column volume (CV); room temperature (rt; r.t. or RT); hour(s) (h or hr); minute(s) (min); retention time (R$_t$); gram(s) (g); milligram(s) (mg); milliliter(s) (mL); microliter(s) (µL); millimole (mmol); volume: volume (V/V). CELITE® is a trademark name for diatomaceous earth. SOLKA FLOC® is a trademark name for powdered cellulose. FLORISIL® is an adsorbent that is comprised hard-powdered synthetic magnesium-silica gel. X or x may be used to express the number of times an action was repeated (e.g., washed with 2×200 mL 1N HCl), or to convey a dimension (e.g., the dimension of a column is 30×250 mm).

In some examples, single stereoisomers were obtained by separation of the isomers from the parent racemate, or made by chiral synthesis (e.g., faster and slower eluting isomers). While it is understood that one of the single isomers is R and the other is S at the relevant chiral center, the absolute stereochemistry of each isomer was not determined unless stated or depicted otherwise (as, for example for Intermediates 1A and 1B).

Intermediates 1A and 1B

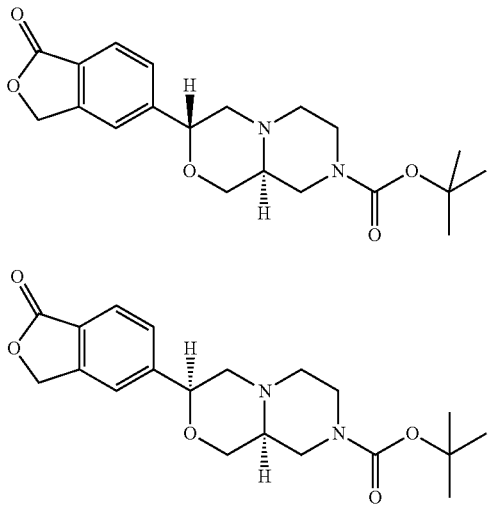

1A: tert-butyl(3R,9aS)-3-(1-oxo-1,3-dihydro-2-benzofuran-5-yl)hexahydropyrazino[2,1-c][1,4]oxazine-8(1H)-carboxylate; 1B: tert-butyl(3S,9aS)-3-(1-oxo-1,3-dihydro-2-benzofuran-5-yl)hexahydropyrazino [2,1-c][1,4]oxazine-8(1H)-carboxylate Step A: 5-ethenyl-2-benzofuran-1(3H)-one: 5-Bromophthalide (50 g, 235 mmol), potassium vinyl trifluoroborate (62.9 g, 469 mmol), and PdCl$_2$(dppf)-CH$_2$Cl$_2$ Adduct (9.58 g, 11.7 mmol) were added to ethanol (500 mL) then TEA (65.4 mL, 469 mmol) was added. The reaction mixture was degassed then heated at reflux for 8 h. The reaction was worked up by diluting with ethyl acetate and washing with brine twice. The organic layer was dried and evaporated to dryness. The crude product was purified by MPLC (silica, 600 g column) with 25% EtOAc/hexane (3 L) then with 30% EtOAc/Hexane (2 L) to yield the title compound.

Step B: 5-(oxiran-2-yl)-2-benzofuran-1(3H)-one: 5-Ethenyl-2-benzofuran-1(3H)-one (28.4 g, 177 mmol) was dissolved in DCM (400 mL) then mCPBA (47.7 g, 213 mmol) was added. The mixture was stirred at room temperature overnight. Some starting olefin remained. Another 25 g of mCPBA was added and the mixture was stirred overnight. The mixture was poured into ice cold Na$_2$SO$_3$ solution (saturated). The layers were separated and the organic layer was washed with 5% NaOH solution, brine, then was dried (MgSO$_4$). The crude product was purified by MPLC (330 g column), eluting with 40% EtOAc/hexane, 2 L, then with 45% EtOAc/hexane, 2 L, to afford 5-(oxiran-2-yl)-2-benzofuran-1(3H)-one. LC-MS: M+1=177.

Step C: tert-butyl(3S)-3-(hydroxymethyl)-4-[2-hydroxy-2-(1-oxo-1,3-dihydro-2-benzofuran-5-yl)ethyl]piperazine-1-carboxylate: 5-(Oxiran-2-yl)-2-benzofuran-1(3H)-one (1.5 g, 8.5 mmol) and commercially available (S)-4-N-BOC-2-hydroxymethyl piperazine (2.394 g, 11.07 mmol) were combined in ethanol (10 mL) in a microwave tube. The mixture was degassed then heated for 60 min at 150° C. LC-MS showed the product peak. The reaction was worked up by adding ethyl acetate and washing once with brine. The organic layer was separated, dried, and concentrated to dryness. The crude product was purified by MPLC using an 80 g Redi-sep column and eluted with 50%-100% EtOAc/hexane yielding the title compound.

Step D: tert-butyl(9aS)-3-(1-oxo-1,3-dihydro-2-benzofuran-5-yl)hexahydropyrazino[2,1-c][1,4]oxazine-8(1H)-carboxylate: tert-Butyl(3S)-3-(hydroxymethyl)-4-[2-hydroxy-2-(1-oxo-1,3-dihydro-2-benzofuran-5-yl)ethyl] piperazine-1-carboxylate (3.3 g, 8.4 mmol) and cyanomethylene tri-n-butylphosphorane (3.65 g, 15.1 mmol) were dissolved in 30 mL of benzene, the solution was degassed, and then heated to 100° C. for 3 h. LC-MS showed the product peak (M+1=389). The reaction mixture was cooled and evaporated to dryness. The residue was purified by MPLC through a 330 g Redi-sep column and eluted with a 15% acetone/85% hexane mixture to yield a cis-trans mixture of the title compound.

Step E: tert-butyl(3R,9aS)-3-(1-oxo-1,3-dihydro-2-benzofuran-5-yl)hexahydropyrazino[2,1-c][1,4]oxazine-8(1H)-carboxylate and tert-butyl(3S,9aS)-3-(1-oxo-1,3-dihydro-2-benzofuran-5-yl)hexahydropyrazino[2,1-c][1,4]oxazine-8 (1H)-carboxylate: The cis-trans isomer mixture from the prior step was separated using a ChiralCEL OD 4.6×250 mm 10 µcolumn eluting with a 45% IPA/55% heptane solvent system. The trans-isomer 1A eluted first at 11.46 min and the cis-isomer 1B second at 17.43 min. 1A: $^1$H-NMR (500 MHz, CDCl$_3$): δ ppm 7.915 (d, J=8 Hz, 1H), 7.56 (s,1H), 7.52 (d, J=8 Hz, 1H), 5.33 (s, 2H), 4.81 (dd, J=2 Hz, 10.5 Hz, 1H), 4.03-4.07 (m, 2H), 4.00 (dd, J=3, 11.25 Hz, 1H), 3.51 (t, J=10.5 Hz, 1H), 3.04 (b, 1 H), 2.96(dd J=2, 11.75 Hz, 1H), 2.76 (d, J=10.5 Hz, 1H), 2.57(b, 1H), 2.21-2.32(m, 3H), 1.5 (s, 9H). 1B: $^1$H-NMR (500 MHz, CDCl$_3$): δ ppm 7.95 (d, J=8 Hz, 1 H), 7.72 (d, J=8 Hz, 1H), 7.70(s,1H), 5.37 (s, 2H), 4.91 (t, J=3.5 Hz, 1H), 3.65-4.07 (b, 2H), 3.64 (dd, J=3, 11.5 Hz, 1H), 3.40 (t, J=11.5 Hz, 1 H), 3.29 (dd, J=3.5, 12 Hz, 1H), 3.02 (b, 1H), 2.82 (dd, J=3.5, 12 Hz, 2H), 2.66-2.67 (b, 1H), 2.50 (t, J=11 Hz, 2H), 1.5 (s, 9H).

Intermediate 2

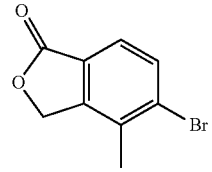

5-bromo-4-methyl-2-benzofuran-1(3H)-one

Step A: (3-bromo-2-methylphenyl)methanol: To a solution of 3-bromo-2-methyl benzoic acid (35.0 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl) methanol.

Step B: 5-bromo-4-methyl-2-benzofuran-1(3H)-one: To a flask charged with (3-bromo-2-methylphenyl)methanol (6.0 g, 30 mmol) was added a 1M TFA solution of thallium trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The solution was filtered through a CELITE pad, washed with EtOAc, adsorbed onto silica and purified by silica gel chromatography to afford the title compound: $^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

Intermediate 3

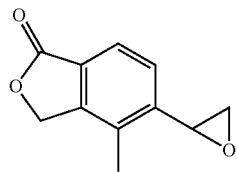

4-methyl-5-oxiran-2-yl-2-benzofuran-1(3H)-one

Step A: 5-ethenyl-4-methyl-2-benzofuran-1(3H)-one: 5-Bromo-4-methyl-2-benzofuran-1(3H)-one (598 mg, 4.47 mmol), potassium vinyl trifluoroborate (507 mg, 2.23 mmol), PdCl$_2$(dppf)-CH$_2$Cl$_2$ Adduct (182 mg, 0.223 mmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% ETOAC/Hexane solvent system to yield 5-ethenyl-4-methyl-2-benzofuran-1(3H)-one. LC-MS: M+1=175.

Step B: 4-methyl-5-oxiran-2-yl-2-benzofuran-1(3H)-one: 5-Ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at RT overnight. The reaction mixture was washed once each with saturated aqueous Na$_2$S$_2$O$_3$, NaHCO$_3$, and brine. The organic layer was dried over Na$_2$SO$_4$, filtered, and evaporated to dryness. The crude material was purified by MPLC through a 120 g Redi-sep column eluting with 0-80% EtOAc/hexane solvent system to yield target 4-methyl-5-oxiran-2-yl-2-benzofuran-1(3H)-one. $^1$H-NMR (500 MHz, CDCl$_3$): δ ppm 7.77 (d, J=8 Hz, 1H), 7.43 (d, J=8 Hz, 1H), 5.30 (s, 2 H), 4.12 (s, 1 H), 3.27 (t, J=4 Hz, 1H), 2.735 (dd, J=2.2, 5.5 Hz, 1H), 2.43 (s, 3H); LC-MS: M+1=191.

Intermediates 3A and 3B (Method 1)

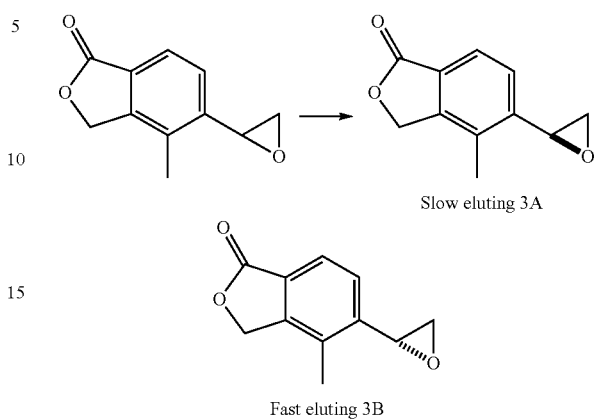

Slow eluting 3A

Fast eluting 3B

3A: 4-methyl-5-[(2S)-oxiran-2-yl]-2-benzofuran-1(3H)-one and 3B: 4-methyl-5-[(2R)-oxiran-2-yl]-2-benzofuran-1(3H)- one: Racemic 4-methyl-5-oxiran-2-yl-2-benzofuran-1 (3H)-one was resolved on a ChiralPak® AD-H column (5×25 cm) under supercritical fluid chromatography (SFC) conditions on a Berger MGIII preparative SFC instrument. The racemate was diluted to 50 mg/mL in 1:1 DCM:MeOH. The separation was accomplished using 10% EtOH/CO$_2$, flow rate 200 mL/min, 100 bar, 25° C. 500 ul Injections were spaced every 2.12 mins. The faster eluting epoxide 3B eluted at 5.2 min, and the slower eluting epoxide 3A eluted at 5.6 min.

Alternatively, the resolution could also be achieved using a mobile phase of 8% MeOH/98% CO$_2$ with a flow rate of 100 ml/min. In that case the sample was prepared by dissolving in methanol, 20 mg/ml, and using a 1 mL volume per injection. After separation, the fractions were dried off via rotary evaporator at bath temperature 40° C.

The absolute stereochemistry of each enantiomer 3A and 3B was inferred based on the X-ray crystal structure determination of a final compound made with 3B, and by Mosher ester and Trost ester HNMR analysis of esters made starting from 3B (used tert-butyl-4-[(2R-2-hydroxy-2-(4-methyl-1-oxo-1,3-dihydro-2-benzofuran-5-yl)ethyl]piperazine-1-carboxylate).

Intermediate 3B (Method 2)

Step A: 3-hydroxymethyl-2-methyl phenol: To a 5 L 3 neck RB equipped with overhead stirrer was charged NaBH$_4$ (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which BF$_3$—OEt$_2$ (321 mL, 2.53 mol) was added slowly over 1.5 hours. The slurry was aged at 10° C.-15° C. for 2 h then assayed for reaction completion (98.5% conversion). The slurry was cooled to <10° C. and quenched with 931 mL MeOH slowly over 1.5 h (gas evolution). The resulting slurry was aged overnight at RT. The batch was cooled to <10° C. then quenched with 1 N HCl (1.5 L) to get a homogeneous solution (pH solution ~1), which was aged for 30 min and then the organic solvents were removed by rotary evaporation to approximately 1.8 L of total reaction volume (bath temperature was set to 50° C.; internal temp of concentrate after rotary evaporation was ~40° C.). The slurry was held at 45° C. for 30 min then cooled slowly to 15° C. The solids were filtered and washed with cold (15° C.) water (2×300 mL), providing 3-hydroxymethyl-2-methyl phenol.

Step B: 4-Bromo-3-hydroxymethyl-2-methyl phenol: 3-Hydroxymethyl-2-methyl phenol (113.9 g, 824.0 mmol) was dissolved in a mixture of acetonitrile (850 mL) and trifluoroacetic acid (750.0 mL, 9,735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5,358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the solids were washed with 4:1 heptane:MTBE (500 mL), followed by heptane (500 mL). The solid was dried under vacuum, providing 4-bromo-3-hydroxymethyl-2-methyl phenol.

Step C: 5-Hydroxy-4-methyl-3H-isobenzofuran-1-one: To a 2 L 3 neck flask equipped with overhead stirrer, $N_2$ inlet, and condenser were charged 4-bromo-3-hydroxymethyl-2-methyl phenol (100 g, 461 mmol), CuCN (83.0 g, 921 mmol), and DMF (500 mL). The solution was sparged with $N_2$ for 15 min then heated to 145° C. to obtain a homogeneous solution. The solution was aged at 145° C. for 2 h, then the reaction mixture was cooled to 95° C. 41.5 mL water was added (sparged with $N_2$), and the reaction aged for 20 h. The reaction was cooled to RT then the solids filtered through solka flok and the cake washed with 50 mL DMF. To a 3 L flask containing 1 L EtOAc was added the DMF filtrate. A precipitate coating formed in bottom of flask. The DMF/EtOAc suspension was filtered through solka flok and the cake was washed with 250 mL EtOAc. The resulting filtrate was washed with 5% brine solution (3×500 mL). The aqueous layers were extracted with 500 mL EtOAc and the combined organics were dried over $MgSO_4$, filtered and evaporated. The solids were slurried in 250 mL MTBE at RT then filtered and washed with 100 mL MTBE. The solids were dried under vacuum at RT, providing 5-hydroxy-4-methyl-3H-isobenzofuran-1-one.

Step D: Trifluoromethanesulfonic acid 4-methyl-1-oxo-1, 3-dihydro-isobenzofuran-5-yl ester 5-Hydroxy-4-methyl-3H-isobenzofuran-1-one (46.8 g, 285 mmol) was suspended in dichloromethane (935 mL) in 2-L roundbottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature <10° C. After stirring the reaction mixture for an additional 15 min, the reaction mixture was quenched with water (200 mL), then stirred with DARCO® KB (activated carbon, 25 g) for 15 min. The biphasic mixture was filtered over SOLKA FLOC, washing with additional dichloromethane, and transferred to a separatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The solid was adsorbed onto silica gel (27.5 g) and eluted through a pad of silica gel (271 g) with 25% ethyl acetate/hexanes. The resulting solution was concentrated under vacuum with the product precipitating during concentration. The suspension was filtered, the solid washed with heptane and dried under vacuum and nitrogen, providing the title compound.

Step E: 5-(1-Butoxy-vinyl)-4-methyl-3H-isobenzofuran-1-one: To a 1 L 3-neck was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol) then $Et_3N$ (35.6 mL, 255 mmol). The solution was sparged with $N_2$ for 20 min. To the solution was added $Pd(OAc)_2$ (1.19 g., 5.32 mmol) and DPPP (2.41 g., 5.85 mmol) and sparged for an additional 10 min then heated to 80° C. After a 1 hr age, the solution was cooled to <10° C. then quenched with 630 mL EtOAc and washed with 5% $NH_4Cl$ (2×315 mL), 10% brine (2×315 mL), dried over $MgSO_4$, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one.

Step F: 5-(2-Bromo-acetyl)-4-methyl-3H-isobenzofuran-1-one: To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portionwise while maintaining Tmax=19° C. The solution was then warmed to RT for 30 minutes. HBr (48%, 0.241 mL) was added and the reaction was aged at RT for approximately 1 h after which 236 mL water was then added to the batch. A water bath is used to maintain temp at 20° C. Another 315 mL of water was added (solvent composition 1:2 THF:water) and the slurry was cooled to 15° C. The resulting solids were filtered and washed with cold 1:2 THF:water (15° C.): 150 mL displacement wash followed by 100 mL slurry wash. The solids were dried under vacuum at RT to provide 5-(2-bromo-acetyl)-4-methyl-3H-isobenzofuran-1-one.

Step G: 4-methyl-5-[(2R)-oxiran-2-yl]-2-benzofuran-1 (3H)-one: 5-(2-Bromo-acetyl)-4-methyl-3H-isobenzofuran-1-one (48.8 g., 181 mmol) was charged to a 5 L 3 neck RB flask equipped with overhead stirrer, thermocouple, and heating mantle. 2-Propanol (1.22 L) was added, followed by 610 mL of pH 7 0.1M potassium phosphate buffer. Buffer solution (610 mL) was charged to a 1.0 L erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the erlenmeyer flask and the mixture was swirled to dissolve the solids. The resulting solution was added to the 5 L round bottom, which was then heated to 28° C. and aged for 6 hours, at which point the reaction was cooled to RT and triethylamine (50.2 mL, 360 mmol) was added. The resulting solution was aged at 40° C. for 1 h. The light slurry solution was cooled to RT, after which 122 g NaCl was added. The solution was aged at RT then extracted with 1.22 L isopropyl acetate (IPAc). The aqueous layer was re-extracted with 400 mL IPAc and the combined organics were washed with 400 mL 20% brine solution, dried over MgSO₄, filtered and concentrated by rotary evaporation. The resulting solids were taken up in 100 mL IPAc (thick slurry). Hexanes were added (400 mL) and the suspension aged at RT then filtered and washed w/ 5:1 Hexanes:IPAc solution (150 mL). The solids were dried under vacuum at RT to provide 4-methyl-5-[(2R)-oxiran-2-yl]-2-benzofuran-1(3H)-one. ¹H NMR (400 MHz, CDCl₃): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H)

Intermediates 4A and 4B

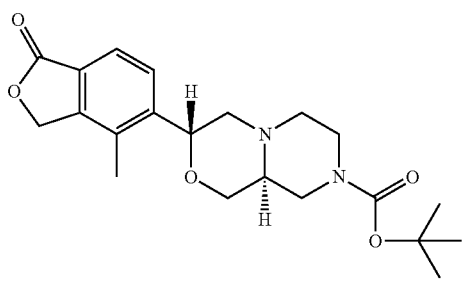

4A

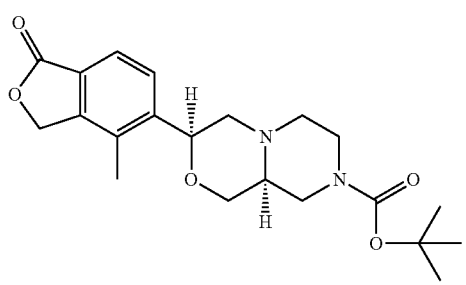

4B

4A: tert-butyl(3R,9aS)-3-(4-methyl-1-oxo-1,3-di-hydro-2-benzofuran-5-yl)hexahydropyrazino[2,1-c][1,4]oxazine-8(1H)-carboxylate and 4B: tert-butyl(3S,9aS)-3-(4-methyl-1-oxo-1,3-di-hydro-2-benzofuran-5-yl)hexahydropyrazino[2,1-c][1,4]oxazine-8(1H)-carboxylate Step A: tert-butyl(3S)-3-(hydroxymethyl)-4-[2-hydroxy-2-(4-methyl-1-oxo-1,3-dihydro-2-benzofuran-5-yl)ethyl]piperazine-1-carboxylate: 4-Methyl-5-oxiran-2-yl-2-benzofuran-1(3H)-one (3.00 g, 15.8 mmol) and (S)-4-N-BOC-2-hydroxymethylpiperazine (5.12 g, 23.7 mmol) were suspended in ethanol (10 mL) in a 20 mL microwave tube. The reaction mixture was degassed and heated in a microwave apparatus for 30 min at 150° C. The reaction mixture was evaporated to dryness, then chromatographed through a 330 g Redi-sep column and eluted with a solvent system of 1:1 EtOAc/hexane to 100% EtOAc to yield the title compound. LC-MS: M+1=407.

Step B: tert-butyl(9aS)-3-(4-methyl-1-oxo-1,3-dihydro-2-benzofuran-5-yl)hexahydropyrazino[2,1-c][1,4]oxazine-8(1H)-carboxylate: tert-Butyl(3S)-3-(hydroxymethyl)-4-[2-hydroxy-2-(4-methyl-1-oxo-1,3-dihydro-2-benzofuran-5-yl)ethyl]piperazine-1-carboxylate (3.3 g, 8.2 mmol) and cyanomethylene tri-n-butylphosphorane (2 equivalents) were dissolved in 45 mL benzene in a sealed and degassed tube. The mixture was heated to 100° C. for 3 h. The reaction mixture was cooled and evaporated to dryness. The residue was purified by chromatography through a 330 g Redi-sep column and eluted with 30% acetone/70% hexane mixture to yield the title compound as a cis-trans mixture. LC-MS: M+1=389.

Step C: Intermediates 4A and 4B: The cis/trans mixture of the product of Step B was separated using a Chiralpak AD 4.6×250 mm 10 g column with a 30% IPA/70% heptane solvent system. The trans isomer 4A eluted first at 15.7 min and the cis-isomer 4B second at 24.9 min. 4A: ¹H-NMR (500 MHz, CDCl₃): δ ppm 7.82 (d, J=8 Hz, 1H) 7.73 (d, J=8 Hz, 1H), 5.28 (s, 2H), 4.97 ppm (dd, J=2.5, 10 Hz, 1H), 4.02 (dd, J=2.5, 11 Hz, 1H), 3.87-4.18 ppm (b, 2 H) 3.53 ppm (t, J=11 Hz, 1 H), 3.04 (b, 1H), 2.88 ppm (d, J=12 Hz, 1H), 2.76 (d, J=11.5 Hz, 1H), 2.54-2.59 (b, 1 H), 2.36 (s, 3H), 2.22-2.34 (m, 3H), 1.50 (s, 9H): LC-MS: M+1=389.

4B: ¹H-NMR (500 MHz, CDCl₃): δ ppm 8.12 (d, J=8 Hz, 1H), 7.79 (d, J=8 Hz, 1H), 5.29 (s, 2H), 5.01 (t, J=4 Hz, 1H), 3.69-4.03 (b, 2H), 3.62 (t, J=8.5 Hz, 1H), 3.38(t, J=7.5 Hz, 1H), 3.23 (dd, J=4, 12 Hz, 1H), 3.09-3.20 ppm (b, 1H), 2.81 (dd, J=4, 12 Hz, 1H), 2.69-2.90 ppm (b, 2H), 2.55-2.58 (b, 2H), 2.38 ppm (s, 3H), 1.50 ppm (s, 9H): LC-MS: M+1=389.

Intermediates 4C and 4D

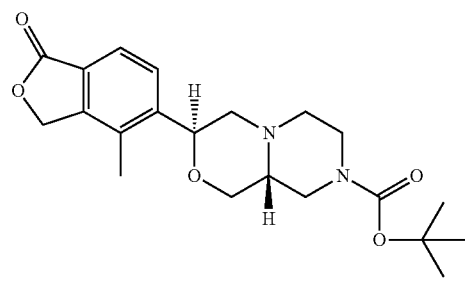

4C

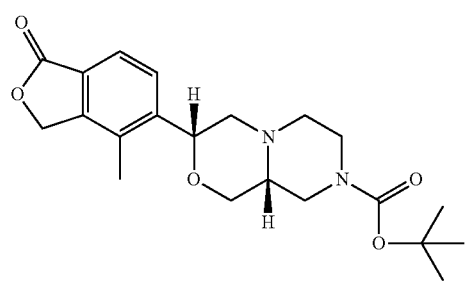

4D

4C: tert-butyl(3S,9aR)-3-(4-methyl-1-oxo-1,3-di-hydro-2-benzofuran-5-yl)hexahydropyrazino[2,1-c][1,4]oxazine-8(1H)-carboxylates 4D: tert-butyl(3R,9aR)-3-(4-methyl-1-oxo-1,3-di-hydro-2-benzofuran-5-yl)hexahydropyrazino[2,1-c][1,4]oxazine-8(1H)-carboxylate Intermediates 4C and 4D were made in a similar fashion to that described above for 4A and 4B, except (R)-4-N-

BOC-2-hydroxymethylpiperazine was used in place of (S)-4-N-BOC-2-hydroxymethylpiperazine. The cis-trans isomers 4C and 4D were separated using a ChiralCEL OD 4.6×250 mm 10 μcolumn with the 20% IPA/80% heptane solvent system. The trans-isomer 4C eluted first at 22.8 min. and the cis-isomer 4D eluted at 37.8 min.: 4C: $^1$H-NMR (500 MHz, CDCl$_3$): δ ppm 7.82 (d, J=8 Hz, 1H) 7.73 (d, J=8 Hz, 1H), 5.28 (s, 2H), 4.97 (dd, J=2.5, 10 Hz, 1H), 4.02 (dd, J=3, 11 Hz, 1H), 4.05-4.20 (b, 2 H) 3.53 (t, J=4 Hz, 1 H), 3.05 (b, 1H), 2.88 (dd, J=2, 11.7 Hz, 1H), 2.75 (d, J=10.5 Hz, 1H), 2.55 (b, 1 H), 2.36 (s, 3H), 2.22-2.36 (m, 3H), 1.51 (s, 9H); LC-MS: M+1=389. 4D: $^1$H-NMR (500 MHz, CDCl$_3$): δ ppm 8.12 (d, J=7.8 Hz, 1H), 7.79 (d, J=8 Hz, 1H), 5.30 (d, J=1.8, 2H), 5.02 (t, J=3.85 Hz, 1H), 3.70-4.05 (b, 2H), 3.62 (dd, J=3, 11.65 Hz,1H), 3.37 (t, J=9 Hz,1H), 3.23 (dd, J=4, 12 Hz,1H), 3.10 (b, 1H), 2.80-2.86 (m, 3H), 2.57 (b, 2H), 2.38 ppm (s, 3H), 1.50 ppm (s, 9H); LC-MS: M+1=389.

Intermediate 5

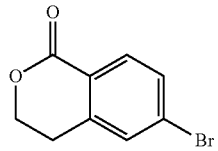 [SMILES: O=C1OCCc2cc(Br)ccc21]

6-bromo-3,4-dihydro-1H-isochromen-1-one

Method A: A 250-mL, three-necked, round-bottomed flask equipped with a septum, nitrogen inlet needle, and thermocouple was charged with diisopropylamine (3.10 g, 30.6 mmol) and 30 mL of THF. The reaction mixture was cooled at –20° C. while n-BuLi (2.5 M, 12.2 mL, 30.6 mmol) was added dropwise via syringe keeping the internal temperature below 0° C. The resulting reaction mixture was stirred at 0° C. for 15 min. The reaction mixture was then cooled at –40° C. while 4-bromo-2-methylbenzonitrile (4.00 g, 20.4 mmol) in 10 mL of THF was added dropwise via syringe over 1 h. An internal temperature of ca. –40° C. was maintained during the addition. The resulting reaction mixture was stirred at –40° C. for 30 min and then charged with DMF (2.98 g, 40.8 mmol, ca. 50 ppm water) in one portion. The reaction mixture was stirred at –40° C. for 15 min. The reaction mixture was quenched with MeOH (5 vol., 20 mL) and then charged with NaBH$_4$ (0.770 g, 20.4 mmol) in one portion and allowed to warm to room temperature. After complete reduction of intermediate aldehyde (as judged by HPLC analysis), the reaction mixture was carefully quenched with 5 M HCl (with cooling) to adjust the pH to 2-3. The reaction mixture was extracted with EtOAc and then solvent-switched to EtOH (40 mL). H$_2$SO$_4$ (98%, 20.0 g, 204 mmol) was added in one portion and the resulting reaction mixture was stirred at reflux for 24 h. After complete cyclization (monitored by HPLC analysis), the reaction mixture was cooled to room temperature and then solvent-switched to EtOAc. The resulting organic layer was washed with water, brine, and solvent-switched to MTBE. Precipitation from 1:1 MTBE:heptane afforded 6-bromo-3,4-dihydro-1H-isochromen-1-one.

Method B: A solution of DIPA (4 M, 270 mL, 1080 mmol) in THF (900 mL) was cooled to –65° C. and hexyl lithium (2.1 M, 505 mL, 1060 mmol) was added dropwise over 15 min maintaining the internal temp <–55° C. Upon completion of the addition, the reaction mixture was warmed up to –40° C. where it was stirred 30 min. To the resulting solution of LDA was added 4-bromo-2-methylbenzoic acid (90 g, 419 mmol) slowly (over 15 min) as a solution in THF (400 mL). The reaction mixture was stirred for 30 min at –40° C. and then warmed to 15° C. at which point paraformaldehyde (50.30 g, 1674 mmol) was added in 3 portions as a solid keeping the internal temperature (ice water bath) below <18° C. Stirring was then continued at room temperature for 1 hour. After a second hour of stirring, the vessel was immersed in an ice water bath and 3N HCl (650 mL) was added at such a rate to keep the internal temperature less than 30° C. The contents of the reaction vessel was subsequently transferred to a separatory funnel where it was extracted 3×400 mL EtOAc and the combined organic phases were then concentrated to ~800 mL total volume. To this was added Amberlyst 15 resin (12 g) and the resulting mixture stirred at 48° C. overnight (~14 h). HPLC analysis the following morning indicated that cyclization to the desired 6-bromo-3,4-dihydro-1H-isochromen-1-one was nearly complete. The resin was removed by filtration and the solution concentrated to ~200 mL total volume at which point the desired product began to precipitate and the solids were then collected by filtration. The cake was subsequently washed with MTBE (2×80 mL) to give the first crop of product. Additional material was salvaged by washing the collected supernatant 2× with 200 mL 10% K$_2$CO$_3$, aq followed by 200 mL 1M H$_3$PO$_4$. After concentration to ~100 mL the precipitated material was collected by filtration, washed with MTBE and then combined with the first crop of 6-bromo-3,4-dihydro-1H-isochromen-1-one and dried.

Intermediate 6A and 6B

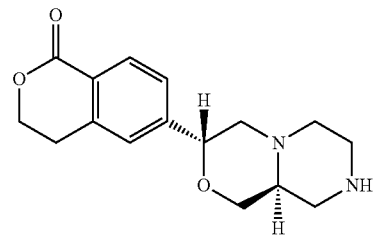

6A

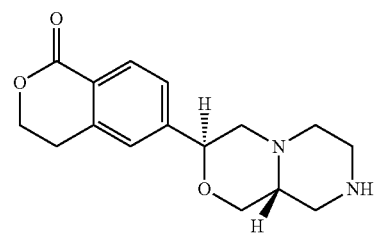

6B

6A: 6-[(3R,9aS)-octahydropyrazino[2,1-c][1,4]oxazin-3-yl]-3,4-dihydro-1H-isochromen-1-one Step A: 6-(bromoacetyl)-3,4-dihydro-1H-isochromen-1-one: 6-Bromo-3,4-dihydro-1H-isochromen-1-one (6.90 g, 30.4 mmol), tributyl(1-ethoxyethenyl)stannane (10.8 mL, 31.9 mmol, 1.05 equiv), and PdCl$_2$(PPh$_3$)$_2$ (1.07 g, 1.52 mmol, 0.05 equiv) were weighed into a 250 mL round bottom flask. To this was added dioxane (70 mL) and the resulting mixture stirred at 80° C. for 4 h. The reaction was not complete by HPLC, therefore another 0.1 equiv of tin reagent was added. After 30 min 6-bromo-3,4-dihydro-1H-isochromen-1-one had been fully consumed as indicated by HPLC. The reaction mixture was cooled to 0° C. and 35 mL THF followed by 14 mL H₂O were added. To this was introduced solid N-bromosuccinimide (5.68 g, 31.9 mmol, 1.05 equiv), added in portions over 5 min. After stirring for 30 min there was still evidence of remaining enol ether, therefore NBS was added in small portions (~300 additional mg added) until it was consumed as evidenced by HPLC. Water was then added and the mixture extracted with EtOAc. The aqueous layer was extracted 2 additional times with EtOAc, the combined organics dried with MgSO₄, filtered and concentrated in vacuo. This was transferred with EtOAc to a 100 mL round bottom flask, the resulting solution concentrated to ~25 mL total volume, at which point hexane (50 mL) was added dropwise. When complete the heterogeneous mixture was stirred for 30 min, then cooled to 0° C. and stirred for 10 min, then filtered and washed twice with hexanes. The desired product was dried under a nitrogen bag, then purified by flash chromatography (12 to 100% EtOAc/Hex) to provide the title compound.

Step B: tert-butyl(9aS)-3-hydroxy-3-(1-oxo-3,4-dihydro-1H-isochromen-6-yl)hexahydropyrazino[2,1-c][1,4]oxazine-8(1H)-carboxylate: 6-(Bromoacetyl)-3,4-dihydro-1H-isochromen-1-one (~1.54 g, ~5.72 mmol, presence of α-chloroketone was noted, ~10%) and commercially available (S)-4-N-BOC-2-hydroxymethylpiperazine (1.24 g, 5.72 mmol) were added to a round bottom flask and diluted with THF (50 mL). Diisopropylethylamine (1.30 mL, 7.44 mmol) was then introduced and the mixture left stirring for 14 h at RT during which time a considerable amount of solid had formed. The reaction mixture was diluted with EtOAc, then washed with saturated NH₄Cl$_{aq}$ followed by H₂O. Both aqueous layers were sequentially back extracted once with another portion of EtOAc, the organics were then combined, dried with MgSO₄, filtered, and concentrated in vacuo. The recovered crude product was subjected to purification by flash chromatography (Biotage, 50% EtOAc/Hex) to afford the title compound.

Step C: 6-[(3R,9aS)-octahydropyrazino[2,1-c][1,4]oxazin-3-yl]-3,4-dihydro-1H-isochromen-1-one: tert-Butyl (9aS)-3-hydroxy-3-(1-oxo-3,4-dihydro-1H-isochromen-6-yl)hexahydropyrazino[2,1-c][1,4]oxazine-8(1H)-carboxylate (1.84 g, 4.55 mmol) was diluted with TFA (18 mL, 234 mmol) and cooled to 0° C. Some off gassing was apparent and after a few minutes a homogenous solution had been formed. Approximately 5 minutes post-TFA addition, Et₃SiH (5.09 mL, 31.8 mmol) was added and the reaction mixture allowed to slowly warm to RT (allowed to warm naturally in the ice bath) where it was stirred for 18 h. The trans:cis diastereomeric ratio appeared to be ~95:5. The reaction vessel was transferred to a rotary evaporator and concentrated in vacuo to a two phase liquid. This crude material was diluted with CH₂Cl₂, washed with aq NaHCO₃, then water. The separately kept aqueous layers were subsequently extracted once with the same portion of CH₂Cl₂, the combined organics dried with MgSO₄, filtered and concentrated in vacuo. The crude residue was dried under house vacuum then the mixture was further purified by flash chromatography (2% MeOH 2% Et₃N in CH₂Cl₂) to afford the title compound.

6B: 6-[(3S,9aR)-octahydropyrazino[2,1-c][1,4]oxazin-3-yl]-3,4-dihydro-1H-isochromen-1-one The same procedure described above to prepare 6-[(3R,9aS)-octahydropyrazino[2,1-c][1,4]oxazin-3-yl]-3,4-dihydro-1H-isochromen-1-one was used to prepare the title compound starting from 6-(bromoacetyl)-3,4-dihydro-1H-isochromen-1-one and commercially available (R)-4-N-BOC-2-hydroxymethylpiperazine; LC-MS (IE, m/z): 289.1 [M+1]⁺.

Intermediate 7 and Isomers 7A and 7B

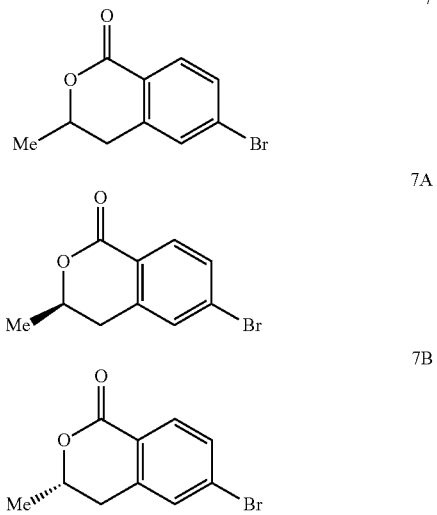

6-bromo-3-methyl-3,4-dihydro-1H-isochromen-1-one and individual isomers 7A: (3R)-6-bromo-3-methyl-3,4-dihydro-1H-isochromen-1-one, and 7B: (3S)-6-bromo-3-methyl-3,4-dihydro-1H-isochromen-1-one: A −78° C. solution of diisopropylamine (13.3 mL, 93.0 mmol)) in THF (155 mL) was treated with n-BuLi (1.6 M in Hexanes; 58 mL, 93 mmol) over a period of 15 minutes using a syringe pump. In a separate flask, a solution of 2-methyl-4-bromo benzoic acid (10.0 g, 46.5 mmol) and HMPA (8.33 mL, 46.5 mmol) in THF (155 mL) was cooled to −78° C. Methyl Lithium (29.1 mL, 46.5 mmol) was added slowly via syringe to the cooled solution. The resulting solution was stirred for 10 minutes and then transferred via cannula to the LDA solution at −78° C. The resulting solution was stirred at −78° C. for an additional 1 h before being quenched with anhydrous acetaldehyde (7.88 mL, 140 mmol) and the reaction was then taken out of the dry ice acetone bath and allowed to stir for an additional 1 h. The flask containing the reaction mixture was then resubmerged in the dry ice acetone bath before it was quenched with 4M HCl in dioxane (50 mL) followed by 25 mL of MeOH. The reaction was stirred at room temp for an additional 1 h. The crude reaction mixture was partitioned between 200 mL ethyl acetate and 200 mL water. The organic layer was washed with water, brine, dried with magnesium sulfate, filtered and concentrated. Purification via MPLC (30-70% DCM/Hexanes) afforded 7 as a racemic mixture which was separable by chiral SFC HPLC using, for example, a Chiralpak AS column to obtain 7A and 7B. ¹H NMR (500 MHz; CDCl₃): δ 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H); LC-MS (IE, m/z): 241 [M+1]⁺.

Intermediate 7A (Method 2)

(3R)-6-bromo-3-methyl-3,4-dihydro-1H-isochromen-1-one

Step A: 4-bromo-N,N-diethyl-2-methylbenzamide: A solution of 4-bromo-2-methylbenzoic acid (25.0 g, 116 mmol) in DCM (400 mL) was treated with oxalyl chloride (11.7 mL, 134 mmol) and a catalytic amount of dry DMF (0.1 mL). The reaction was allowed to stir under nitrogen for 2 hours at room temperature. Removal of excess solvent gave crude acid chloride which was redissolved in DCM (400 mL). The mixture was then cooled to 0° C. and triethyl amine (40.5 mL, 291 mmol) was added followed by the slow addition of diethyl amine (24.3 mL, 233 mmol). The reaction was then allowed to warm to room temperature overnight. The crude mixture was then diluted with 400 mL of water and extracted with DCM (3×500 mL). The combined organic layers were then washed with brine (200 mL), dried over magnesium sulfate, filtered and then concentrated. The crude material was purified via MPLC (10% EtOAc/Hex) to afford 4-bromo-N,N-diethyl-2-methylbenzamide: LC-MS: $(M+H)^+$ 270.

Step B: 4-bromo-N,N-diethyl-2-(2-oxopropyl)benzamide: A 2M solution of LDA (35.2 mL, 70.3 mmol) in THF (176 mL) cooled to −78° C. was treated with slow addition of 4-bromo-N,N-diethyl-2-methylbenzamide (19 g, 70.3 mmol) in dry THF (176 mL). The reaction was allowed to stir at −78° C. for 1 hour before it was quenched with N-methoxy-N-methylacetamide (22.43 mL, 211 mmol) and allowed to slowly warm to room temp. The reaction was stirred overnight and then partitioned between 1N HCl (200 mL) and EtOAc (400 mL). The aqueous layer was further extracted with EtOAc (2×150 mL). The combined organic layers were washed with brine (150 mL), dried over magnesium sulfate, filtered and concentrated. The crude material was an oil out of which the product precipitated. The oil was decanted off and the solid was washed with hexanes and dried using a buchner funnel to afford 4-bromo-N,N-diethyl-2-(2-oxopropyl)benzamide: LC-MS: $(M+H)^+$ 312.

Step C: 4-bromo-N,N-diethyl-2-[(2R)-2-hydroxypropyl]benzamide: A flask equipped with an overhead stirrer was charge with pH=8 Phosphate Buffer (156 mL, 31.2 mmol) followed by D-glucose (1.298 g, 7.21 mmol) and then warmed to 30° C. Next, 135 mg glucose dehydrogenase and 270 mg NADP+ disodium was added to the glucose/buffer solution at once, a homogeneous solution was obtained after 1 min agitating. Next, 577 mg of keto-reductase enzyme KRED P1B2 (available from Codexis, Inc., 200 Penobscot Drive, Redwood City, Calif. 94063, www.codexis.com, tel. 1-650-421-8100) was added to the reaction vessel and stirred at 500 rpm at 30° C. until enzyme was wetted (about 40 min). Lastly, a solution of 4-bromo-N,N-diethyl-2-(2-oxopropyl)benzamide (1.5 g, 4.80 mmol) dissolved in DMSO (14.56 mL) (pre-warmed on stir plate to 30° C.) was added to the reaction over ~3 min and agitated at 30° C. (400 rpm) overnight.

After 48 hours the reaction was cooled to room temperature and then 75 g of potassium carbonate was added to the reaction in portions and stirred for 15 minutes until enzyme clumped together when stirring is stopped. Next, acetonitrile (50 mL) was poured into the reaction flask and the layers were thoroughly mixed. Stirring was stopped after 15-20 minutes, the layers allowed to separate and the upper layer decanted off. This was repeated two more times with additional 50 mL of acetonitrile. The combined organic layers were then filtered through a medium porosity funnel, concentrated and then 50 ml MTBE was added to the concentrate and stirred for 5 min and then transferred to a separatory funnel and the layers separated. The aqueous layer was extracted further another 50 mL MTBE. The combined organic extracts were dried over magnesium sulfate, filtered and concentrated. Purification via MPLC (30-70% EtOAc/Hex) afforded 4-bromo-N,N-diethyl-2-[(2R)-2-hydroxypropyl]benzamide.

Step D: (3R)-6-bromo-3-methyl-3,4-dihydro-1H-isochromen-1-one: A solution of 4-bromo-N,N-diethyl-2-[(2R)-2-hydroxypropyl]benzamide (12.2 g, 38.8 mmol) dissolved in 4N HCl in dioxane (200 mL) was stirred at room temperature and monitored by TLC. After 3 days the reaction was partitioned between EtOAc (300 mL) and water (300 mL). The aqueous phase was further extracted with EtOAc (2×250 mL). The combined organic layers were then washed with water (200 mL), brine (200 mL), dried over magnesium sulfate, filtered and concentrated. The crude material was then purified via MPLC (15-30% EtOAc/Hexane) to afford (3R)-6-bromo-3-methyl-3,4-dihydro-1H-isochromen-1-one: $^1$H NMR (500 MHz; CDCl$_3$): 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H); LC-MS: $(M+1)^+$ 241.

Intermediate 7B (Method 2)

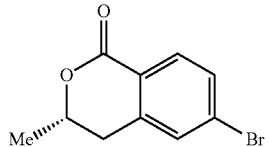 [SMILES: C[C@H]1Cc2cc(Br)ccc2C(=O)O1]

(3S)-6-bromo-3-methyl-3,4-dihydro-1H-isochromen-1-one: (3S)-6-Bromo-3-methyl-3,4-dihydro-1H-isochromen-1-one was prepared in a similar manner as (3R)-6-Bromo-3-methyl-3,4-dihydro-1H-isochromen-1-one except using keto-reductase enzyme KRED P1H9 (available from Codexis, Inc., 200 Penobscot Drive, Redwood City, Calif. 94063, www.codexis.com, tel. 1-650-421-8100) in Step C, which gave the opposite enantiomer of the resulting alcohol.

Intermediates 8A and 8B

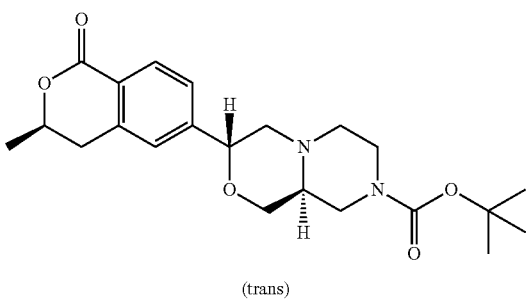

8A (trans)

-continued

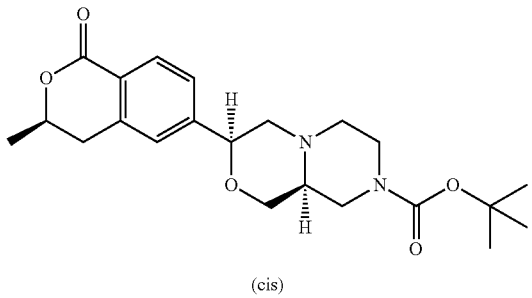

(cis)

8A: tert-Butyl (3R,9aS)-3-[(3R)-3-methyl-1-oxo-3,4-dihydro-1H-isochromen-6-yl]hexahydropyrazino[2,1-c][1,4]oxazine-8(1H)-carboxylate 8B: tert-Butyl (3S,9aS)-3-[(3R)-3-methyl-1-oxo-3,4-dihydro-1H-isochromen-6-yl]hexahydropyrazino[2,1-c][1,4]oxazine-8(1H)-carboxylate Step A: (3R)-6-ethenyl-3-methyl-3,4-dihydro-1H-isochromen-1-one: A solution of (3R)-6-bromo-3-methyl-3,4-dihydro-1H-isochromen-1-one (2.4 g, 9.96 mmol) and triethylamine (2.78 mL, 19.91 mmol) in EtOH (39.8 mL) was added to a microwave vial containing PdCl$_2$(dppf)-CH$_2$Cl$_2$, (0.406 g, 0.498 mmol) and potassium vinyltrifluoroborate (2.000 g, 14.93 mmol). The contents of the vial were heated to 100° C. for 1 hour after which the mixture was cooled, diluted with chloroform (50 mL) and washed with aqueous ammonium chloride (25 mL). The organic layer was then dried over magnesium sulfate, filtered and the solvent was evaporated under reduced pressure. MPLC purification (15-60% EtOAc/Hex) gave the title compound.

Step B: (3R)-3-methyl-6-(oxiran-2-yl)-3,4-dihydro-1H-isochromen-1-one: A solution of 6-ethenyl-3-methyl-3,4-dihydro-1H-isochromen-1-one (1.69 g, 8.98 mmol) in DCM (60 mL) was treated with mCPBA (3.100 g, 17.96 mmol) overnight at room temperature. The reaction was then diluted with water (50 mL) and DCM (50 mL). The organic layer was further washed successively with saturated aqueous sodium bicarbonate (30 mL), water (30 mL), and brine (30 mL). The organic layer was then dried over magnesium sulfate, filtered and concentrated. The residue was purified via MPLC (15-40% EtOAc/Hex) to give the title compound.

Step C: tert-butyl (3S)-3-(hydroxymethyl)-4-{2-hydroxy-2-[(3R)-3-methyl-1-oxo-3,4-dihydro-1H-isochromen-6-yl]ethyl}piperazine-1-carboxylate: A solution of (3R)-3-methyl-6-(oxiran-2-yl)-3,4-dihydro-1H-isochromen-1-one (325 mg, 1.59 mmol) and tert-butyl (3S)-3-(hydroxymethyl)piperazine-1-carboxylate (345 mg, 1.59 mmol dissolved in EtOH (7 mL)) was heated in a sealed tube to 155° C. for 3 hours in the microwave. The reaction was cooled and concentrated to give crude product which was purified via MPLC (40-100% EtOAc/Hexane) to give the title compound as a mixture of diastereomers.

Step D: tert-Butyl (3R,9aS)-3-[(3R)-3-methyl-1-oxo-3,4-dihydro-1H-isochromen-6-yl]hexahydropyrazino[2,1-c][1,4]oxazine-8(1H)-carboxylate and tert-Butyl (3S,9aS)-3-[(3R)-3-methyl-1-oxo-3,4-dihydro-1H-isochromen-6-yl]hexahydropyrazino[2,1-c][1,4]oxazine-8(1H)-carboxylate: A sealed tube containing tert-butyl (3S)-3-(hydroxymethyl)-4-{2-hydroxy-2-[(3R)-3-methyl-1-oxo-3,4-dihydro-1H-isochromen-6-yl]ethyl}piperazine-1-carboxylate as a mixture of diastereomers (530 mg, 1.26 mmol) and cyanomethylenetributylphosphorane (304 mg, 1.26 mmol) dissolved in anhydrous benzene (8 mL) was degassed twice with nitrogen and then heated using a microwave to 135° C. for 2.5 hours. The reaction was allowed to cool and the crude mixture was concentrated and purified on MPLC (20-65% EtOAc/Hex) to afford a mixture of diastereomers as well as recovered starting material. The cis/trans mixture was purified via chiral HPLC (10% EtOH/Heptane) using AS column to give the trans isomer as the faster eluting peak and the cis isomer as the slower eluting peak. Alternatively, the mixture can be separated by chiral SFC-HPLC (40% 2:1MeOH:MeCN/CO$_2$) using an IC column.

8A: $^1$H NMR (500 MHz; CDCl$_3$): 8.08 (d, J=8.1 Hz, 1H), 7.35 (d, J=8.0 Hz, 1H), 7.28 (s, 1H), 4.70 (m, 2H), 4.00 (bs, 2H), 3.96 (dd, J=3.0, 11.3 Hz, 2H), 3.48 (t, J=10.7 Hz, 1H), 2.95 (m, 4H), 2.74 (d, J=10.5 Hz, 1H), 2.2 (m, 3H), 1.53 (d, J=6.4 Hz, 3H), 1.49 (s, 9H);

LC-MS: (M+1)$^+$ 403; 8B: $^1$H NMR (500 MHz; CDCl$_3$): 8.10 (d, J=8.2 Hz, 1H), 7.54 (d, J=8.0 Hz, 1H), 7.40 (s, 1H), 4.81 (bt, 1H), 4.71 (m, 1H), 3.62 (dd, J=2.8, 11.5 Hz, 1H), 3.41 (m, 1H), 3.25 (dd, J=3.7, 12.1 Hz, 1H), 2.95 (m, 4H), 2.76 (m, 3H), 2.50 (m, 2H), 2.28 (m, 1H), 1.54 (d, J=6.2 Hz, 3H), 1.49 (s, 9H); LC-MS: (M+1)$^+$ 403.

Intermediate 9A and 9B

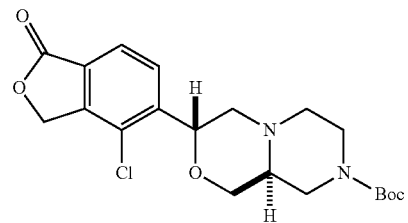

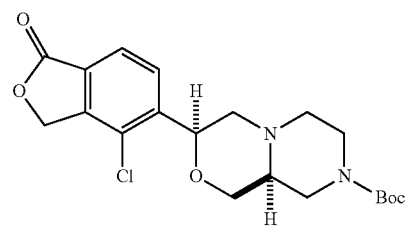

9A: tert-butyl (3R,9aS)-3-(4-chloro-1-oxo-1,3-dihydro-2-benzofuran-5-yl)hexahydropyrazino[2,1-c][1,4]oxazine-8(1H)-carboxylate 9B: tert-butyl (3S,9aS)-3-(4-chloro-1-oxo-1,3-dihydro-2-benzofuran-5-yl)hexahydropyrazino[2,1-c][1,4]oxazine-8(1H)-carboxylate Step A: 2-chloro-3-(hydroxymethyl)phenol: To a solution of 2-chloro-3-hydroxybenzaldehyde (8.10 g, 51.7 mmol) in MeOH was added NaBH$_4$ (1.96 g, 51.7 mmol) at 0° C. The reaction was allowed to stir for 30 minutes. TLC showed clean conversion to a more polar spot. The reaction was diluted with EtOAc (400 mL), washed with water and brine, dried over sodium sulfate, and concentrated. The crude product was used in Step B without further purification.

Step B: 4-bromo-2-chloro-3-(hydroxymethyl)phenol: To the flask charged with 2-chloro-3-(hydroxymethyl)phenol from Step A and a stir bar was added NBS (10.8 g, 60.5 mmol) and TFA (50 mL). The reaction was allowed to stir for 16 hours at RT. TLC showed complete reaction at that point. The solvent was removed under vacuum. The residue was re-dissolved in EtOAc, washed with water, and purified by silica gel flash chromatography. A pair of regio-isomers was collected from the separation. The less polar spot was the desired 4-bromo-2-chloro-3-(hydroxymethyl)phenol according to NMR analysis.

Step C: 4-chloro-5-hydroxy-2-benzofuran-1(3H)-one: To a flask charged with 4-bromo-2-chloro-3-(hydroxymethyl)phenol (2.44 g, 10.3 mmol) and a stir bar was added CuCN (2.76 g, 30.8 mmol) and DMF (25 mL). The flask was fitted with a condenser and purged three times with Nitrogen. The solution was then heated to 145° C. for 2 hours. At that point, water (0.555 mL, 30.8 mmol) was added to the reaction via a syringe, and the reaction was kept at 100° C. for another 24 hours. The reaction was cooled to RT, diluted with DCM (100 mL), and filtered through a pad of CELITE to remove the solids. The filtrate was washed with saturated NH$_4$OAc, dried over sodium sulfate, concentrated and purified by silica gel flash chromatography. 4-Chloro-5-hydroxy-2-benzofuran-1(3H)-one was collected after removal of solvents.

Step D: 4-chloro-5-ethenyl-2-benzofuran-1(3H)-one: To a cold solution of 4-chloro-5-hydroxy-2-benzofuran-1(3H)-one (1.39 g, 7.53 mmol) in DCM (25 mL) was added Hunig's Base (3.29 mL, 18.8 mmol) and trifluoromethanesulfonic anhydride (2.54 mL, 15.1 mmol). The mixture was allowed to stir for 16 hours. Analysis by TLC showed complete consumption of all SM. The reaction was diluted with Hexane and washed with water. The solution was dried with sodium sulfate, concentrated, and purified by flash chromatography on a silica column. The solvent was removed under reduced pressure to give intermediate triflate: LC-MS (M+1=317). To the triflate was added a stir bar, potassium vinyltrifluoroborate (1.33 g, 9.90 mmol), PdCl$_2$(dppf) (0.243 g, 0.332 mmol), triethylamine (1.89 mL, 13.3 mmol), and iso-propanol (50 mL). The mixture was purged three times with nitrogen, and heated to 60° C. for 2 hours. TLC showed complete reaction at that point. Most of the solvent was removed under vacuum. The crude residue was diluted with EtOAc (200 mL), washed with brine, dried over sodium sulfate, adsorbed onto silica gel, and purified by flash chromatography to give the title compound.

Step E: 4-chloro-5-oxiran-2-yl-2-benzofuran-1(3H)-one: To a solution of 4-chloro-5-ethenyl-2-benzofuran-1(3H)-one (1.1 g, 5.7 mmol) in DCM (40 mL) was added mCPBA (1.9 g, 8.5 mmol). The solution was stirred at RT for 16 hours. Analysis by TLC and LC showed formation of the desired product, along with some untouched starting material. The reaction was diluted with DCM (200 mL), washed with aqueous Na$_2$S$_2$O$_3$ and Na$_2$CO$_3$, dried over sodium sulfate, concentrated, and purified by silica gel flash chromatography to afford the title compound.

Step F-G: tert-butyl (3R,9aS)-3-(4-chloro-1-oxo-1,3-dihydro-2-benzofuran-5-yl)hexahydropyrazino[2,1-c][1,4]oxazine-8(1H)-carboxylate and tert-butyl (3S,9aS)-3-(4-chloro-1-oxo-1,3-dihydro-2-benzofuran-5-yl)hexahydropyrazino[2,1-c][1,4]oxazine-8(1H)-carboxylate
The title compounds were prepared from 4-chloro-5-(oxiran-2-yl)-2-benzofuran-1(3H)-one in two steps in an analogous fashion as that described for the synthesis of 4A: tert-butyl(3R,9aS)-3-(4-methyl-1-oxo-1,3-dihydro-2-benzofuran-5-yl)hexahydropyrazino[2,1-c][1,4]oxazine-8(1H)-carboxylate and 4B: tert-butyl(3S,9aS)-3-(4-methyl-1-oxo-1,3-dihydro-2-benzofuran-5-yl)hexahydropyrazino[2,1-c][1,4]oxazine-8(1H)-carboxylate. The crude product mixture was adsorbed onto silica gel, and purified by flash chromatography. The top product spot was determined by NMR to be the trans-isomer 9A, and more polar product spot was the cis-isomer 9B: $^1$H-NMR (500 MHz, CDCl$_3$) δ ppm 9A: 7.83 (d, J=7.5 Hz, 1H), 7.78 (d, J=8.0 Hz, 1H), 5.26 (s, 2H), 5.10 (d, J=10.5 Hz, 1H), 3.98 (d, J=11.5 Hz, 1H), 3.90 (broad, 1H), 3.52 (t, J=10.5 Hz, 1H), 3.05 (d, J=11.5 Hz, 1H), 3.03 (broad, 1H), 2.75 (d, J=11 Hz, 1H), 2.54 (broad, 1H), 2.30 (t, J=10 Hz, 1H), 2.22 (t, J=11 Hz, 1H), 2.07 (t, J=10.5 Hz, 1H), 1.46 (s, 9H); 9B: 8.20 (d, J=7.5 Hz, 1H), 7.82 (d, J=8.0 Hz, 1H), 5.28 (s, 2H), 5.13 (s, 1H), 3.85 (broad, 1H), 3.71 (d, J=11.5, 1H), 3.49 (m, 1H), 3.09 (dd, J=12, 5.0 Hz, 1H), 3.05 (m, 1H), 2.91 (m, 1H), 2.88-2.80 (m, 2H), 2.64 (m, 1H), 1.47 (s, 9H).

Intermediate 10 (trans)

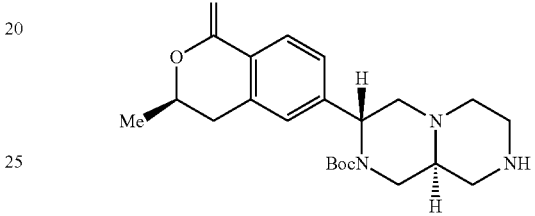

(3R,9aS)-tert-butyl 3-((R)-3-methyl-1-oxoisochroman-6-yl)hexahydro-1H-pyrazino[1,2-a]pyrazine-2(6H)-carboxylate Step A: (3S)-tert-butyl 4-(2-hydroxy-2-((R)-3-methyl-1-oxoisochroman-6-yl)ethyl)-3-(hydroxymethyl)piperazine-1-carboxylate: (3R)-3-methyl-6-(oxiran-2-yl)isochroman-1-one (0.750 g, 3.62 mmol) and (S)-tert-butyl 3-(hydroxymethyl)piperazine-1-carboxylate (0.953 g, 4.41 mmol) in ethanol (12 mL) was heated in microwave at 150° C. for 1.5 h. The reaction solution was concentrated and the residue was purified on Biotage using 40-100% ethyl acetate/hexane to give the title compound: LC/MS: (M+1)$^+$: 421.15;

Step B: (3S)-benzyl 4-(2-hydroxy-2-((R)-3-methyl-1-oxoisochroman-6-yl)ethyl)-3-(hydroxymethyl)piperazine-1-carboxylate: To the solution of (3S)-tert-butyl 4-(2-hydroxy-2-((R)-3-methyl-1-oxoisochroman-6-yl)ethyl)-3-(hydroxymethyl)piperazine-1-carboxylate (2630 mg, 6.25 mmol) in methylene chloride (10 mL) was added trifluoroacetic acid (10 mL, 130 mmol) at rt for 1 h. After removing the volatile the residue was dissolved in methylene chloride (100 mL). To the above solution was added triethylamine (4.36 mL, 31.3 mmol) and benzyl chloroformate (0.986 mL, 6.56 mmol) at 0° C. for 0.5 h. The reaction was quenched by water followed by addition of saturated sodium carbonate. The mixture was extracted with methylene chloride, dried over sodium sulfate, concentrated and the residue was purified on Biotage using 40-100% EtOAc/hexane to give the title compound: LC/MS: (M+1)$^+$: 455.10.

Step C: (9aR)-benzyl 8-allyl-7-((R)-3-methyl-1-oxoisochroman-6-yl)hexahydro-1H-pyrazino[1,2-a]pyrazine-2(6H)-carboxylate: A solution of (3S)-benzyl 4-(2-hydroxy-2-((R)-3-methyl-1-oxoisochroman-6-yl)ethyl)-3-(hydroxymethyl)piperazine-1-carboxylate (2.07 g, 4.55 mmol) in thionyl chloride (30.0 mL, 411 mmol) was heated at reflux for 1 h. After removing the volatiles, the residue was dissolved in N,N-dimethylformamide (20 mL) and treated with allylamine (1.879 mL, 25.05 mmol) at 0° C. The resulting solution was treated with sodium iodide (0.0680 g, 0.455 mmol) and heated at 90° C. for 1 h. The solution was diluted in ethyl acetate (300 mL) and was washed with saturated sodium bicarbonate three times, dried over sodium sulphate concentrated and the residue was purified on Biotage using 40-100% ethyl acetate/hexane to give the title compound: LC/MS: (M+1)$^+$: 476.14.

Step D: (3R,9aS)-8-benzyl 2-tert-butyl 3-((R)-3-methyl-1-oxoisochroman-6-yl)tetrahydro-1H-pyrazino[1,2-a]pyrazine-2,8(9H,9aH)-dicarboxylate and (3S,9aS)-8-benzyl 2-tert-butyl 3-((R)-3-methyl-1-oxoisochroman-6-yl)tetrahydro-1H-pyrazino[1,2-a]pyrazine-2,8(9H,9aH)-dicarboxylate: The mixture of (9aR)-benzyl 8-allyl-7-((R)-3-methyl-1-oxoisochroman-6-yl)hexahydro-1H-pyrazino[1,2-a]pyrazine-2(6H)-carboxylate (1160 mg, 2.439 mmol), 1,3-dimethylpyrimidine-2,4,6(1H,3H,5H)-trione (1143 mg, 7.320 mmol) and tetrakis(triphenylphosphine)palladium (0) (141 mg, 0.122 mmol) in methylene chloride (10 mL) was heated at 35° C. for 4 h. After cooling to rt, di-tert-butyl dicarbonate (639 mg, 2.93 mmol) and triethylamine (1371 µL, 9.760 mmol) was added and the resulting solution was stirred at rt overnight. After concentration, the residue was purified on Biotage using 20-100% EtOAc/hexane to give (3S,9aS)-8-benzyl 2-tert-butyl 3-((R)-3-methyl-1-oxoisochroman-6-yl)tetrahydro-1H-pyrazino[1,2-a]pyrazine-2,8(9H,9aH)-dicarboxylate (less polar). LC/MS: (M+1)$^+$: 536.27, $^1$HNMR (500 MHz, CDCl$_3$) δ 8.092-8.066(m, 1H), 7.579-7.564(m,1H), 7.478-7.7.462(m,1H), 7.391-7.315(m, 5H), 5.419(broad, 1H), 5.162(s,2H), 4.722-4.705(broad, 1H), 4.109-3.967(m,2H), 3.820-3.790 (m,1H), 3.350-3.237 (m, 1H), 3.016-2.929(m,3H), 2.904-2.773(broad, 1H), 2.655-2.531(m, 3H), 2.202-2.113(m, 2H), 1.600 (s, 3H), 1.523(s, 9H); and (3R,9aS)-8-benzyl 2-tert-butyl 3-((R)-3-methyl-1-oxoisochroman-6-yl)tetrahydro-1H-pyrazino[1,2-a]pyrazine-2,8(9H,9aH)-dicarboxylate (more polar). LC/MS: (M+1)$^+$: 536.27, $^1$HNMR (500 MHz, CDCl$_3$) δ 8.054-8.038(d, J=8.1 Hz, 1H), 7.701-7.660(m, 1H), 7.495-7.474(m,1H), 7.375(broad, 5H), 5.158(s, 2H), 4.695-4.653 (m, 1H), 4.606(broad, 1H), 4.152-4.034(m, 2H), 3.839-3.806(m, 1H), 3.043-2.916(m, 5H), 2.893-790(broad, 2H), 2.338-2.226 (m, 3H), 1.533-1.521(d, 6.3 Hz,3H), 1.209(s, 9H).

Step E: (3R,9aS)-tert-butyl 3-((R)-3-methyl-1-oxoisochroman-6-yl)hexahydro-1H-pyrazino[1,2-a]pyrazine-2(6H)-carboxylate: To the solution of (3R,9aS)-8-benzyl 2-tert-butyl 3-((R)-3-methyl-1-oxoisochroman-6-yl)tetrahydro-1H-pyrazino[1,2-a]pyrazine-2,8(9H,9aH)-dicarboxylate (0.590 g, 1.10 mmol) in methanol (20 mL) was added palladium on carbon (10%, 0.117 g, 0.110 mmol) and the mixture was subjected to hydrogenation at rt overnight. After filtration the filtrate was concentrated to give the title compound. LC/MS: (M+1)$^+$: 402.18.

Intermediate 11 (cis)

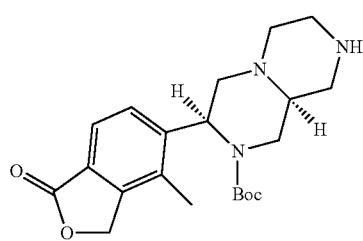 [SMILES: Cc1c([C@H]2CN3CCNC[C@H]3CN2C(=O)OC(C)(C)C)ccc2c1COC2=O]

(3S,9aS)-tert-butyl 3-(4-methyl-1-oxo-1,3-dihydroisobenzofuran-5-yl)hexahydro-1H-pyrazino[1,2-a]pyrazine-2(6H)-carboxylate Title compound was synthesized following an analogous procedure to that described for the synthesis of (3R,9aS)-tert-butyl 3-((R)-3-methyl-1-oxoisochroman-6-yl)hexahydro-1H-pyrazino[1,2-a]pyrazine-2(6H)-carboxylate 10 starting from 4-methyl-5-oxiran-2-yl-2-benzofuran-1(3H)-one and (S)-tert-butyl 3-(hydroxymethyl)piperazine-1-carboxylate; except in this case, the cis isomer from separation of the cis and trans isomers is described.
LC/MS: (M+1)$^+$: 388.10.

Intermediate 12

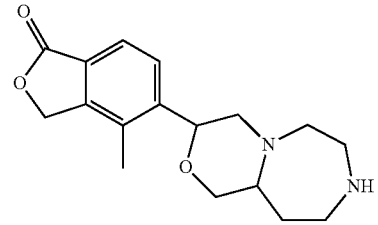 [SMILES: Cc1c(C2CN3CCNCCC3CO2)ccc2c1COC2=O]

4-methyl-5-(octahydro-H-[1,4]oxazino[4,3-d][1,4]diazepin-3-yl)isobenzofuran-1(3H)-one Step A: tert-butyl 1,4-dibenzyl-1,4-diazepane-5-carboxylate. To the solution of N$^1$,N$^2$-dibenzylethane-1,2-diamine (3.18 g, 13.24 mmol) in methylene chloride (200 mL) was added diisopropylethylamine (5.78 mL, 33.1 mmol) followed by addition of a solution of tert-butyl 2,4-dibromobutanoate in DCM (6 mL) dropwise, the resulting solution was stirred at rt overnight, and then heated at reflux for 6 h. After cooling to rt, the solution was washed with 10% sodium carbonate (100 mL), the aqueous was extracted with DCM (2×60 mL). The combined organic phase was dried over sodium sulphate, concentrated and the residue was purified on Biotage using 10-40% ethyl acetate/hexane to give title compound. LC/MS: (M+1)$^+$: 381.30;

Step B: (1,4-dibenzyl-1,4-diazepan-5-yl)methanol To the solution of tert-butyl 1,4-dibenzyl-1,4-diazepane-5-carboxylate (0.83 g, 2.2 mmol) in tetrahydrofuran (20 mL) was added lithium aluminum hydride (4.36 mL, 1N, 4.36 mmol) dropwise at rt. The resulting mixture was stirred at rt for 0.5 h before quenching by water under nitrogen (dropwise very slowly) followed by addition of sodium hydroxide solution (5N, 20 mL). The mixture was extracted with DCM (150 mL×3). The combined organic phase was dried over Na$_2$SO$_4$, concentrated and the residue was purified on Biotage using ethyl acetate to give title compound. LC/MS: (M+1)$^+$: 311.23;

Step C: (1,4-diazepan-5-yl)methanol The solution of (1,4-dibenzyl-1,4-diazepan-5-yl)methanol (554 mg, 1.79 mmol) in methanol (20 mL) in the presence of palladium on carbon (10%, 190 mg, 1.79 mmol) was hydrogenated at 40 psi overnight. After filtration through CELITE under N$_2$, the filtrate was concentrated to give (1,4-diazepan-5-yl)methanol. LC/MS: (M+1)$^+$: 131.19;

Step D: tert-butyl 5-(hydroxymethyl)-1,4-diazepane-1-carboxylate To the solution of (1,4-diazepan-5-yl)methanol (222 mg, 1.71 mmol) in dioxane (20 mL) was added sodium hydroxide solution (10 mL, 1N, 10 mmol) followed by addition of di-tert-butyl dicarbonate (0.356 mL, 1.54 mmol) in dioxane (4 mL) dropwise at 0° C. and the resulting solution was stirred at 0° C. for 2 h. After removing the volatile, the aqueous was extracted with methylene chloride (6×20 mL) and 30% isopropanol/chloroform (20 mL). The combined organic phase was dried over sodium sulphate and concentrated to give title compound. LC/MS: (M+1)+: 231.17;

Step E: tert-butyl 3-hydroxy-3-(4-methyl-1-oxo-1,3-dihydroisobenzofuran-5-yl)hexahydro-1H-[1,4]oxazino[4,3-d][1,4]diazepine-8(9H)-carboxylate To the solution of (tert-butyl 5-(hydroxymethyl)-1,4-diazepane-1-carboxylate (400 mg, 1.49 mmol) in tetrahydrofuran (30 mL) was added 5-(2-bromoacetyl)-4-methylisobenzofuran-1(3H)-one (342 mg, 1.49 mmol) and diisopropylethylamine (0.65 mL, 3.7 mmol) and the resulting solution was stirred at rt for 1 day. The reaction mixture was partitioned between DCM (100 mL) and saturated sodium bicarbonate solution. The aqueous phase was extracted with DCM (2×100 mL), the combined organic phase was dried over sodium sulphate, concentrated and the residue was purified on Biotage using 40-100% ethyl acetate/hexane to give title compound. LC/MS: (M+1)+: 419.23;

Step F: 4-methyl-5-(octahydro-1H-[1,4]oxazino[4,3-d][1,4]diazepin-3-yl)isobenzofuran-1(3H)-one The solution of tert-butyl 3-hydroxy-3-(4-methyl-1-oxo-1,3-dihydroisobenzofuran-5-yl)hexahydro-1H-[1,4]oxazino[4,3-d][1,4]diazepine-8(9H)-carboxylate (390 mg, 0.932 mmol) and triethylsilane (0.595 mL, 3.73 mmol) in trifluoroacetic acid (6 mL, 78 mmol) was heated at reflux for 2 h. After removing the volatile, the residue was treated with hydrogen chloride solution (4N, 4 Ml) in dioxane. The mixture was concentrated to give title compound as hydrogen chloride salt. LC/MS: (M+1)+: 303.10.

Intermediate 13

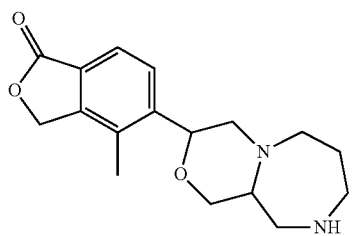 [SMILES: Cc1c(C2CN3CCCNCC3CO2)ccc2c1COC2=O]

4-methyl-5-(octahydro-1H-[1,4]oxazino[4,3-a][1,4]diazepin-3-yl)isobenzofuran-1(3H)-one Step A: N¹,N³-dibenzylpropane-1,3-diamine. A solution of propane-1,3-diamine (5.00 g, 67.5 mmol), benzaldehyde (15.1 mL, 148 mmol) and toluenesulfonic acid (12 mg, 0.067 mmol) in benzene (300 mL) was heated under Dean-Stark reflux for 2 h. After cooling down to rt, the solution was washed with saturated sodium carbonate solution, dried over sodium sulphate, concentrated and the residue was dissolved in tetrahydrofuran (100 mL) and treated with lithium aluminum hydride (4.00 g, 105 mmol) at 0° C. by portions and the resulting mixture was stirred at rt for 1 h before quenched by addition of water (20 mL) dropwise very slowly under N₂ followed by addition of sodium hydroxide (30 mL, 5N). The mixture was extracted by methylene chloride (3×100 mL). The combined organic phase was washed with water (200 mL), dried over sodium sulphate, and concentrated to give title compound. LC/MS: (M+1)+: 255.17;

Step B: ethyl 1,4-dibenzyl-1,4-diazepane-2-carboxylate. To the solution of N¹,N³-dibenzylpropane-1,3-diamine (4.00 g, 15.4 mmol) and ethyl 2,3-dibromopropanoate (4.31 g, 16.9 mmol) in benzene (100 mL) was added diisopropylethylamine (6.72 mL, 38.5 mmol) dropwise, the resulting solution was heated at 60° C. overnight. After removing the volatiles, the residue was partitioned between methylene chloride (100 mL) and 10% sodium carbonate solution (100 mL). The aqueous phase was extracted with methylene chloride (2×100 mL). The combined the organic phase was dried over sodium sulphate, concentrated, and the residue was purified on Biotage using 40% ethyl acetate/hexane to give ethyl 1,4-dibenzyl-1,4-diazepane-2-carboxylate. LC/MS: (M+1)+: 353.27;

Step C: (1,4-dibenzyl-1,4-diazepan-2-yl)methanol To the solution of 1,4-dibenzyl-1,4-diazepane-2-carboxylate (1.43 g, 4.06 mmol) in tetrahydrofuran (40 mL) was added lithium aluminum hydride (1.0M, 8.11 mL, 8.11 mmol) at 0° C. dropwise and the resulting mixture was stirred at rt for 0.5 h before quenched by water under N₂ dropwise very slowly followed by addition of sodium hydroxide solution (5N, 20 mL). The mixture was extracted with methylene chloride (3×150 mL). The combined organic phase was dried over sodium sulphate, concentrated and the residue was purified on Biotage using 20-40% ethyl acetate/hexane to give title compound. LC/MS: (M+1)+: 311.23;

Step D: (1,4-diazepan-2-yl)methanol To the solution of (1,4-dibenzyl-1,4-diazepan-2-yl)methanol (1.11 g, 3.58 mmol) in methanol (20 mL) was added palladium on carbon (10%, 0.381 g, 3.58 mmol) under N₂, the resulting suspension was subjected to hydrogenation at 40 psi overnight. After filtration under N₂ through CELITE, the filtrate was concentrated to give (1,4-diazepan-2-yl)methanol. LC/MS: (M+1)+: 131.19;

Step E: tert-butyl 3-(hydroxymethyl)-1,4-diazepane-1-carboxylate To the solution of 1,4-diazepan-2-yl)methanol (459 mg, 3.53 mmol) in dioxane (40 mL) and water 10 mL was added sodium hydroxide (14.1 mL, 14.1 mmol) and di-tert-butyl dicarbonate (819 µL, 3.53 mmol) in 4 mL dioxane dropwise at 0° C. for 3 h. After removing the volatile, the residue was extracted with methylene chloride (20 mL×10), the combined organic phase was dried over sodium sulphate, concentrated to give title compound. LC/MS: (M+1)+: 231.23;

Step F: tert-butyl 3-hydroxy-3-(4-methyl-1-oxo-1,3-dihydroisobenzofuran-5-yl)hexahydro-1H-[1,4]oxazino[4,3-a][1,4]diazepine-9(6H)-carboxylate. To the solution of tert-butyl 3-(hydroxymethyl)-1,4-diazepane-1-carboxylate. (600 mg, 2.61 mmol) in tetrahydrofuran (30 mL) was added 5-(2-bromoacetyl)-4-methylisobenzofuran-1(3H)-one (701 mg, 2.61 mmol) and diisopropylethylamine (1.14 mL, 6.51 mmol) and the resulting solution was stirred at rt for 1 day. The reaction mixture was partitioned between methylene chloride (100 mL) and saturated sodium bicarbonate solution, the aqueous phase was extracted with methylene chloride (2×100 mL), the combined organic phase was dried over sodium sulphate, concentrated and the residue was purified on Biotage using 40-100% ethyl acetate/hexane to give title compound. LC/MS: (M+1)+: 419.23;

Step G: 4-methyl-5-(octahydro-1H-[1,4]oxazino[4,3-a][1,4]diazepin-3-yl)isobenzofuran-1(3H)-one A solution of tert-butyl 3-hydroxy-3-(4-methyl-1-oxo-1,3-dihydroisobenzofuran-5-yl)hexahydro-1H-[1,4]oxazino[4,3-a][1,4]diazepine-9(6H)-carboxylate. (127 mg, 0.303 mmol) and triethylsilane (0.097 mL, 0.61 mmol) in trifluoroacetic acid (2.0 mL, 26 mmol) was heated at reflux for 2 h. The mixture was concentrated and the residue was treated with hydrogen chloride/dioxane (2N, 2 mL) and concentrated to give title compound as hydrogen chloride salt. LC/MS: (M+1)⁺: 303.16.

Intermediates 14 (Isomer Mixture), 14A and 14B

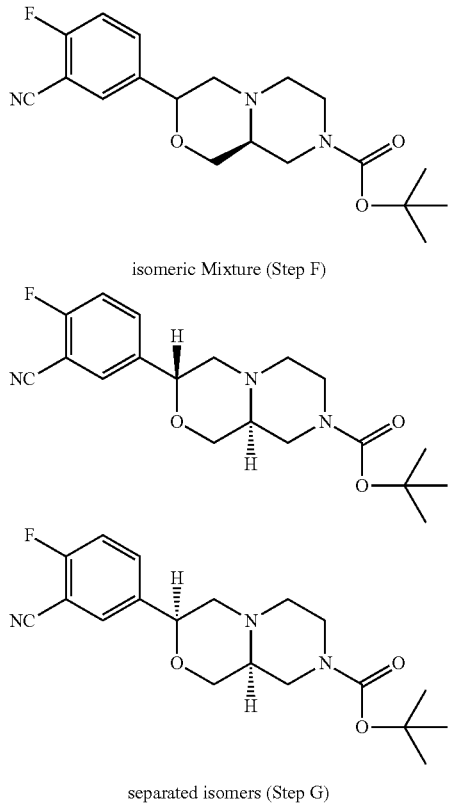

isomeric Mixture (Step F)

separated isomers (Step G)

tert-butyl (3R,9aS)-3-(3-cyano-4-fluorophenyl)hexahydropyrazino[2,1-c][1,4]oxazine-8(1H)-carboxylate and tert-butyl (3S,9aS)-3-(3-cyano-4-fluorophenyl)hexahydropyrazino[2,1-c][1,4]oxazine-8(1H)-carboxylate Step A: 2-fluoro-5-(1-hydroxyethyl)benzonitrile: 3-Cyano-4-fluorobenzaldehyde (2.17 g, 14.7 mmol) was dissolved in THF (50 mL) then cooled to −70° C. To this mixture was added methyl magnesiumbromide (5.34 mL, 16.0 mmol). The mixture was stirred for 1 h, then was quenched with brine and extracted with ether. The ethereal layer was separated, dried over Na₂SO₄, filtered, and evaporated to dryness. The residue was purified by MPLC chromatography through a 120 g Redi-sep column using 0-50% EtOAc/hexane eluent to yield 2-fluoro-5-(1-hydroxyethyl) benzonitrile: LC-MS: M+1=166.

Step B: 5-acetyl-2-fluorobenzonitrile: 2-Fluoro-5-(1-hydroxyethyl)benzonitrile (0.80 g, 4.8 mmol) was dissolved in DCM (50 mL). To this mixture was added pyridinium dichromate (2.73 g, 7.27 mmol) and the mixture was stirred at RT overnight. FLORISIL (26 g) was added to the reaction mixture which was then diluted with 50 mL of ether and filtered through a pad of CELITE. The filtrate was evaporated to dryness and the residue was purified by MPLC through a 120 g Redi-sep column, eluting with 0-100% EtOAc/hexane to yield 5-acetyl-2-fluorobenzonitrile.

Step C: 5-(bromoacetyl)-2-fluorobenzonitrile: 5-Acetyl-2-fluorobenzonitrile (400 mg, 2.45 mmol) was dissolved in THF (20 mL) then copper (II) bromide (1.10 g, 4.90 mmol) was added and the mixture was stirred at RT for 48 h. The reaction mixture was diluted with 20 mL of ether then washed with water, followed by brine. The organic layer was separated, dried over Na₂SO₄, and filtered. The filtrate was evaporated to dryness then purified by MPLC chromatography through an 80 g Redi-sep column with 0-50% ethyl acetate/hexane eluent to yield 5-(bromoacetyl)-2-fluorobenzonitrile: LC-MS: M+1=244.

Step D: tert-butyl (3S)-4-[2-(3-cyano-4-fluorophenyl)-2-oxoethyl]-3-(hydroxymethyl)piperazine-1-carboxylate: 5-(Bromoacetyl)-2-fluorobenzonitrile (590 mg, 2.44 mmol) and (S)-4-N-BOC-2-hydroxymethyl-piperazine (527 mg, 2.44 mmol) were dissolved in THF (40 mL) at 0° C. then TEA (247 mg, 2.44 mmol) was added. The reaction mixture was stirred at RT for 16 h, then poured into water and extracted with ethyl acetate. The organic layer was dried over Na₂SO₄, filtered, and evaporated to dryness. The crude product was purified by MPLC through an 80 g Redi-sep column using 0-100% EtOAc/hexane to yield the title compound.

Step E: tert-butyl (3S)-4-[2-(3-cyano-4-fluorophenyl)-2-hydroxyethyl]-3-(hydroxymethyl)piperazine-1-carboxylate: tert-Butyl (3S)-4-[2-(3-cyano-4-fluorophenyl)-2-oxoethyl]-3-(hydroxymethyl)piperazine-1-carboxylate (800 mg, 2.12 mmol) was dissolved in ethanol (50 mL) then sodium borohydride (321 mg, 8.48 mmol) was added and the mixture was stirred at RT for 16 h. LC-MS analysis showed product to be present. The ethanol was removed and the residue was redissolved in EtOAc and stirred with 1N HCl for 5 min. The mixture was then neutralized with saturated aqueous NaHCO₃ and extracted twice with EtOAc. The organic layers were washed with brine, dried over Na₂SO₄, filtered, and evaporated to dryness to yield the title compound. LC-MS: M+1=280.

Step F: tert-butyl (9aS)-3-(3-cyano-4-fluorophenyl)hexahydropyrazino[2,1-c][1,4]oxazine-8(1H)-carboxylate: tert-Butyl (3S)-4-[2-(3-cyano-4-fluorophenyl)-2-hydroxyethyl]-3-(hydroxymethyl)piperazine-1-carboxylate (358 mg, 0.944 mmol) was dissolved in DCM (25 mL) and cooled to 0° C. To this mixture was added TEA (0.197 mL, 1.42 mmol) followed by methanesulfonyl chloride (0.096 mL, 1.2 mmol). The mixture was warmed to RT and stirred overnight. The reaction mixture was washed twice with brine, dried, and evaporated to dryness. The residue was purified by chromatography through a 40 g Redi-sep column, eluting with EtOAc/Hex 0-100% to yield the intermediate chloride (470 mg, 1.81 mmol). This chloride was then dissolved in THF (25 mL) and tetrabutylammonium chloride (436 mg, 1.18 mmol) was added at 0° C. followed by NaH (47.2 mg, 1.18 mmol) then the mixture was stirred at reflux overnight. The reaction mixture was diluted with EtOAc and washed with brine. The organic layer was dried over Na₂SO₄, filtered, and evaporated to dryness. The crude residue was purified by MPLC chromatography through a 40 g Redi-sep column, eluting with 0-100% ethyl acetate to yield the title compound as a mixture of two isomers: ¹H-NMR (500 MHz, CDCl₃): δ ppm 7.86 (d, J=5.5Hz, 0.5 H), 7.75-7.81 (m, 0.5H), 7.65 (d, J=6 Hz, 1H), 7.58-7.61 (m, 0.5 H), 7.19-7.24 (q, 1 H), 4.79 (s, 0.5H), 4.66 d, J=10.5 Hz, 0.5H), 3.96 (dd, J=3, 11 Hz, 1H), 3.55-4.0 (b, 2H), 3.54 (dd, J=2.5, 11.5 Hz, 0.5 H), 3.46 (t, J=10.5 Hz, 0.5H), 3.24 (t, J=8.5 Hz, 0.5 H), 3.18 (d, J=2.5 Hz, 0.5 H) 3. (b, 2H), 2.89 (dd, J=2.1, 11.5 Hz, 0.5 H), 2.7-2.8 (m, 2H), 2.5 (b, 1H), 2.38-2.45 (m, 1 H), 2.25 (t, J=8.5 Hz, 1H), 2.17 (t, J=11 Hz, 1 H), 1.48 (s,9H); LC-MS: M+1=362.

Step G: tert-butyl (3R,9aS)-3-(3-cyano-4-fluorophenyl) hexahydropyrazino[2,1-c][1,4]oxazine-8(1H)-carboxylate and tert-butyl (3S,9aS)-3-(3-cyano-4-fluorophenyl)hexahydropyrazino[2,1-c][1,4]oxazine-8(1H)-carboxylate: The title compounds were obtained by preparative HPLC separation of the mixture of isomers obtained in the prior step.

Intermediates 15A and 15B (Method 1)

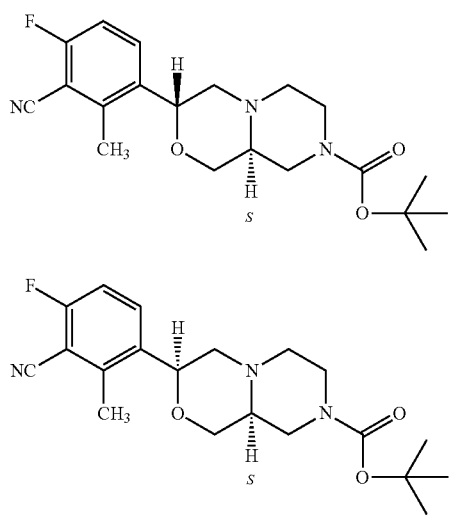

15A: tert-butyl (3R,9aS)-3-(3-cyano-4-fluoro-2-methylphenyl)hexahydropyrazino[2,1-c][1,4]oxazine-8(1H)-carboxylate 15B: tert-butyl (3S,9aS)-3-(3-cyano-4-fluoro-2-methylphenyl)hexahydropyrazino[2,1-c][1,4]oxazine-8(1H)-carboxylate Step A: 3-bromo-6-fluoro-2-methylbenzonitrile (Method A): Commercially available 2-fluoro-6-methylbenzonitrile (Apollo Scientific, 15.0 g, 111 mmol) was dissolved in triflic acid (75 mL) at 0° C. then NBS (20.7 g, 117 mmol) was added. The reaction mixture was stirred at RT for 1 h then poured into ice water and extracted twice with DCM. The organic layer was washed with brine, dried over Na$_2$SO$_4$, then filtered and evaporated to dryness to yield 3-bromo-6-fluoro-2-methylbenzonitrile: LC-MS: M+1=216.

Alternate Step A (Method B): To a 3 L 3 Neck RB equipped with overhead stirrer was charged 2-Fluoro-6-methyl-benzonitrile (191.8 g., 1419 mmol) and MsOH (563 mL, 8516 mmol). NBS (265 g., 1490 mmol) was added portionwise to this stirred solution over 30 minutes, and the mixture was stirred at 50° C. for 33 hours. By this time, HPLC shows the reaction to be mostly complete, so the reaction was poured into 1 L of ice (exotherm noted), diluted with 700 mL 30% EtOAc/Hexanes, and agitated. The aqueous layer was cut, and the organics washed 2× with 1N NaOH and with water. The aqueous cuts were observed to be significantly enriched with impurities. The organics were dried over MgSO$_4$, concentrated, then stored in a −10° C. freezer overnight. Precipitate formed over this time, and was filtered and washed with 5% EtOAc/Hexanes. A second crop of precipitate was combined with the first crop to provide 3-bromo-6-fluoro-2-methyl-benzonitrile.

Step B: 3-ethenyl-6-fluoro-2-methylbenzonitrile: 3-Bromo-6-fluoro-2-methylbenzonitrile (23.6 g, 110 mmol), potassium vinyl trifluoroborate (29.5 g, 221 mmol), PdCl$_2$ (dppf)-CH$_2$Cl$_2$ Adduct (4.03 g, 5.51 mmol), and TEA (30.7 mL, 221 mmol) were added to 250 mL of ethanol. The reaction mixture was degassed then stirred at reflux for 4 h. LC-MS confirmed the presence of product. The reaction mixture was diluted with ethyl acetate, washed twice with brine, dried, and evaporated to dryness. The crude material was then purified by MPLC chromatography using a 330 g Redi-sep column and eluting with a 10% EtOAc/Hexane solvent system to yield 3-ethenyl-6-fluoro-2-methylbenzonitrile.

Step C: 6-fluoro-2-methyl-3-(oxiran-2-yl)benzonitrile: 3-Ethenyl-6-fluoro-2-methylbenzonitrile (14.9 g, 92.0 mmol) was added to DCM (400 mL) at 0° C. then mCPBA (47.85 g, 277.5 mmol) was added and the mixture was stirred at RT for 72 h. The reaction mixture was washed with saturated aqueous Na$_2$S$_2$O$_3$, then with 1N NaOH, and brine. The organic layer was separated, dried over Na$_2$SO$_4$, filtered, and evaporated to dryness. The crude product was purified by chromatography through a 330 g Redi-sep column, eluting with 0-100% hexane/DCM solvent system to afford 6-fluoro-2-methyl-3-(oxiran-2-yl)benzonitrile. LC-MS: M+1=178.

Step D: tert-butyl (3S)-4-[2-(3-cyano-4-fluoro-2-methylphenyl)-2-hydroxyethyl]-3-(hydroxymethyl)piperazine-1-carboxylate: 6-Fluoro-2-methyl-3-(oxiran-2-yl)benzonitrile (12.0 g, 67.7 mmol) and (S)-4-N-BOC-2-hydroxymethyl-piperazine (22.0 g. 102 mmol) were suspended in ethanol (100 mL) then heated in a microwave apparatus for 30 minutes at 150° C. The reaction mixture was cooled and evaporated dryness. The residue was purified by MPLC chromatography through a 330 g Redi-sep column eluting with 5% MeOH/95% EtOAc solvent system to yield the title compound. LC-MS: M+1=394.

Step E: tert-butyl (9aS)-3-(3-cyano-4-fluoro-2-methylphenyl)hexahydropyrazino[2,1-c][1,4]oxazine-8(1H)-carboxylate: tert-Butyl (3S)-4-[2-(3-cyano-4-fluoro-2-methylphenyl)-2-hydroxyethyl]-3-(hydroxymethyl)piperazine-1-carboxylate (18.5 g, 47.0 mmol) and cyanomethylenetri-n-butylphosphorane (20.4 g, 85.0 mmol) were dissolved in 180 mL of benzene. The reaction mixture was degassed and heated to 100° C. for 16 h. LC-MS analysis indicated product peak (M+1=376). The reaction was cooled and evaporated to dryness. The residue was purified by chromatography through a 330 g Redi-sep column, eluting with a 20% acetone/80% hexane mixture to yield a cis-trans mixture of the title compound.

Step F: tert-butyl(3R,9aS)-3-(3-cyano-4-fluoro-2-methylphenyl)hexahydropyrazino[2,1-c][1,4]oxazine-8(1H)-carboxylate and tert-butyl(3S,9aS)-3-(3-cyano-4-fluoro-2-methylphenyl)hexahydropyrazino[2,1-c][1,4]oxazine-8 (1H)-carboxylate: The cis-trans isomers of the product of Step E were separated using a Chiralpak AD 4.6×250 mm 10 g column with 20% IPA/80% heptane solvent system: 15A (trans-isomer eluted first): $^1$H-NMR (500 MHz, CDCl$_3$): δ ppm 7.74 (dd, J=6, 8.5 Hz, 1H), 7.095 (t, J=8.5 Hz, 1H), 4.838 (d, J=10 Hz,1 H), 3.98 (dd, J=3, 11.5 Hz, 1H), 3.84-4.21 (b, 2 H), 3.50 (t, J=11 Hz, 1H), 2.98-3.18 (b, 1H), 2.85 (dd, J=2, 11.5 Hz, 1H), 2.75 (d, J=10 Hz, 1H), 2.6 ppm (s, 3 H), 2.45-2.68 (b, 1H), 2.24-2.31 (m, 2H), 2.16 (t, J=11 Hz, 1H), 1.50 ppm (s, 9H); LC-MS: M+1=376; 15B (cis-isomer eluted second): $^1$H-NMR (500 MHz, CDCl$_3$): δ ppm 8.20 (t, J=6.95 Hz, 1H), 7.06 (t, J=8.5 Hz, 1H), 4.91 (t, J=3.5 Hz, 1H), 3.70-4.07 (b, 2H), 3.55 (d, J=11 Hz, 1H), 3.26 (t, J=9 Hz, 1H), 3.15 (dd, J=3, 12 Hz, 1H), 2.98-3.11 (b, 1H), 2.82 (dd, J=4, 12 Hz, 2H), 2.63 (s, 3H), 2.59-2.7 (b, 1H), 2.44-2.49 (m,2H), 1.50 (s, 9H); LC-MS: M+1=376.

Intermediate 15B (Method 2)

Step A: 2-Fluoro-6-methyl-benzonitrile: A 10 L round bottom flask equipped with adapter, thermocouple and stir bar was charged with DMA (6 L) and degassed under vacuum and purged with N$_2$ three times. To the mixture was added Palladium Tetrakis triphenylphosphine (87.5 g, 72.0 mmol) and the mixture was degassed under vacuum and purged with N$_2$ three times. The reaction was heated to 80° C. for 30 min. 3-Fluoro-2-iodotoluene (575 g, 2.4 mol) and Zinc Cyanide (171.7 g, 1.46 mol) were added and the mixture was degassed under vacuum and purged with N$_2$ three times. The reaction mixture was heated to 80° C. for 16 h and then allowed to cool to RT. The solution was added to a 2.0 L aqueous solution of 1N NH$_4$OH and extracted three times with 1.5 L EtOAc. The extracts were washed with 2 L brine, dried over Na$_2$SO$_4$, filtered and concentrated. The crude product was treated with mCPBA in cooled DCM and then purified by chromatography (PE/EA=10:1) to get the title compound.

Step B: 3-Bromo-6-fluoro-2-methyl-benzonitrile: To a 3 L 3 Neck round bottomed flask equipped with overhead stirrer was charged 2-Fluoro-6-methyl-benzonitrile (191.8 g., 1419 mmol) and MsOH (563 mL, 8516 mmol). NBS (265 g., 1490 mmol) was added portionwise to this stirred solution over 30 minutes, and the mixture was stirred at 50° C. for 33 hours. By that time, HPLC showed the reaction to be mostly complete, so the reaction was poured into 1 L of ice (exotherm noted), diluted with 700 mL 30% EtOAc/Hexanes, and agitated. The aqueous layer was cut, and the organics washed 2× with 1N NaOH and with water. The organics were dried over MgSO$_4$, concentrated, then stored in a −10° C. freezer overnight. Precipitate formed over this time, and was filtered and washed with 5% EtOAc/Hexanes, providing a first crop of product. A second crop of precipitate provided further 3-Bromo-6-fluoro-2-methyl-benzonitrile.

Step C: 3-(2-Bromo-acetyl)-6-fluoro-2-methyl-benzonitrile: Degassed tributyl(1-ethoxyvinyl)tin (200 mL, 591 mmol) was added to a stirred, room temperature mixture of 3-Bromo-6-fluoro-2-methyl-benzonitrile (115 g, 537 mmol) and cis-PdCl$_2$(PPh$_3$)$_2$ (18.9 g, 26.9 mmol) in degassed Dioxane (1149 mL) and the mixture was stirred at 100° C. for 22 hours. By this time HPLC showed complete conversion of starting material (requires at least 12 hours), completion of the reaction can be seen by plating of palladium metal onto the side of the flask. At this time the reaction was cooled to 0° C. and THF (575 mL) and Water (230 mL) were added followed by NBS (110 g, 618 mmol) (added portionwise over 15 min, maintaining internal temperature <5° C.). After 30 minutes, HPLC showed full consumption of the intermediate enol ether. The solution was diluted with MTBE (1000 mL) and washed with 0.5% aqueous HBr (3×500 mL), then washed with water. The organics were dried over MgSO$_4$, filtered and concentrated. A precipitate was generated, and the solid was filtered and washed several times with hexanes. It was dried by nitrogen sweep, providing 3-(2-Bromo-acetyl)-6-fluoro-2-methyl-benzonitrile.

Step D: (3R,9aS)-3-(3-Cyano-4-fluoro-2-methyl-phenyl)-3-hydroxy-hexahydro-pyrazino[2,1-c][1,4]oxazine-8-carboxylic acid tert-butyl ester: Diisopropylethylamine (44.0 mL, 252 mmol) was added to a stirred, room temperature mixture of 72 wt % 3-(2-Bromo-acetyl)-6-fluoro-2-methyl-benzonitrile (69 g, 194 mmol) and (S)-4-N-Boc-2-hydroxymethyl-piperazine (42.0 g, 194 mmol) in THF (1000 mL) and the mixture was stirred at room temperature for 18 h. The reaction was diluted with 1 L EtOAc, washed 2× with 500 mL 10% w/w NaHCO$_3$ aqueous solution, dried over MgSO$_4$, filtered and concentrated. The residue was purified by column chromatography on silica gel (40-80% EtOAc/Hexanes, linear gradient), to give the title compound.

Step E: (S)-3-(3-Cyano-4-fluoro-2-methyl-phenyl)-6,7,9,9a-tetrahydro-1H-pyrazino[2,1-c][1,4]oxazine-8-carboxylic acid tert-butyl ester: Mesyl-Cl (17.2 mL, 221 mmol) was slowly added dropwise to a stirred, <5° C. internal temperature mixture of (3R,9aS)-3-(3-Cyano-4-fluoro-2-methyl-phenyl)-3-hydroxy-hexahydro-pyrazino[2,1-c][1,4]oxazine-8-carboxylic acid tert-butyl ester (66.6 g, 170 mmol) and triethylamine (71.1 mL, 510 mmol) in CH$_2$Cl$_2$ (1000 mL), and the reaction was allowed to warm to room temperature for 30 minutes, by which time reaction was complete. The solution was washed with 500 mL 10% w/w NaHCO$_3$ aqueous solution. The organics were dried over MgSO$_4$, filtered and concentrated. The resulting material was taken up in a minimal amount of EtOAc (125 mL) with some heating (solution kept <50° C.) until all solids dissolved. The solution was allowed to cool with stirring, then dropwise overnight 350 mL hexanes was added. By the next morning the solution had clarified and there was considerable powder. The solids were collected by filtration and washed with 20% EtOAc/Hexanes, providing product. The mother liquors were concentrated until precipitate appeared, which was filtered to give additional (S)-3-(3-Cyano-4-fluoro-2-methyl-phenyl)-6,7,9,9a-tetrahydro-1H-pyrazino[2,1-c][1,4]oxazine-8-carboxylic acid tert-butyl ester.

Step F: (3S,9aS)-3-(3-Cyano-4-fluoro-2-methyl-phenyl)-hexahydro-pyrazino[2,1-c][1,4]oxazine-8-carboxylic acid tert-butyl ester: To a 1 L 3 neck RB was charged 5% Pd/CaCO$_3$ (10.0 g., 4.02 mmol), MeOH (405 mL), and (S)-3-(3-Cyano-4-fluoro-2-methyl-phenyl)-6,7,9,9a-tetrahydro-1H-pyrazino[2,1-c][1,4]oxazine-8-carboxylic acid tert-butyl ester (15.0 g., 40.2 mmol). The solution was sparged with N$_2$ for 5 min, then put under an atmosphere of hydrogen with balloon pressure and warmed to 40° C. with stirring. After 38 h, HPLC shows full conversion of the olefin, with a 5:1 cis:trans ratio of diastereomers. The suspension was cooled to room temperature, filtered through a pad of CELITE and concentrated. The residue was purified via column chromatography (60-100% EtOAc/Hexanes, linear gradient), to provide the title compound. $^1$H NMR (400 MHz, CDCl$_3$): δ 8.18 (m, 1H), 7.03 (t, J=7.9 Hz, 1H), 4.87 (s, 1H), 4.10-3.60 (m, 2H), 3.56 (d, J=10.5 Hz, 1H), 3.25-2.88 (m, 3H), 2.80-2.35 (m, 8H), 1.50 (s, 9H).

Intermediate 15A (Method 2)

A three-necked, round-bottomed flask equipped with a nitrogen inlet adapter, thermocouple, and a septum was charged with (3R,9aS)-3-(3-Cyano-4-fluoro-2-methyl-phenyl)-3-hydroxy-hexahydro-pyrazino[2,1-c][1,4]oxazine-8-carboxylic acid tert-butyl ester (330 g, 840 mmol), TFA (1.65 L, 21 mol), and 3300 mL of DCM. Et$_3$SiH (292 g, 2.52 mol, 3 equiv) was added in one portion and the reaction mixture stirred at room temperature for 24 h. The reaction mixture was concentrated and azeotroped with toluene (100 mL) to remove the TFA. The resulting material was dissolved in DCM (1.7 L) and carefully charged with 2.5 M Na₂CO₃ (pH should be basic). Boc₂O (218 g, 1.2 equiv) was added in one portion and the reaction mixture was stirred at room temperature for 2 h. The organic layer was separated, concentrated, and purified via column chromatography (0-30% acetone-hexanes) to give a mixture of product cis/trans isomers. Chiral SFC purification (Berger Multi-Gram™ SFC, Mettler Toledo Co, Ltd, AD 250 mm*50 mm, 5 um column, A: supercritical CO₂, B: methanol, A:B=85:15 at 150 mL/min) afforded the major trans diastereomer 15A as well as the cis diastereomer 15B.

Intermediates 15C and 15D (Method 1)

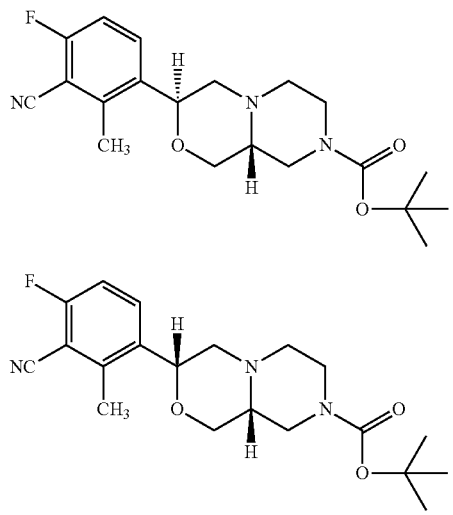

15C: tert-butyl(3S,9aR)-3-(3-cyano-4-fluoro-2-methylphenyl)hexahydropyrazino[2,1-c][1,4]oxazine-8(1H)-carboxylate 15D: tert-butyl(3R,9aR)-3-(3-cyano-4-fluoro-2-methylphenyl)hexahydropyrazino[2,1-c][1,4]oxazine-8(1H)-carboxylate Step A: tert-butyl (3R)-4-[2-(3-cyano-4-fluoro-2-methylphenyl)-2-hydroxylethyl]-3-(hydroxymethyl)piperazine-1-carboxylate: 6-Fluoro-2-methyl-3-(2-oxiranyl)benzonitrile (prepared as described above, 4.80 g, 27.1 mmol) and (R)-4-N-BOC-2-hydroxymethyl-piperazine (8.79 g. 40.6 mmol) were suspended in EtOH (30 mL) and heated in a microwave apparatus at 150° C. for 1 h. The reaction mixture was cooled and evaporated to dryness. The residue was purified by chromatography through a 330 g ISCO Redi-sep column eluting with ethyl acetate to 5% MeOH/ethyl acetate to yield the title compound. LC-MS: M+1=394;

Step B: tert-butyl(3S,9aR)-3-(3-cyano-4-fluoro-2-methylphenyl)hexahydropyrazino[2,1-c][1,4]oxazine-8(1H)-carboxylate and tert-butyl(3R,9aR)-3-(3-cyano-4-fluoro-2-methylphenyl)hexahydropyrazino[2,1-c][1,4]oxazine-8(1H)-carboxylate: tert-Butyl (3R)-4-[2-(3-cyano-4-fluoro-2-methylphenyl)-2-hydroxylethyl]-3-(hydroxymethyl)piperazine-1-carboxylate (7.14 g, 18.2 mmol) and cyanomethylene tributylphosphorane (7.88 g, 32.7 mmol) were dissolved in benzene (60.0 mL) then heated at 100° C. overnight. The reaction mixture was cooled and evaporated to dryness. The residue was purified by chromatography through a 330 g ISCO Redi-sep column eluting with 10% acetone/DCM-to 20% acetone DCM to yield trans-cis mixture. The isomers were resolved by chiral HPLC (70 mL/min of 15% 2:1 MeOH:MeCN:CO₂ on a 30×250 mm Chiralpak IC column (Diacel Chemical Industries, LTD.) at 100 bar and 35° C., 230 nM). Isomer 15C (faster eluting): ¹H-NMR (500 MHz, CDCl₃): δ ppm 7.73 (dd, J=9.0, 6.0 Hz, 1H), 7.09 (t, J=8.4 Hz, 1H), 4.83 (d, J=9.3 Hz,1 Hz, 1 H), 4.05(b, 2H), 3.98 (dd, J=11.25, 2.7, 1H), 3.49 (t, J=10.5 Hz, 1H), 3.031(b, 1H), 2.84 (d, J=11, 6 Hz, 1H), 2.74 (d,J=11.5 Hz, 1H), 2.59 (s, 3H), 2.54 (b, 1H), 2.22-2.30 (m, 2H), 2.146 (t, J=11.0 Hz, 1H), 1.5 (s, 9H): Isomer 15D (slower eluting): ¹H-NMR (500 MHz, CDCl₃): δ ppm 8.19 (b, 1H), 7.05 (t, J=8.5 Hz, 1H), 4.90 (s,1 H), 3.98(b, 3H), 3.54 (d, J=12.5 Hz, 1H), 3.24(b, 1H), 3.14(dd, J=12, 2.5 Hz, 1H), 3.05 (b, 1H), 2.80(dd, J=11.25, 2.5 Hz, 2H), 2.68(b, 1H), 2.63 (s, 3H), 2.46 (b, 1H), 1.5 (s, 9H).

Intermediate 15C and 15D (Method 2)

Step A: 2-Fluoro-6-methyl-benzonitrile: A 10 L round bottom flask equipped with adapter, thermocouple and stir bar was charged with DMA (6 L) and degassed under vacuum and purged with N₂ three times. To the mixture was added palladium tetrakis triphenylphosphine (87.5 g, 72.0 mmol) and the mixture was degassed under vacuum and purged with N₂ three times. The reaction was heated to 80° C. for 30 min. 3-Fluoro-2-iodotoluene (575 g, 2.4 mol) and zinc cyanide (171.7 g, 1.46 mol) were added and the mixture was degassed under vacuum and purged with N₂ three times. The reaction mixture was heated to 80° C. for 16 h and then allowed to cool to RT. The solution was added to a 2.0 L aqueous solution of 1N NH₄OH, which was extracted three times with 1.5 L EtOAc, washed with 2 L brine, dried over Na₂SO₄, filtered and concentrated. The crude product was treated with mCPBA in cooled DCM and then purified by chromatography (PE/EA=10:1) to get the title compound.

Step B: 3-Bromo-6-fluoro-2-methyl-benzonitrile: To a 3 L 3 Neck round bottomed flask equipped with overhead stirrer was charged 2-fluoro-6-methyl-benzonitrile (191.8 g., 1419 mmol) and MsOH (563 mL, 8516 mmol). NBS (265 g., 1490 mmol) was added portionwise to this stirred solution over 30 minutes, and the mixture was stirred at 50° C. for 33 hours. The reaction was poured into 1 L of ice, diluted with 700 mL 30% EtOAc/Hexanes, and agitated. The aqueous layer was cut, and the organics washed 2× with 1N NaOH and with water. The organics were dried over MgSO₄, concentrated, then stored in a –10° C. freezer overnight. Precipitate formed over this time, and was filtered and washed with 5% EtOAc/Hexanes, providing a first crop of product. A second crop of precipitate provided additional 3-Bromo-6-fluoro-2-methyl-benzonitrile.

Step C: 3-(2-Bromo-acetyl)-6-fluoro-2-methyl-benzonitrile: Degassed tributyl(1-ethoxyvinyl)tin (200 mL, 591 mmol) was added to a stirred, room temperature mixture of 3-bromo-6-fluoro-2-methyl-benzonitrile (115 g, 537 mmol) and cis-PdCl₂(PPh₃)₂ (18.9 g, 26.9 mmol) in degassed dioxane (1149 mL) and the mixture was stirred at 100° C. for 22 hours. Completion of the reaction could be seen by plating of palladium metal onto the side of the flask. The reaction was cooled to 0° C. and THF (575 mL) and Water (230 mL) were added followed by NBS (110 g, 618 mmol) (added portionwise over 15 min, maintaining internal temperature <5° C.). After 30 minutes, HPLC showed full consumption of the intermediate enol ether. The solution was diluted with MTBE (1000 mL) and washed with 0.5% aqueous HBr (3×500 mL), then washed with water. The organics were dried over MgSO$_4$, filtered and concentrated. A precipitate was generated, and the solid was filtered and washed several times with hexanes. It was dried by nitrogen sweep, providing 3-(2-Bromo-acetyl)-6-fluoro-2-methyl-benzonitrile.

Step D: (3S,9aR)-3-(3-Cyano-4-fluoro-2-methyl-phenyl)-3-hydroxy-hexahydro-pyrazino[2,1-c][1,4]oxazine-8-carboxylic acid tert-butyl ester: Diisopropylethylamine (156 mL, 894 mmol) was added to a stirred, room temperature mixture of 3-(2-Bromo-acetyl)-6-fluoro-2-methyl-benzonitrile (176 g, 688 mmol) and (R)-4-N-Boc-2-hydroxymethyl-piperazine (149 g, 688 mmol) in THF (3500 mL) and the mixture was stirred at room temperature for 18 h. The reaction was diluted with 3 L EtOAc, washed 2× with 1500 mL 10% w/w NaHCO$_3$ aqueous solution, dried over MgSO$_4$, filtered and concentrated. The residue was purified by column chromatography on silica gel (40-80% EtOAc/Hexanes, linear gradient), to provide the title compound.

Step E: 17C and 17D: A 5000-mL, three-necked, round-bottomed flask equipped with a nitrogen inlet adapter, thermocouple, and a septum was charged with the product of Step D (273 g, 696.2 mmol), TFA (1340 mL, 17.45 mol, 25 equiv), and 1300 mL of DCM. Et$_3$SiH (333 mL, 2.1 mol, 3 equiv) was added in one portion and the reaction mixture was stirred at room temperature for 12 h. The reaction mixture was concentrated to remove the TFA. The resulting material was dissolved in DCM (600 mL) and carefully charged with 2.5 M Na$_2$CO$_3$ (1400 mL, 3.5 mol, 5 equiv) (pH should be basic). Boc$_2$O (243 mL, 1.05 mol, 1.5 equiv) was added in one portion and the reaction mixture was stirred at room temperature for 2 h. The organic layer was separated, concentrated, and purified via column chromatography (0-30% acetone-hexanes) to give the product (ca. 2:1 trans:cis), which was separated by Chiral SFC to give both single isomers: Chiral SFC HPLC separation conditions: Instrument: Berger MultiGram SFC, Mettler Toledo Co, Ltd.; Column: Chiralpak AD column (Diacel Chemical Industries, LTD.) 250 mm×50 mm, 5 um.; Mobile phase: A: Supercritical CO$_2$, B: MeOH, A:B=85:15 at 150 mL/min.; Column Temp: 38° C.; Nozzle Pressure: 100 Bar; Nozzle Temp: 60° C.; Evaporator Temp: 20° C.; Trimmer Temp: 25° C.; Wavelength: 235 nm. 15C trans isomer $^1$H NMR 400 MHz, CDCl$_3$ δ: 7.720-7.683 (dd, J=9,6 Hz, 1H), 7.056 (t, J=8 Hz, 1H), 4.811-4.787 (d, J=9 Hz, 1H), 3.962-3.928 (dd, J=9,6 Hz, 3H), 3.465(t, J=10 Hz 1H),3.002 (s, 1H), 2.826-2.797 (d, J=11 Hz, 1H), 2.719 (s,1H), 2.638-2.559 (m, 4H), 2.091-2.253 (m, 3H), 1.469 (s,9H); 15D cis isomer $^1$H NMR 400 MHz, CDCl$_3$ δ: 8.182-8.146 (t, J=7 Hz, 1H), 7.019 (t, J=9 Hz, 1H), 4.873 (s,1H), 3.952-3.711 (m, 2H), 3.530-3.503 (d, J=11 Hz, 1H), 3.215-3.020 (m, 3H), 2.801-2.761 (d, J=16 Hz, 1H), 2.593 (s, 4H), 2.452-2.430 (m, 3H), 1.463 (s, 9H).

Intermediate 16A

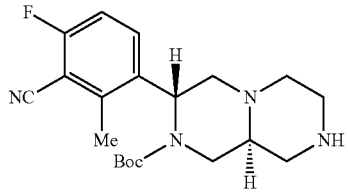

(3R,9aS)-tert-butyl 3-(3-cyano-4-fluoro-2-methyl-phenyl)hexahydro-1H-pyrazino[1,2-a]pyrazine-2(6H)-carboxylate Step A: (3S)-tert-butyl 4-(2-(3-cyano-4-fluoro-2-methylphenyl)-2-hydroxyethyl)-3-(hydroxymethyl)piperazine-1-carboxylate: A mixture of 6-fluoro-2-methyl-3-(oxiran-2-yl)benzonitrile (785 mg, 4.43 mmol) and (S)-tert-butyl 3-(hydroxymethyl)piperazine-1-carboxylate (1340 mg, 6.2 mmol) in ethanol (10 mL) was heated in microwave at 150° C. for 3 h. The volatile was evaporated and the residue was purified on Biotage using 40-100% ethyl acetate/hexane to give the title compound: LC/MS: (M+1)$^+$: 394.19.

Step B: (3S)-benzyl 4-(2-(3-cyano-4-fluoro-2-methylphenyl)-2-hydroxyethyl)-3-(hydroxymethyl)piperazine-1-carboxylate: To a solution of (3S)-tert-butyl 4-(2-(3-cyano-4-fluoro-2-methylphenyl)-2-hydroxyethyl)-3-(hydroxymethyl)piperazine-1-carboxylate (2.87 g, 7.32 mmol) in methylene chloride (20 mL) was added trifluoroacetic acid (20 mL) at rt, and the resulting solution was stirred at rt for 1 h. After removing the volatile solvents, the residue was dissolved in methylene chloride (50 mL). To the above solution was added triethylamine (6.12 mL, 43.9 mmol) and benzyl chloroformate (1.1 mL, 7.3 mmol) dropwise at 0° C. The reaction solution was stirred at 0° C. for 1 h before quenching with saturated sodium bicarbonate solution (200 mL). The mixture was then extracted with methylene chloride (3×100 mL). The combined organic phase was dried over sodium sulphate and concentrated to give the title compound. LC/MS: (M+1)$^+$: 428.18.

Step C: (7R,9aR)-benzyl 8-allyl-7-(3-cyano-4-fluoro-2-methylphenyl)hexahydro-1H-pyrazino[1,2-a]pyrazine-2(6H)-carboxylate and (7S,9aR)-benzyl 8-allyl-7-(3-cyano-4-fluoro-2-methylphenyl)hexahydro-1H-pyrazino[1,2-a]pyrazine-2(6H)-carboxylate: A solution of (3S)-benzyl 4-(2-(3-cyano-4-fluoro-2-methylphenyl)-2-hydroxyethyl)-3-(hydroxymethyl)piperazine-1-carboxylate (1.68 g, 3.93 mmol) in sulfonyl chloride (14.0 g, 118 mmol) was heated at 90° C. for 1 h. After removing the volatile, the residue was dissolved in DMF (16 mL), treated with allylamine (1.726 mL, 23.58 mmol) and sodium iodide (0.059 g, 0.39 mmol) in a sealed tube at 0° C. and the resulting mixture was heated at 90° C. for 1 h. The mixture was diluted in ethyl acetate (300 mL), was washed with saturated sodium bicarbonate (3×200 mL), dried over sodium sulphate, concentrated, and the residue was purified on Biotage using 40-80% ethyl acetate/hexane to give the title compound (more polar on TLC). LC/MS: (M+1)$^+$: 449.24.

Step D: (3R,9aS)-8-benzyl 2-tert-butyl 3-(3-cyano-4-fluoro-2-methylphenyl)tetrahydro-1H-pyrazino[1,2-a]pyrazine-2,8(9H,9aH)-dicarboxylate: A mixture of (7R,9aR)-benzyl 8-allyl-7-(3-cyano-4-fluoro-2-methylphenyl)hexahydro-1H-pyrazino[1,2-a]pyrazine-2(6H)-carboxylate (1260 mg, 2.81 mmol), 1,3-dimethylpyrimidine-2,4,6(1H,3H,5H)-trione (1316 mg, 8.430 mmol) and tetrakis(triphenylphosphine)palladium(0) (162 mg, 0.140 mmol) in methylene chloride (10 mL) was heated at 35° C. for 4 h. After cooling to rt, di-tert-butyl dicarbonate (736 mg, 3.37 mmol) and triethylamine (1579 μL, 11.24 mmol) were added and the resulting solution was stirred at rt overnight. After concentration, the residue was purified on Biotage using 40% EtOAc/hexane to give the title compound. LC/MS: (M+1)$^+$: 509.32.

Step E: (3R,9aS)-tert-butyl 3-(3-cyano-4-fluoro-2-methylphenyl)hexahydro-1H-pyrazino[1,2-a]pyrazine-2(6H)-carboxylate: To a solution of (3R,9aS)-8-benzyl 2-tert-butyl 3-(3-cyano-4-fluoro-2-methylphenyl)tetrahydro-1H-pyrazino[1,2-a]pyrazine-2,8(9H,9aH)-dicarboxylate (600 mg, 1.180 mmol) in MeOH (100 mL) was added Palladium on carbon (10%,126 mg, 0.118 mmol) and the resulting mixture was subjected to hydrogenation at rt overnight. The reaction mixture was filtered through CELITE, washed with mixture of methanol and methylene chloride (1:1) and the filtrate was concentrated to give the title compound: LC/MS: (M+1)+: 375.28.

Intermediate 16B

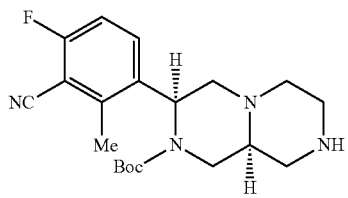 [SMILES: Cc1c([C@H]2CN3CCNC[C@H]3CN2C(=O)OC(C)(C)C)ccc(F)c1C#N]

(3S,9aS)-tert-butyl 3-(3-cyano-4-fluoro-2-methylphenyl)hexahydro-1H-pyrazino[1,2-a]pyrazine-2(6H)-carboxylate Step A: (3S,9aS)-8-benzyl 2-tert-butyl 3-(3-cyano-4-fluoro-2-methylphenyl)tetrahydro-1H-pyrazino[1,2-a]pyrazine-2,8(9H,9Ah)-dicarboxylate: A mixture of (7S,9aR)-benzyl 8-allyl-7-(3-cyano-4-fluoro-2-methylphenyl)hexahydro-1H-pyrazino[1,2-a]pyrazine-2(6H)-carboxylate (518 mg, 1.155 mmol), 1,3-dimethylpyrimidine-2,4,6(1H,3H,5H)-trione (518 mg, 1.16 mmol) and tetrakis(triphenylphosphine)palladium(0) (66.7 mg, 0.058 mmol) in methylene chloride (10 mL) was heated at 35° C. for 4 h. After cooling to rt, di-tert-butyl dicarbonate (302 mg, 1.39 mmol) and triethylamine (649 μL, 4.62 mmol) was added and the resulting solution was stirred at rt overnight. After concentration, the residue was purified on Biotage using 40% EtOAc/hexane to give the title compound: LC/MS: (M+1)+: 509.26.

Step B: (3S,9aS)-tert-butyl 3-(3-cyano-4-fluoro-2-methylphenyl)hexahydro-1H-pyrazino[1,2-a]pyrazine-2(6H)-carboxylate: To a solution of (3S,9aS)-8-benzyl 2-tert-butyl 3-(3-cyano-4-fluoro-2-methylphenyl)tetrahydro-1H-pyrazino[1,2-a]pyrazine-2,8(9H,9Ah)-dicarboxylate (0.78 g, 1.534 mmol) in MeOH (100 Ml) was added palladium on carbon (10%,0.163 g, 0.153 mmol) and the resulting mixture was subjected to hydrogenation at rt overnight. The reaction mixture was filtered through CELITE, washed with mixture of methanol and methylene chloride (1:1) and the filtrate was concentrated to give the title compound: LC/MS: (M+1)+: 375.28.

Intermediates 17A and 17B

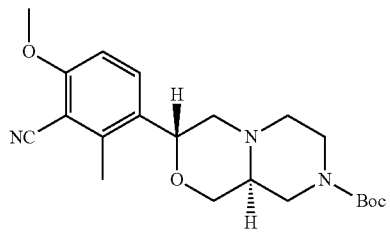

17A

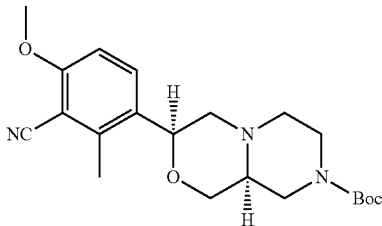

17B

17A: tert-butyl (3R,9aS)-3-(3-cyano-4-methoxy-2-methylphenyl)hexahydropyrazino[2,1-c][1,4]oxazine-8(1H)-carboxylate 17B: tert-butyl (3S,9aS)-3-(3-cyano-4-methoxy-2-methylphenyl)hexahydropyrazino[2,1-c][1,4]oxazine-8(1H)-carboxylate Step A: 3-bromo-6-methoxy-2-methylbenzonitrile: To a solution of 2-bromo-3-methylphenol (10.0 g, 53.5 mmol) in DMF (60 ml) was added sodium hydride (2.78 g, 69.5 mmol) in small portions at 0° C., which was followed by addition of MeI (6.69 mL, 107 mmol). TLC showed formation of a slightly less polar spot right away. The reaction was diluted with EtOAc (400 mL), washed with water 3 times, dried over Na2SO4, and concentrated. The crude product was used in the next step without further purification. To the flask charged with the above material and a stir bar was added CuCN (9.9 g, 109 mmol) and DMF (100 mL). The mixture was purged three times with nitrogen, and heated to 150° C. for 24 hours. TLC showed formation of a more polar spot. The reaction was cooled to RT, diluted with DCM (400 mL), and filtered through a pad of CELITE to remove the solids. The filtrate was washed with saturated NH4OAc and brine, dried over sodium sulfate, concentrated to afford a brownish solid (4.8 g, 60% yield). The resulting nitrile was used in the following step without further purification. To a flask charged with the nitrile and a stir bar was added NBS (6.4 g, 36 mmol) and TFA (60 mL). The reaction was allowed to stir at RT for 16 hours. TLC showed clean formation of a slightly more polar spot. The solvent was removed under vacuum, and the residue was purified by silica gel flash chromatography. After removal of solvent, 3-bromo-6-methoxy-2-methylbenzonitrile was collected.

Step B: 3-(bromoacetyl)-6-methoxy-2-methylbenzonitrile: To a flask charged with 3-bromo-6-methoxy-2-methylbenzonitrile (0.98 g, 4.33 mmol) and a stir bar was added Bis(triphenylphosphinepalladium(II) chloride (0.152 g, 0.217 mmol), tributyl(1-ethoxyethenyl)stannane (2.35 g, 6.50 mmol), and dioxane (20 mL). The mixture was fitted with a condensor and purged three times with nitrogen, and heated to 100° C. for 3 hours. The reaction was cooled, and to the solution was added THF (16 mL) and water (8 mL). After cooling the solution to 0° C. with an ice bath, NBS (1.543 g, 8.67 mmol) was added into the reaction. The dark solution turned brownish orange within 5 minutes. TLC showed a more polar spot. The reaction was diluted with EtOAc (100 mL), washed with brine, dried over sodium sulfate, and purified by flash chromatography to afford the title compound.

Step C: tert-butyl (3S)-4-[2-(3-cyano-4-methoxy-2-methylphenyl)-2-oxoethyl]-3-(hydroxymethyl)piperazine-1-carboxylate: To a solution of the 3-(bromoacetyl)-6-methoxy-2-methylbenzonitrile (2.25 g, 8.40 mmol) in THF was added tert-butyl (3S)-3-(hydroxymethyl)piperazine-1-carboxylate (2.18 g, 10.8 mmol) and Hunig's Base (2.93 mL, 16.8 mmol). The reaction was allowed to stir at RT for 16 hours. TLC showed good reaction at that point. The crude reaction was adsorbed onto silica gel, and purified by silica gel flash chromatography to afford the title compound.

Step D: tert-butyl (3R,9aS)-3-(3-cyano-4-methoxy-2-methylphenyl)hexahydropyrazino[2,1-c][1,4]oxazine-8 (1H)-carboxylate and tert-butyl (3S,9aS)-3-(3-cyano-4-methoxy-2-methylphenyl)hexahydropyrazino[2,1-c][1,4] oxazine-8(1H)-carboxylate: To a solution of tert-butyl (3S)-4-[2-(3-cyano-4-methoxy-2-methylphenyl)-2-oxoethyl]-3-(hydroxymethyl)piperazine-1-carboxylate (800 mg, 1.983 mmol) and triethylsilane (1.58 mL, 9.91 mmol) in DCM (10 mL) was dropped TFA (5 mL) slowly. The reaction was allowed to stir at RT for 72 hours. LC showed quite clean reaction. The volatiles were removed under vacuum, and the residue was redissolved in DCM. To this solution was added Boc anhydride (1.08 g, 4.96 mmol) and saturated sodium carbonate (5 mL). TLC showed complete protection within 30 minutes. The reaction was diluted with water, extracted with DCM, dried over sodium sulfate, and purified by silica gel flash chromatography to afford a colorless oil (220 mg, 29% yield). NMR analysis suggested that it was a mixture of the trans, and cis-isomers in the ratio of about 3:1. The isomers were separated by chiral preparative HPLC (Chiralpak AD-SFC conditions) to give the trans-isomer 17A and the cis-isomer 17B: $^1$H-NMR (500 MHz, CDCl$_3$) δ ppm 17A: 7.61 (d, J=9.0 Hz, 1H), 6.81 (d, J=9.0 Hz, 1H), 4.77 (d, J=10 Hz, 1H), 4.05 (m, 2H), 3.93 (d, J=11.5 Hz, 1H), 3.90 (s, 3H), 3.46 (t, J=11 Hz, 1H), 3.01 (d, J=17.5 Hz, 1H), 3.00 (broad, 1H), 2.80 (d, J=11.5 Hz, 1H), 2.71 (d, J=9.0 Hz, 1H), 2.52 (s, 3H), 2.50 (m, 1H), 2.23 (q, J=12 Hz, 1H), 2.14 (t, J=11.5 Hz, 1H), 1.47 (s, 9H); 17B: 8.06 (d, J=9.0 Hz, 1H), 6.77 (d, J=9.0 Hz, 1H), 4.84 (s, 1H), 3.91 (s, 3H), 3.50 (d, J=11.5 Hz, 1H), 3.26 (m, 1H), 3.11 (d, J=1.5 Hz, 1H), 3.01 (s, 1H), 2.75 (m, 2H), 2.66 (m, 1H), 2.54 (s, 3H), 2.44 (m, 2H), 1.46 (s, 9H).

Intermediates 18A and 18B

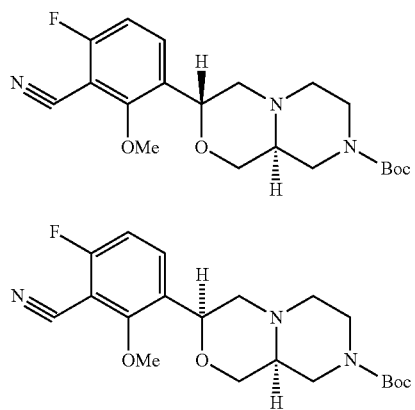

18A: tert-butyl (3R,9aS)-3-(3-cyano-4-fluoro-2-methoxyphenyl)hexahydropyrazino[2,1-c][1,4]oxazine-8(1H)-carboxylate and 18B: tert-butyl (3S,9aS)-3-(3-cyano-4-fluoro-2-methoxyphenyl)hexahydropyrazino[2,1-c][1,4]oxazine-8(1H)-carboxylate Step A: 3-bromo-6-fluoro-2-methoxybenzonitrile (Method 1): 2-Fluoro-6-methoxybenzonitrile (8.30 g, 54.9 mmol) was dissolved in triflic acid (75 mL) at 0° C. then NBS (10.3 g, 57.7 mmol) was added. The reaction mixture was stirred at RT for 1 h. LC-MS showed no starting material peak. The reaction mixture was poured into ice and extracted twice with DCM. The combined organic layers were washed with brine, dried over Na$_2$SO$_4$, filtered, and evaporated to dryness. The residue was purified by chromatography through a 330 g Redi-Sep column and eluted with 10% to 50% EtOAc/hexane solvent system to yield the title compound.

Step B: 3-ethenyl-6-fluoro-2-methoxybenzonitrile: 3-bromo-6-fluoro-2-methoxybenzonitrile (4.40 g, 19.1 mmol), potassium vinyl trifluoroborate (5.12 g, 38.3 mmol), PdCl$_2$(dppf)-CH$_2$Cl$_2$ Adduct (0.7 g, 1 mmol) and TEA (5.33 mL, 38.3 mmol) were added to 80 mL ethanol in a 200 mL flask. The reaction mixture was degassed and heated to reflux for 4 h. The reaction mixture was cooled and then most of the EtOH was removed. The residue was diluted with ethyl acetate. The mixture was washed with brine twice. The organic layer was separated and dried over Na$_2$SO$_4$, filtered, and evaporated to dryness. The residue was purified through a 330 g RediSep column and eluted with 10% EtOAc/hexane solvent system to yield the title compound.

Step C: 6-fluoro-2-methoxy-3-(oxiran-2-yl)benzonitrile: 3-Ethenyl-6-fluoro-2-methoxybenzonitrile (1.67 g, 9.43 mmol) was added to DCM (50 mL) at 0° C. then mCPBA (4.88 g, 28.3 mmol) was added and the reaction mixture was stirred at RT for 16 h. The reaction mixture was washed with saturated aqueous Na$_2$S$_2$O$_3$, then with 1N NaOH followed by brine. The organic layer was separated and dried over Na$_2$SO$_4$, filtered, and evaporated to dryness. The crude product was purified by chromatography through a 120 g Redi-sep column and eluting with a 0-100% EtOAc/hexane solvent system. Isolated the title compound.

Step D: tert-butyl (3S)-4-[2-(3-cyano-4-fluoro-2-methoxyphenyl)-2-hydroxyethyl]-3-(hydroxymethyl)piperazine-1-carboxylate: 6-Fluoro-2-methoxy-3-(oxiran-2-yl)benzonitrile (1.4 g, 7.3 mmol) and (S)-4-N-BOC-2-hydroxymethylpiperazine (3.13 g, 14.5 mmol) were suspended in ethanol (15 mL) then heated in a microwave apparatus for 60 min at 150° C. The reaction mixture was cooled and evaporated to dryness. The residue was purified by chromatography through a 40 g Redi-sep column and eluting with 5% MeOH/95% EtOAc to yield the title compound: LC-MS: M+1=410;

Step E: tert-butyl (9aS)-3-(3-cyano-4-fluoro-2-methoxyphenyl)hexahydropyrazino[2,1-c][1,4]oxazine-8(1H)-carboxylate: tert-Butyl (3S)-4-[2-(3-cyano-4-fluoro-2-methoxyphenyl)-2-hydroxyethyl]-3-(hydroxymethyl) piperazine-1-carboxylate (2 g, 4.88 mmol) and cyanomethylenetri-n-butylphosphorane (2.122 g, 8.79 mmol) were dissolved in 15 mL benzene. The reaction mixture was degassed and heated to 100° C. for 16 hrs. LC-MS showed product peak at 2.07 (M+1=380). The reaction was cooled and evaporated to dryness. The residue was chromatographed through a 80 g Redi-sep column and eluted with 40% EtOAc/60% hexane mixture to yield cis-trans mixture of the title compound.

Step F: Trans Isomer (3R,9aS) 18A and Cis Isomer (3S,9aS) 18B: The isomers were separated by Chirapak AD-H 250 mm×30 mm I.D. with 85% SFC CO$_2$ and 15% EtOH. The trans-isomer eluted first, then the cis-isomer. 18A: $^1$H-NMR (500 MHz, CDCl$_3$): δ ppm 7.72 ppm (t, J=8 Hz, 1H), 6.96 (t, J=8 Hz, 1H), 4.92 (d, J=9.5 Hz, 1 H), 4.17 (s, 3H), 4.03 (b, 2H), 3.96 (d, J=11 Hz, 1H), 3.49 (t, J=10.5 Hz, 1H), 3.05 (b, 1H), 2.95 (d, J=10.5 Hz, 1H), 2.74 (s,1H), 2.54 (b, 1H), 2.24 (d, J=10.5 Hz, 2 H), 2.07 (t, J=10.5 Hz, 1H), 1.50 (s, 9H); LC-MS: M+1=392; 18B: $^1$H-NMR (500 MHz, CDCl$_3$): δ ppm 8.28 (b,1H), 6.96 (t, J=8.5 Hz, 1H), 5.06 (s, 1H), 4.16 (s, 3H), 3.80-4.05 ppm (b, 2H), 3.80 (s, 1H), 3.74 (s, 1H), 3.423 (b, 1H), 3.04 (d, J=10.5 Hz, 1H), 2.81(b, 3H), 2.56 (b, 2H) 2.68, 1.50 (s, 9H); LC-MS: M+1=392.

Method 2 for Making
3-bromo-6-fluoro-2-methoxybenzonitrile

Step A: 1-bromo-4-fluoro-2-methoxybenzene: A solution of 2-bromo-5-fluorophenol (15 g, 79 mmol) in 125 mL of anhydrous DMF was added K$_2$CO$_3$ (17.0 g, 138 mmol) and MeI (14.0 g, 102 mmol) under cooling, then the reaction was stirred at room temperature for 3 hours. The mixture was poured to water, extracted with diethyl ether, washed with water and brine, dried over anhydrous Na$_2$SO$_4$ and concentrated to give 1-bromo-4-fluoro-2-methoxybenzene.

Step B: 3-bromo-6-fluoro-2-methoxybenzoic acid: A solution of dry diisopropylamine (10 g, 99 mmol) in dry THF under nitrogen was cooled with a −78° C. bath, n-butyl lithium (2.50 M in hexane, 40 mL, 99 mmol) was added and the solution was stirred at −78° C. for 20 minutes. 1-Bromo-4-fluoro-2-methoxybenzene (17.0 g, 82.5 mmol) was added. After stirring at −78° C. for 2 hours, the solution was bubbled with CO$_2$ and then warmed to 0° C. Then 1 N HCl was added until pH=3-4 and the mixture was extracted with AcOEt. The combined organic layers were washed with brine, dried over anhydrous sodium sulphate and concentrated to afford 3-bromo-6-fluoro-2-methoxybenzoic acid.

Step C: 3-bromo-6-fluoro-2-methoxybenzamide: Oxalyl chloride (15 mL) was added dropwise at 0° C. to a suspension of 3-bromo-6-fluoro-2-methoxybenzoic acid (15 g, 60 mmol) in 100 mL of DCM with 0.5 mL of DMF. The mixture was stirred at 25° C. for 2 hours and the clear solution was concentrated to dryness under reduced pressure. The residue dissolved in 60 mL of anhydrous acetonitrile was added to 600 mL of aqueous NH$_3$.H$_2$O at 0° C. and stirred for 2 hours, then filtered to give 3-bromo-6-fluoro-2-methoxybenzamide.

Step D: 3-bromo-6-fluoro-2-methoxybenzonitrile: A solution of 3-bromo-6-fluoro-2-methoxybenzamide (14 g, 61 mmol) in 100 mL of DMF was added 2,4,6-trichloro-[1,3,5]triazine (12.3 g, 67.0 mmol) portionwise at 0° C. and stirred for 2 hours before poured to ice/water. The white solid was collected by filtration and was washed with water, dissolved in DCM, dried over anhydrous Na$_2$SO$_4$ and concentrated to afford 3-bromo-6-fluoro-2-methoxybenzonitrile.

$^1$H-NMR (400 MHz, CDCl3) δ ppm 7.71-7.74 (m, 1H), 6.84-6.88 (m, 1H), 4.09 (s, 3H);

Intermediates 19A and 19B

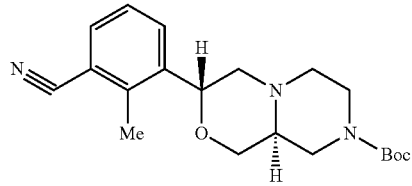

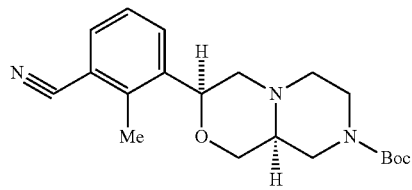

tert-butyl (3R,9aS)-3-(3-cyano-2-methylphenyl)hexahydropyrazino[2,1-c][1,4]oxazine-8(1H)-carboxylate and tert-butyl (3S,9aS)-3-(3-cyano-2-methylphenyl)hexahydropyrazino[2,1-c][1,4]oxazine-8(1H)-carboxylate Step A: 3-bromo-2-methylbenzonitrile was prepared starting from commercially available 3-bromo-2-methylbenzoic acid using an analogous sequence to that described in Method 2, Steps C and D, for making 3-bromo-6-fluoro-2-methoxybenzonitrile.

Step B: The preparation of the title compounds was accomplished in an analogous fashion as that described for making Intermediates 17A and 17B (Method 1) starting with 3-bromo-2-methylbenzonitrile in place of 3-bromo-6-fluoro-2-methoxybenzonitrile. The trans and cis were separated with AD-H column, 30×250 mm, 25% IPA (0.2% DEA)/CO$_2$, 70 mL/min, 100 bar, 50 in MeOH, 35 C, 220 nm. S-trans isomer (eluted first)—$^1$H-NMR (500 MHz, CDCl$_3$): δ ppm 7.74 (d, J=7.5 Hz, 1H), 7.57 (d, J=7.5 Hz, 1H), 7.34-7.32 (m, 1H), 4.87 (d, J=10 Hz, 1H), 4.07-4.02 (m, 2H), 3.98-3.96 (m, 2H), 3.52-3.48 (m, 1H), 2.86 (d, J=10 Hz, 1H), 2.75-2.73 (m, 1H), 2.59 (s, 3H), 2.29-2.24 (m, 2H), 2.19-2.15 (m, 2H), 1.49-1.48 (m, 9H); LC/MS: [(M+1)]$^+$=358: S-cis isomer (eluted second)—$^1$H-NMR (500 MHz, CDCl$_3$): δ ppm 8.14 (d, J=7 Hz, 1H), 7.59 (d, J=8 Hz, 1H), 7.32-7.31 (m, 1H), 4.93 (s, 1H), 4.08-4.03 (m, 2H), 3.59-3.56 (m, 2H), 3.31 (s, 1H), 3.18-3.15 (m, 2H), 2.82-2.87 (m, 2H), 2.65 (s, 3H), 2.53-2.49 (m, 2H), 1.49 (s, 9H); LC/MS: [(M+1)]$^+$=358.

Intermediates 20A and 20B

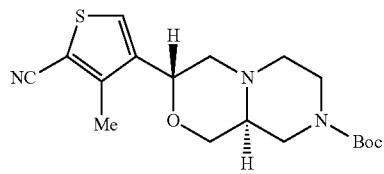

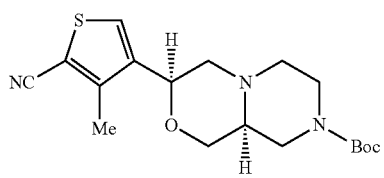

20A tert-butyl(3R,9aS)-3-(5-cyano-4-methylthiophen-3-yl)hexahydropyrazino[2,1-c][1,4]oxazine-8(1H)-carboxylate and tert-butyl(3S,9aS)-3-(5-cyano-4-methylthiophen-3-yl)hexahydropyrazino[2,1-c][1,4]oxazine-8(1H)-carboxylate and tert-butyl(3S,9aS)-3-(5-cyano-4-methylthiophen-3-yl)hexahydropyrazino[2,1-c][1,4]oxazine-8(1H)-carboxylate and tert-butyl(3S,9aS)-3-(5-cyano-4-methylthiophen-3-yl)hexahydropyrazino[2,1-c][1,4]oxazine-8(1H)-carboxylate Step A: 2,4-dibromo-3-methylthiophene: To a solution of 2,3,5-tribromo-4-methylthiophene (46.2 g, 138 mmol) in 500 mL of THF was added dropwise n-BuLi (55.2 mL, 138.0 mmol) at −70° C. The mixture was stirred at −70° C. for 15 minutes and 50 mL of water was added slowly. The resulting mixture was allowed to warm to room temperature and stirred for 10 minutes and extracted with EtOAc. The organic layers were washed with water and brine, dried over anhydrous $Na_2SO_4$ and concentrated to give crude 2,4-dibromo-3-methylthiophene.

Step B: 4-bromo-3-methylthiophene-2-carbonitrile: A mixture of 2,4-dibromo-3-methylthiophene (20.0 g, 78.1 mmol) and CuCN (6.30 g, 70.3 mmol) in 150 mL of DMF was stirred at reflux for 4 hours before cooling down. The reaction mixture was poured into 1 L of ether with stirring and the precipitate was removed by filtration. The filtrate was washed with water (3×100 mL), brine (100 mL), dried over anhydrous $Na_2SO_4$ and concentrated. The residue was purified by silica column chromatography (PE:EtOAc=50:1) to afford title compound.

Step C: 4-ethenyl-3-methylthiophene-2-carbonitrile: A mixture of 4-bromo-3-methylthiophene-2-carbonitrile (3.00 g, 14.8 mmol), potassium vinyltrifluoroborate (2.40 g, 17.8 mmol) and Pd(dppf)Cl$_2$ (0.5 g) in 30 mL of EtOH and 30 mL of TEA was refluxed under Ar for 4 hours. The reaction mixture was concentrated, and the residue was purified by column chromatography (petrol ether:EtOAc=50:1) to afford 4-ethenyl-3-methylthiophene-2-carbonitrile.

Step D: 3-methyl-4-(oxiran-2-yl)thiophene-2-carbonitrile: A suspension of 4-ethenyl-3-methylthiophene-2-carbonitrile (1.70 g, 11.4 mmol) in 30 mL of t-Bu-OH and 60 mL of water was added NBS (2.40 g, 13.7 mmol) portionwise. The mixture was stirred at 90° C. for 1 hour then cooled down to 10° C. Then a solution of NaOH (0.7 g in 10 mL of water, 17.5 mmol) was added dropwise and stirred for 15 minutes. The reaction mixture was extracted with EtOAc twice and concentrated. The residue was purified by silica column chromatography (petrol ether:EtOAc=20:1) to afford 3-methyl-4-(oxiran-2-yl)thiophene-2-carbonitrile.

Step E: tert-butyl(3S)-4-[2-(5-cyano-4-methylthiophen-3-yl)-2-hydroxyethyl]-3-(hydroxymethyl)piperazine-1-carboxylate: A mixture of 3-methyl-4-(oxiran-2-yl)thiophene-2-carbonitrile (1.3 g, 7.9 mmol) and tert-butyl (3S)-3-(hydroxymethyl)piperazine-1-carboxylate (2.0 g, 9.5 mmol) in 5 mL of EtOH was heated in a microwave apparatus at 140° C. for 90 minutes and then cooled down. The reaction mixture was concentrated, and the residue was purified by column chromatography (DCM:MeOH=10:1) to afford the title compound.

Step F: tert-butyl(3R,9aS)-3-(5-cyano-4-methylthiophen-3-yl)hexahydropyrazino[2,1-c][1,4]oxazine-8(1H)-carboxylate and tert-butyl(3S,9aS)-3-(5-cyano-4-methylthiophen-3-yl)hexahydropyrazino[2,1-c][1,4]oxazine-8(1H)-carboxylate: tert-Butyl (3S)-4-[2-(5-cyano-4-methylthiophen-3-yl)-2-hydroxyethyl]-3-(hydroxymethyl)piperazine-1-carboxylate (1.40 g, 3.67 mmol) and cyanomethylene tributylphosphorane (1.59 g, 6.61 mmol) were dissolved in benzene (15 mL) in a microwave tube then sealed, degassed and heated to 100° C. overnight. The reaction mixture was cooled and the benzene was evaporated off. The residue was then purified by chromatography through a 80 g Redi-sep column eluting with acetone:DCM (5:95).

Cis-Isomer 20A, (tert-butyl(3S,9aS), eluted first): $^1$H-NMR (500 MHz, CDCl$_3$): δ ppm 8.06 (s, 1H), 4.76 (s, 1 H), 4.00 (b, 1H), 3.79 (d, J=11 Hz, 0.5H), 3.70 (d, J=10 Hz, 0.5 H), 3.42 (d, J=11.5 Hz, 1H), 3.15 (t, J=10.5 Hz, 1H), 3.10 (s, 0.5H), 3.08 (s, 0.5H), 2.99 (b, 1H), 2.75 (t, J=13.0 Hz, 2H), 2.46 (b, 1H), 2.41 (s, 3H), 2.24-2.40 (m, 2H), 1.45 (s, 9H); LC-MS: M+1=264. Trans-isomer 20B (tert-butyl(3R,9aS), eluted second): $^1$H-NMR (500 MHz, CDCl$_3$): δ ppm 7.50 (s, 1H), 4.66 (d, J=10 Hz, 1 H), 3.80-4.15 (m, 3H), 3.45 (t, J=10 Hz, 1H), 3.02( b,1H), 2.89 (d, J=11.5 Hz, 1H), 2.75 (d, J=9.5 Hz, 1H), 2.53 (b, 1H), 2.43 (s, 3H), 2.27 (t, J=10.5 Hz, 3H), 1.49 (s, 9H); LC-MS: M+1=264.

Intermediates 21A and 21B

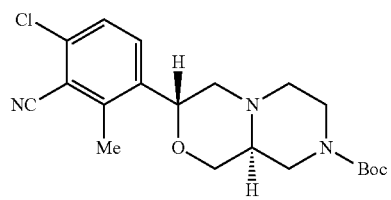

21A

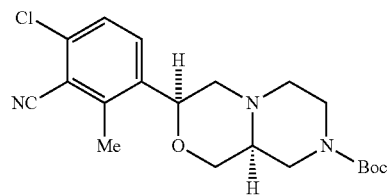

21B tert-butyl(3R,9aS)-3-(4-chloro-3-cyano-2-methylphenyl)hexahydropyrazino[2,1-c][1,4]oxazine-8(1H)-carboxylate and tert-butyl(3S,9aS)-3-(4-chloro-3-cyano-2-methylphenyl)hexahydropyrazino[2,1-c][1,4]oxazine-8(1H)-carboxylate The title compounds were prepared by an analogous method to that described for the synthesis of tert-butyl(3R,9aS)-3-(3-cyano-4-fluoro-2-methylphenyl)hexahydropyrazino[2,1-c][1,4]oxazine-8(1H)-carboxylate and tert-butyl(3S,9aS)-3-(3-cyano-4-fluoro-2-methylphenyl)hexahydropyrazino[2,1-c][1,4]oxazine-8(1H)-carboxylate above (Method 1) starting from 2-chloro-6-methylbenzonitrile. The isomers were separated by Chiralcel OD, 20×250 mm, 50 mL/min, 100 bar, 30% MeOH/CO$_2$, 35 C, ~50 mg/mL in MeOH/DCM, 220 nm. The trans Isomer 21A eluted out first while the cis Isomer 21B eluted second: Trans Isomer 21A: ¹H-NMR (500 MHz, CDCl₃): δ ppm 7.67 (d, J=8.5 Hz, 1H), 7.39(d, J=8 Hz, 1H), 4.88 (d, J=9 Hz, 1H), 4.06-3.99 (m, 3H), 3.58-3.50 (m, 3H), 2.93-2.81 (m, 2H), 2.61 (s, 3H), 2.37-2.29 (m, 3H), 2.20-2.16 (m, 2H), 1.51 (s, 9H); LC/MS: [(M+1)]⁺=392; Cis Isomer 21B: ¹H-NMR (500 MHz, CDCl₃): δ ppm 8.11 (d, J=3 Hz, 1H), 4.92 (s, 2H), 4.05-3.52 (m, 2H), 3.27-3.22 (m, 2H), 3.16-3.05 (m, 3H), 2.83-2.82 (m, 2H), 2.652 (s, 3H), 2.52-2.39 (m, 2H), 1.50 (s, 9H); LC/MS: [(M+1)]⁺=392.

Intermediates 22A and 22B

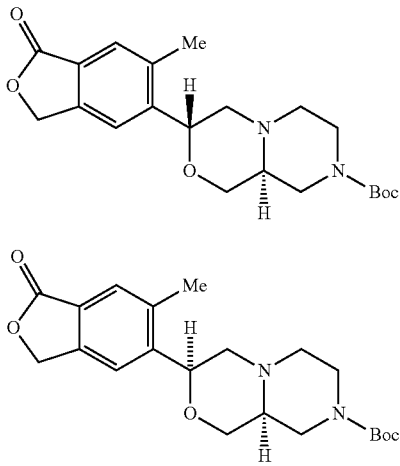

tert-butyl(3R,9aS)-3-(6-methyl-1-oxo-1,3-dihydro-2-benzofuran-5-yl)hexahydropyrazino[2,1-c][1,4]oxazine-8(1H)-carboxylate and tert-butyl(3S,9aS)-3-(6-methyl-1-oxo-1,3-dihydro-2-benzofuran-5-yl)hexahydropyrazino[2,1-c][1,4]oxazine-8(1H)-carboxylate Step A: 5-(prop-2-en-1-yl)-2-benzofuran-1(3H)-one: A mixture of 5-bromo-2-benzofuran-1(3H)-one (15.0 g, 70.4 mmol), allyl-tributyl-stannane (25.6 g, 77.5 mmol), LiCl (11.8 g, 282 mmol) and Pd(PPh₃)₄ (1.2 g, 1 mmol) in 100 mL toluene was heated under N₂ at 90-100° C. overnight. After cooling to r.t., the mixture was diluted with 250 mL EtOAc and filtered. The filtrate was washed with water and brine, dried over anhydrous Na₂SO₄ and concentrated to dryness. The residue was purified via silica column chromatography (DCM/Petrol Ether=1:5) to give 5-(prop-2-en-1-yl)-2-benzofuran-1(3H)-one.

Step B: 5-(2-hydroxyethyl)-2-benzofuran-1(3H)-one: To a solution of 5-(prop-2-en-1-yl)-2-benzofuran-1(3H)-one (13.5 g, 45.2 mmol) in 200 mL DCM/MeOH (V/V=1:1) was bubbled O₃ at −78° C. for 30 min, and N₂ was bubbled for another 15 min at −78° C. Then 20 mL of Me₂S were added, and the mixture was stirred at r.t. overnight before concentrating to dryness. The residue was dissolved in MeOH (100 mL) and then cooled to 0° C. NaBH₄ (5.90 g, 155 mmol) was added in portions. The resulting mixture was stirred at 0° C. for 1 hr, then quenched with citric acid (aq.) and extracted with EtOAc (3×500 mL). The combined organic layers were washed with NaHCO₃ (aq.) and brine, dried over anhydrous Na₂SO₄ and concentrated to dryness. The residue was purified via silica column chromatography (EtOAc/Petrol Ether=1:5) to give 5-(2-hydroxyethyl)-2-benzofuran-1(3H)-one.

Step C: 5-(2-hydroxyethyl)-6-iodo-2-benzofuran-1(3H)-one: To a cooled (0° C.) solution of 5-(2-hydroxyethyl)-2-benzofuran-1(3H)-one (9.00 g, 50.6 mmol) in 100 mL of TfOH was added NIS (12.5 g, 55.6 mmol), then the mixture was stirred at 0° C. for 2 hrs and then poured into ice-water (500 mL). The solution was extracted with EtOAc (3×500 mL) and the combined organic layers were washed with saturated NaHCO₃ solution and brine, and dried over anhydrous sodium sulfate, filtered and concentrated. The residue was purified by silica column chromatography (EtOAc/Petrol Ether=1:5) to give 5-(2-hydroxyethyl)-6-iodo-2-benzofuran-1(3H)-one and its separated regioisomer.

Step D: 5-(2-hydroxyethyl)-6-methyl-2-benzofuran-1(3H)-one: To a flask charged with 5-(2-hydroxyethyl)-6-iodo-2-benzofuran-1(3H)-one (6.00 g, 19.7 mmol) and a stir bar was added Pd₂(dba)₃ (452 mg, 0.493 mmol), PPh₃ (1.00 g, 3.95 mmol) and NMP (50 mL). The mixture was purged with N₂ and heated to 50° C. for 10 min, followed by addition of CuI (375 mg, 1.97 mmol). Then the mixture was heated for another 10 min, after which Sn(CH₃)₄ (5.30 g, 29.6 mmol) was added into the reaction, and it was heated to 120° C. for 2 h. After cooling to room temperature, the mixture was diluted with saturated NH₄Cl (200 mL) and extracted with EtOAc (3×200 mL). The combined organic layers were washed with water and brine, dried over anhydrous sodium sulfate, filtered and concentrated. The residue was purified by preparative HPLC to give 5-(2-hydroxyethyl)-6-methyl-2-benzofuran-1(3H)-one.

Step E: 2-(6-methyl-1-oxo-1,3-dihydro-2-benzofuran-5-yl)ethyl methanesulfonate: To a solution of 5-(2-hydroxyethyl)-6-methyl-2-benzofuran-1(3H)-one (1.20 g, 6.25 mmol) and TEA (2.5 g, 25 mmol) in DCM (100 mL) was added MsCl (1.40 g, 12.5 mmol) at 0° C. The mixture was stirred at ambient temperature overnight, then was washed with water and brine. The organic layer was dried and concentrated to dryness. The resulting 2-(6-methyl-1-oxo-1,3-dihydro-2-benzofuran-5-yl)ethyl methanesulfonate was used for the next step without any purification.

Step F: 5-ethenyl-6-methyl-2-benzofuran-1(3H)-one: To a mixture of 2-(6-methyl-1-oxo-1,3-dihydro-2-benzofuran-5-yl)ethyl methanesulfonate (2.0 g, 7.4 mmol) and TEA (5 mL) in DCM (50 mL) was added DBU (5 mL) slowly at 0° C. The mixture was stirred at r.t. overnight, and then diluted with 50 mL of DCM, washed with 2 N HCl in three times and brine. The organic layer was dried and concentrated to dryness. The residue was purified by prep-TLC to give 5-ethenyl-6-methyl-2-benzofuran-1(3H)-one.

Step G: 6-methyl-5-(oxiran-2-yl)-2-benzofuran-1(3H)-one: A solution of 5-ethenyl-6-methyl-2-benzofuran-1(3H)-one (1.00 g, 5.75 mmol) in 50 mL of DCM was slowly added mCPBA (3.50 g, 17.4 mmol) in 50 mL of DCM at 0° C. Warmed to room temperature, the mixture was stirred for 2 days. The mixture was washed with aqueous Na₂SO₃ until the KI paper didn't change color. The organic layers was washed with brine and then concentrated. The residue was purified via column chromatography to give the product title compound.

Step H: tert-butyl(3S)-3-(hydroxymethyl)-4-[2-hydroxy-2-(6-methyl-1-oxo-1,3-dihydro-2-benzofuran-5-yl)ethyl]piperazine-1-carboxylate: A mixture of 6-methyl-5-(oxiran-2-yl)-2-benzofuran-1(3H)-one (750 mg, 3.95 mmol) and tert-butyl (3S)-3-(hydroxymethyl)piperazine-1-carboxylate (1.02 g, 4.74 mmol) in EtOH (5 mL) was reacted under microwave condition (140° C.) for 90 min. After cooling to r.t., the mixture was concentrated to dryness. The residue was purified by prep-TLC to give title compound.

Step I: tert-butyl(3R,9aS)-3-(6-methyl-1-oxo-1,3-dihydro-2-benzofuran-5-yl)hexahydropyrazino[2,1-c][1,4]oxazine-8(1H)-carboxylate and tert-butyl(3S,9aS)-3-(6-methyl-1-oxo-1,3-dihydro-2-benzofuran-5-yl) hexahydropyrazino[2,1-c][1,4]oxazine-8(1H)-carboxylate
The synthesis of the title compounds was achieved in an analogous fashion to that previously described for isomers tert-butyl(3R,9aS)-3-(4-methyl-1-oxo-1,3-dihydro-2-benzofuran-5-yl)hexahydropyrazino[2,1-c][1,4]oxazine-8(1H)-carboxylate and tert-butyl(3S,9aS)-3-(4-methyl-1-oxo-1,3-dihydro-2-benzofuran-5-yl)hexahydropyrazino[2,1-c][1,4]oxazine-8(1H)-carboxylate (Steps B-C) starting from tert-butyl (3S)-3-(hydroxymethyl)-4-[2-hydroxy-2-(6-methyl-1-oxo-1,3-dihydro-2-benzofuran-5-yl)ethyl]piperazine-1-carboxylate. The isomers were separated by Chiralcel OD-H, 4.6×250, 20% IPA/CO$_2$, 2.1 mL/min, 100 bar, 40 C. The trans isomer eluted first, while the cis isomer eluted second. trans-Isomer 22A: $^1$H-NMR (500 MHz, CDCl$_3$): δ ppm 7.72 (s,1H), 7.68 (s, 1H), 5.31 (s, 2H), 4.95 (d, J=10 Hz, 1H), 4.07-3.99 (m, 3H), 3.56-3.52 (m, 1H), 2.77-2.493 (m, 5H), 2.32-2.14 (m, 2H), 1.63 (s, 3H), 1.54-1.49 (m, 9H); LC/MS: [(M+1)]$^+$=389; cis-Isomer 22B: LC/MS: [(M+1)]$^+$=389.

Intermediate 23

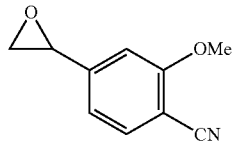 [SMILES: COc1cc(C2CO2)ccc1C#N]

2-Methoxy-4-(oxiran-2-yl)benzonitrile

Step A: 4-Formyl-2-methoxyphenyl trifluoromethanesulfonate: To a solution of vanillin (20 g, 131 mmol) in DMF (200 mL) at room temperature was added potassium carbonate (36.30 g, 263 mmol) and 4-nitrophenyl trifluoromethanesulfonate (53.5 g, 197 mmol) and the reaction mixture was stirred for 8 hr. EtOAc (600 mL) was added to the reaction mixture and the organic layer was washed three times with water, dried, filtered, and concentrated. The crude compound was then purified by flash chromatography (ethylacetate/hexanes 1:9-3:7) to provide the title compound.

Step B: 4-Formyl-2-methoxybenzonitrile: A mixture of the sulfonate (37.0 g, 130 mmol), zinc cyanide (61.1 g, 521 mmol) and tetrakis triphenylphosphine palladium (0) (22.57 g, 19.53 mmol) in DMF (300 mL) were stirred at 110° C. for 8 hr. EtOAc was added to the reaction mixture and the organic layer was washed two times with water, dried, filtered and concentrated. The crude product was then purified by column chromatography (silica gel, ethylacetate/hexanes 3:7) which afforded the title compound: LC/MS: (IE, m/z) [M+1]$^+$=162.34.

Step C: 2-Methoxy-4-(oxiran-2-yl)benzonitrile: To a cool solution of NaH (0.16 g, 3.9 mmol) in THF (40 mL) was added dropwise a solution of trimethylsulfonium iodide (0.91 g, 4.5 mmol) in DMSO (20 mL). The resulting mixture was stirred at 0° C. under N$_2$ for 20 min. A solution of 4-formyl-2-methoxybenzonitrile (0.60 g, 3.72 mmol) in THF (20 mL) was added. The resulting reaction mixture was stirred at 0° C. under N$_2$ for 1 hr, and then it was warmed gradually to room temperature and stirred at that temperature for 12 hr. The starting material was consumed as indicated by TLC (25% ethyl acetate/hexanes). The reaction mixture was cooled to 0° C. and quenched with dropwise addition of water. The mixture was extracted with ethyl acetate (2×70 mL). The combined organic layers were washed with water, brine, then dried (MgSO$_4$) and filtered. The filtrate was concentrated in vacuo. The residue was purified via column chromatography (silica gel, 10-30% EtOAc-hexanes) to afford 2-methoxy-4-(oxiran-2-yl)benzonitrile: $^1$H NMR (CDCl$_3$, 500 MHz) δ 7.57 (d, J=8 Hz, 1H), 6.99 (dd, J=1.1 Hz, J=1.2 Hz, 1H), 6.89 (s, 1H), 3.97 (s, 3H), 3.94-3.92 (m, 1H), 3.22 (dd, J=5.2, Hz, J=4.1 Hz, 1H), 2.77 (d, J=2.5 Hz, 1H); LC/MS: (IE, m/z) [M+1]$^+$=176.33.

Intermediates 24A and 24B

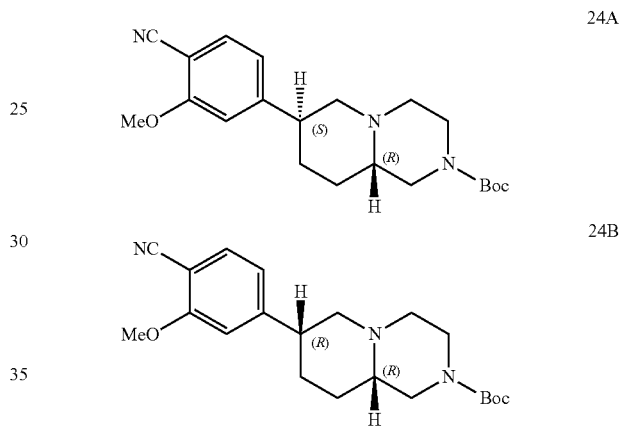

24A: tert-Butyl (3S,9aR)-3-(4-cyano-3-methoxyphenyl)hexahydropyrazino[2,1-c][1,4]oxazine-8(1H)-carboxylate and 24B: tert-Butyl (3R,9aR)-3-(4-cyano-3-methoxyphenyl)hexahydropyrazino[2,1-c][1,4]oxazine-8(1H)-carboxylate Step A: tert-Butyl (3R)-4-[2-(4-cyano-3-methoxyphenyl)-2-hydroxyethyl]-3(hydroxymethyl)piperazine1-carboxylate: A Pyrex vessel was charged with magnetic stirring bar, (2.0 g, 11.42 mmol) of 2-methoxy-4-(oxiran-2-yl)benzonitrile, (3.70 g, 17.12 mmol) of tert-butyl (3R)-3-(hydroxymethyl)piperazine-1-carboxylate, and 6 mL of EtOH. Then it was introduced in the microwave reactor and irradiated at 150° C. for 3 h. The mixture was cooled to room temperature and the solvent was evaporated and the resulting residue was purified by column chromatography (silica gel, 1-20% dichloromethane/MeOH) which afforded the product as a mixture of two diastereomers (1:1) LC/MS: (IE, m/z) [(M+1)-t-Bu]$^+$=336.41

Step B: tert-Butyl (9aR)-3-(4-cyano-3-methoxyphenyl) hexahydropyrazino[2,1-c][1,4]oxazine-8(1H)-carboxylate: The isomeric mixture of the prior step (3.48 g, 8.89 mmol, 1:1) in benzene was treated with (tributyl-λ$^5$-phosphanylidene) acetonitrile (3.22 g, 13.3 mmol). The reaction mixture was microwaved for 3 hr at 135° C. in a Biotage apparatus. Then the mixture was cooled to room temperature, and solvent removal gave crude product. The crude product was chromatographed (silica gel, hexanes/EtOAc 9:1-3:7, as eluent) to give an isomeric mixture of the bicyclic title compound.

Step C: tert-Butyl(3S,9aR)-3-(4-cyano-3-methoxyphenyl)hexahydropyrazino[2,1-c][1,4]oxazine-8(1H)-carboxylate and tert-Butyl(3R,9aR)-3-(4-cyano-3-methoxyphenyl)hexahydropyrazino[2,1-c][1,4]oxazine-8(1H)-carboxylate:
The isomeric mixture was further separated into its enantiomers using a 21×250 mm ChiralCel OJ-H, column, eluting with 15% MeOH/CO$_2$ with a flow rate of 50 mL/min, 100 bar, 59 mg/mL in MeOH, 35 C, 220 nm, Thr=200: trans-Isomer 24A: $^1$H NMR (CDCl$_3$, (trans) isomer, 500 MHz) δ 7.54 (d, J=7.9 Hz, 1H), 7.05 (s, 1H), 6.97 (d, J=7.9 Hz, 1H), 4.72 (d, J=8.9 Hz, 1H), 4.12-4.0 (m, 2H), 3.98 (s, 3H), 3.49 (t, J=9.4 Hz, J=9.0 Hz, 1H), 3.03 (bs, 1H), 2.94 (d, J=11.2 Hz, 1H), 2.76 (d, J=9 Hz, 1H), 2.56 (bs, 1H), 2.29-2.192 (m, 3H), 1.69 (bs, 1H), 1.50 (s, 9H); LC/MS: (IE, m/z) [(M+1)-t-Bu]$^+$=318.40; cis-Isomer 24B: $^1$H NMR (CDCl$_3$, (cis) isomer, 500 MHz) δ 7.58 (d, J=7.9 Hz, 1H), 7.21 (s, 1H), 7.17 (d, J=7.8 Hz, 1H), 4.82 (bs, 1H), 4.06-3.99 (m, 2H), 3.98 (s, 3H), 3.64 (bs, 1H), 3.43 (bs, 1H), 3.23 (d, J=11.6 Hz, 1H), 3.05 (bs, 1H), 2.81 (bs, 2H), 2.72-2.42 (m, 3H), 1.50 (s, 9H); LC/MS: (IE, m/z) [(M+1)-t-Bu]$^+$=318.35.

Intermediates 24C and 24D

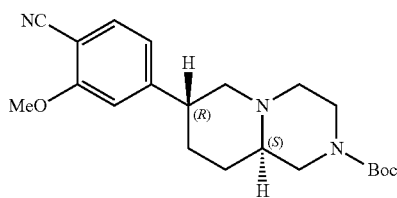

24C

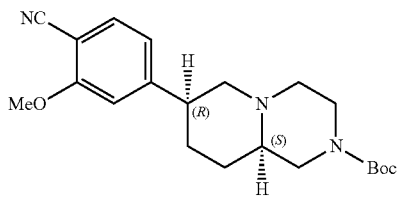

24D

24C: tert-Butyl (3R,9aS)-3-(4-cyano-3-methoxyphenyl)hexahydropyrazino[2,1-c][1,4]oxazine-8(1H)-carboxylate and 24D: tert-Butyl (3S,9aS)-3-(4-cyano-3-methoxyphenyl)hexahydropyrazino[2,1-c][1,4]oxazine-8(1H)-carboxylate Step A: tert-Butyl (3S)-4-[2-(4-cyano-3-methoxyphenyl)-2-hydroxyethyl]-3-(hydroxymethyl)piperazine-1-carboxylate: A Pyrex vessel was charged with magnetic stirring bar, (0.350 g, 2.00 mmol) of 2-methoxy-4-(oxiran-2-yl)benzonitrile, (0.457 g, 2.20 mmol) of tert-butyl (3S)-3-(hydroxymethyl)piperazine-1-carboxylate, and 6 mL of EtOH. Then it was introduced in the microwave reactor and irradiated at 150° C. for 3 hr. Then the mixture was cooled to room temperature and the solvent was evaporated and the resulting residue was purified by column chromatography (silica gel, 1-20% dichloromethane/MeOH) which afforded the title compound as a mixture of two diastereomers (1:1). LC/MS: (IE, m/z) [(M+1)-t-Bu]$^+$=336.1.

Step B: tert-Butyl (9aS)-3-(4-cyano-3-methoxyphenyl)hexahydropyrazino[2,1-c][1,4]oxazine-8(1H)-carboxylate:
The isomeric mixture of the prior step (0.55 g, 1.40 mmol, 1:1) in benzene was treated with (tributyl-λ$^5$-phosphanylidene) acetonitrile (0.678 g, 2.81 mmol). The reaction mixture was microwaved for 3 hr at 135° C. in a Biotage apparatus. Then the mixture was cooled to room temperature, and solvent removal gave crude product. The crude product was chromatographed (silica gel, hexanes/EtOAc 9:1-3:7, as eluent) to give an isomeric mixture of the bicyclic title compound LC/MS: (IE, m/z) [(M+1)-t-Bu]$^+$=318.06.

Step C: 29C and 29D: tert-Butyl (9aS)-3-(4-cyano-3-methoxyphenyl)hexahydropyrazino[2,1-c][1,4]oxazine-8(1H)-carboxylate was further separated into its enantiomers using a 21×250 mm ChiralCel OJ-H, column, eluting with 15% MeOH/CO$_2$ with a flow rate of 50 mL/min, 100 bar, 59 mg/mL in MeOH, 35C, 220 nm, Thr=200: trans-Isomer 24C: $^1$H NMR (CDCl$_3$, (trans) isomer, 500 MHz) δ 7.55 (d, J=8.0 Hz, 1H), 7.06 (s, 1H), 6.97 (d, J=8.0 Hz, 1H), 4.71 (d, J=9.4 Hz, 1H), 4.12-4.0 (m, 2H), 3.98 (s, 3H), 3.48 (t, J=9.4 Hz, J=10.3 Hz, 1H), 3.03 (bs, 1H), 2.94 (d, J=11.0 Hz, 1H), 2.76 (d, J=7.8 Hz, 1H), 2.54 (bs, 1H), 2.29-2.192 (m, 3H), 1.51 (s, 9H); LC/MS: (IE, m/z) [(M+1)-t-Bu]$^+$=318.17; cis-Isomer 24D: $^1$H NMR (CDCl$_3$, (cis) isomer, 500 MHz) δ 7.58 (d, J=8.0 Hz, 1H), 7.22 (s, 1H), 7.17 (d, J=7.8 Hz, 1H), 4.82 (bs, 1H), 4.06-3.99 (m, 2H), 3.98 (s, 3H), 3.64 (bs, 1H), 3.43 (bs, 1H), 3.23 (dd, J=3.6 Hz, J=3.7 Hz, 1H), 3.01 (bs, 1H), 2.80 (bs, 2H), 2.72-2.42 (m, 3H), 1.50 (s, 9H); LC/MS: (IE, m/z) [(M+1)-t-Bu]$^+$=318.35.

Intermediate 25

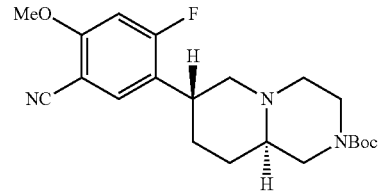 [SMILES: COc1cc(F)c([C@H]2CC[C@@H]3CN(C(=O)OC(C)(C)C)CCN3C2)cc1C#N]

tert-butyl (3R,9aS)-3-(5-cyano-2-fluoro-4-methoxyphenyl)hexahydropyrazino[2,1-c][1,4]oxazine-8(1)-carboxylate)-carboxylate Step A: 5-bromo-4-fluoro-2-methoxybenzonitrile: To a 500 mL flask was added 4-fluoro-2-methoxybenzonitrile (9.00 g, 59.5 mmol), NBS (12.7 g, 71.5 mmol) and TFA (40 mL); the resulting mixture was stirred for 4 h at 65° C. Analysis of the reaction by LC indicated completion of the reaction. The reaction mixture was concentrated to dryness, treated with EtOAc (200 mL) and washed with brine and water, dried (Na$_2$SO$_4$), filtered and concentrated to dryness. The resulting organic residue was purified by MPLC with the solvent systems of hexanes/EtOAc=1/1 to furnish the desired product: LC/MS: [(M+2)]$^+$=232;

Step B: 5-ethenyl-4-fluoro-2-methoxybenzonitrile: 5-Ethyenyl-4-fluoro-2-methoxybenzonitrile was prepared from 4-bromo-2-fluoro-6-methoxybenzonitrile using potassium vinyl trifluoroborate and PdCl$_2$(dppf)$_2$ in an analogous fashion as described for 4-ethenyl-3-methyl-2-(methyloxy) benzonitrile above: LC/MS: [(M+1)]$^+$=178

Step C: 4-fluoro-2-methoxy-5-(oxiran-2-yl)benzonitrile: The title compound was prepared from 5-ethyenyl-4-fluoro- 2-methoxybenzonitrile using mCPBA in an analogous fashion to that described for 6-fluoro-2-methyl-3-(oxiran-2-yl)benzonitrile (Step C, Intermediates 15A/15B): LC/MS: [(M+1)]$^+$=194.

Steps D: tert-butyl (3R,9aS)-3-(5-cyano-2-fluoro-4-methoxyphenyl)hexahydropyrazino[2,1-c][1,4]oxazine-8(1)-carboxylate)-carboxylate: The title compound was prepared from 4-fluoro-2-methoxy-5-(oxiran-2-yl)benzonitrile in an analogous fashion as described for tert-Butyl (3R,9aS)-3-(4-cyano-3-methoxyphenyl)hexahydropyrazino[2,1-c][1,4]oxazine-8(1H)-carboxylate Intermediate 24C. Trans and cis were resolved by AD column, 30×250 mm, 20% 2:1 MeOH:MeCN/CO$_2$, 70 ml/min, 100 bar, 250 mg/ml in MeOH/MeCN, 35 C, 230 nm; $^1$H-NMR (500 MHz, CDCl$_3$) δ ppm 7.75 (d, J=7.5 Hz, 1H), 6.67 (d, J=11.5 Hz, 1H), 4.88 (d, J=10 Hz, 1H), 3.94 (s, 3H), 3.49-3.45 (m, 2H), 2.94-2.91 (m, 2H), 2.75-2.73 (m, 1H), 2.28-2.23 (m, 4H), 2.17-2.13 (m, 2H), 1.5 (s, 9H).

Intermediates 26A and 26B

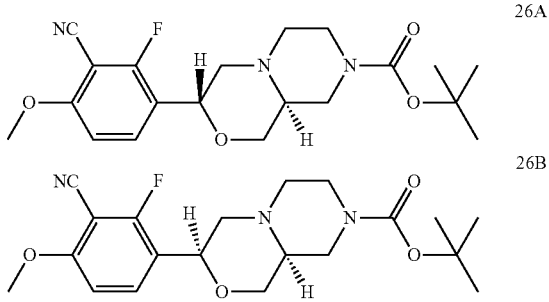

26A: tert-butyl(3R,9aS)-3-(3-cyano-2-fluoro-4-methoxyphenyl)hexahydropyrazino[2,1-c][1,4]oxazine-8(1H)-carboxylate 26B: tert-butyl(3S,9aS)-3-(3-cyano-2-fluoro-4-methoxyphenyl)hexahydropyrazino[2,1-c][1,4]oxazine-8(1H)-carboxylate Step A: 2-fluoro-6-methoxy-3-nitrobenzonitrile To a flask containing 2,6-difluoro-3-nitrobenzonitrile (15 g, 81 mmol) was added MeOH (40 mL); to this solution was slowly added triethylamine (10.7 mL, 81.0 mmol). The resulting mixture was stirred at room temperature for 2 h. Analysis of the reaction mixture by LC as well as TLC (hexanes/EtOAc=1/0.3) indicated that reaction had gone to completion. The solvent was removed and the resulting organic residue was then dissolved in methylene chloride, washed with brine, dried over Na$_2$SO$_4$, filtered, concentrated, and separated over silica gel to give 2-fluoro-6-(methyloxy)-3-nitrobenzonitrile.

Step B: 3-amino-2-fluoro-6-methoxybenzonitrile

To a flask containing 2-fluoro-6-(methyloxy)-3-nitrobenzonitrile (2.00 g, 10.2 mmol) and a stir bar was added Pd on carbon (109 mg, 1 mmol), MeOH (15 mL), and few drops of AcOH. The reaction mixture was stirred under H$_2$ (balloon) for 1 h. Analysis of the reaction progress by LC as well as TLC (hexanes/EtOAc=1/1) indicated that reaction was complete. The reaction mixture was filtered through CELITE, and the resulting solution was concentrated to dryness to furnish 3-amino-2-fluoro-6-(methyloxy)benzonitrile.

Step C: 3-bromo-2-fluoro-6-methoxybenzonitrile

To a flask containing a stir bar were added Copper (II) Bromide (6.2 g, 28 mmol), tert-butyl nitrite (4.3 mL, 33 mmol), followed by acetonitrile (20 mL). The flask was placed in an oil bath at 60° C. under N$_2$ and stirred for 30 min. To the flask was added 3-amino-2-fluoro-6-(methyloxy)benzonitrile (3.70 g, 22.3 mmol) in acetonitrile (10 mL). The resulting mixture was stirred at 60° C. under N$_2$ for 20 min. TLC (hexanes/EtOAc=1/1) analysis showed that the reaction was complete. The flask was taken out of the oil bath and cooled to room temperature. It was then treated with 2M HCl (2 mL) and extracted with diethyl ether several times. The organic layer was then combined and washed with water, dried over Na$_2$SO$_4$, filtered, and concentrated to dryness. The residue was then purified by MPLC over silica gel to give 3-bromo-2-fluoro-6-(methyloxy)benzonitrile.

Step D: 3-ethenyl-2-fluoro-6-methoxybenzonitrile

To a 20 mL microwave tube was added 3-bromo-2-fluoro-6-(methyloxy)benzonitrile (1 g, 4.35 mmol), Potassium vinyltrifluoroborate (1.2 g, 8.7 mmol), Pd(dppf)Cl$_2$ (355 mg, 0.435 mmol), TEA (1 mL) and EtOH (15 mL). The reaction mixture was heated in a microwave reactor at 150° C. for 45 min. TLC showed clean and complete reaction. The organic residue was dissolved in EtOAc (500 mL) and the solution was washed with brine, dried over sodium sulfate, filtered and concentrated. The resulting organic residue was subjected to MPLC purification over silica gel to give 3-ethenyl-2-fluoro-6-(methyloxy)benzonitrile.

Step E: 2-fluoro-6-methoxy-3-(oxiran-2-yl)benzonitrile

To a solution of 3-ethenyl-2-fluoro-6-(methyloxy)benzonitrile (2.00 g, 11.3 mmol) in DCM (20 mL) was slowly added mCPBA (3.50 g, 20.3 mmol) at 0° C. The flask was warmed to room temperature and the mixture was then stirred for 12 hours. Analysis by TLC as well as LC indicated that reaction had gone to completion. The mixture was washed with aqueous Na$_2$S$_2$O$_3$, NaHCO$_3$, and water. The organic layer was washed with brine and then concentrated. The residue was purified over silica gel to give title compound;

Step F: tert-butyl (3S)-4-[2-(3-cyano-2-fluoro-4-methoxyphenyl)-2-hydroxyethyl]-3-(hydroxymethyl)piperazine-1-carboxylate To a microwave tube containing a stir bar was added 2-fluoro-6-methoxy-3-(oxiran-2-yl)benzonitrile (0.480 g, 2.45 mmol) and tert-butyl (3S)-3-(hydroxymethyl)piperazine-1-carboxylate (1.00 g, 4.92 mmol); the resulting mixture was purged with N$_2$ and the tube was heated in a microwave reactor for 1 h at 150° C. TLC analysis of the reaction mixture showed the completion of the reaction. The solution was concentrated to dryness and absorbed into silica gel and was subjected for purification over a silica column to give title compound Step G: Intermediates 26A and 26B: To a 20 mL size microwave tube containing a stir bar was added tert-butyl (3S)-4-[2-(3-cyano-2-fluoro-4-methoxyphenyl)-2-hydroxyethyl]-3-(hydroxymethyl)piperazine-1-carboxylate (0.6 g, 1.48 mmol), Cyanomethylene tri-n-Butylphosphorane (0.65 g, 2.68 mmol) methylene and anhydrous toluene (15 mL). The tube was degassed and purged with N$_2$ followed by heating at 100° C. for 12 h. Analysis of the reaction by LC and TLC (10% MeOH in DCM) showed consumption of starting material and formation of product. Solution was concentrated to dryness and the organic residue was then purified over silica gel with the solvent system of 30%

Acetone in DCM to furnish the diastereomer mixture of 26A and 26B. Individual Isomers 26A and 26B were obtained by further separation of the mixture using a chiral column. 26A: ¹H-NMR (CDCl₃, 500 MHz), δ 7.708-7.675 (m, 1 H), 6.802 (d, J=9 Hz, 1H), 4.923 (d, J=9.5 Hz, 1H), 3.992-3.912 (m, 4H), 3.523-3.493 (m, 5H), 3.033-2.746 (m, 3H), 2.288-2.143 (m, 2H),1.503 (s, 9H); 26B: (after Boc was removed with 4M HCl) ¹H-NMR (DMSO, 500 MHz), δ 8.028-7.997 (m, 1H), 7.112 (d, J=9 Hz, 1H), 4.972-4.962 (m, 1H), 3.938 (s, 3H), 3.838-3.682 (m, 6H), 3.335-3.207 (m, 4H), 3.109-2.991 (m, 2H)

Intermediates 27A and 27B

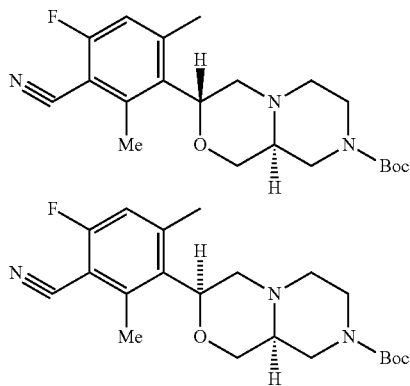

Trans isomer: tert-butyl (3R,9aS)-3-(5-cyano-4-fluoro-2-methylphenyl)hexahydropyrazino[2,1-c][1,4]oxazine-8(1H)-carboxylate; and cis-isomer: tert-butyl (3S,9aS)-3-(5-cyano-4-fluoro-2-methylphenyl) hexahydropyrazino[2,1-c][1,4]oxazine-8(1H)-carboxylate The preparation of the title compounds was achieved in an analogous fashion to that described previously for Intermediates tert-butyl (3R,9aS)-3-(3-cyano-4-fluoro-2-methylphenyl)hexahydropyrazino[2,1-c][1,4]oxazine-8(1H)-carboxylate and tert-butyl(3S,9aS)-3-(3-cyano-4-fluoro-2-methylphenyl)hexahydropyrazino[2,1-c][1,4]oxazine-8 (1H)-carboxylate from 5-bromo-2-fluoro-4-methylbenzonitrile. 5-Bromo-2-fluoro-4-methylbenzonitrile was prepared in a similar fashion to that described for 3-bromo-6-fluoro-2-methylbenzonitrile (I-15A/15B method 1 Step A). In the final step, tert-butyl (3S)-4-[2-(5-cyano-4-fluoro-2-methylphenyl)-2-hydroxyethyl]-3-(hydroxymethyl) piperazine-1-carboxylate (1.44 g, 3.66 mmol) and cyanomethylene tri-n-butylphosphorane (1.59 g, 6.59 mmol) were dissolved in benzene (15 mL) in a microwave tube then sealed, degassed and heated to 100° C. overnight. The reaction was cooled and the benzene was evaporated off. The residue was then chromatographed through an 80 g Redi-sep column and eluted with ethyl acetate:hexane (0-50%). The first eluent was the cis isomer title compound and the second eluent was the trans isomer title compound. Isomer A: ¹H-NMR (500 MHz, CDCl₃): δ ppm 8.24 (s, 1H), 7.06 (d, J=9.5 Hz,1 H), 4.88 (s, 1H), 4.06-3.60 (m,2H), 3.52 (s, 1 H), 3.23 (s, 1H), 3.14 (d, J=12.5 Hz, 1H), 3.09 (b, 1H), 2.90 (s, 2H), 2.63 (b, 1H), 2.49 (s, 3H), 2.40 (b, 2H), 1.51 (s, 9H); Isomer B: ¹H-NMR (500 MHz, CDCl₃): δ ppm 7.77 (d, J=6.5 Hz, 1H), 7.03 (d, J=9.5 Hz,1H), 4.80 (d, J=9.5 Hz, 1 H), 4.03-4.15 (b, 1H), 3.99 (d, J=10.5 Hz, 2H), 3.49 (t, J=11 Hz, 1H), 3.03 (b, 1H), 2.85 (d, J=11 Hz, 1H), 2.74 (d, J=9.5 Hz, 1H), 2.54 (b, 1H), 2.45 (s, 3H), 2.26-2.30 (m, 2H), 2.15 (t, J=11 Hz, 1H), 1.51 (s, 9H).

Intermediate 28

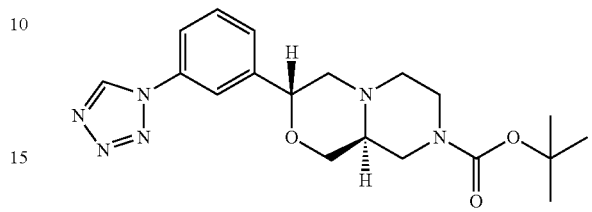

tert-butyl (3R,9aS)-3-[3-(1H-tetrazol-1-yl)phenyl] hexahydropyrazino[2,1-c][1,4]oxazine-8(1H)-carboxylate Step A: (S)-tert-butyl 3-(hydroxymethyl)-4-(2-(3-nitrophenyl)-2-oxoethyl)piperazine-1-carboxylate: 2-Bromo-1-(3-nitrophenyl)ethanone (1.01 g, 4.14 mmol) was dissolved in THF (20 mL) and added (S)-tert-butyl 3-(hydroxymethyl) piperazine-1-carboxylate (1.074 g, 4.97 mmol) followed by Hunig's base (1.45 mL, 8.28 mmol) then stirred at room temperature overnight. The reaction was poured into water and extracted with EtOAc (2×). The organic layer was separated, dried over Na₂SO₄, filtered and concentrated. The product was purified by chromatography through a 120 g ISCO Redi-sep column eluting with 0-70% ethyl acetate/hexane to yield the title compound.

Step B: (9aS)-tert-butyl 3-(3-nitrophenyl)hexahydropyrazino[2,1-c][1,4]oxazine-8(1H-carboxylate: (S)-tert-butyl 3-(hydroxymethyl)-4-(2-(3-nitrophenyl)-2-oxoethyl)piperazine-1-carboxylate (1.5 g, 3.95 mmol) was dissolved in mixture of DCM (10 mL)/TFA (5 ml) then added triethylsilane (3.16 mL, 19.8 mmol) and stirred at room temperature overnight. The reaction mixture was concentrated. The residue was dissolved in DCM (15 mL) with saturated aqueous NaHCO₃ (15 ml) and di-tert-butyl dicarbonate (2.157 g, 9.88 mmol) was added then stirred for 2 hrs. The reaction was extracted with DCM (2×). The combined DCM was washed with brine, dried over Na₂SO₄, filtered and evaporated to dryness. The product was chromatographed through 120 g ISCO Redi-sep column and eluted with 10-70% ethyl acetate/hexane to yield the title compound; the product was almost exclusively the trans isomer.

Step C: (9aS)-tert-butyl 3-(3-aminophenyl)hexahydropyrazino[2,1-c][1,4]oxazine-8(1H)-carboxylate: (9aS)-tert-Butyl 3-(3-nitrophenyl)hexahydropyrazino[2,1-c][1,4]oxazine-8(1H)-carboxylate (1.37 g, 3.77 mmol, mostly trans isomer) was dissolved in ethyl acetate (30 mL) then added 10% Pd/C (0.1 g, 0.940 mmol). The mixture was stirred under a balloon of hydrogen overnight. The reaction mixture was filtered and concentrated to yield (9aS)-tert-butyl 3aminophenyl)hexahydropyrazino[2,1-c][1,4]oxazine-8 (1H)-carboxylate (trans isomer).

Step D: tert-butyl (3R,9aS)-3-[3-(1H-tetrazol-1-yl)phenyl]hexahydropyrazino[2,1-c][1,4]oxazine-8(1H)-carboxylate: (9aS)-tert-Butyl 3-(3-aminophenyl) hexahydropyrazino [2,1-c][1,4]oxazine-8(1H)-carboxylate (1.27 g, 3.81 mmol, trans isomer), sodium azide (0.446 g, 6.86 mmol) and triethyl orthoformate (1.27 mL, 7.62 mmol) were stirred in acetic acid (15 mL) then refluxed for 3 hrs. The reaction was concentrated and taken up with ethyl acetate then washed with NaHCO₃, dried over Na₂SO₄, filtered and concentrated. The product was purified by chromatography through a 120 g ISCO Redi-sep column eluting with 2.5% MeOH/DCM to yield the title compound: LC-MS (IE, m/z): 387 [M+1]; ¹H-NMR (600 MHz, CDCl₃) δ ppm 9.008 (s, 1H), 7.752(s, 1H), 7.653 (d, J=8 Hz, 1H), 7.566 (t, J=7.8 Hz, 1H), 7.488 (d, J=7.70 Hz, 1H), 4.768 (dd, J=10.8, 1.8 Hz, 1H), 4.009 (b, 1H), 3.982 (dd, J=11.1, 3.2 Hz, 2H), 3.488(t, J=10.8 Hz, 1 H), 3.013 (b, 1H), 2.971 (dd, J=11.7, 2.2 Hz, 1H), 2.748 (d, J=10.1 Hz, 1H), 2.529 (b, 1H), 2.297-2.231 (m, 3H), 1.481 (s, 9H).

Intermediate 29

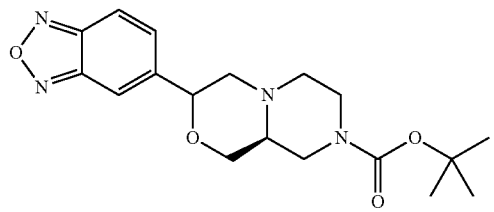

tert-butyl (9aS)-3-(2,1,3-benzoxadiazol-5-yl)hexahydropyrazino[2,1-c][1,4]oxazine-8(1H)-carboxylate Step A: 5-ethenyl-2,1,3-benzoxadiazole: 5-bromo-2,1,3-benzoxadiazole (4.0 g, 20 mmol), potassium vinyltrifluoroborate (5.40 g, 40.2 mmol) and Pd(dppf)Cl₂ (1.6 g, 2 mmol) in TEA (5.2 mL) and EtOH (15 mL) were added to a flask containing a stir bar, and the flask was then heated at 80° C. for 12 h. The organic residue was dissolved in EtOAc (500 mL) and the solution was washed with brine, dried over sodium sulfate, filtered and concentrated. The resulting organic residue was subjected to purification over silica gel to give the title compound.

Step B: 5-(oxiran-2-yl)-2,1,3-benzoxadiazole: To a solution of 5-ethenyl-2,1,3-benzoxadiazole (1.80 g, 12.3 mmol) in DCM (20 mL) was slowly added mCPBA (3.8 g, 22 mmol) at 0° C. The flask was warmed to room temperature; the mixture was then stirred for 12 hours. TLC as well as LC indicated that reaction had gone to completion. The mixture was washed with aqueous Na₂S₂O₃, NaHCO₃, and water. The organic layers was washed with brine and then concentrated. The residue was purified over silica gel to afford the title compound.

Step C: tert-butyl (3S)-4-[2-(2,1,3-benzoxadiazol-5-yl)-2-hydroxyethyl]-3-(hydroxymethyl)piperazine-1-carboxylate: To a microwave tube containing a stir bar was added 5-(oxiran-2-yl)-2,1,3-benzoxadiazole (1.2 g, 7.4 mmol), Boc-piperizine alcohol (2.8 g, 13.3 mmol); the resulting mixture was dissolved in anhydrous toluene (15 mL), purged with N₂ and the tube was heated in a microwave reactor for 1 h at 150° C. TLC analysis of the rectrion mix. showed the completion of the reaction. The solution was concentrated to dryness and absorbed into silica gel and was subjected for purification over a silica column to give the title compound.

Step D: tert-butyl (9aS)-3-(2,1,3-benzoxadiazol-5-yl) hexahydropyrazino[2,1-c][1,4]oxazine-8(1H)-carboxylate: To a 20 mL size microwave tube containing a stir bar was added tert-butyl (3S)-4-[2-(2,1,3-benzoxadiazol-5-yl)-2-hydroxyethyl]-3-(hydroxymethyl)piperazine-1-carboxylate (0.80 g, 2.1 mmol), cyanomethylene tri-n-Butylphosphorane (0.92 g, 3.8 mmol) and anhydrous toluene (15 mL). The tube was degassed and purged with N₂ followed by heating at 100° C. for 12 h. The solution was concentrated to dryness and the organic residue was then purified over silica gel with the solvent systems of 30% Acetone in DCM to furnish the title compound: ¹H-NMR (CDCl3, 500 MHz), δ 7.854-7.832 (m, 2H), 7.428 (d, J=9 Hz, 1H), 4.754 (d, J=10.5 Hz, 1H), 4.041-4.015 (m, 3H), 3.774-3.733 (m, 2H), 3.517 (t, J=11 Hz, 1H), 3.011 (d, J=11.5 Hz, 1H), 2.782 (d, J=9.5 Hz, 1H), 2.335-2.240 (m, 3H), 1.510 (s, 9H).

Intermediates 30A and 30B

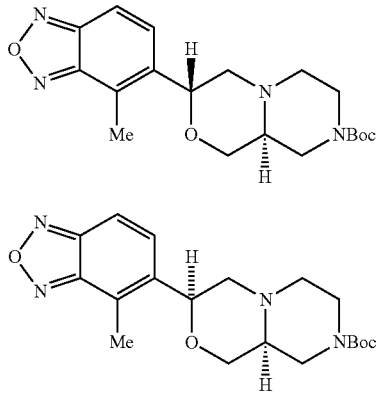

tert-butyl(3R,9aS)-3-(4-methyl-2,1,3-benzoxadiazol-5-yl)hexahydropyrazino[2,1-c][1,4]oxazine-8(1H)-carboxylate and tert-butyl(3S,9aS)-3-(4-methyl-2,1,3-benzoxadiazol-5-yl)hexahydropyrazino[2,1-c][1,4]oxazine-8(1H)-carboxylate Step A: 1-methoxy-2-methyl-3,4-dinitrobenzene: To cooled (0° C.) fuming nitric acid (100 mL) was added slowly 2-methyl-3-nitroanisole (13.0 g, 77.8 mmol) in ten times. After the addition, the mixture was warmed to r.t. and stirred for 4 h, then poured into ice-water (500 g). The resulting mixture was extracted with EtOAc (3×500 mL). The combined organic layers were washed with water, saturated NaHCO₃, brine, dried over Na₂SO₄, and concentrated to dryness. The residue was purified by silica column chromatography (petroleum ether/EtOAc=20:1) to obtain the pure product 1-methoxy-2-methyl-3,4-dinitrobenzene.

Step B: 2-azido-4-methoxy-3-methyl-1-nitrobenzene: To a solution of 1-methoxy-2-methyl-3,4-dinitrobenzene (3.4 g, 16 mmol) in 60 mL of DMSO was added NaN₃ (2.1 g, 32 mmol) at one portion and the reaction was stirred for 72 hours at room temperature. Then the reaction was poured into 500 mL of ice water, and then was extracted with DCM (100 mL×3). The combined organic layers were washed with water, dried and concentrated to about 100 mL of solvent. Then 100 mL of toluene was added and the residual DCM was removed under reduced pressure, the toluene solution of 2-azido-4-methoxy-3-methyl-1-nitrobenzene was used directly the next step.

Step C: 6-methoxy-7-methyl-2,1,3-benzoxadiazole 1-oxide: The toluene solution of 2-azido-4-methoxy-3-methyl-1-nitrobenzene was refluxed for 96 hours under Ar, then the solvent was removed under reduced pressure and the residue was purified by silica gel column to give 6-methoxy-7-methyl-2,1,3-benzoxadiazole 1-oxide.

Step D: 5-methoxy-4-methyl-2,1,3-benzoxadiazole: To a solution of 6-methoxy-7-methyl-2,1,3-benzoxadiazole 1-oxide (6.80 g, 37.7 mmol) in 150 mL of toluene was added PPh$_3$ at one portion and the mixture was refluxed for 3 hours under Ar. Then the solvent was removed under reduced pressure and the residue was purified by silica gel column to give the title compound.

Step E: 4-methyl-2,1,3-benzoxadiazol-5-ol: To a solution of 5-methoxy-4-methyl-2,1,3-benzoxadiazole (3.00 g, 18.2 mmol) in 120 mL of DCE was added 17.6 mL of BBr$_3$ at one portion and the mixture was stirred at reflux for 12 hours under Ar, then the solvent was removed under reduced pressure and the residue was purified by silica gel column to give 4-methyl-2,1,3-benzoxadiazol-5-ol.

Step F: 4-methyl-2,1,3-benzoxadiazol-5-yl trifluoromethanesulfonate: To a solution of 4-methyl-2,1,3-benzoxadiazol-5-ol (2.10 g, 17.9 mmol) in 40 mL of dry DCM was added Tf$_2$O (7.61 g, 26.9 mmol) dropwise at −78° C. under Ar and stirred for 5 minutes, then Et$_3$N (2.73 g, 26.9 mmol) was added dropwise to the mixture and the reaction was stirred at 0° C. for 4 hours. Then the reaction was poured into 200 mL of ice water and extracted with DCM (50 mL×3). The combined organic layers were washed with brine, dried and concentrated, the residue was purified by silica gel column to give the title compound.

Step G: 5-ethenyl-4-methyl-2,1,3-benzoxadiazole: The mixture of 4-methyl-2,1,3-benzoxadiazol-5-yl trifluoromethanesulfonate (3.90 g, 13.8 mmol), potassium vinyltrifluoroborate (2.22 g, 16.6 mmol) and Pd (dppf)$_2$Cl$_2$ (0.5 g) in 50 mL of EtOH and 15 mL of TEA was refluxed under Ar for 4 hours. After concentration, the residue was purified by silica column chromatography (PE:EtOAc=20:1) to afford 5-ethenyl-4-methyl-2,1,3-benzoxadiazole.

Step H: 4-methyl-5-(oxiran-2-yl)-2,1,3-benzoxadiazole: A mixture of 5-ethenyl-4-methyl-2,1,3-benzoxadiazole (1.4 g, 8.4 mmol) and mCPBA (85%, 2.57 g, 12.6 mmol) in 200 mL of DCM was stirred at room temperature for 96 hours. The reaction mixture was cooled to 0° C. and was washed subsequently with saturated NaHCO$_3$ (50 mL), saturated Na$_2$SO$_3$ (50 mL), 5% NaOH (50 mL×2) and brine (50 mL), dried over anhydrous Na$_2$SO$_4$ and concentrated. The residue was purified by silica column chromatography (PE:EtOAc=5:1) to afford the title compound.

Step I-J: tert-butyl(3R,9aS)-3-(4-methyl-2,1,3-benzoxadiazol-5-yl)hexahydropyrazino[2,1-c][1,4]oxazine-8(1H)-carboxylate and tert-butyl(3S,9aS)-3-(4-methyl-2,1,3-benzoxadiazol-5-yl)hexahydropyrazino[2,1-c][1,4]oxazine-8(1H)-carboxylate: The title compound was prepared from 4-methyl-5-(oxiran-2-yl)-2,1,3-benzoxadiazole in a similar fashion to that described for: Intermediates 17A and 17B (Method 1). The isomers were separated by Chiralcel OD-H, 4.6×250, 20% MeOH/CO$_2$, 2.4 mL/min, 100 bar, 40 C. The trans-isomer 30A eluted first, while the cis-isomer 30B eluted second: trans-$^1$H-NMR (500 MHz, CDCl$_3$): δ ppm 7.69-7.42 (m, 2H), 5.03 (d, J=5.2 Hz, 1H), 4.11-3.99 (m, 3H), 3.56-3.53 (m, 2H), 3.11-3.03 (m, 2H), 2.84-2.74 (m, 4H), 1.62 (s, 3H), 1.56-1.52 (m, 9H); cis-$^1$H-NMR (500 MHz, CDCl$_3$): δ ppm 8.01 (d, J=2.8 Hz, 1H) 7.72 (d, J=3.4 Hz, 1H), 5.02 (s, 1H), 4.01-3.52 (m, 4H), 3.20-2.72 (m, 7H), 1.61 (s, 3H), 1.55 (s, 9H).

Intermediate 31A

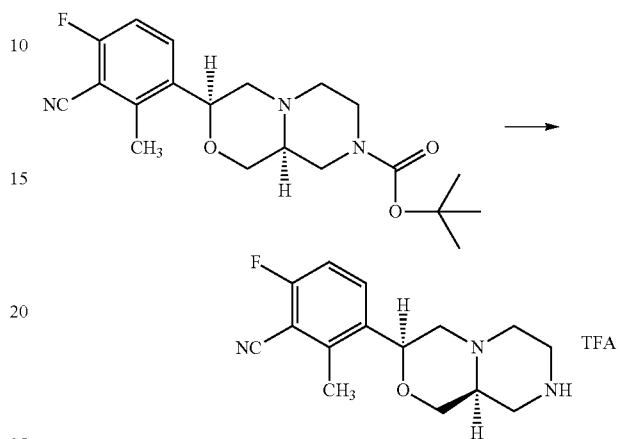

6-fluoro-2-methyl-3-[(3S,9aS)-octahydropyrazino[2,1-c][1,4]oxazin-3-yl]benzonitrile 2,2,2-trifluoroacetate: tert-Butyl (3S,9aS)-3-(3-cyano-4-fluoro-2-methylphenyl)hexahydropyrazino[2,1-c][1,4]oxazine-8(1H)-carboxylate (1.88 g, 5.01 mmol) was treated with 10 mL TFA at RT for 1 h. The TFA was then removed under reduced pressure to yield the title compound. LC-MS: M+1=276: $^1$H-NMR (600 MHz, DMSO) δ ppm 7.954 (dd, J=8.7, 6.25 Hz, 1H), 7.412 (t, J=8.85 Hz, 1H), 4.939 (dd, J=8.4, 2.75 Hz, 1 H), 3.848 (d, J=11.8 Hz, 1H), 3.762 (b, 1 H), 3.189-3.536 (m, 8H), 3.072 (d, J=12 Hz, 1H), 2.485 (s, 3H).

Intermediate 31B

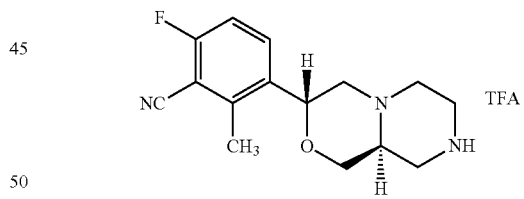

6-fluoro-2-methyl-3-[(3R,9aS)-octahydropyrazino[2,1-c][1,4]oxazin-3-yl]benzonitrile 2,2,2-trifluoroacetate: tert-Butyl (3R,9aS)-3-(3-cyano-4-fluoro-2-methylphenyl)hexahydropyrazino[2,1-c][1,4]oxazine-8(1H)-carboxylate (1.73 g, 4.61 mmol) was treated with 10 mL TFA at RT for 1 h. The trifluoroacetic acid was then removed under reduced pressure to yield the title compound. LC-MS: M+1=276: $^1$H-NMR (600 MHz, DMSO) δ ppm 7.724 (dd, J=9.0, 6.2 Hz,1H), 7.353 (t, J=8.85 Hz, 1H), 4.738 (d, J=10.3 Hz, 1 H), 3.924 (d, J=11.10 Hz, 1H), 3.386 (t, J=11.65 Hz, 1 H), 3.285(d, J=12.3 Hz, 1H), 3.20 (d, J=11.8 Hz, 1H), 3.01 (b, 1H), 2.934 (d, J=11.6 Hz, 1H), 2.884 (d, J=11.0 Hz, 1H), 2.642(b, 1 H), 2.476 (s, 3H), 2.47(b, 1H), 2.329-2.367 (m, 1H), 2.054-2.089(m,1H).

Intermediate 31C-1 (Method 1)

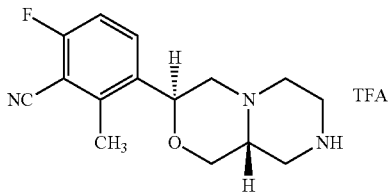 [SMILES: Cc1c([C@H]2CN3CCNC[C@@H]3CO2)ccc(F)c1C#N]

6-fluoro-2-methyl-3-[(3S,9aR)-octahydropyrazino[2,1-c][1,4]oxazin-3-yl]benzonitrile 2,2,2-trifluoroacetate: (3S,9aR)-tert-Butyl 3-(3-cyano-4-fluoro-2-methylphenyl)hexahydropyrazino[2,1-c][1,4]oxazine-8(1H)-carboxylate (3.00 g, 7.99 mmol) was dissolved in TFA (10 mL) and stirred for 1 hr. The trifluoroacetic acid was removed under reduced pressure and azeotroped with dichloroethane (3×) then was dried over high vacuum to yield the title compound: LC-MS (IE, m/z): 276 [M+1]$^+$; $^1$H-NMR (500 MHz, DMSO) δ ppm 7.755 (dd, J=8.75, 6.2 Hz, 1H), 7.38 (t, J=8.85 Hz, 1H), 4.80 (d, J=10.1 Hz, 1H), 3.98 (dd, J=11.25, 2.5 Hz, 1H), 3.456 (t, J=10.7 Hz, 1 H), 3.354 (d, J=12.6 Hz, 1H), 3.273 (d, J=11.8 Hz, 1H), 2.984-3.089 (m, 3H), 2.715 (t, J=11.37 Hz, 1H), 2.639 (t, J=10 Hz, 1H), 2.50 (s, 3H), 2.46 (b, 1H), 2.337 (t. J=10.9 Hz, 1H).

Intermediate 31C-2 (Method 2)

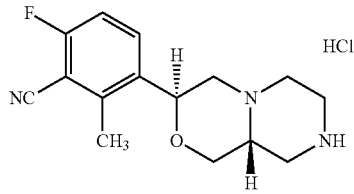 [SMILES: Cc1c([C@H]2CN3CCNC[C@@H]3CO2)ccc(F)c1C#N ; Cl]

6-fluoro-2-methyl-3-[(3S,9aR)-octahydropyrazino[2,1-c][1,4]oxazin-3-yl]benzonitrile Hydrochloride: (3S,9aR)-tert-Butyl 3-(3-cyano-4-fluoro-2-methylphenyl)hexahydropyrazino[2,1-c][1,4]oxazine-8(1H)-carboxylate (158.8 g, 423.0 mmol) was suspended with 318 mL of 2-propanol. The resulting slurry was treated with HCl solution in 2-propanol (5.5 M, 1000 mL, 5499 mmol), and the mixture was heated to 50° C. for 2 hours. The mixture was concentrated to remove approximately 400 mL of 2-propanol, then was cooled to rt and agitated overnight. The mixture was filtered to collect the solid product and the wet cake was washed with 50 mL of 2-propanol. The filter cake was dried under vacuum for two days at 40° C. with nitrogen bleed to afford the title compound.

Intermediate 31D

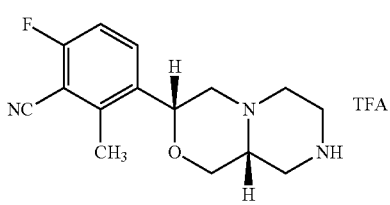 [SMILES: Cc1c([C@@H]2CN3CCNC[C@@H]3CO2)ccc(F)c1C#N]

6-fluoro-2-methyl-3-[(3R,9aR)-octahydropyrazino[2,1-c][1,4]oxazin-3-yl]benzonitrile 2,2,2-trifluoroacetate: (3R,9aR)-tert-Butyl 3-(3-cyano-4-fluoro-2-methylphenyl)hexahydropyrazino[2,1-c][1,4]oxazine-8(1H)-carboxylate (1.09 g, 2.90 mmol) was stirred in trifluoroacetic acid (10 mL) for 1 h then concentrated and azeotroped with dichloroethane (3×) to yield the title compound. LC-MS (IE, m/z): 276 [M+1]$^+$; $^1$H-NMR (500 MHz, DMSO) δ ppm 7.989 (t, J=6.4 Hz,1H), 7.416(t, J=8.85 Hz, 1H), 4.959 (dd, J=7.75, 2.35 Hz, 1 H), 3.855 (d, J=11.9 Hz, 1H), 3.755 (b, 1 H), 3.236-3.54 (m, 8H), 3.066 (d, J=11.5 Hz, 1H), 2.50 (s, 3H).

Intermediate 32A

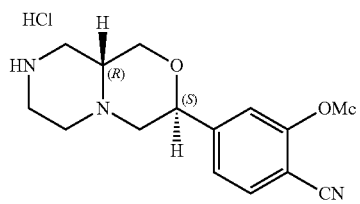

2-Methoxy-4-[(3S,9aR)-octahydropyrazino[2,1-c][1,4]oxazin-3-yl]benzonitrile hydrochloride: tert-Butyl (3S,9aR)-3-(4-cyano-3-methoxyphenyl)hexahydropyrazino[2,1-c][1,4]oxazine-8(1H)-carboxylate (520 mg, 1.39 mmol) was dissolved in 10 Ml of 4 M HCl in dioxane and stirred at room temperature for 8 h. The mixture was concentrated to ¼ the original volume and diluted with 10 Ml of diethyl ether. The precipitate was filtered and dried under high vacuum to offer the title amine HCl salt: $^1$H NMR (DMSO-d$_6$, E (trans) isomer, 500 MHz) δ 7.76 (d, J=8.0 Hz, 1H), 7.25 (s, 1H), 7.11 (d, J=7.9 Hz, 1H), 5.0 (bs, 1H), 4.17 (bs, 1H), 3.94 (s, 3H), 3.85-3.60 (bs, 2H), 3.62-3.34 (m, 6H), 1.69 (bs, 2H); LC/MS: (IE, m/z) [M+1]$^+$=274.

Intermediate 32B

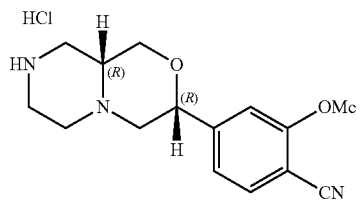

2-Methoxy-4-[(3R,9aR)-octahydropyrazino[2,1-c][1,4]oxazin-3-yl]benzonitrile hydrochloride tert-Butyl (3R,9aR)-3-(4-cyano-3-methoxyphenyl)hexahydropyrazino[2,1-c][1,4]oxazine-8(1H)-carboxylate (120 mg, 0.321 mmol) was dissolved in 10 Ml of 4 M HCl in dioxane and stirred at room temperature for 8 h. The mixture was concentrated to ¼ the original volume and diluted with 10 Ml of diethyl ether. The precipitate was filtered and dried under high vacuum to offer amine HCl salt: NMR (DMSO-d$_6$, Z (cis) isomer, 500 MHz) δ 7.77 (d, J=7.9 Hz, 1H), 7.32 (s, 1H), 7.19 (d, J=7.9 Hz, 1H), 4.95 (bs, 1H), 4.08 (bs, 2H), 3.96 (s, 3H), 3.85-3.60 (bs, 3H), 3.58-3.34 (m, 6H); LC/MS: (IE, m/z) [M+1]$^+$=274.

Intermediate 32C

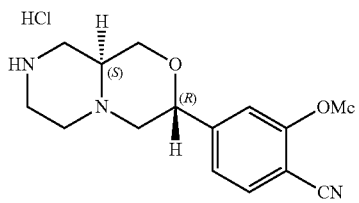

2-Methoxy-4-[(3R,9aS)-octahydropyrazino[2,1-c][1,4]oxazin-3-yl]benzonitrile hydrochloride tert-Butyl (3R,9aS)-3-(4-cyano-3-methoxyphenyl)hexahydropyrazino[2,1-c][1,4]oxazine-8(1H)-carboxylate (90.0 mg, 0.241 mmol) was dissolved in 5 mL of 4 M HCl in dioxane and stirred at room temperature for 8 h. The mixture was concentrated to ¼ the original volume and diluted with 10 mL of diethyl ether. The precipitate was filtered and dried under high vacuum to offer amine HCl salt: $^1$H NMR (DMSO-d$_6$, E (trans) isomer, 500 MHz) δ 7.68 (d, J=8.0 Hz, 1H), 7.19 (s, 1H), 7.07 (d, J=8.0 Hz, 1H), 4.65 (dd, J=1.8 Hz, J=1.6 Hz, 1H), 3.91 (s, 3H), 3.82 (dd, J=3.0 Hz, 1H), 3.32-3.27 (m, 2H), 2.87-2.62 (m, 5H), 2.24-1.98 (m, 3H); LC/MS: (IE, m/z) [M+1]$^+$=274.

Intermediate 32D

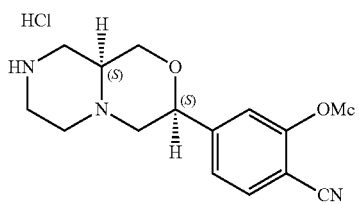

2-Methoxy-4-[(3S,9aS)-octahydropyrazino[2,1-c][1,4]oxazin-3-yl]benzonitrile hydrochloride tert-Butyl (3S,9aS)-3-(4-cyano-3-methoxyphenyl)hexahydropyrazino[2,1-c][1,4]oxazine-8(1H)-carboxylate (38.0 mg, 0.102 mmol) was dissolved in 10 mL of 4 M HCl in dioxane and stirred at room temperature for 8 h. The mixture was concentrated to ¼ the original volume and diluted with 5 mL of diethyl ether. The precipitate was filtered and dried under high vacuum to offer amine HCl salt: $^1$H NMR (DMSO-d$_6$, Z (cis) isomer, 500 MHz) δ 7.77 (d, J=7.9 Hz, 1H), 7.32 (s, 1H), 7.19 (d, J=7.9 Hz, 1H), 4.95 (bs, 1H), 4.08 (bs, 2H), 3.96 (s, 3H), 3.85-3.60 (bs, 3H), 3.58-3.34 (m, 6H); LC/MS: (IE, m/z) [M+1]$^+$=274.

The intermediates shown in Table 1 below were prepared in an analogous fashion to that described for the syntheses of Intermediates 31A: 6-fluoro-2-methyl-3-[(3S,9aS)-octahydropyrazino[2,1-c][1,4]oxazin-3-yl]benzonitrile 2,2,2-trifluoroacetate, and 32D: 2-methoxy-4-[(3S,9aS)-octahydropyrazino[2,1-c][1,4]oxazin-3-yl]benzonitrile hydrochloride, using either HCl or TFA to remove the Boc protective group present in the corresponding Boc-piperazine precursor. The acid used in the reaction and the mass spec data are provided in Table 1 for each example. It is understood that the resulting intermediates may be TFA or HCl salts, or they may be obtained as free base amines by routine partitioning of the product with an organic solvent and a basic aqueous solution such as saturated sodium bicarbonate solution and concentration of the resulting organic solution.

TABLE 1

| INTERMEDIATE #, conditions | Structure of INTERMEDIATE and MS characterization |
|---|---|
| 33A TFA | MS (M + H)$^+$ 275 |
| 33B TFA | MS (M + H)$^+$ 275 |
| 34A TFA | MS (M + H)$^+$ 289 |
| 34B TFA | MS (M + H)$^+$ 289 |
| 34C TFA | MS (M + H)$^+$ 289 |

TABLE 1-continued
| INTER-MEDIATE #, conditions | Structure of INTERMEDIATE and MS characterization |
|---|---|
| 34D TFA | 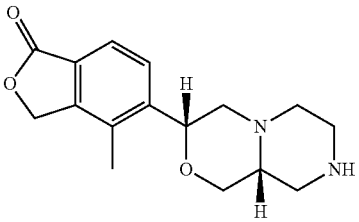<br>MS (M + H)⁺ 289 |
| 35A HCl | 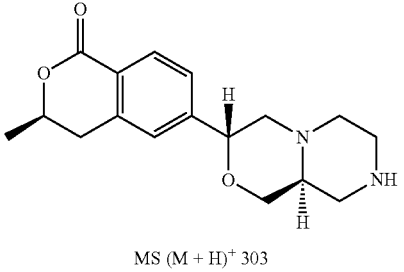 [SMILES: C[C@@H]1Cc2cc([C@@H]3CN4CCNC[C@H]4CO3)ccc2C(=O)O1]<br>MS (M + H)⁺ 303 |
| 36A TFA | 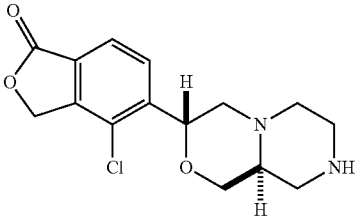<br>MS (M + H)⁺ 309 |
| 36B TFA | 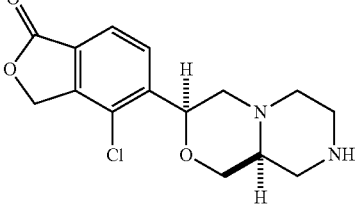<br>MS (M + H)⁺ 309 |
| 37A HCl | 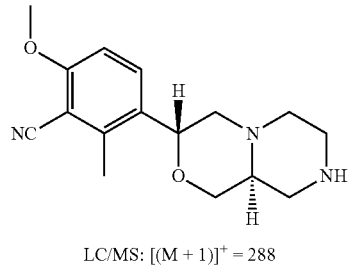 [SMILES: COc1ccc([C@@H]2CN3CCNC[C@H]3CO2)c(C)c1C#N]<br>LC/MS: [(M + 1)]⁺ = 288 |
| 37B HCl | 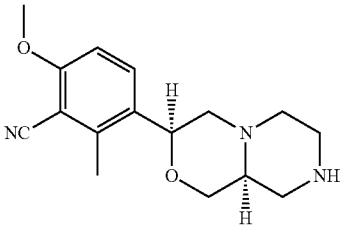<br>LC/MS: [(M + 1)]⁺ = 288 |
| 38A TFA | 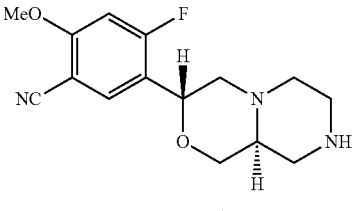<br>LC/MS: [(M + 1)]⁺ = 292 |
| 39A TFA | 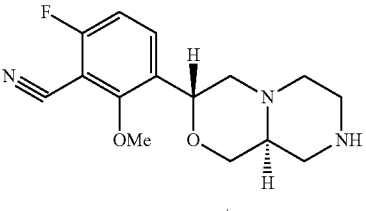<br>LC/MS: [(M + 1)]⁺ = 292 |
| 39B TFA | 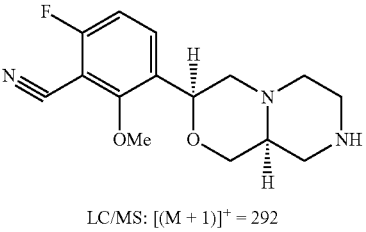 [SMILES: COc1c([C@H]2CN3CCNC[C@H]3CO2)ccc(F)c1C#N]<br>LC/MS: [(M + 1)]⁺ = 292 |
| 40A TFA | 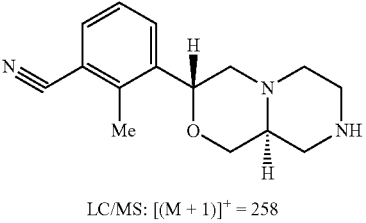 [SMILES: Cc1c(C#N)cccc1[C@@H]1CN2CCNC[C@H]2CO1]<br>LC/MS: [(M + 1)]⁺ = 258 |
| 40B TFA | 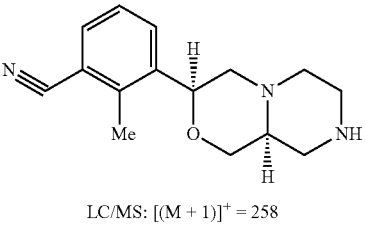 [SMILES: Cc1c(C#N)cccc1[C@H]1CN2CCNC[C@H]2CO1]<br>LC/MS: [(M + 1)]⁺ = 258 |

TABLE 1-continued
| INTERMEDIATE #, conditions | Structure of INTERMEDIATE and MS characterization |
|---|---|
| 41A TFA | 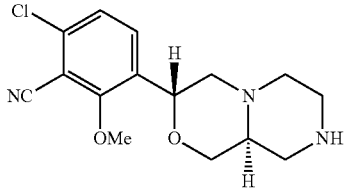 LC/MS: [(M + 1)]⁺ = 292 |
| 41B TFA | 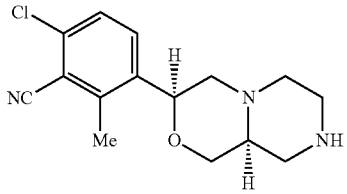 LC/MS: [(M + 1)]⁺ = 292 |
| 42A TFA | 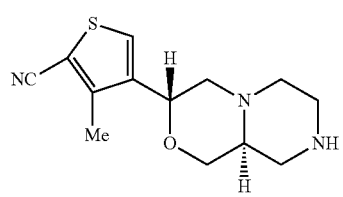 LC/MS: [(M + 1)]⁺ = 264 |
| 42B TFA | 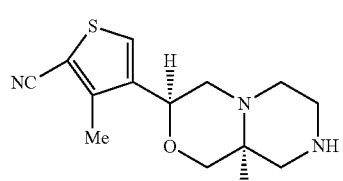 LC/MS: [(M + 1)]⁺ = 264 |
| 43A TFA | 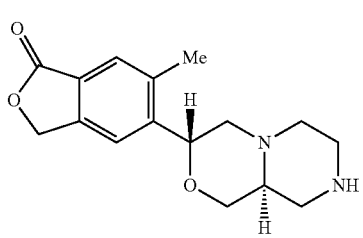 LC/MS: [(M + 1)]⁺ = 289 |
| 43B | 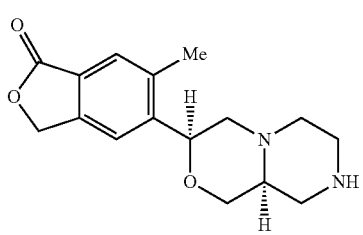 LC/MS: [(M + 1)]⁺ = 289 |
| 44 TFA | 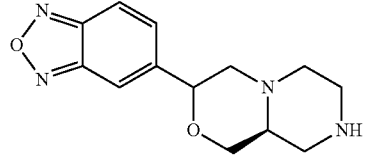 LC/MS: [(M + 1)]⁺ = 261 |
| 45A TFA | 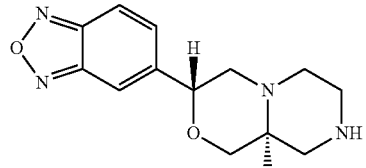 LC/MS: [(M + 1)]⁺ = 275 |
| 45B TFA | 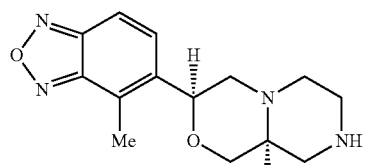 LC/MS: [(M + 1)]⁺ = 275 |
| 46 TFA | 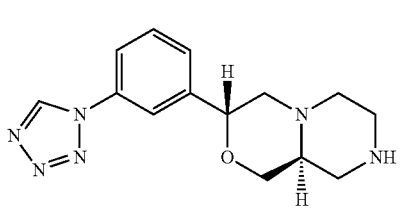 LC-MS: 287 [M + 1]⁺ |
| 47B TFA | 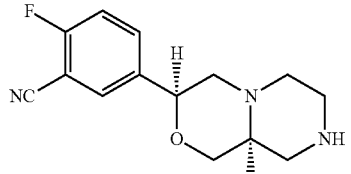 LC/MS: (M + H)⁺ 262 |
| 47A TFA | 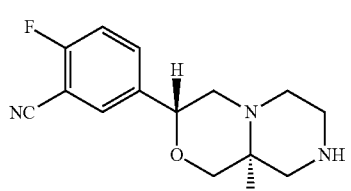 LC/MS: (M + 1)⁺ 262 |

TABLE 1-continued

| INTERMEDIATE #, conditions | Structure of INTERMEDIATE and MS characterization |
|---|---|
| 48A TFA | 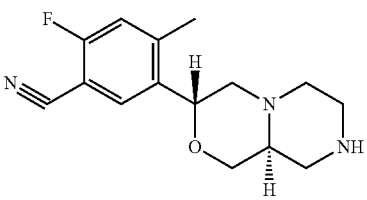<br>LC/MS: $[(M + 1)]^+ = 276$ |
| 49A TFA | 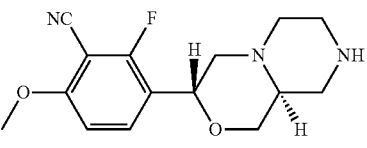<br>LC/MS: $[(M + 1)]^+ = 292$ |

Intermediate 50

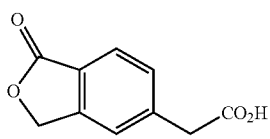 [SMILES: O=C(O)Cc1ccc2c(c1)COC2=O]

(1-oxo-1,3-dihydro-2-benzofuran-5-yl)acetic acid

Step A: tert-butyl (1-oxo-1,3-dihydro-2-benzofuran-5-yl) acetate: To a 20 mL microwave tube charged with 5-bromo-2-benzofuran-1(3H)-one (500 mg, 2.35 mmol) and palladium tetrakis triphenylphosphine (136 mg, 0.117 mmol) in THF (5 mL) was added (2-tert-butoxy-2-oxoethyl) (chloro) zinc (6.57 mL, 0.5 M, 3.29 mmol). The mixture was purged with nitrogen 3 times, and heated to 105° C. for 30 minutes in a microwave reactor. The reaction mixture was poured into water and filtered then extracted with ethyl acetate twice. The organic layer was washed with brine, dried, and evaporated to dryness. The residue was purified by MPLC on a 40 g ISCO Redi-Sep column to yield title compound. $^1$H-NMR (500 MHz, CDCl$_3$) δ ppm 7.89 (d, J=7.7 Hz, 1H), 7.46 (d, J=8.3 Hz, 1H), 7.44 (s, 1H), 5.33 (s, 2H), 3.69 (s, 2H), 1.47 (s, 9H).

Step B: (1-oxo-1,3-dihydro-2-benzofuran-5-yl)acetic acid: tert-Butyl (1-oxo-1,3-dihydro-2-benzofuran-5-yl)acetate (1.2 g, 4.8 mmol) was dissolved in TFA and stirred at room temperature for one h. The reaction mixture was concentrated and pumped under vacuum overnight to afford the title compound. LC-MS (IE, m/z): 193.2 [M+1]$^+$.

Intermediate 51

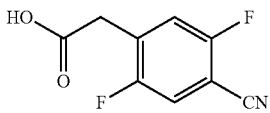 [SMILES: N#Cc1cc(F)c(CC(=O)O)cc1F]

(4-cyano-2,5-difluorophenyl)acetic acid

Step A: di-tert-butyl (4-cyano-2,5-difluorophenyl)propanedioate: A suspension of NaH (60% in mineral oil, 2.6 g, 64 mmol) in dry DMF (120 mL) was stirred and cooled to 0° C., and di-tert-butyl malonate (9.0 g, 41 mmol) was added over 30 min. The mixture was allowed to warm to room temperature before addition of 2,4,5-trifluorobenzonitrile (5.0 g, 32 mmol). After being heated at 80° C. for 8 h with stirring, the reaction mixture was cooled to room temperature and poured into a mixture of ice-water (100 mL) and AcOEt (200 mL). Layers were separated, and the organic layer was washed successively with water, and brine, then dried over MgSO$_4$ and concentrated. The residue was purified by flash chromatography (silica gel, EtOAc/hexanes, 2:8) to give the title compound. LCMS: [(M+1)-t-Bu]$^+$=239.3.

Step B: (4-cyano-2,5-difluorophenyl)acetic acid: TFA (30 mL) was added to a solution of di-tert-butyl (4-cyano-2,5-difluorophenyl) propanedioate (10.0 g, 28.3 mmol) in dichloromethane (30 mL) at room temperature. The reaction mixture was stirred over night, then concentrated under reduced pressure, and the residue was treated with Et$_2$O (100 mL) to induce crystallization. The solids were collected by filtration to give title compound. $^1$H NMR (500 MHz, DMSO-d$_6$) δ 12.7 (bs, 1H), 7.96 (dd, J=5.3 Hz, J=5.3 Hz, 1H), 7.61 (dd, J=5.9 Hz, J=5.7 Hz, 1H), 3.76 (s, 2H); LC/MS: [(M+1)+H$_2$O]$^+$=216.2.

Intermediate 52

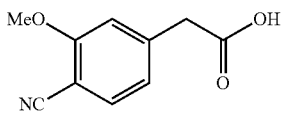

(4-cyano-3-methoxyphenyl)acetic acid

Step A: Ethyl (3-methoxy-4-{[(trifluoromethyl)sulfonyl]oxy}phenyl)acetate: Ethyl (4-hydroxy-3-methoxyphenyl) acetate, 12.0 g, 57 mmol was dissolved in anhydrous dichloromethane (200 mL). 4-Dimethylaminopyridine (0.70 g, 0.10 equiv) was added, followed by triethylamine (9.6 mL, 69 mmol). The solution was then cooled to in a dry ice and acetone bath while under nitrogen. Trifluoromethanesulfonic anhydride (9.6 mL, 57 mmol) was slowly added and the reaction mixture was allowed to warm to ambient temperature. The reaction mixture was then diluted with dichloromethane (200 mL) and washed with water (2×100 mL). The organic layer was dried over magnesium sulfate, filtered, and concentrated to dryness under reduced pressure to yield the triflate. LC/MS [(M+1)-CO$_2$Et]$^+$=269.0.

Step B: Ethyl (4-cyano-3-methoxyphenyl)acetate: The crude triflate (16.6 g) was dissolved in anhydrous dimethylformamide (100 mL). Zinc cyanide (3.4 g, 29 mmol) was added, and the solution was purged thoroughly with nitrogen. Tetrakis(triphenylphosphine)palladium(0) (5.6 g, 4.9 mmol) was then added and the reaction mixture was heated to 80° C. for 4 h. After allowing to cool to ambient temperature and diluting with water (200 mL), ethyl acetate (400 mL) was added. The combined layers were filtered to remove any solids, the filtrate transferred to a separatory funnel, and the layers separated. The aqueous layer was re-extracted with ethyl acetate (2×100 mL), the organic portions were combined and dried over magnesium sulfate. The dry organics were then filtered and evaporated to dryness under reduced pressure and excess dimethylformamide was removed by evaporation in vacuo at 65° C. for 1.5 h to yield the crude title compound. The crude product was purified through silica gel chromatography (ethyl acetate/hexanes, 2:3) to yield the title nitrile. LC/MS (M+1)$^+$=220.17;

Step C: (4-Cyano-3-methoxyphenyl)acetic acid: Aqueous LiOH (0.096 g, 2.9 mmol, in 2 mL of water) was added to a stirred solution of ethyl (4-cyano-3-methoxyphenyl)acetate (0.50 g, 2.9 mmol) in THF:CH$_3$OH) 5:1 (23 mL), and the solution was stirred at room temperature overnight. After acidification to Ph 3 with 1 N HCl, the aqueous was extracted with AcOEt (2×50 mL). The organic phase was washed with brine, dried (MgSO$_4$), and evaporated under reduced pressure to give the (4-cyano-3-methoxyphenyl) acetic acid, which was used without further purification. NMR (500 MHz, DMSO-d$_6$), δ 12.52 (s, 1H), 7.65 (d, J=8.0 Hz, 1H), 7.17 (s, 1H), 7.0 (d, J=7.8.0 Hz, 1H), 3.89 (s, 3H), 3.69 (s, 2H); LC/MS (M+1)$^+$=192.16.

Intermediate 53

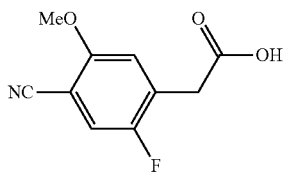 [SMILES: COc1cc(CC(=O)O)c(F)cc1C#N]

(4-cyano-2-fluoro-5-methoxyphenyl)acetic acid

Step A: di-tert-Butyl (4-cyano-2-fluoro-5-methoxyphenyl)propanedioate: A suspension of NaH (60% in mineral oil, 0.33 g, 8.3 mmol) in dry DMF (20 mL) was stirred and cooled to 0° C., and di-tert-butyl malonate (1.5 g, 7.1 mmol) was added. The mixture was allowed to warm to room temperature before addition of 4,5-difluoro-2-methoxybenzonitrile (1.0 g, 5.9 mmol). The mixture was heated at 80° C. for 4 h with stirring, then the reaction mixture was cooled to room temperature and poured into a mixture of ice-water (100 mL) and AcOEt (100 mL). The layers were separated, and the organic layer was washed successively with water, and brine, then dried over Na$_2$SO$_4$ and concentrated. The residue was purified by flash chromatography (silica gel, EtOAc/hexanes, 0->10%) to give the title compound: LCMS: [(M+1)-t-Bu, CO2-t-Bu]$^+$=210.1;

Step B: (4-cyano-2-fluoro-5-methoxyphenyl) acetic acid: TFA (5 mL) was added to a solution of di-tert-butyl (4-cyano-5-fluoro-2-methoxyphenyl) propanedioate (1.3 g, 28.3 mmol) in of dichloromethane (5 mL) at room temperature. The reaction mixture was stirred over night, then concentrated under reduced pressure, and the residue was treated with Et$_2$O (10 mL) to induce crystallization. The solids were collected by filtration to give the title compound. $^1$H NMR (500 MHz, CD$_3$OD) δ 7.44 (d, J=5.3 Hz, 1H), 7.19 (d, J=5.4 Hz, 1H), 3.96 (s, 3H), 3.78 (s, 2H); LC/MS: [(M+1)]$^+$=210.1.

Intermediate 54

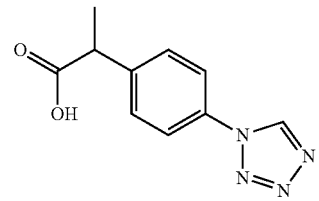 [SMILES: CC(C(=O)O)c1ccc(-n2cnnn2)cc1]

2-[4-(1H-tetrazol-1yl)phenyl]propanoic acid

Step A: 2-(4-aminophenyl)propionic acid: 2-(4-nitrophenyl) propionic acid (5 g, 25.6 mmol) was dissolved in ethyl acetate (50 mL) and palladium on carbon (1 g, 9.4 mmol) was added then stirred under hydrogen balloon overnight. The product precipitated out. Added methanol to dissolved product then filtered off the palladium catalyst. The filtrate was concentrated and the residue was triturated with EtOAc to yield title compound. LC-MS (IE, m/z): 166 [M+1]$^+$;

Step B: 2-[4-(1H-tetrazol-1yl)phenyl]propanoic acid Triethyl orthoformate (5.29 mL, 31.8 mmol) and 2-(4-aminophenyl) propionic acid (3.26 g, 19.7 mmol) were suspended in acetic acid (50 mL) then added sodium azide (1.924 g, 29.6 mmol). The mixture was refluxed for 3 hours then let stirred at room temperature overnight. The reaction was poured into water (60 ml) and extracted with ethyl acetate (60 ml). The organic layer was separated and dried over MgSO4. The mixture was filtered and concentrated to yield title compound. LC-MS (IE, m/z): 219 [M+1]$^+$.

Intermediate 55

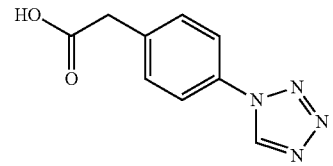 [SMILES: O=C(O)Cc1ccc(-n2cnnn2)cc1]

[4-(1H-tetrazol-1-yl)phenyl]acetic acid

The title compound could be prepared in an analogous fashion to that described for 2-[4-(1H-tetrazol-1yl)phenyl]propanoic acid I-54 (Step B) from commercially available 4-aminophenylacetic acid. LC-MS (IE, m/z): 205 [M+1]$^+$ Alternatively, the title compound is commercially available from a number of different vendors including Matrix Scientific (catalog number 011841) and Oakwood Products, Inc (catalog number 028142). Lastly, a synthesis of the title compound has been previously reported (Aridoss, G.; Laali, K. K. *Eur. J. Org. Chem.*, 2011, 15, 2827-2835).

Intermediate 56

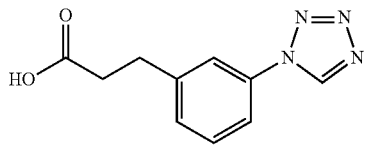 [SMILES: O=C(O)CCc1cccc(-n2cnnn2)c1]

3-[3-(1H-tetrazol-1-yl)phenyl]propanoic acid

To a solution of 3-(3-aminophenyl)propanoic acid (500 mg, 3.03 mmol) in glacial acetic acid (5 mL) was added triethyl orthoformate (1.51 mL, 9.08 mmol) and sodium azide (590 mg, 9.08 mmol). The reaction mixture was heated at 80° C. for 3 hours in a sealed vial and then cooled to ambient temperature. Once cooled, water (5 mL) was added and the aqueous layer was extracted with ethyl acetate (3×20 mL). The combined organic layers were then dried over sodium sulfate, filtered and concentrated in vacuo to afford crude title compound which was used without further purification. LC-MS: (M+H)$^+$ 219.

Intermediate 57

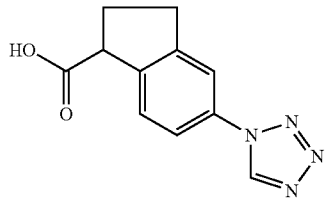 [SMILES: O=C(O)C1CCc2cc(-n3cnnn3)ccc21]

5-(1H-tetrazol-1-yl)indane-1-carboxylic acid

Step A: N-(2,3-dihydro-1H-inden-5-yl)acetamide: A solution of indan-5-amine (43 g, 0.31 mol) and TEA (51.3 mL, 0.370 mol) in 400 mL of anhydrous DCM was added a solution of AcCl (23.6 mL, 0.340 mol) in 100 mL of anhydrous DCM dropwise at 0° C. then and stirred for 0.5 h at r.t. After the reaction was completed, the reaction mixture was added 500 mL of DCM, washed with water, 10% HCl solution, 10% NaHCO$_3$ and brine. The organic phase was dried over anhydrous Na$_2$SO$_4$ and concentrated to give N-(2,3-dihydro-1H-inden-5-yl)acetamide.

Step B: N-(1-oxo-2,3-dihydro-1H-inden-5-yl)acetamide: A solution of N-(2,3-dihydro-1H-inden-5-yl)acetamide (50 g, 0.29 mol) in 150 mL of acetic acid and 40 mL of acetic anhydride was added a solution of chromium trioxide in a mixed solution (30 mL of water and 140 mL of acetic acid) dropwise at 10° C. by external cooling. After stirring overnight, the solution was poured into 2 L of ice water under vigorously stirring. The resulting solid was filtered, washed with cooled EtOH to give N-(1-oxo-2,3-dihydro-1H-inden-5-yl)acetamide.

Step C: N-(1-cyano-2,3-dihydro-1H-inden-5-yl)acetamide: To a stirring ice-cooled mixture of N-(1-oxo-2,3-dihydro-1H-inden-5-yl)acetamide (10.00 g, 52.9 mmol), TosMIC (15.50 g, 80.0 mmol) in 100 mL of anhydrous DME was added a solution of NaOMe (1.84 g of Na in 20 mL of anhydrous of MeOH) dropwise. After the addition was completed, the mixture was stirred overnight at ambient temperature. The reaction mixture was quenched with 4 N HCl at 0° C. and extracted with DCM. The extract was washed with brine, dried over anhydrous Na$_2$SO$_4$ and concentrated. The residue was purified with silica gel column chromatograph to give N-(1-cyano-2,3-dihydro-1H-inden-5-yl)acetamide.

Step D: 5-aminoindane-1-carboxylic acid: A mixture of N-(1-cyano-2,3-dihydro-1H-inden-5-yl)acetamide (19.7 g, 0.105 mol) in 175 mL of concentrated hydrogen chloride was refluxed for two days. The reaction mixture was concentrated under reduce pressure, and the residue was basified with saturated NaOH to Ph 4~5. The mixture was extracted with EtOAc and the extract was dried over anhydrous Na$_2$SO$_4$ and concentrated. The residue was purified with silica gel column chromatograph to afford 5-aminoindane-1-carboxylic acid.

Step E: 5-(1H-tetrazol-1-yl)indane-1-carboxylic acid: A solution of 5-aminoindane-1-carboxylic acid (2.95 g, 16.7 mmol), sodium azide (1.20 g, 18.3 mmol) and triethyl orthoformate (7.42 g, 50.1 mmol) in 20 mL of acetic acid was heated to 100° C. for 3 hrs. After the reaction was completed, the mixture was cooled to ambient temperature. The solution was removed under vacuum and the residue was diluted with EtOAc, washed with brine, dried over anhydrous Na$_2$SO$_4$ and concentrated. The residue was purified with silica gel column chromatograph to give the crude product, then re-crystallization from DCM to yield 5-(1H-tetrazol-1-yl)indane-1-carboxylic acid. $^1$H-NMR (400 MHz, DMSO) δ ppm 10.0 (s, 1H), 7.75 (s, 1H), 7.66-7.69 (m, 1H), 7.55 (d, J=8.1 Hz, 1H), 4.02~4.06 (m, 1H), 2.88~3.08 (m, 2H), 2.31 (q, J=8.1 Hz, 2H).

Intermediate 58

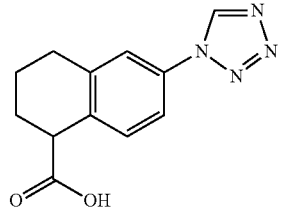 [SMILES: O=C(O)C1CCCc2cc(-n3cnnn3)ccc21]

6-(1H-tetrazol-1-yl)-1,2,3,4-tetrahydronaphthalene-1-carboxylic acid

Step A: N-(5-cyano-7,8-dihydronaphthalen-2-yl)acetamide: N-(5-oxo-5,6,7,8-tetrahydronaphthalen-2-yl)acetamide (5.00 g, 24.6 mmol) was dissolved in benzene then zinc iodide (0.079 g, 0.246 mmol) and trimethylsilylcyanide (6.56 mL, 49.2 mmol) were added and the mixture was refluxed for 1 h. Next, the benzene was evaporated off and isopropanol —HCl saturated solution (20 ml) was added to the residue and the mixture was refluxed for 1 hr. The suspension was stirred overnight. The reaction was poured into water and extracted with ethyl acetate (2×). The organic layer was washed with 1N NaOH (1×), 1N HCl (1×), brine (1×) then dried and evaporated to dryness. The residue was purified by chromatography through a 330 g ISCO Redi-Sep with 5% MeOH/DCM solvent system to yield N-(5-cyano-7,8-dihydronaphthalen-2-yl) acetamide. LC-MS: M+1=213.

Step B: N-(5-cyano-5,6,7,8-tetrahydronaphthalen-2yl)acetamide: N-(5-cyano-7,8-dihydronaphthalen-2-yl) acetamide (3.4 g, 16 mmol) was stirred in a 1:1 mixture of 1,2-dimethoxyethane and ethanol (40 mL) and cooled to 0° C. NaBH$_4$ (2.121 g, 56.1 mmol) was added and the reaction was refluxed for 20 hrs. The reaction was quenched with acetone then concentrated to dryness. The residue was taken up with saturated NH$_4$Cl and DCM. The phases separated and the aqueous layer was re-extracted with DCM (2×). The organic layer was dried with MgSO$_4$, filtered and concentrated. The residue was purified by chromatography thru a 220 g ISCO Redi-sep column using 5% MeOH/DCM solvent system to yield N-(5-cyano-5,6,7,8-tetrahydronaphthalen-2yl) acetamide. LC-MS: M+1=215;

Step C: 6-amino-1,2,3,4-tetrahydronaphthalene-1-carboxylic acid: N-(5-cyano-5,6,7,8-tetrahydronaphthalen-2yl) acetamide (2.31 g, 10.78 mmol) was refluxed in hydrochloric acid (15 mL) for 5 hrs then cooled room temperature. The precipitates were filtered and washed with 5% EtOH/Et$_2$O then with ether to yield the title compound. LC-MS: M+1=192;

Step D: Methyl 6-amino-1,2,3,4-tetrahydronaphthalene-1-carboxylate: Thionyl chloride (1.359 mL, 18.62 mmol) was added to 6-amino-1,2,3,4-tetrahydronaphthalene-1-carboxylic acid (2.12 g, 9.31 mmol) in methanol (15 mL) then refluxed for 5 hrs. The reaction was cooled and concentrated then took up with ethyl acetate and washed with NaHCO$_3$ (1×), brine 1×, dried over Na$_2$SO$_4$, filtered and evaporated to dryness. The residue was chromatographed thru 120 g ISCO Redi-sep and eluted out with 5% MeOH/DCM to yield title compound. LC-MS: M+1=206

Step E: Methyl 6-(1H-tetrazol-1-yl)-1,2,3,4-tetrahydronaphthalene-1-carboxylate: Methyl 6-amino-1,2,3,4-tetrahydronaphthalene-1-carboxylate (1.49 g, 7.26 mmol) was stirred in acetic acid (20 mL) and added triethyl orthoformate (2.42 mL, 14.52 mmol) followed by sodium azide (0.849 g, 13.1 mmol) then heated to reflux for 3 h. LC-MS showed starting material and product. Temperature was decreased to 80° C. and continued heating overnight. The reaction was concentrated then took up residue with ethyl acetate and washed with NaHCO$_3$ solution followed by brine. The organic layer was dried over Na$_2$SO$_4$, filtered and concentrated. The residue was chromatographed thru a 120 g ISCO Redi-sep column and eluted with 50% EtOAc/hexane to yield the title compound. LC-MS: M+1=259

Step F: 6-(1H-tetrazol-1-yl)-1,2,3,4-tetrahydronaphthalene-1-carboxylic acid: Methyl 6-(1H-tetrazol-1-yl)-1,2,3,4-tetrahydronaphthalene-1-carboxylate (1.77 g, 6.85 mmol) was stirred in a mixture of tetrahydrofuran (20 ml) and water (20.00 ml) then added lithium hydroxide (0.374 g, 8.91 mmol). Small amount of methanol was added to the reaction to ensure a homogeneous mixture. After 1 hour, reaction showed SM still present. More lithium hydroxide (0.374 g, 8.91 mmol) was added and stirred. When the hydrolysis was complete, 1N HCl was added to the reaction until a pH ~7 was obtained. The reaction was extracted with EtOAc. The organic layer was separated and dried over Na$_2$SO$_4$ then filtered and concentrated to yield the title compound. $^1$H-NMR (600 MHz, CDCl3) δ ppm 8.966 (d, J=2.3 Hz, 1H), 7.488 (s, 1H), 7.475 (t, J=7.9 Hz, 1H), 7.458 (t, J=8.05 Hz, 1H), 3.943 (t, J=5.6 Hz, 1H), 2.934-2.981(m, 1H), 2.85-2.902 (m, 1H), 2.273-2.321 (m, 1H), 2.607-2.121 (m, 1H), 1.983-2.052(m, 1H), 1.855-1.913 (m, 1H).

Intermediate 59

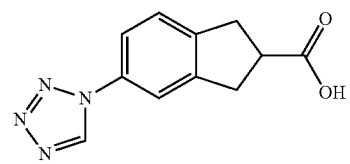 [SMILES: O=C(O)C1Cc2ccc(-n3cnnn3)cc2C1]

5-(1H-tetrazol-1-yl)-2,3-dihydro-1H-indene-2-carboxylic acid

Step A: ethyl 5-bromo-1-oxo-2,3-dihydro-1H-indene-2-carboxylate: A suspension of NaH (19.00 g, 474.0 mmol, 60% in mineral oil) and compound diethyl carbonate (43.5 mL, 355.5 mmol) in anhydrous THF (200 mL) was added a solution of compound 5-bromo-2,3-dihydro-1H-inden-1-one (50.00 g, 237.0 mmol) in anhydrous THF (100 mL) dropwise at ambient temperature, kept the reaction temperature blow 40° C. After the addition, the mixture was refluxed for 1 h under nitrogen atmosphere. The reaction mixture was quenched with water after the temperature of inter below 20° C. The mixture was acidified with conc. HCl, extracted with EtOAc. The combined organic phase was washed with brine, dried over anhydrous sodium sulfate and concentrated under vacuum to give the title compound.

Step B: ethyl 5-bromo-2,3-dihydro-1H-indene-2-carboxylate

A solution of compound ethyl 5-bromo-1-oxo-2,3-dihydro-1H-indene-2-carboxylate (62.00 g, 219.1 mmol) in 300 mL of TFA was added Et$_3$SiH (210 mL, 1.32 mol) and the mixture was stirred at ambient temperature overnight. The reaction mixture was concentrated under vacuum and the residue was purified with silica gel column chromatograph to give the title compound.

Step C: ethyl 5-(1,3-dioxo-1,3-dihydro-2H-isoindol-2-yl)-2,3-dihydro-1H-indene-2-carboxylate A solution of compound ethyl 5-bromo-2,3-dihydro-1H-indene-2-carboxylate (20.0 g, 74.4 mmol) in 150 mL of DMA was added potassium phthalimide (15.2 g, 81.9 mmol) and CuI (28.34 g, 148.8 mmol) and the mixture was stirred at 150° C. under nitrogen atmosphere overnight. The reaction mixture was concentrated under vacuum, and the residue was dissolved in DCM, filtered through CELITE. The filtration was concentrated and purified with silica gel column chromatograph to give the title compound.

Step D: ethyl 5-amino-2,3-dihydro-1H-indene-2-carboxylate: A mixture of ethyl 5-(1,3-dioxo-1,3-dihydro-2H-isoindol-2-yl)-2,3-dihydro-1H-indene-2-carboxylate (14.04 g, 41.87 mmol) in 200 mL of EtOH was added NH$_2$NH$_2$.H$_2$O (13.08 g, 209.34 mmol, 85% in water) was heated to reflux for 3 h. The solvent was removed under vacuum and the residue was dissolved in water. The mixture was extracted with EtOAc, and the combined organic phase was washed with brine, dried over anhydrous sodium sulfate and concentrated. The residue was purified with silica gel column chromatograph to give ethyl 5-amino-2,3-dihydro-1H-indene-2-carboxylate.

Step E: ethyl 5-(1H-tetrazol-1-yl)-2,3-dihydro-1H-indene-2-carboxylate: A solution of compound ethyl 5-amino-2,3-dihydro-1H-indene-2-carboxylate (4.00 g, 19.52 mmol) and triethyl orthoformate (8.67 g, 58.54 mmol) in 40 mL of AcOH was added sodium azide (1.40 g, 21.48 mmol). The resulting mixture was heated to 100° C. for 3 h. The mixture was cooled to ambient temperature and concentrated under vacuum. The residue was dissolved in EtOAc, washed with brine, dried over anhydrous Na$_2$SO$_4$ and concentrated. The residue was purified with silica gel column chromatograph to give the title compound.

Step F: 5-(1H-tetrazol-1-yl)-2,3-dihydro-1H-indene-2-carboxylic acid: To a solution of compound ethyl 5-(1H-tetrazol-1-yl)-2,3-dihydro-1H-indene-2-carboxylate (4.93 g, 19.11 mmol) in 100 mL of MeOH/THF/H$_2$O (2/2/1) was added LiOH.H$_2$O (4.01 g, 95.55 mmol), and the mixture was stirred at ambient temperature overnight. The solvents were removed under vacuum, and the residue was added 50 mL of water and extracted with ether. The aqueous layer was then acidified with 4 N HCl to pH=3 in ice bath, and extracted with EtOAc. The combined organic phase was washed with brine, dried over anhydrous sodium sulfate and concentrated. The residue was re-crystallized from DCM to give the title compound. $^1$H-NMR (400 MHz, MeOD) δ ppm 9.68 (s, 1H), 7.69 (s, 1H), 7.61~7.63 (m, 1H), 7.43~7.45 (d, J=8.1 Hz, 1H), 3.40~3.45 (m, 1H), 3.18~3.31 (m, 4H).

Intermediate 60

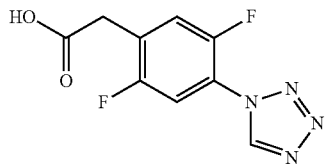 [SMILES: O=C(O)Cc1cc(F)c(-n2cnnn2)cc1F]

[2,5-difluoro-4-(1H-tetrazol-1-yl)phenyl]acetic acid

Step A: diethyl (2,5-difluoro-4-nitrophenyl)propanedioate: To an ice-cooled slurry of NaH (475 mg, 11.8 mmol, 60%) in dry DMF (10 mL) was added CH$_2$(COOEt)$_2$ dropwise under an N$_2$ atmosphere. After 20 minutes, 1,2,4-trifluoro-5-nitrobenzene (1 g, 5.6 mmol) was added dropwise over 10 minutes and the mixture was stirred at –6° C. overnight. After the reaction was completed, the mixture was diluted with water and extracted with EtOAc. The organic layer washed with brine, dried over anhydrous Na$_2$SO$_4$ and concentrated. The residue was purified by chromatography to give diethyl (2,5-difluoro-4-nitrophenyl)propanedioate.

Step B: (2,5-difluoro-4-nitrophenyl)acetic acid: A mixture of diethyl (2,5-difluoro-4-nitrophenyl)propanedioate (700 mg, 2.2 mmol) with HOAc (10 mL) and HCl (6 N, 10 mL) was heated under N$_2$ at 120° C. for 2.5 hours and then allowed to cool and stirred overnight. Most of the solvent was removed by evaporation and then water was added. The mixture was extracted with EtOAc. The organic layer washed with brine, dried over anhydrous Na$_2$SO$_4$ and concentrated to give (2,5-difluoro-4-nitrophenyl)acetic acid.

Step C: (4-amino-2,5-difluorophenyl)acetic acid: To a solution of (2,5-difluoro-4-nitrophenyl)acetic acid (440 mg, 2.03 mmol) in 20 ml of EtOAc was added HOAc (121 mg, 2.03 mmol) and 200 mg of Pd/C was stirred at room temperature under H$_2$ atmosphere for 3 hours. The reaction mixture was filtrated and concentrated to give the title compound.

Step D: [2,5-difluoro-4-(1H-tetrazol-1-yl)phenyl]acetic acid: A solution of (4-amino-2,5-difluorophenyl)acetic acid (380 mg, 2.0 mmol) and triethyl orthoformate (902 mg, 6.1 mmol) in HOAc (10 mL) was added sodium azide (158 mg, 2.44 mmol) and the mixture was heated to 100° C. for 3 hours. After the reaction was completed, the reaction mixture was cooled to ambient temperature. The solvent was removed under vacuum. The residue was dissolved in EtOAc, washed with water, dried over anhydrous sodium sulfate, and concentrated to give the title compound.

Intermediate 61

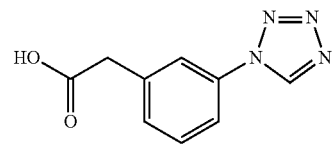 [SMILES: O=C(O)Cc1cccc(-n2cnnn2)c1]

[3-(1H-tetrazol-1-yl)phenyl]acetic acid

Step A: methyl (3-nitrophenyl)acetate: (3-Nitrophenyl) acetic acid (400 mg, 2.21 mmol) was dissolved in a 1:1 mixture of MeOH/Et$_2$O (10 mL) and cooled to 0° C. To this solution was added a 2M solution of trimethylsilyldiazomethane (5.5 mL, 11.05 mmol). The reaction was quenched by the addition of glacial acetic acid (7 mL) and concentrated in vacuo to afford crude title compound which was used without further purification: LC-MS: (M+H)$^+$ 196;

Step B: methyl (3-aminophenyl)acetate: Under an atmosphere of nitrogen, a MeOH (6 mL) solution of methyl (3-nitrophenyl)acetate (431 mg, 2.21 mmol) was added to palladium on carbon (5 mg, 0.044 mmol). The reaction mixture was then subjected to 1 atm of hydrogen at ambient temperature. After 15 hours, the reaction mixture was filtered over CELITE and concentrated in vacuo to furnish crude methyl (3-aminophenyl)acetate which was used without further purification. LC-MS: (M+H)$^+$ 166;

Step C: methyl[3-(1H-tetrazol-1-yl)phenyl]acetate: To a solution of (3-aminophenyl)acetate (365 mg, 2.21 mmol) in glacial acetic acid (4 mL) was added triethyl orthoformate (370 μL, 2.21 mmol) and sodium azide (144 mg, 2.21 mmol). The reaction mixture was heated at 80° C. for 3 hours in a sealed vial and then cooled to ambient temperature. Once cooled, water (1.5 mL) and solid sodium bicarbonate were added until a pH range of 6-7 was achieved. The aqueous layer was extracted with ethyl acetate (3×10 mL). The combined organic layers were then dried over sodium sulfate, filtered and concentrated in vacuo to furnish crude methyl [3-(1H-tetrazol-1-yl)phenyl]acetate which was used without further purification. LC-MS: (M+H)$^+$ 219;

Step D: [3-(1H-tetrazol-1-yl)phenyl]acetic acid: To a solution of methyl [3-(1H-tetrazol-1-yl)phenyl]acetate (482 mg, 2.21 mmol) in THF (10 mL) was added 1.5 mL of 5N aqueous sodium hydroxide solution. The reaction mixture was allowed to stir at ambient temperature for 30 minutes and then concentrated in vacuo. The crude residue was dissolved in 4 mL of a 1N aqueous hydrochloric acid solution and extracted with DCM (3×20 mL). The combined organic layers were then dried over sodium sulfate, filtered and concentrated in vacuo to afford crude title compound which was used without further purification. LC-MS: (M+H)$^+$ 205.

Intermediate 62

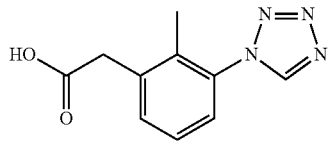 [SMILES: Cc1c(CC(=O)O)cccc1-n1cnnn1]

[2-methyl-3-(1H-tetrazol-1-yl)phenyl]acetic acid

Step A: methyl (2-methyl-3-nitrophenyl)acetate: To a solution of (2-methyl-3-nitrophenyl)acetic acid (1.50 g, 7.69 mmol) in methanol (30 mL) was added sulfuric acid (2.60 mL, 48.8 mmol). The reaction mixture was heated at 82° C. for 15 hours then cooled to ambient temperature. Once cooled, the reaction was concentrated in vacuo. The residue was diluted with water and extracted with ethyl acetate. The combined organic layers were dried over sodium sulfate, filtered and concentrated in vacuo to afford crude methyl (2-methyl-3-nitrophenyl)acetate which was used without further purification. LC-MS: (M+H)$^+$ 210;

Step B: methyl (3-amino-2-methylphenyl)acetate: Under an atmosphere of nitrogen, a DCM (10 mL) solution of methyl (2-methyl-3-nitrophenyl)acetate (1.71 g, 8.17 mmol) was added to palladium on carbon (342 mg, 3.21 mmol). The reaction mixture was then subjected to 1 atm of hydrogen at ambient temperature. After 20 hours, the reaction mixture was filtered over CELITE and concentrated in vacuo to furnish crude methyl (3-amino-2-methylphenyl)acetate which was used without further purification. LC-MS: (M+H)$^+$ 180;

Step C: methyl [2-methyl-3-(1H-tetrazol-1-yl)phenyl]acetate: To a solution of methyl (3-amino-2-methylphenyl)acetate (400 mg, 2.23 mmol) in glacial acetic acid (5 mL) was added triethyl orthoformate (1.11 mL, 6.70 mmol) and sodium azide (435 mg, 6.70 mmol). The reaction mixture was heated at 80° C. for 3 hours in a sealed vial and then cooled to ambient temperature. Once cooled, water (5 mL) was added and the aqueous layer was extracted with EtOAc (3×20 mL). The combined organic layers were then dried over sodium sulfate, filtered and concentrated in vacuo to afford title compound which was used without further purification. LC-MS: (M+H)$^+$ 233;

Step D: [2-methyl-3-(1H-tetrazol-1-yl)phenyl]acetic acid: To a solution of methyl [2-methyl-3-(1H-tetrazol-1-yl)phenyl]acetate (800 mg, 3.41 mmol) in THF/MeOH/H$_2$O (6 mL/2 mL/2 mL) was added 4.1 mL of 5N aqueous sodium hydroxide solution. The reaction mixture was allowed to stir at ambient temperature for 45 minutes and then acidified with 1N aqueous hydrochloric acid solution. The aqueous was extracted with DCM (3×20 mL). The combined organic layers were then dried over sodium sulfate, filtered and concentrated in vacuo to afford crude title compound which was used without further purification. LC-MS: (M+H)$^+$ 219.

Intermediate 63

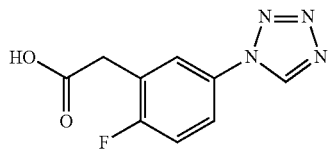 [SMILES: O=C(O)Cc1cc(-n2cnnn2)ccc1F]

[2-fluoro-5-(1H-tetrazol-1-yl)phenyl]acetic acid

Step A: methyl (2-fluoro-5-nitrophenyl)acetate: To a solution of (2-fluoro-5-nitrophenyl)acetic acid (5 g, 25 mmol) in methanol (75 mL) was added sulfuric acid (8.50 mL, 159 mmol). The reaction mixture was heated at 82° C. for 15 hours then cooled to ambient temperature. Once cooled, the reaction was concentrated in vacuo. The residue was diluted with water and extracted with ethyl acetate. The combined organic layers were dried over sodium sulfate, filtered and concentrated in vacuo to afford crude methyl (2-fluoro-5-nitrophenyl)acetate which was used without further purification. LC-MS: (M+H)$^+$ 214;

Step B: methyl (5-amino-2-fluorophenyl)acetate: Under an atmosphere of nitrogen, a DCM (5 mL) solution of methyl (2-fluoro-5-nitrophenyl)acetate (500 mg, 2.34 mmol) was added to palladium on carbon (100 mg, 0.094 mmol). The reaction mixture was then subjected to 1 atm of hydrogen at ambient temperature. After 15 hours, the reaction mixture was filtered over CELITE and concentrated in vacuo. The crude material was purified via MPLC (0-50% EtOAc/Hex gradient) to afford methyl (5-amino-2-fluorophenyl)acetate. LC-MS: (M+H)$^+$ 184;

Step C: methyl [2-fluoro-5-(1H-tetrazol-1-yl)phenyl]acetate: To a solution of methyl (5-amino-2-fluorophenyl)acetate (600 mg, 3.28 mmol) in glacial acetic acid (10 mL) was added triethyl orthoformate (1.63 mL, 9.83 mmol) and sodium azide (639 mg, 9.83 mmol). The reaction mixture was heated at 80° C. for 3 hours in a sealed vial and then cooled to ambient temperature. Once cooled, water (5 mL) was added and the aqueous layer was extracted with ethyl acetate (3×20 mL). The combined organic layers were then dried over sodium sulfate, filtered and concentrated in vacuo to afford methyl [2-fluoro-5-(1H-tetrazol-1-yl)phenyl]acetate which was used without further purification. LC-MS: (M+H)$^+$ 237.

Step D: [2-fluoro-5-(1H-tetrazol-1-yl)phenyl]acetic acid To a solution of methyl [2-fluoro-5-(1H-tetrazol-1-yl)phenyl]acetate (860 mg, 3.64 mmol) in THF/MeOH/H$_2$O (6 mL/2 mL/2 mL) was added 4.1 mL of 5N aqueous sodium hydroxide solution. The reaction mixture was allowed to stir at ambient temperature for 45 minutes and then acidified with 1N aqueous hydrochloric acid solution. The aqueous was extracted with DCM (3×20 mL). The combined organic layers were then dried over sodium sulfate, filtered and concentrated in vacuo to afford crude title compound which was used without further purification. LC-MS: (M+H)$^+$ 223.

Intermediate 64

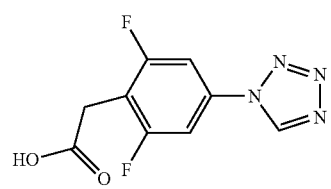 [SMILES: O=C(O)Cc1c(F)cc(-n2cnnn2)cc1F]

[2,6-Difluoro-4-(1H-tetrazol-1-yl)phenyl]acetic acid

Step A: tert-butyl (4-amino-2,6-difluorophenyl)acetate: To a solution of 4-bromo-3,5-difluoroaniline (400 mg, 1.92 mmol) in THF (8 mL) were added Pd$_2$(dba)$_3$ (141 mg, 0.154 mmol), X-Phos (110 mg, 0.231 mmol). The reaction mixture was degassed and filled with nitrogen, followed by addition of 2-(tert-butoxy)-2-oxoethyzink chloride (9.62 mL, 4.81 mmol). The reaction mixture was heated at 60° C. overnight, cooled to RT, quenched with sat NH$_4$Cl, and extracted with EtOAc. The organic layer was washed with brine, dried over Na₂SO₄, and concentrated. The residue was purified with preparative TLC (1500 uM, hex/EA=3/1) to give title compound. LC/MS [(M+1)]⁺=244.20, [(M+1-56)]⁺=188.21.

Step B: tert-butyl [2,6-difluoro-4-(1H-tetrazol-1-yl)phenyl]acetate: To a solution of tert-butyl (4-amino-2,6-difluorophenyl)acetate (388 mg, 1.60 mmol) in EtOAc (5 mL) was added trimethylsilyl trifluoroacetate (0.468 mL, 2.71 mmol) at room temperature. After stirred 5 min, triethyl orthoformate (0.478 mL, 2.87 mmol) was added. After stirred another 5 min, azidotrimethylsilane (0.336 ml, 2.55 mmol) was added. The reaction mixture was stirred at room temperature overnight, was then concentrated. The residue was purified with preparative TLC (hex/EA=3/1) to give title compound. LC/MS: [(M+1)]⁺=297.26, [(M+1-56)]⁺=241.29;

Step C: [2,6-Difluoro-4-(1H-tetrazol-1-yl)phenyl]acetic acid: To a solution of tert-butyl [2,6-difluoro-4-(1H-tetrazol-1-yl)phenyl]acetate (435 mg, 1.47 mmol) in DCM containing thioanisole (1.04 mL, 8.81 mmol) was added TFA (1.70 mL, 22.02 mmol) at 0° C. The mixture was stirred at RT overnight, concentrated. The residue was triturated with ether:hexane (1:1) three times, then with ACN to provide the title compound. LC-MS: [(M+1)]⁺=241.24

Intermediate 65

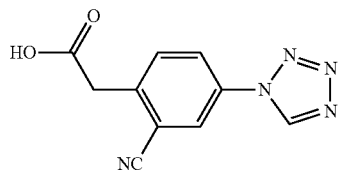 [SMILES: N#Cc1cc(-n2cnnn2)ccc1CC(=O)O]

2-(2-cyano-4-(1H-tetrazol-1-yl)phenyl)acetic acid

Step A: tert-Butyl 2-(4-amino-2-cyanophenyl)acetate: To a solution of 5-amino-2-bromobenzonitrile (400 mg, 2.03 mmol) in THF (8 mL) were added Pd₂(dba)₃ (149 mg, 0.162 mmol), X-Phos (116 mg, 0.244 mmol). The reaction mixture was degassed and filled with nitrogen, followed by addition of 2-(tert-butoxy)-2-oxoethyzink chloride (10.15 mL, 5.08 mmol). The reaction mixture was heated at 60° C. overnight, cooled to RT, quenched with sat NH₄Cl, and extracted with EtOAc. The organic layer was washed with brine, dried over Na₂SO₄, and concentrated. The residue was purified with preparative TLC (1500 uM, hex/EA=7/3) to give tert-butyl 2-(4-amino-2-cyanophenyl)acetate. LC/MS: [(M+23)]⁺=255.2

Step B: tert-Butyl 2-(2-cyano-4-(1H-tetrazol-1-yl)phenyl)acetate :To a solution of tert-butyl 2-(4-amino-2-cyanophenyl)acetate (180, 0.775 mmol) in EtOAc (2.5 mL) was added trimethylsilyl trifluoroacetate (0.228 mL, 1.32 mmol) at room temperature. After stirred 5 min, triethyl orthoformate (0.232 mL, 1.40 mmol) was added. After stirred another 5 min, azidotrimethylsilane (0.163 ml, 1.24 mmol) was added. The reaction mixture was stirred at room temperature overnight, was then concentrated. The residue was purified with preparative TLC (hex/EA=7/3) to give title compound. LC/MS: [(M+1)]⁺=286.18

Step C: 2-(2-cyano-4-(1H-tetrazol-1-yl)phenyl)acetic acid: To a solution of tert-Butyl 2-(2-cyano-4-(1H-tetrazol-1-yl)phenyl)acetate (140 mg, 0.491 mmol) in DCM containing thioanisole (0.348 mL, 2.94 mmol) was added TFA (0.567 mL, 7.34 mmol) at 0° C. The mixture was stirred at RT overnight, concentrated to dryness to give 2-(2-cyano-4-(1H-tetrazol-1-yl)phenyl)acetic acid. LC/MS: [(M+1)]⁺=230.18

Intermediate 66

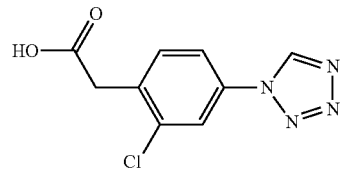 [SMILES: O=C(O)Cc1ccc(-n2cnnn2)cc1Cl]

2-(2-chloro-4-(1H-tetrazol-1-yl)phenyl)acetic acid

Step A: methyl 2-(4-amino-2-chlorophenyl)acetate: Methyl 2-(2-chloro-4-nitrophenyl)acetate (365 mg, 1.59 mmol) was suspended in AcOH (5 mL) at RT with vigorously stirring. Zinc (1040 mg, 15.9 mmol) was added slowly (exothermic reaction). The mixture was stirred at 50° C. for 2 hours, and filtered. The filter cake was washed with EtOAc. The filtrate was concentrated to give methyl 2-(4-amino-2-chlorophenyl)acetate. LC/MS: [(M+1)]⁺=200.23.

Step B: Methyl 2-(2-chloro-4-(1H-tetrazol-1-yl)phenyl)acetate: To a solution of methyl 2-(4-amino-2-chlorophenyl)acetate (323 mg, 1.62 mmol) in EtOAc (8 mL) was added trimethylsilyl trifluoroacetate (0.475 mL, 2.75 mmol) at room temperature. After stirred 5 min, triethyl orthoformate (0.485 mL, 2.91 mmol) was added. After stirred another 5 min, azidotrimethylsilane (0.340 ml, 2.59 mmol) was added. The reaction mixture was stirred at room temperature overnight, was then concentrated. The residue was purified with preparative TLC (hex/EA=1/1) to give title compound. LC/MS: [(M+1)]⁺=253.12.

Step C: 2-(2-chloro-4-(1H-tetrazol-1-yl)phenyl)acetic acid: To a solution of methyl 2-(2-chloro-4-(1H-tetrazol-1-yl)phenyl)acetate (250 mg, 0.989 mmol) in THF (3 mL) was added 1 M aqueous solution of LiOH (2.97 mL, 2.97 mmol). The mixture was stirred at RT for 2 hours, acidified with 1 N HCl, and extracted with EtOAc. The organic layer was concentrated to dryness to give 2-(2-chloro-4-(1H-tetrazol-1-yl)phenyl)acetic acid. LC/MS: [(M+1)]⁺=239.08.

EXAMPLE 1A

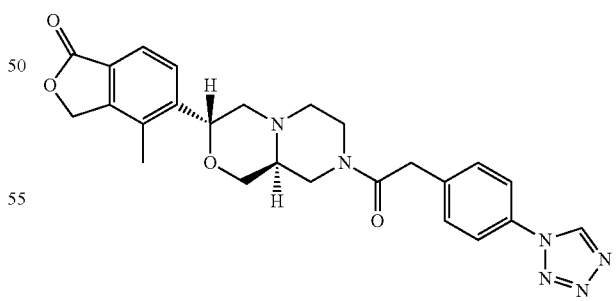

4-methyl-5-[(3R,9aS)-8-{[4-(1H-tetrazol-1-yl)phenyl]acetyl}octahydropyrazino[2,1-c][1,4]oxazin-3-yl]-2-benzofuran-1(3H)-one 4-Methyl-5-((3R,9aS)-octahydropyrazino[2,1-c][1,4]oxazin-3-yl)isobenzofuran-1(3H)-one   2,2,2-trifluoroacetate (25 mg, 0.062 mmol) was dissolved in DCM (5 ml) and TEA was added (26.0 μl, 0.186 mmol) followed by 2-(4-(1H-tetrazol-1-yl)phenyl)acetic acid (13.96 mg, 0.068 mmol) and EDC (19.53 mg, 0.102 mmol). The reaction was stirred for 1 hr. then poured into brine. The layers were separated and the DCMG fraction was dried (Na$_2$SO$_4$) and concentrated. The residue was purified by prep-plate silica gel using 5% (NH$_4$OH:MeOH 1:9) in DCM solvent system to yield the title compound. LC-MS (IE, m/z): 475 [M+1]$^+$; $^1$H-NMR (500 MHz, DMSO) δ ppm 10.077(s, 1H), 7.849 (t, J=4.1 Hz, 2H), 7.688(d, J=7.8 Hz, 1H), 7.615(t, J=7.35 Hz, 1H), 7.507 (t, J=7.1 Hz, 2H), 5.402 (m, 2H), 4.895 (d, J=9.6 Hz, 1 H), 4.339(t, J=11.2 Hz, 1H) 4.055(d, J=10.1 Hz, 2H), 3.879 (m, 2H), 3.43 (t, J=10.8 Hz, 1H), 3.224(t, J=11.7 Hz, 0.5H), 2.906 (d, J=0.7 Hz, 1H), 2.784(m, 2.0H), 2.344(t, J=13.2 Hz, 0.5H), 2.286 (s, 3H), 2.00-2.191 (m, 3H).

EXAMPLE 1B

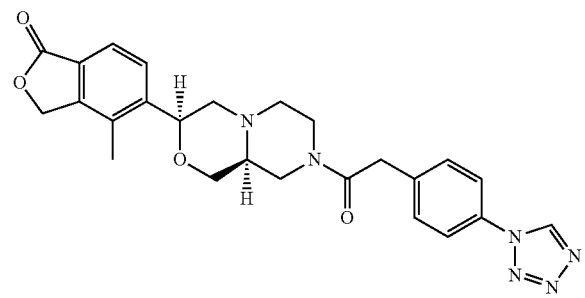 [SMILES: Cc1c([C@H]2CN3CCN(C(=O)Cc4ccc(-n5cnnn5)cc4)C[C@H]3CO2)ccc2c1COC2=O]

4-methyl-5-[(3S,9aS)-8-{[4-(1H-tetrazol-1-yl)phenyl]acetyl}octahydropyrazino[2,1-c][1,4]oxazin-3-yl]-2-benzofuran-1(3H)-one 4-methyl-5-((3S,9aS)-octahydropyrazino[2,1-c][1,4]oxazin-3-yl)isobenzofuran-1 (3H)-one 2,2,2-trifluoroacetate (20.5 mg, 0.051 mmol) was dissolved in DCM (5 ml) and TEA was added (21.30 μl, 0.153 mmol) followed by 2-(4-(1H-tetrazol-1-yl)phenyl)acetic acid (11.4 mg, 0.056 mmol) and EDC (19.53 mg, 0.102 mmol). The reaction was stirred for 1 hr. then poured into brine. The layers were separated, and the DCM fraction was dried (Na2SO4) and concentrated. The residue was purified by prep-plate silica gel using 5% (NH$_4$OH:MeOH 1:9) in DCM solvent system to yield the title compound. LC-MS (IE, m/z): 475 [M+1]$^+$; $^1$H-NMR (500 MHz, DMSO) δ ppm 10.074 (s, 1H), 8.025 (d, J=3.9 Hz, 1H), 7.846 (d, J=5.7 Hz, 2H), 7.682 (d, J=5.3 Hz, 1H), 7.50 (d, J=7.1 Hz, 2H), 5.411 (s, 2H), 4.988 (s, 1 H), 4.23 (d, J=11.9, Hz, 0.5H), 4.161 (d, J=11.9, Hz, 0.5H), 3.851 (b, 3H), 3.599 (b, 1H), 3.1-3.3 (m, 3H), 2.89 (b, 1H), 2.367-2.66 (m, 4H), 2.29 (s, 3H).

EXAMPLE 2

Racemate and Isomers 2A and 2B

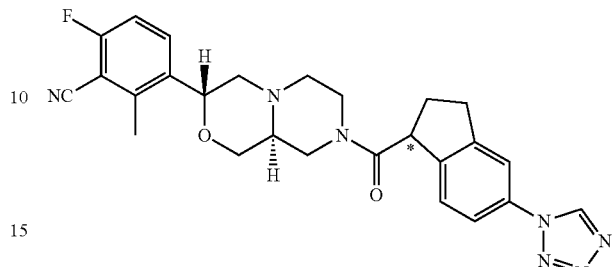

3-((3R,9aS)-8-((R)-5-(1H-tetrazol-1-yl)-2,3-dihydro-1H-indene-1carbonyl)octahydropyrazino[2,1-c][1,4]oxazin-3-yl)-6-fluoro-2-methylbenzonitrile and 3-((3R,9aS)-8-((S)-5-(1H-tetrazol-1-yl)-2,3-dihydro-1H-indene-1carbonyl)octahydropyrazino[2,1-c][1,4]oxazin-3-yl)-6-fluoro-2-methylbenzonitrile 6-Fluoro-2-methyl-3-((3R,9aS)-octahydropyrazino[2,1c][1,4]oxazin-3-yl)benzonitrile 2,2,2-trifluoroacetate (0.100 g, 0.257 mmol) was stirred in DCM (10 ml) then added TEA (0.143 ml, 1.027 mmol) followed by 5-(1H-tetrazol-1-yl)-2,3-dihydro-1H-indene-1-carboxylic acid (0.059 g, 0.257 mmol), HOBT (0.059 g, 0.385 mmol) and EDC (0.123 g, 0.642 mmol). The mixture was stirred at room temperature for another 3 hrs. then poured into brine and extracted with more DCM. The DCM layer was separated and dried over Na$_2$SO$_4$ then filtered and concentrated. The residue was purified by MPLC with a 40 g ISCO Redi-Sep column and using 5% (NH4OH:MeOH 1:9) in DCM solvent system to yield 3-((3R,9aS)-8-(5-(1H-tetrazol-1-yl)-2,3-dihydro-1H-indene-1-carbonyl)octahydropyrazino[2,1-c][1,4]oxazin-3-yl)-6-fluoro-2-methylbenzonitrile diastereomers mixture. The diastereomers were separated by prep SFC using 40% 2:1 MeOH:MeCN/CO$_2$ on Chiralcel OD (21×250 mm column, 60 ml/min, 100 bar, 20 mg/ml in MeCN, 35° C., 230 nm.). Diastereomer 2A: (faster eluting) LC-MS (IE, m/z): 488 [M+1]$^+$; $^1$H-NMR (600 MHz, DMSO) δ ppm 10.027(s, 1H), 7.769(s, 1H), 7.739(m, 1 H), 7.756(d, J=7.8 Hz, 1H), 7.421(t, J=8.4 Hz, 1H), 7.346 (d, J=8.4 Hz, 1H), 4.956 (s, 1 H), 4.548 (m, 2H) 4.371(b, 1H), 4.188(m, 1H), 3.68 (m, 1H), 3.46 (b, 3H), 3.28 (b, 2H), 3.06 (m, 1H), 2.96 (m, 1H), 2.87 (m, 1.5H), 2.64 (b, 0.5H), 2.47 (s, 3H), 2.41 (m, 1H), 2.24 (m, 0.5H), 2.15 (m, 0.5H). Diastereomer 2B: (slower eluting) LC-MS (IE, m/z): 488 [M+1]$^+$; $^1$H-NMR (600 MHz, DMSO) δ ppm 10.026(s, 1H), 7.76 (s, 1H), 7.746 (m, 1 H), 7.668(m, 1H), 7.420(m, 1H), 7.355 (t, J=7.8 Hz, 1H), 4.953 (s, 1 H), 4.548(m, 2H) 4.366(b, 1H), 4.190(m, 1H), 3.66 (b, 2H), 3.478 (m, 1H), 3.366 (b, 1.5H), 3.185 (b, 0.5H), 3.03 (m, 1H), 2.963 (m, 3.5H), 2.71 (b, 0.5H), 2.472 (s, 3H), 2.411 (m, 1H), 2.192(m, 0.5H), 2.086 (m, 0.5H).

The Examples in Table 2 were prepared in an analogous fashion to that described for the synthesis of Examples 1A, 1B, and 2 above from the appropriate amine and carboxylic acid Intermediates (commercially available or prepared as described above).

TABLE 2

| Example No. | EXAMPLE STRUCTURE | Characterization MS and/or HNMR |
|---|---|---|
| 3 | 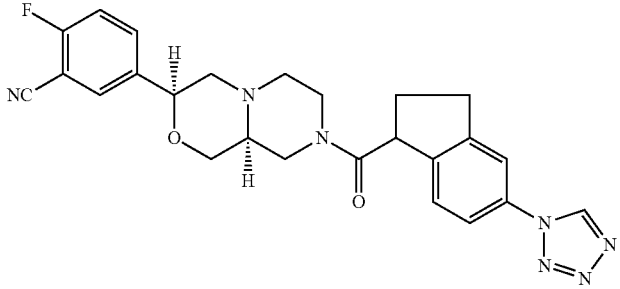 [SMILES: N#Cc1cc([C@H]2CN3CCN(C(=O)C4CCc5cc(-n6cnnn6)ccc54)C[C@H]3CO2)ccc1F]<br>2-fluoro-5-[(3S,9aS)-8-{[5-(1H-tetrazol-1-yl)-2,3-dihydro-1H-inden-1-yl]carbonyl}octahydropyrazino[2,1-c][1,4]oxazin-3-yl]benzonitrile | LC/MS (M + H) 474<br>Mixture of two isomers at indane |
| 4 | 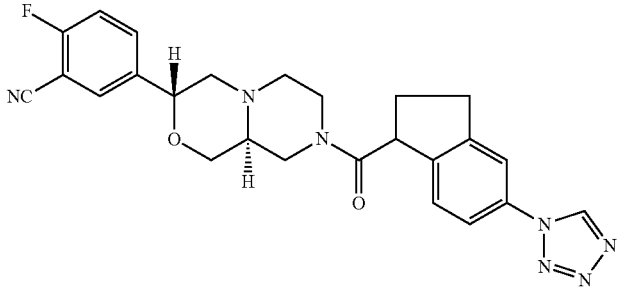 [SMILES: N#Cc1cc([C@@H]2CN3CCN(C(=O)C4CCc5cc(-n6cnnn6)ccc54)C[C@H]3CO2)ccc1F]<br>2-fluoro-5-[(3R,9aS)-8-{[5-(1H-tetrazol-1-yl)-2,3-dihydro-1H-inden-1-yl]carbonyl}octahydropyrazino[2,1-c][1,4]oxazin-3-yl]benzonitrile | LC/MS (M + H) 474<br>Mixture of two isomers at indane |
| 5 | 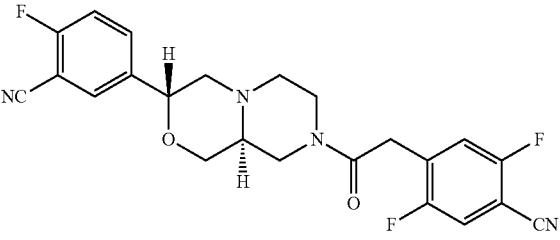 [SMILES: N#Cc1cc([C@@H]2CN3CCN(C(=O)Cc4cc(F)c(C#N)cc4F)C[C@H]3CO2)ccc1F]<br>4-{2-[(3R,9aS)-3-(3-cyano-4-fluorophenyl)hexahydropyrazino[2,1-c][1,4]oxazin-8(1H)-yl]-2-oxoethyl}-2,5-difluorobenzonitrile | LC/MS (M + H) 441 |
| 6 | 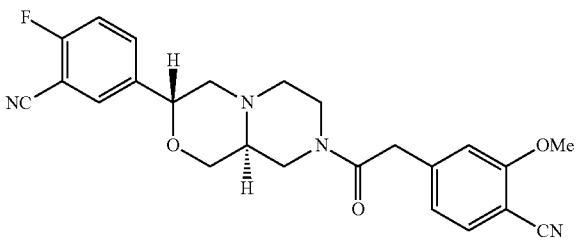 [SMILES: COc1cc(CC(=O)N2CCN3C[C@@H](c4ccc(F)c(C#N)c4)OC[C@@H]3C2)ccc1C#N]<br>4-{2-[(3R,9aS)-3-(3-cyano-4-fluorophenyl)hexahydropyrazino[2,1-c][1,4]oxazin-8(1H)-yl]-2-oxoethyl}-2,5-difluorobenzonitrile | LC/MS (M + H) 435 |

TABLE 2-continued

| Example No. | EXAMPLE STRUCTURE | Characterization MS and/or HNMR |
|---|---|---|
| 7 | 5-[(3S,9aS)-8-{[4-(1H-tetrazol-1-yl)phenyl]acetyl}octahydropyrazino[2,1-c][1,4]oxazin-3-yl]-2-benzofuran-1(3H)-one | LC/MS (M + H) 461 |
| 8 | 5-[(3R,9aS)-8-{[4-(1H-tetrazol-1-yl)phenyl]acetyl}octahydropyrazino[2,1-c][1,4]oxazin-3-yl]-2-benzofuran-1(3H)-one | LC/MS (M + H) 461 |
| 9 | 5-fluoro-2-methoxy-4-{2-oxo-2-[(3S,9aS)-3-(1-oxo-1,3-dihydro-2-benzofuran-5-yl)hexahydropyrazino[2,1-c][1,4]oxazin-8(1H)-yl]ethyl}benzonitrile | LC/MS (M + H) 466 |
| 10 | 5-fluoro-2-methoxy-4-{2-oxo-2-[(3R,9aS)-3-(1-oxo-1,3-dihydro-2-benzofuran-5-yl)hexahydropyrazino[2,1-c][1,4]oxazin-8(1H)-yl]ethyl}benzonitrile | LC/MS (M + H) 466 |

TABLE 2-continued

| Example No. | EXAMPLE STRUCTURE | Characterization MS and/or HNMR |
|---|---|---|
| 11 | 5-[(3S,9aS)-8-{[5-(1H-tetrazol-1-yl)-2,3-dihydro-1H-inden-1-yl]carbonyl}octahydropyrazino[2,1-c][1,4]oxazin-3-yl]-2-benzofuran-1(3H)-one | LC/MS (M + H) 487 Mixture of two isomers at indane |
| 12 | 5-[(3R,9aS)-8-{[5-(1H-tetrazol-1-yl)-2,3-dihydro-1H-inden-1-yl]carbonyl}octahydropyrazino[2,1-c][1,4]oxazin-3-yl]-2-benzofuran-1(3H)-one | LC/MS (M + H) 487 Mixture of two isomers at indane |
| 13 | 4-methyl-5-[(3R,9aR)-8-{[4-(1H-tetrazol-1-yl)phenyl]acetyl}octahydropyrazino[2,1-c][1,4]oxazin-3-yl]-2-benzofuran-1(3H)-one | LC/MS (M + H) 475 |

TABLE 2-continued

| Example No. | EXAMPLE STRUCTURE | Characterization MS and/or HNMR |
|---|---|---|
| 14 | 4-methyl-5-[(3S,9aR)-8-{[4-(1H-tetrazol-1-yl)phenyl]acetyl}octahydropyrazino[2,1-c][1,4]oxazin-3-yl]-2-benzofuran-1(3H)-one | LC/MS (M + H) 475 |
| 15 | 6-[(3R,9aS)-8-{[4-(1H-tetrazol-1-yl)phenyl]acetyl}octahydropyrazino[2,1-c][1,4]oxazin-3-yl]-3,4-dihydro-1H-isochromen-1-one | LC/MS (M + H) 475 |
| 16 | 5-fluoro-2-methoxy-4-{2-[(3S,9aS)-3-(4-methyl-1-oxo-1,3-dihydro-2-benzofuran-5-yl)hexahydropyrazino[2,1-c][1,4]oxazin-8(1H)-yl]-2-oxoethyl}benzonitrile | LC/MS (M + H) 480 |
| 17 | 5-fluoro-2-methoxy-4-{2-[(3R,9aS)-3-(4-methyl-1-oxo-1,3-dihydro-2-benzofuran-5-yl)hexahydropyrazino[2,1-c][1,4]oxazin-8(1H)-yl]-2-oxoethyl}benzonitrile | LC/MS (M + H) 480 |

TABLE 2-continued

| Example No. | EXAMPLE STRUCTURE | Characterization MS and/or HNMR |
|---|---|---|
| 18 | 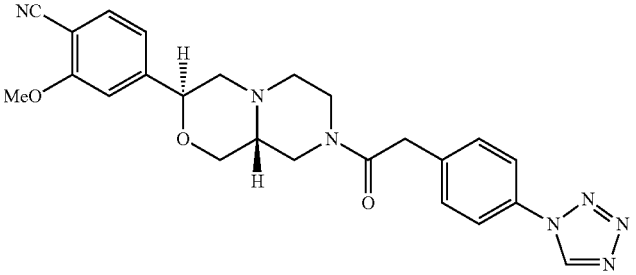 [SMILES: COc1cc([C@H]2CN3CCN(C(=O)Cc4ccc(-n5cnnn5)cc4)C[C@@H]3CO2)ccc1C#N]<br>2-methoxy-4-[(3S,9aR)-8-{[4-(1H-tetrazol-1-yl)phenyl]acetyl}octahydropyrazino[2,1-c][1,4]oxazin-3-yl]benzonitrile | LC/MS (M + H) 460 |
| 19 | 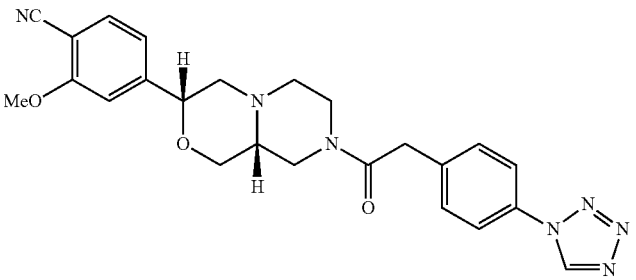 [SMILES: COc1cc([C@@H]2CN3CCN(C(=O)Cc4ccc(-n5cnnn5)cc4)C[C@@H]3CO2)ccc1C#N]<br>2-methoxy-4-[(3R,9aR)-8-{[4-(1H-tetrazol-1-yl)phenyl]acetyl}octahydropyrazino[2,1-c][1,4]oxazin-3-yl]benzonitrile | LC/MS (M + H) 460 |
| 20 | 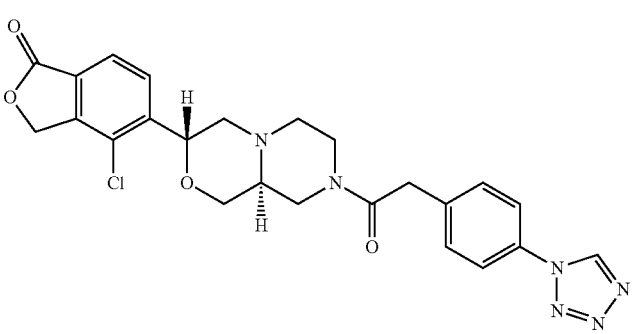 [SMILES: O=C1OCc2c1ccc([C@@H]1CN3CCN(C(=O)Cc4ccc(-n5cnnn5)cc4)C[C@H]3CO1)c2Cl]<br>4-chloro-5-[(3R,9aS)-8-{[4-(1H-tetrazol-1-yl)phenyl]acetyl}octahydropyrazino[2,1-c][1,4]oxazin-3-yl]-2-benzofuran-1(3H)-one | LC/MS (M + H) 495 |
| 21 | 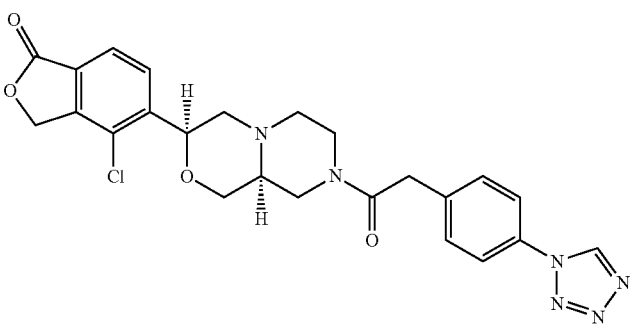 [SMILES: O=C1OCc2c1ccc([C@H]1CN3CCN(C(=O)Cc4ccc(-n5cnnn5)cc4)C[C@H]3CO1)c2Cl]<br>4-chloro-5-[(3S,9aS)-8-{[4-(1H-tetrazol-1-yl)phenyl]acetyl}octahydropyrazino[2,1-c][1,4]oxazin-3-yl]-2-benzofuran-1(3H)-one | LC/MS (M + H) 495 |

TABLE 2-continued

| Example No. | EXAMPLE STRUCTURE | Characterization MS and/or HNMR |
|---|---|---|
| 22 | 6-[(3R,9aS)-8-{[5-(1H-tetrazol-1-yl)-2,3-dihydro-1H-inden-1-yl]carbonyl}octahydropyrazino[2,1-c][1,4]oxazin-3-yl]-3,4-dihydro-1H-isochromen-1-one | LC/MS (M +H) 501; Mixture of two isomers at indane |
| 23 | 6-fluoro-2-methyl-3-{(3S,9aS)-8-[(1-oxo-1,3-dihydro-2-benzofuran-5-yl)acetyl]octahydropyrazino[2,1-c][1,4]oxazin-3-yl}benzonitrile | LC/MS (M + H) 450 |
| 24 | 6-fluoro-2-methyl-3-{(3R,9aS)-8-[(1-oxo-1,3-dihydro-2-benzofuran-5-yl)acetyl]octahydropyrazino[2,1-c][1,4]oxazin-3-yl}benzonitrile | LC/MS (M + H) 450 |
| 25 | 2-fluoro-6-methoxy-3-[(3R,9aS)-8-{[4-(1H-tetrazol-1-yl)phenyl]acetyl}octahydropyrazino[2,1-c][1,4]oxazin-3-yl]benzonitrile | LC/MS (M + H) 478 |

TABLE 2-continued

| Example No. | EXAMPLE STRUCTURE | Characterization MS and/or HNMR |
|---|---|---|
| 26 | 6-methoxy-2-methyl-3-[(3R,9aS)-8-{[4-(1H-tetrazol-1-yl)phenyl]acetyl}octahydropyrazino[2,1-c][1,4]oxazin-3-yl]benzonitrile | LC/MS (M + H) 474 |
| 27 | 4-fluoro-2-methoxy-5-[(3R,9aS)-8-{[4-(1H-tetrazol-1-yl)phenyl]acetyl}octahydropyrazino[2,1-c][1,4]oxazin-3-yl]benzonitrile | LC/MS (M + H) 478 |
| 28 | 2-methoxy-4-{2-oxo-2-[(3S,9aR)-3-(1-oxo-3,4-dihydro-1H-isochromen-6-yl)hexahydropyrazino[2,1-c][1,4]oxazin-8(1H)-yl]ethyl}benzonitrile | LC/MS (M + H) 462 |
| 29 | 2-methoxy-4-{2-oxo-2-[(3R,9aS)-3-(1-oxo-3,4-dihydro-1H-isochromen-6-yl)hexahydropyrazino[2,1-c][1,4]oxazin-8(1H)-yl]ethyl}benzonitrile | LC/MS (M + H) 462 |

TABLE 2-continued

| Example No. | EXAMPLE STRUCTURE | Characterization MS and/or HNMR |
|---|---|---|
| 30 | 5-fluoro-2-methoxy-4-{2-oxo-2-[(3R,9aS)-3-(1-oxo-3,4-dihydro-1H-isochromen-6-yl)hexahydropyrazino[2,1-c][1,4]oxazin-8(1H)-yl]ethyl}benzonitrile | LC/MS (M + H) 480 |
| 31 | 5-fluoro-2-methoxy-4-{2-oxo-2-[(3S,9aR)-3-(1-oxo-3,4-dihydro-1H-isochromen-6-yl)hexahydropyrazino[2,1-c][1,4]oxazin-8(1H)-yl]ethyl}benzonitrile | LC/MS (M + H) 480 |
| 32 | 6-fluoro-2-methoxy-3-[(3R,9aS)-8-{[4-(1H-tetrazol-1-yl)phenyl]acetyl}octahydropyrazino[2,1-c][1,4]oxazin-3-yl]benzonitrile | LC/MS (M + H) 478 |
| 33 | 6-fluoro-2-methoxy-3-[(3S,9aS)-8-{[4-(1H-tetrazol-1-yl)phenyl]acetyl}octahydropyrazino[2,1-c][1,4]oxazin-3-yl]benzonitrile | LC/MS (M + H) 478 |

TABLE 2-continued

| Example No. | EXAMPLE STRUCTURE | Characterization MS and/or HNMR |
|---|---|---|
| 34 | 6-chloro-2-methyl-3-[(3R,9aS)-8-{[4-(1H-tetrazol-1-yl)phenyl]acetyl}octahydropyrazino[2,1-c][1,4]oxazin-3-yl]benzonitrile | LC/MS (M + H) 478 |
| 35 | 6-chloro-2-methyl-3-[(3S,9aS)-8-{[4-(1H-tetrazol-1-yl)phenyl]acetyl}octahydropyrazino[2,1-c][1,4]oxazin-3-yl]benzonitrile | LC/MS (M + H) 478 |
| 36 | 6-chloro-2-methyl-3-[(3S,9aS)-8-{[5-(1H-tetrazol-1-yl)-2,3-dihydro-1H-inden-1-yl]carbonyl}octahydropyrazino[2,1-c][1,4]oxazin-3-yl]benzonitrile | LC/MS (M + H) 504 Mixture of two diastereomers at indane |
| 37 | 6-chloro-2-methyl-3-[(3R,9aS)-8-{[5-(1H-tetrazol-1-yl)-2,3-dihydro-1H-inden-1-yl]carbonyl}octahydropyrazino[2,1-c][1,4]oxazin-3-yl]benzonitrile | LC/MS (M + H) 504 Mixture of two diastereomers at indane |

TABLE 2-continued

| Example No. | EXAMPLE STRUCTURE | Characterization MS and/or HNMR |
|---|---|---|
| 38 | 2-fluoro-4-methyl-5-[(3R,9aS)-8-{[4-(1H-tetrazol-1-yl)phenyl]acetyl}octahydropyrazino[2,1-c][1,4]oxazin-3-yl]benzonitrile | LC/MS (M + H) 462 |
| 39 | 3-methyl-4-[(3R,9aS)-8-{[4-(1H-tetrazol-1-yl)phenyl]acetyl}octahydropyrazino[2,1-c][1,4]oxazin-3-yl]thiophene-2-carbonitrile | LC/MS (M + H) 450 |
| 40 | 3-methyl-4-[(3S,9aS)-8-{[4-(1H-tetrazol-1-yl)phenyl]acetyl}octahydropyrazino[2,1-c][1,4]oxazin-3-yl]thiophene-2-carbonitrile | LC/MS (M + H) 450 |
| 41 | 6-methyl-5-[(3R,9aS)-8-{[4-(1H-tetrazol-1-yl)phenyl]acetyl}octahydropyrazino[2,1-c][1,4]oxazin-3-yl]-2-benzofuran-1(3H)-one | LC/MS (M + H) 475 |

TABLE 2-continued

| Example No. | EXAMPLE STRUCTURE | Characterization MS and/or HNMR |
|---|---|---|
| 42 | 2-methyl-3-[(3R,9aS)-8-{[4-(1H-tetrazol-1-yl)phenyl]acetyl}octahydropyrazino[2,1-c][1,4]oxazin-3-yl]benzonitrile | LC/MS (M + H) 444 |
| 43 | 2-methyl-3-[(3S,9aS)-8-{[4-(1H-tetrazol-1-yl)phenyl]acetyl}octahydropyrazino[2,1-c][1,4]oxazin-3-yl]benzonitrile | LC/MS (M + H) 444 |
| 44 | 6-fluoro-2-methyl-3-[(3S,9aS)-8-{[5-(1H-tetrazol-1-yl)-2,3-dihydro-1H-inden-2-yl]carbonyl}octahydropyrazino[2,1-c][1,4]oxazin-3-yl]benzonitrile | LC/MS (M + H) 488 Mixture of two isomers at indane center |
| 45 | 6-fluoro-2-methyl-3-[(3R,9aS)-8-{2-[4-(1H-tetrazol-1-yl)phenyl]propanoyl}octahydropyrazino[2,1-c][1,4]oxazin-3-yl]benzonitrile | LC/MS (M + H) 476 Mixture of two isomers at carbon alpha to carbonyl |

TABLE 2-continued

| Example No. | EXAMPLE STRUCTURE | Characterization MS and/or HNMR |
|---|---|---|
| 46 | 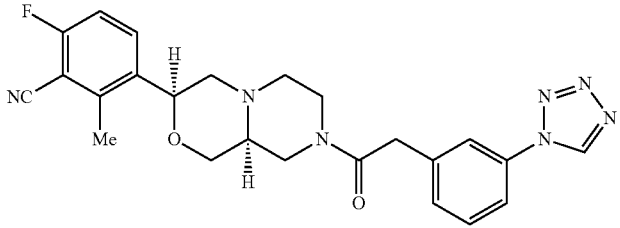 [SMILES: Cc1c([C@H]2CN3CCN(C(=O)Cc4cccc(-n5cnnn5)c4)C[C@H]3CO2)ccc(F)c1C#N]<br>6-fluoro-2-methyl-3-[(3S,9aS)-8-{[3-(1H-tetrazol-1-yl)phenyl]acetyl}octahydropyrazino[2,1-c][1,4]oxazin-3-yl]benzonitrile | LC/MS (M + H) 462 |
| 47 | 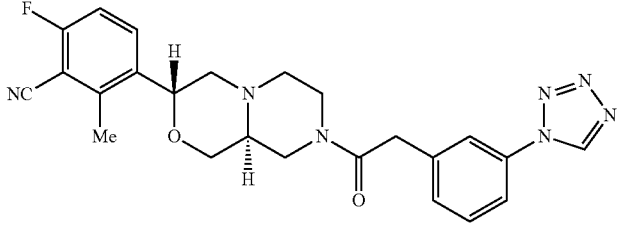 [SMILES: Cc1c([C@@H]2CN3CCN(C(=O)Cc4cccc(-n5cnnn5)c4)C[C@H]3CO2)ccc(F)c1C#N]<br>6-fluoro-2-methyl-3-[(3R,9aS)-8-{[3-(1H-tetrazol-1-yl)phenyl]acetyl}octahydropyrazino[2,1-c][1,4]oxazin-3-yl]benzonitrile | LC/MS (M + H) 462 |
| 48 | 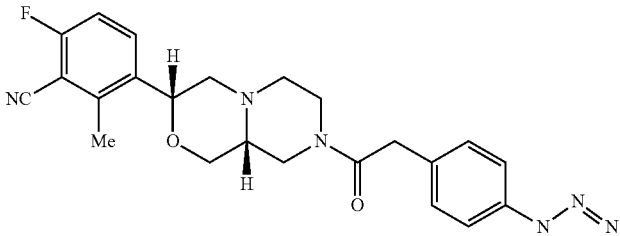<br>6-fluoro-2-methyl-3-[(3R,9aR)-8-{[3-(1H-tetrazol-1-yl)phenyl]acetyl}octahydropyrazino[2,1-c][1,4]oxazin-3-yl]benzonitrile | LC/MS (M + H) 462 |
| 49 | 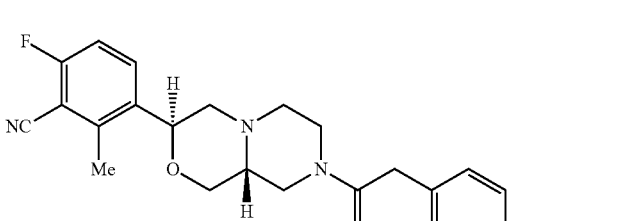<br>6-fluoro-2-methyl-3-[(3S,9aR)-8-{[3-(1H-tetrazol-1-yl)phenyl]acetyl}octahydropyrazino[2,1-c][1,4]oxazin-3-yl]benzonitrile | LC/MS (M + H) 462 |

| Example No. | EXAMPLE STRUCTURE | Characterization MS and/or HNMR |
|---|---|---|
| 50 | 4-methyl-5-(9-{[4-(1H-tetrazol-1-yl)phenyl]acetyl}octahydro-1H-[1,4]oxazino[4,3-a][1,4]diazepin-3-yl)-2-benzofuran-1(3H)-one | LC/MS (M + H) 489<br>Mixture of isomers |
| 51 | 4-methyl-5-(8-{[4-(1H-tetrazol-1-yl)phenyl]acetyl}octahydro-1H-[1,4]oxazino[4,3-a][1,4]diazepin-3-yl)-2-benzofuran-1(3H)-one | LC/MS (M + H) 489<br>Mixture of isomers |
| 52 | 3-[(3R,9aS)-8-{[2,6-difluoro-4-(1H-tetrazol-1-yl)phenyl]acetyl}octahydropyrazino[2,1-c][1,4]oxazin-3-yl]-6-fluoro-2-methylbenzonitrile | LC/MS (M + H) 498 |
| 53 | 3-[(3R,9aR)-8-{[2,6-difluoro-4-(1H-tetrazol-1-yl)phenyl]acetyl}octahydropyrazino[2,1-c][1,4]oxazin-3-yl]-6-fluoro-2-methylbenzonitrile | LC/MS (M + H) 498 |

| Example No. | EXAMPLE STRUCTURE | Characterization MS and/or HNMR |
|---|---|---|
| 54 | 3-[(3R,9aR)-8-{[2,5-difluoro-4-(1H-tetrazol-1-yl)phenyl]acetyl}octahydropyrazino[2,1-c][1,4]oxazin-3-yl]-6-fluoro-2-methylbenzonitrile | LC/MS (M + H) 498 |
| 55 | 3-[(3R,9aS)-8-{[2,5-difluoro-4-(1H-tetrazol-1-yl)phenyl]acetyl}octahydropyrazino[2,1-c][1,4]oxazin-3-yl]-6-fluoro-2-methylbenzonitrile | LC/MS (M + H) 498 |
| 56 | 6-fluoro-2-methyl-3-[(3R,9aR)-8-{[3-(1H-tetrazol-1-yl)phenyl]acetyl}octahydropyrazino[2,1-c][1,4]oxazin-3-yl]benzonitrile | LC/MS (M + H) 462 |
| 57 | 6-fluoro-2-methyl-3-[(3S,9aR)-8-{[3-(1H-tetrazol-1-yl)phenyl]acetyl}octahydropyrazino[2,1-c][1,4]oxazin-3-yl]benzonitrile | LC/MS (M + H) 462 |

TABLE 2-continued

| Example No. | EXAMPLE STRUCTURE | Characterization MS and/or HNMR |
|---|---|---|
| 58 | 6-fluoro-3-[(3S,9aR)-8-{[2-fluoro-5-(1H-tetrazol-1-yl)phenyl]acetyl}octahydropyrazino[2,1-c][1,4]oxazin-3-yl]-2-methylbenzonitrile | LC/MS (M + H) 480 |
| 59 | 6-fluoro-3-[(3R,9aR)-8-{[2-fluoro-5-(1H-tetrazol-1-yl)phenyl]acetyl}octahydropyrazino[2,1-c][1,4]oxazin-3-yl]-2-methylbenzonitrile | LC/MS (M + H) 480 |
| 60 | 6-fluoro-2-methyl-3-[(3R,9aR)-8-{[2-methyl-3-(1H-tetrazol-1-yl)phenyl]acetyl}octahydropyrazino[2,1-c][1,4]oxazin-3-yl]benzonitrile | LC/MS (M + H) 476 |
| 61 | 6-fluoro-2-methyl-3-[(3S,9aR)-8-{[2-methyl-3-(1H-tetrazol-1-yl)phenyl]acetyl}octahydropyrazino[2,1-c][1,4]oxazin-3-yl]benzonitrile | LC/MS (M + H) 476 |

TABLE 2-continued

| Example No. | EXAMPLE STRUCTURE | Characterization MS and/or HNMR |
|---|---|---|
| 62 | 6-methoxy-2-methyl-3-[(3S,9aS)-8-{[5-(1H-tetrazol-1-yl)-2,3-dihydro-1H-inden-1-yl]carbonyl}octahydropyrazino[2,1-c][1,4]oxazin-3-yl]benzonitrile | LC/MS (M + H) 500 Mixture of two diastereomers at indane center |
| 63 | 6-methoxy-2-methyl-3-[(3R,9aS)-8-{[5-(1H-tetrazol-1-yl)-2,3-dihydro-1H-inden-1-yl]carbonyl}octahydropyrazino[2,1-c][1,4]oxazin-3-yl]benzonitrile | LC/MS (M + H) 500 Mixture of two diastereomers at indane center |
| 64 | 2-methoxy-4-[(3R,9aR)-8-{[5-(1H-tetrazol-1-yl)-2,3-dihydro-1H-inden-1-yl]carbonyl}octahydropyrazino[2,1-c][1,4]oxazin-3-yl]benzonitrile | LC/MS (M + H) 486 Mixture of two diastereomers at indane center |
| 65 | 2-methoxy-4-[(3R,9aS)-8-{[5-(1H-tetrazol-1-yl)-2,3-dihydro-1H-inden-1-yl]carbonyl}octahydropyrazino[2,1-c][1,4]oxazin-3-yl]benzonitrile | LC/MS (M + H) 486 Mixture of two diastereomers at indane center |

TABLE 2-continued

| Example No. | EXAMPLE STRUCTURE | Characterization MS and/or HNMR |
|---|---|---|
| 66 | 2-methoxy-4-[(3S,9aS)-8-{[5-(1H-tetrazol-1-yl)-2,3-dihydro-1H-inden-1-yl]carbonyl}octahydropyrazino[2,1-c][1,4]oxazin-3-yl]benzonitrile | LC/MS (M + H) 486 Mixture of two diastereomers at indane center |
| 67 | 3-[(3R,9aS)-8-{[2-cyano-4-(1H-tetrazol-1-yl)phenyl]acetyl}octahydropyrazino[2,1-c][1,4]oxazin-3-yl]-6-fluoro-2-methylbenzonitrile | LC/MS (M + H) 487 |
| 68 | 3-[(3R,9aR)-8-{[2-cyano-4-(1H-tetrazol-1-yl)phenyl]acetyl}octahydropyrazino[2,1-c][1,4]oxazin-3-yl]-6-fluoro-2-methylbenzonitrile | LC/MS (M + H) 487 |
| 69 | 3-[(3R,9aR)-8-{[2-chloro-4-(1H-tetrazol-1-yl)phenyl]acetyl}octahydropyrazino[2,1-c][1,4]oxazin-3-yl]-6-fluoro-2-methylbenzonitrile | LC/MS (M + H) 496 |

TABLE 2-continued

| Example No. | EXAMPLE STRUCTURE | Characterization MS and/or HNMR |
|---|---|---|
| 70 | 3-[(3R,9aS)-8-{[2-chloro-4-(1H-tetrazol-1-yl)phenyl]acetyl}octahydropyrazino[2,1-c][1,4]oxazin-3-yl]-6-fluoro-2-methylbenzonitrile | LC/MS (M + H) 496 |
| 71 | 4-methyl-5-[(3S,9aS)-8-{3-[3-(1H-tetrazol-1-yl)phenyl]propanoyl}octahydropyrazino[2,1-c][1,4]oxazin-3-yl]-2-benzofuran-1(3H)-one | LC/MS (M + H) 489 |
| 72 | 6-fluoro-2-methyl-3-[(3R,9aS)-8-{3-[3-(1H-tetrazol-1-yl)phenyl]propanoyl}octahydropyrazino[2,1-c][1,4]oxazin-3-yl]benzonitrile | LC/MS (M + H) 476 |
| 73 | 6-fluoro-2-methyl-3-[(3S,9aS)-8-{3-[3-(1H-tetrazol-1-yl)phenyl]propanoyl}octahydropyrazino[2,1-c][1,4]oxazin-3-yl]benzonitrile | LC/MS (M + H) 476 |

TABLE 2-continued

| Example No. | EXAMPLE STRUCTURE | Characterization MS and/or HNMR |
|---|---|---|
| 74 | 6-fluoro-2-methyl-3-[(3S,9aS)-8-{[5-(1H-tetrazol-1-yl)-2,3-dihydro-1H-inden-2-yl]carbonyl}octahydropyrazino[2,1-c][1,4]oxazin-3-yl]benzonitrile | LC/MS (M + H) 476 Mixture of two diastereomers at indane center |
| 75 | (3S,9aS)-3-(4-methyl-2,1,3-benzoxadiazol-5-yl)-8-{[4-(1H-tetrazol-1-yl)phenyl]acetyl}octahydropyrazino[2,1-c][1,4]oxazine | LC/MS (M + H) 461 |
| 76 | (3R,9aS)-3-(4-methyl-2,1,3-benzoxadiazol-5-yl)-8-{[4-(1H-tetrazol-1-yl)phenyl]acetyl}octahydropyrazino[2,1-c][1,4]oxazine | LC/MS (M + H) 461 |
| 77 | (3R,9aS)-3-(2,1,3-benzoxadiazol-5-yl)-8-{[4-(1H-tetrazol-1-yl)phenyl]acetyl}octahydropyrazino[2,1-c][1,4]oxazine | LC/MS (M + H) 447 |

| Example No. | EXAMPLE STRUCTURE | Characterization MS and/or HNMR |
|---|---|---|
| 78 | (3R,9aS)-3-(2,1,3-benzoxadiazol-5-yl)-8-{[5-(1H-tetrazol-1-yl)-2,3-dihydro-1H-inden-1-yl]carbonyl}octahydropyrazino[2,1-c][1,4]oxazine | LC/MS (M + H) 473 Mixture of two diastereomers at indane center |
| 79 | 5-[(3R,9aR)-8-{[2,6-difluoro-4-(1H-tetrazol-1-yl)phenyl]acetyl}octahydropyrazino[2,1-c][1,4]oxazin-3-yl]-4-methyl-2-benzofuran-1(3H)-one | LC/MS (M + H) 511 |
| 80 | (3R,9aS)-8-{[5-(1H-tetrazol-1-yl)-2,3-dihydro-1H-inden-1-yl]carbonyl}-3-[3-(1H-tetrazol-1-yl)phenyl]octahydropyrazino[2,1-c][1,4]oxazine | LC/MS (M + H) 499 Single isomer with unknown absolute stereochemistry at indane center; faster eluting isomer from SFC chiral HPLC separation with Chiralcel OJ column |
| 81 | 4-methyl-5-[(3S,9aS)-8-{[5-(1H-tetrazol-1-yl)-2,3-dihydro-1H-inden-1-yl]carbonyl}octahydropyrazino[2,1-c][1,4]oxazin-3-yl]-2-benzofuran-1(3H)-one | LC/MS (M + H) 501 Single isomer with unknown absolute stereochemistry at indane center; slower eluting isomer from SFC chiral HPLC separation with Chiralpak AS column |

TABLE 2-continued

| Example No. | EXAMPLE STRUCTURE | Characterization MS and/or HNMR |
|---|---|---|
| 82 | 3-methyl-4-[(3R,9aS)-8-{[5-(1H-tetrazol-1-yl)-2,3-dihydro-1H-inden-1-yl]carbonyl}octahydropyrazino[2,1-c][1,4]oxazin-3-yl]thiophene-2-carbonitrile | LC/MS (M + H) 476 Single isomer with unknown absolute stereochemistry at indane center; faster eluting isomer from SFC chiral HPLC separation with Chiralpak AS column |
| 83 | 3-methyl-4-[(3R,9aS)-8-{[5-(1H-tetrazol-1-yl)-2,3-dihydro-1H-inden-1-yl]carbonyl}octahydropyrazino[2,1-c][1,4]oxazin-3-yl]thiophene-2-carbonitrile | LC/MS (M + H) 476 Single isomer with unknown absolute stereochemistry at indane center; slower eluting isomer from SFC chiral HPLC separation with Chiralpak AS column |
| 84 | (3R)-3-methyl-6-[(3R,9aS)-8-{[5-(1H-tetrazol-1-yl)-2,3-dihydro-1H-inden-1-yl]carbonyl}octahydropyrazino[2,1-c][1,4]oxazin-3-yl]-3,4-dihydro-1H-isochromen-1-one | LC/MS 515 (M + H)+ Single isomer with unknown absolute stereochemistry at indane center; OD column, faster eluting isomer |
| 85 | (3R)-3-methyl-6-[(3R,9aS)-8-{[5-(1H-tetrazol-1-yl)-2,3-dihydro-1H-inden-1-yl]carbonyl}octahydropyrazino[2,1-c][1,4]oxazin-3-yl]-3,4-dihydro-1H-isochromen-1-one | LC/MS 515 (M + H)+ Single isomer with unknown absolute stereochemistry at indane center; OD column, slower eluting isomer |

TABLE 2-continued

| Example No. | EXAMPLE STRUCTURE | Characterization MS and/or HNMR |
|---|---|---|
| 86 | 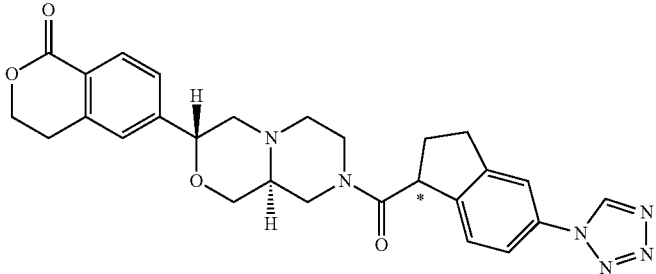 [SMILES: O=C1OCCc2cc([C@@H]3CN4CCN(C(=O)C5CCc6cc(-n7cnnn7)ccc65)C[C@H]4CO3)ccc21]<br>6-[(3R,9aS)-8-{[5-(1H-tetrazol-1-yl)-2,3-dihydro-1H-inden-1-yl]carbonyl}octahydropyrazino[2,1-c][1,4]oxazin-3-yl]-3,4-dihydro-1H-isochromen-1-one | LC/MS 501 (M + H)+ Single isomer with unknown absolute stereochemistry at indane center; Chiralcel OJ HPLC column, faster eluting isomer |
| 87 | 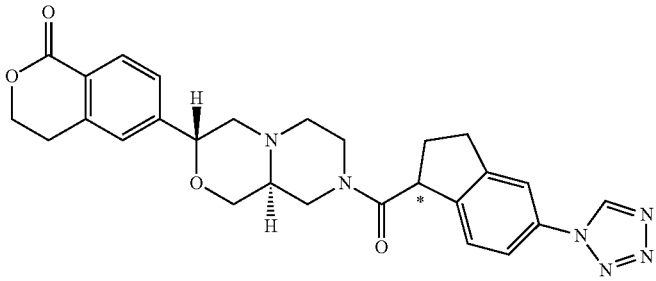 [SMILES: O=C1OCCc2cc([C@@H]3CN4CCN(C(=O)C5CCc6cc(-n7cnnn7)ccc65)C[C@H]4CO3)ccc21]<br>6-[(3R,9aS)-8-{[5-(1H-tetrazol-1-yl)-2,3-dihydro-1H-inden-1-yl]carbonyl}octahydropyrazino[2,1-c][1,4]oxazin-3-yl]-3,4-dihydro-1H-isochromen-1-one | LC/MS 501 (M + H)+ Single isomer with unknown absolute stereochemistry at indane center; Chiralcel OJ HPLC column, slower eluting isomer |
| 88 | 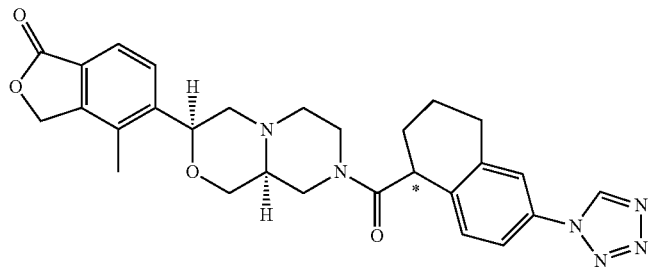 [SMILES: Cc1c([C@H]2CN3CCN(C(=O)C4CCCc5cc(-n6cnnn6)ccc54)C[C@H]3CO2)ccc2c1COC2=O]<br>4-methyl-5-[(3S,9aS)-8-{[6-(1H-tetrazol-1-yl)-1,2,3,4-tetrahydronaphthalen-1-yl]carbonyl}octahydropyrazino[2,1-c][1,4]oxazin-3-yl]-2-benzofuran-1(3H)-one | LC/MS 515 (M + H)+ Single isomer with unknown absolute stereochemistry at tetrahydronaphthalene center; SFC on AS HPLC column, slower eluting isomer |
| 89 | 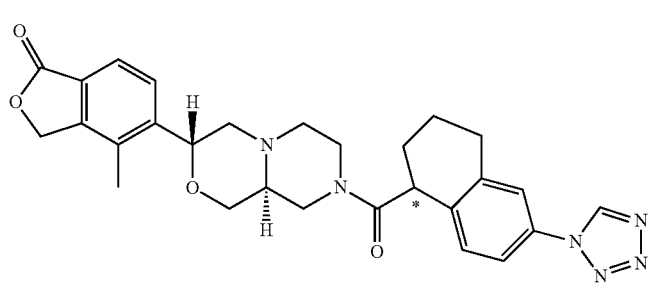 [SMILES: Cc1c([C@@H]2CN3CCN(C(=O)C4CCCc5cc(-n6cnnn6)ccc54)C[C@H]3CO2)ccc2c1COC2=O]<br>4-methyl-5-[(3R,9aS)-8-{[6-(1H-tetrazol-1-yl)-1,2,3,4-tetrahydronaphthalen-1-yl]carbonyl}octahydropyrazino[2,1-c][1,4]oxazin-3-yl]-2-benzofuran-1(3H)-one | LC/MS 515 (M + H)+ Single isomer with unknown absolute stereochemistry at tetrahydronaphthalene center; SFC on AS HPLC column, slower eluting isomer |

TABLE 2-continued

| Example No. | EXAMPLE STRUCTURE | Characterization MS and/or HNMR |
|---|---|---|
| 90 | 6-[(3R,9aS)-8-{[6-(1H-tetrazol-1-yl)-1,2,3,4-tetrahydronaphthalen-1-yl]carbonyl}octahydropyrazino[2,1-c][1,4]oxazin-3-yl]-3,4-dihydro-1H-isochromen-1-one | LC/MS 515 (M + H)+ Single isomer with unknown absolute stereochemistry at tetrahydronaphthalene center; SFC on AS HPLC column, faster eluting isomer |
| 91 | 6-fluoro-2-methyl-3-[(3R,9aS)-8-{[6-(1H-tetrazol-1-yl)-1,2,3,4-tetrahydronaphthalen-1-yl]carbonyl}octahydropyrazino[2,1-c][1,4]oxazin-3-yl]benzonitrile | LC/MS 502 (M + H)+ Single isomer with unknown absolute stereochemistry at tetrahydronaphthalene center; SFC HPLC on Chiralcel OD-H column, faster eluting isomer |
| 92 | 6-fluoro-2-methyl-3-[(3R,9aS)-8-{[6-(1H-tetrazol-1-yl)-1,2,3,4-tetrahydronaphthalen-1-yl]carbonyl}octahydropyrazino[2,1-c][1,4]oxazin-3-yl]benzonitrile | LC/MS 502 (M + H)+ Single isomer with unknown absolute stereochemistry at tetrahydronaphthalene center; SFC HPLC on Chiralcel OD-H column, slower eluting isomer |
| 93 | 6-fluoro-2-methyl-3-[(3S,9aS)-8-{[6-(1H-tetrazol-1-yl)-1,2,3,4-tetrahydronaphthalen-1-yl]carbonyl}octahydropyrazino[2,1-c][1,4]oxazin-3-yl]benzonitrile | LC/MS 502 (M + H)+ Single isomer with unknown absolute stereochemistry at tetrahydronaphthalene center; SFC HPLC on Chiralpak AD column, faster eluting isomer |

TABLE 2-continued

| Example No. | Example Structure | Characterization MS and/or HNMR |
|---|---|---|
| 94 | 6-fluoro-2-methyl-3-[(3R,9aR)-8-{[6-(1H-tetrazol-1-yl)-1,2,3,4-tetrahydronaphthalen-1-yl]carbonyl}octahydropyrazino[2,1-c][1,4]oxazin-3-yl]benzonitrile | LC/MS 502 (M + H)+ Single isomer with unknown absolute stereochemistry at tetrahydronaphthalene center; SFC HPLC on Chiralcel OJ column, faster eluting |
| 95 | 6-fluoro-2-methyl-3-[(3S,9aR)-8-{[6-(1H-tetrazol-1-yl)-1,2,3,4-tetrahydronaphthalen-1-yl]carbonyl}octahydropyrazino[2,1-c][1,4]oxazin-3-yl]benzonitrile | LC/MS 502 (M + H)+ Single isomer with unknown absolute stereochemistry at tetrahydronaphthalene center; SFC HPLC on Chiralcel OD column, faster eluting |
| 96 | 3-methyl-4-[(3R,9aS)-8-{[6-(1H-tetrazol-1-yl)-1,2,3,4-tetrahydronaphthalen-1-yl]carbonyl}octahydropyrazino[2,1-c][1,4]oxazin-3-yl]thiophene-2-carbonitrile | LC/MS 490 (M + H)+ Single isomer with unknown absolute stereochemistry at tetrahydronaphthalene center; SFC HPLC on Chiralcel OD column, faster eluting |
| 97 | 3-methyl-4-[(3S,9aS)-8-{[6-(1H-tetrazol-1-yl)-1,2,3,4-tetrahydronaphthalen-1-yl]carbonyl}octahydropyrazino[2,1-c][1,4]oxazin-3-yl]thiophene-2-carbonitrile | LC/MS 490 (M + H)+ Single isomer with unknown absolute stereochemistry at tetrahydronaphthalene center; SFC HPLC on Chiralcel OD column, faster eluting |

TABLE 2-continued

| Example No. | EXAMPLE STRUCTURE | Characterization MS and/or HNMR |
|---|---|---|
| 98 | 6-fluoro-2-methyl-3-[(3S,9aS)-8-{[5-(1H-tetrazol-1-yl)-2,3-dihydro-1H-inden-1-yl]carbonyl}octahydropyrazino[2,1-c][1,4]oxazin-3-yl]benzonitrile | LC/MS 488 (M + H)+ Single isomer with unknown absolute stereochemistry at indane center; faster eluting isomer from SFC HPLC on Chiralpak AS column |

EXAMPLE 99

3-((3R,9aR)-8-(2-(4-(1H-tetrazol-1-yl)phenyl)acetyl) octahydro-1H-pyrazino[1,2-a]pyrazin-3-yl)-6-fluoro-2-methylbenzonitrile Step A: (3R,9aS)-tert-butyl 8-(2-(4-(1H-tetrazol-1-yl) phenyl)acetyl)-3-(3-cyano-4-fluoro-2-methylphenyl)hexahydro-1H-pyrazino[1,2-a]pyrazine-2(6H)-carboxylate: To a solution of (3R,9aS)-tert-butyl 3-(3-cyano-4-fluoro-2-methylphenyl)hexahydro-1H-pyrazino[1,2-a]pyrazine-2(6H)-carboxylate (21.4 mg, 0.057 mmol) and 2-(4-(1H-tetrazol-1-yl)phenyl)acetic acid (16.34 mg, 0.080 mmol) in DMF (1 mL) was added HATU (32.6 mg, 0.086 mmol) and diisopropylethylamine (29.9 µL, 0.171 mmol). The resulting solution was stirred at rt for 1 h. Ethyl acetate (10 mL) was added and the mixture was washed with sat. sodium bicarbonate three times, dried over sodium sulphate, concentrated and the residue was purified on TLC using 10% MeOH/DCM to give the title compound. (M+1)+: 561.30.

Step B: 3-((3R,9aR)-8-(2-(4-(1H-tetrazol-1-yl)phenyl) acetyl)octahydro-1H-pyrazino[1,2-a]pyrazin-3-yl)-6-fluoro-2-methylbenzonitrile: To the solution of (3R,9aS)-tert-butyl 8-(2-(4-(1H-tetrazol-1-yl)phenyl)acetyl)-3-(3-cyano-4-fluoro-2-methylphenyl)hexahydro-1H-pyrazino[1,2-a]pyrazine-2(6H)-carboxylate (32 mg, 0.057 mmol) in dichloromethane (1 mL) was added thioanisole (27 µL, 0.228 mmol) and trifluoroacetic acid (1 mL) at 0° C. and the resulting solution was stirred at rt for 1 h. After removing the volatiles, the residue was partitioned between methylene chloride and sat. sodium bicarbonate. The alkaline phase was extracted with methylene chloride twice, and the combined organic phase was dried over sodium sulphate, concentrated and the residue was purified on TLC using 10% MeOH/DCM to give the title product. (M+1)+: 461.24. ¹HNMR (500 MHz, CDCl₃) δ 9.030 (s, 1H), 7.870-7.812(m, 1H), 7.714-7.687(m, 2H), 7.495-7.478(m,2H), 7.058-7.025 (m, 1H), 4.632-4.537 (m, 1H), 4.189-3.750(m, 1H), 3.843 (S, 2H), 3.750-3.370(m, 1H), 3.126-2.815 (m, 2H), 2.891-2.730(m, 4H), 2.607(s, 3H), 2.219-2.018(m, 4H).

The Examples in Table 3 were prepared in an analogous fashion to that described for the synthesis of Example 99 from the appropriate amine and carboxylic acid Intermediates (prepared as described above).

TABLE 3

| EXAMPLE No. | EXAMPLE STRUCTURE | Characterization MS and/or HNMR↓ |
|---|---|---|
| 100 | 4-methyl-5-[(3S,9aR)-8-{[4-(1H-tetrazol-1-yl)phenyl]acetyl}octahydro-2H-pyrazino[1,2-a]pyrazin-3-yl]-2-benzofuran-1(3H)-one | LC/MS (M + H) 474 |

TABLE 3-continued

| EXAMPLE No. | EXAMPLE STRUCTURE | Characterization MS and/or HNMR↓ |
|---|---|---|
| 101 | 6-fluoro-2-methyl-3-[(3S,9aR)-8-{[4-(1H-tetrazol-1-yl)phenyl]acetyl}octahydro-2H-pyrazino[1,2-a]pyrazin-3-yl]benzonitrile | LC/MS (M + H) 461 |
| 102 | 3-[(3R,9aR)-8-{[2,6-difluoro-4-(1H-tetrazol-1-yl)phenyl]acetyl}octahydro-2H-pyrazino[1,2-a]pyrazin-3-yl]-6-fluoro-2-methylbenzonitrile | LC/MS (M + H) 497 |
| 103 | 3-[(3S,9aR)-8-{[2,6-difluoro-4-(1H-tetrazol-1-yl)phenyl]acetyl}octahydro-2H-pyrazino[1,2-a]pyrazin-3-yl]-6-fluoro-2-methylbenzonitrile | LC/MS (M + H) 497 |
| 104 | (3R)-3-methyl-6-[(3R,9aR)-8-{[4-(1H-tetrazol-1-yl)phenyl]acetyl}octahydro-2H-pyrazino[1,2-a]pyrazin-3-yl]-3,4-dihydro-1H-isochromen-1-one | LC/MS (M + H) 488 |

TABLE 3-continued

| EXAMPLE No. | EXAMPLE STRUCTURE | Characterization MS and/or HNMR↓ |
|---|---|---|
| 105 | 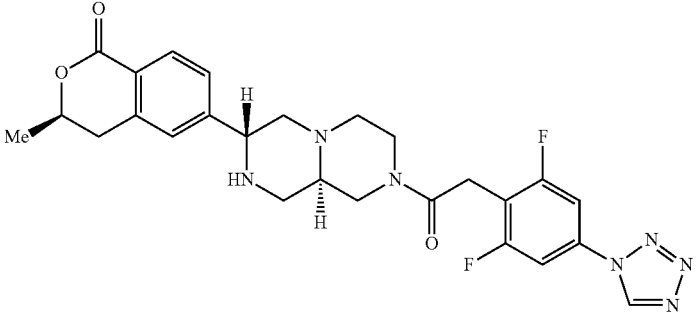<br>(3R)-6-[(3R,9aR)-8-{[2,6-difluoro-4-(1H-tetrazol-1-yl)phenyl]acetyl}octahydro-2H-pyrazino[1,2-a]pyrazin-3-yl]-3-methyl-3,4-dihydro-1H-isochromen-1-one | LC/MS (M + H) 524 |

The following Thallium Flux Assay and/or the Electrophysiology Assay were performed on each of the final product compounds in the Examples unless otherwise noted in an Example.

Thallium Flux Assay

Cell Culture Conditions—HEK293 cells stably expressing hROMK (hK$_{ir}$1.1) were grown at 37° C. in a 10% CO$_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 mL Calcium/Magnesium-free PBS. Add 5 mL of 1× trypsin (prepared in Ca/Mg Free PBS) to T-225 flask and return flask to 37° C./CO$_2$ incubator for 2-3 minutes. To dislodge the cell, gently bang the side of the flask with your hand. Triturate the cells completely and then transfer the cells to 25 mL complete media. Centrifuge at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)
FluxOR™ Reagent (Component A)
FluxOR™ Assay Buffer (Component B)—10× Concentrate
PowerLoad™ Concentrate (Component C)—100× Concentrate
Probenecid (Component D)—Lyophilized sample is kept at −20° C. Water soluble, 100× after solubilization in 1 mL water. Store at 4° C.
FluxOR™ Chloride-free Buffer (Component E)—5× Concentrate
Potassium sulfate (K$_2$SO$_4$) Concentrate (Component F)—125 mM in water. Store at 4° C.
Thallium sulfate (Tl$_2$SO$_4$) Concentrate (Component G)—50 mM in water. Store at 4° C.
DMSO (dimethyl sulfoxide, Component H)—1 mL (100%)

Reagent Preparation: FluxOR Working Solutions
1000× FluxOR™ Reagent: Reconstitute a vial of component A in 100 µl DMSO; Mix well; Store 10 µl aliquots at −20° C.
1× FluxOR™ Assay Buffer: Dilute Component B 10-fold with water; Adjust pH to 7.4 with Hepes/NaOH; Filter and store at 4° C.
Probenecid/Assay Buffer: 100 mL of 1× FluxOR™ Assay Buffer; 1 mL of reconstituted component D; Store at 4° C.
Loading Buffer (per microplate): 10 µl 1000× FluxOR™ Reagent; 100 µl component C; 10 mL Probenecid/Assay Buffer
Compound Buffer (per microplate): 20 mL Probenecid/Assay Buffer; 0.3 mM ouabain (10 mM ouabain in water can be stored in amber bottle/aluminum foil at room temperature); Test compound
1× FluxOR™ Chloride-Free Buffer: Prepare 1× working solution in water. Can be stored at room temperature
Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium/0.3 mM Potassium). Store at 4° C. when not in use. If kept sterile, this solution is good for months.

Assay Protocol—The ROMK channel functional thallium flux assay is performed in 384 wells, using the FLIPR-Tetra instrument. HEK-hKir1.1 cells are seeded in Poly-D-Lysine microplates and kept in a 37° C.-10% CO$_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer±test compound followed by 30 min incubation at ambient temperature, where the Thallium/Potassium stimulant is added to the microplate.

Step Protocol
1. Seed HEK-hKir1.1 cells (50 µl at 20,000 cells/well) in 384-well PDL coated Microplates
2. Allow cells to adhere overnight in humidified 37° C./10% CO$_2$ incubator
3. Completely remove cell growth media from microplate and replace with 25 µl loading buffer 4. Incubate Microplate at room temperature, protected form light, for 90 min
5. Remove loading buffer and replace with 25 μl 1× Assay Buffer±test compound.
6. Incubate microplate at room temperature, protected from light, for 30 min
7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation—The fluorescence intensity of wells containing 3 μM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 μM in this assay. Alternatively, the control could be another compound (outside the scope of Formula I) that has an $IC_{50}$ potency in this assay of less than 1 μM.

Electrophysiology Assay

Block of Kir1.1 (ROMK1) currents was examined by whole cell voltage clamp (Hamill et. al. Pfluegers Archives 391:85-100 (1981)) using the IonWorks Quattro automated electrophysiology platform (Molecular Devices, Sunnyvale, Calif.). Chinese hamster ovary cells stably expressing Kir1.1 channels were maintained in T-75 flasks in cell culture media in a humidified 10% $CO_2$ incubator at 37° C. Prior to an experiment, Kir1.1 expression was induced by overnight incubation with 1 mM sodium butyrate. On the day of the experiment, cells were dissociated with 2.5 mL of Versene (Invitrogen 15040-066) for approximately 6 min at 37° C. and suspended in 10 mL of bath solution containing (in mM): 150 NaCl, 10 KCl, 2.7 $CaCl_2$, 0.5 $MgCl_2$, 5 HEPES, pH 7.4. After centrifugation, the cell pellet was resuspended in approximately 4.0 mL of bath solution and placed in the IonWorks instrument. The intracellular solution consisted of (in mM): 80 K gluconate, 40 KCl, 20 KF, 3.2 $MgCl_2$, 3 EGTA, 5 Hepes, pH 7.4. Electrical access to the cytoplasm was achieved by perforation in 0.13 mg/mL amphotericin B for 4 min. Amphotericin B (Sigma A-4888) was prepared as a 40 mg/mL solution in DMSO. Voltage protocols and current recordings were performed using the IonWorks HT software/hardware system. Currents were sampled at 1 kHz. No correction for liquid junction potentials was used. The test pulse, consisting of a 100 ms step to 0 mV from a holding potential of −70 mV, followed by a 100 ms voltage ramp from −70 mV to +70 mV, was applied before and after a 6 min compound incubation period. Test compounds were prepared by diluting DMSO stock solutions into the bath solution at 3× the final concentration and placed in the instrument in 96-well polypropylene plates. Current amplitudes were measured using the IonWorks software. To assess compound potency, the fractional block during the voltage step to 0 mV was calculated in Microsoft Excel (Microsoft, Redmond, Calif.), and dose-response curves were fitted with Igor Pro 4.0 (WaveMetrics, Lake Oswego, Oreg.). Normally, a control compound is included to support that the assay is giving consistent results compared to previous measurements, although the control is not required to obtain the results for the test compounds. The control can be any compound of Formulas I-V of the present invention, preferably with an $IC_{50}$ potency of less than 1 μM in this assay. Alternatively, the control could be another compound (outside the scope of Formulas I-V) that has an $IC_{50}$ potency in this assay of less than 1 μM.

Data collected for compounds in the Examples of the present invention using the Thallium Flux Assay and the Electrophysiology Assay are shown in Table 4 below. All of the tested final product compounds in the Examples (diastereomeric mixtures and individual diastereomers) had $IC_{50}$ potencies less than 1 μM in one or both of the Thallium Flux Assay and the Electrophysiology Assay.

TABLE 4

| EXAMPLE No. | Thallium Flux $IC_{50}$ (μM) | Electrophysiology $IC_{50}$ (μM) |
| --- | --- | --- |
| 1A | 0.03 | 0.10 |
| 1B |  | 0.33 |
| 2A | 0.17 | 0.14 |
| 2B | 0.29 | 0.15 |
| 3 |  | 0.18 |
| 4 |  | 0.19 |
| 5 |  | 0.12 |
| 6 |  | 0.16 |
| 7 |  | 0.17 |
| 8 |  | 0.14 |
| 9 |  | 0.14 |
| 10 | 0.13 | 0.09 |
| 11 |  | 0.34 |
| 12 |  | 0.25 |
| 13 | 0.12 | 0.15 |
| 14 | 0.11 | 0.14 |
| 15 | 0.05 | 0.08 |
| 16 |  | 0.18 |
| 17 |  | 0.16 |
| 18 | 0.25 | 0.11 |
| 19 | 0.17 | 0.07 |
| 20 | 0.58 | 0.06 |
| 21 | 0.10 | 0.10 |
| 22 | 0.14 | 0.13 |
| 23 | 0.07 | 0.07 |
| 24 | 0.06 | 0.08 |
| 25 | 0.15 | 0.20 |
| 26 | 0.14 | 0.26 |
| 27 | 0.18 | 0.39 |
| 28 | 0.33 | 0.13 |
| 29 | 0.30 | 0.13 |
| 30 | 0.10 | 0.11 |
| 31 | 0.57 | 0.12 |
| 32 | 0.10 | 0.14 |
| 33 | 0.11 | 0.13 |
| 34 | 0.19 | 0.20 |
| 35 | 0.76 | 0.26 |
| 36 | 0.73 | 0.31 |
| 37 | 0.20 | 0.32 |
| 38 | 0.11 | 0.18 |
| 39 | 0.06 | 0.06 |
| 40 | 0.09 | 0.08 |
| 41 | 0.32 | 0.09 |
| 42 | 0.09 | 0.13 |
| 43 | 0.14 | 0.17 |
| 44 | 0.37 | 0.16 |
| 45 | 0.33 | 0.21 |

TABLE 4-continued

| EXAMPLE No. | Thallium Flux IC$_{50}$ (µM) | Electrophysiology IC$_{50}$ (µM) |
| --- | --- | --- |
| 46 | 0.24 | 0.14 |
| 47 | 0.30 | 0.09 |
| 48 | 0.28 | 0.16 |
| 49 | 0.20 | 0.14 |
| 50 | 0.74 | 0.18 |
| 51 | 0.69 | 0.67 |
| 52 | 0.17 | 0.07 |
| 53 | 0.18 | 0.11 |
| 54 | 0.10 | 0.10 |
| 55 | 0.13 | 0.10 |
| 56 | 0.20 | 0.06 |
| 57 | 0.14 | 0.05 |
| 58 | 0.18 | 0.08 |
| 59 | 0.36 | 0.14 |
| 60 | 0.44 | 0.42 |
| 61 | 0.34 | 0.24 |
| 62 | 0.20 | 0.65 |
| 63 | 0.18 | 0.45 |
| 64 | 0.27 | 0.21 |
| 65 | 0.40 | 0.35 |
| 66 | 0.37 | 0.49 |
| 67 | 0.13 | 0.17 |
| 68 | 0.21 | 0.12 |
| 69 | 0.10 | 0.11 |
| 70 | 0.25 | 0.16 |
| 71 | 0.49 | |
| 72 | 0.27 | |
| 73 | 0.14 | |
| 74 | 0.37 | 0.16 |
| 75 | 0.21 | 0.12 |
| 76 | 0.22 | 0.22 |
| 77 | 0.15 | 0.05 |
| 78 | 0.21 | 0.10 |
| 79 | 0.26 | 0.19 |
| 80 | 0.13 | 0.28 |
| 81 | 0.23 | 0.26 |
| 82 | 0.33 | 0.11 |
| 83 | 0.14 | 0.09 |
| 84 | 0.40 | 0.24 |
| 85 | 0.15 | 0.20 |
| 86 | 0.09 | 0.34 |
| 87 | 0.08 | 0.20 |
| 88 | 0.38 | 0.46 |
| 89 | 0.49 | 0.46 |
| 90 | 0.43 | 0.26 |
| 91 | 0.19 | 0.39 |
| 92 | 0.74 | 0.30 |
| 93 | 0.27 | 0.39 |
| 94 | 0.52 | 0.36 |
| 95 | 0.58 | 0.32 |
| 96 | 0.46 | 0.19 |
| 97 | 0.62 | 0.28 |
| 98 | 0.17 | 0.14 |
| 99 | 0.07 | 0.18 |
| 100 | 0.43 | 0.25 |
| 101 | 0.06 | 0.05 |
| 102 | 0.15 | 0.16 |
| 103 | 0.11 | 0.08 |
| 104 | 0.29 | 0.38 |
| 105 | 0.36 | 0.18 |

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula I:

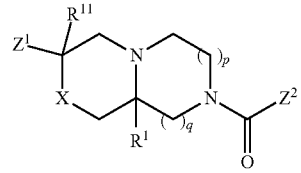

or a pharmaceutically acceptable salt thereof wherein:
X is O or NH;
p is an integer selected from 1 (one) or 2 (two), and q is an integer selected from 1 (one) or 2 (two), provided that only one of p and q can be 2;
Z$^1$ is

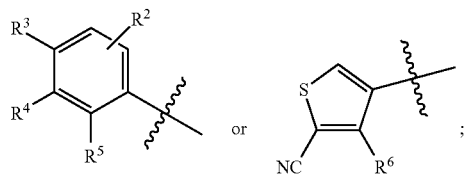

R$^1$ is —H or —C$_{1-4}$alkyl;
R$^2$ is —H, —F, —Cl, —C$_{1-6}$alkyl, —C$_{3-6}$cycloalkyl or —OC$_{1-4}$alkyl;
R$^3$ is —H, —F, —Cl, —CN, —C$_{1-6}$alkyl, —C$_{3-6}$cycloalkyl, OC$_{1-4}$alkyl or N-tetrazolyl optionally substituted with —CH$_3$;
R$^4$ is —H, —F, —Cl, —CN, —C$_{1-6}$alkyl, —C$_{3-6}$cycloalkyl, —OC$_{1-4}$alkyl or N-tetrazolyl optionally substituted with —CH$_3$;
or R$^3$ and R$^4$ are joined together with the phenyl ring to which they are attached to form a bicyclic ring system that is:

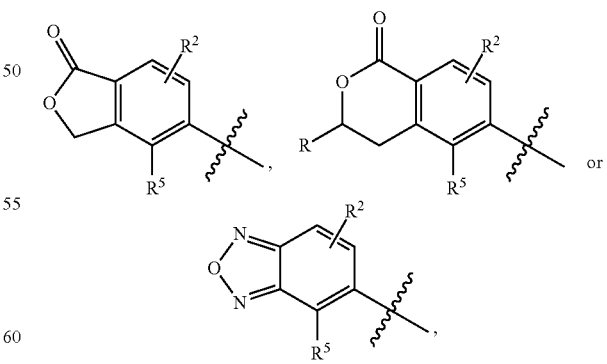

wherein R is —H or —C$_{1-4}$alkyl;
R$^5$ is —H, —F, —Cl, —CN, —C$_{1-4}$alkyl, —C$_{3-6}$cycloalkyl or —OC$_{1-4}$alkyl;
provided that when R$^3$ and R$^4$ are not joined together, then either (a) one of $R^3$, $R^4$ or $R^5$ is —CN and the others are not —CN, or (b) one of $R^3$ or $R^4$ is N-tetrazolyl optionally substituted with —CH$_3$ and the other is not N-tetrazolyl optionally substituted with —CH$_3$;

$R^6$ is —H or —C$_{1-6}$alkyl;

$Z^2$ is

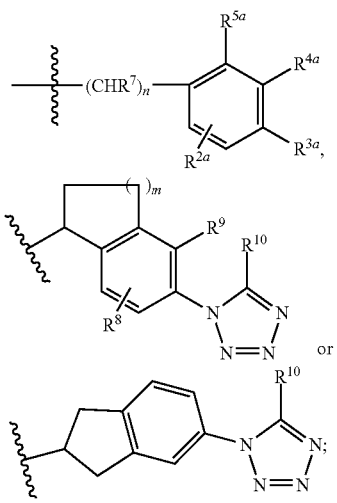

n is an integer selected from 1 (one) or 2 (two);

m is an integer selected from 1 (one) or 2 (two);

$R^{2a}$ is —H, —F, —Cl, —C$_{1-6}$alkyl, —C$_{3-6}$cycloalkyl or —OC$_{1-4}$alkyl;

$R^{3a}$ is —H, —F, —Cl, —CN, —C$_{1-6}$alkyl, —C$_{3-6}$cycloalkyl, —OC$_{1-4}$alkyl or N-tetrazolyl optionally substituted with —CH$_3$;

$R^{4a}$ is —H, —F, —Cl, —CN, —C$_{1-6}$alkyl, —C$_{3-6}$cycloalkyl, —OC$_{1-4}$alkyl or N-tetrazolyl optionally substituted with —CH$_3$;

or $R^{3a}$ and $R^{4a}$ are joined together with the phenyl ring to which they are attached to form:

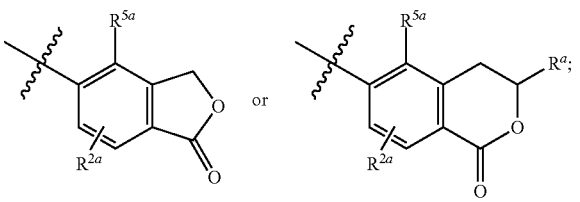

wherein $R^a$ is —H or —C$_{1-4}$alkyl;

$R^{5a}$ is —H, —F, —Cl, —CN, —C$_{1-4}$alkyl, —C$_{3-6}$cycloalkyl or —OC$_{1-4}$alkyl;

provided that when $R^{3a}$ and $R^{4a}$ are not joined together, then either (a) only one of $R^{3a}$, $R^{4a}$ or $R^{5a}$ is —CN and the others are not —CN, or (b) only one of $R^{3a}$ or $R^{4a}$ is N-tetrazolyl optionally substituted with —CH$_3$ and the other is not N-tetrazolyl optionally substituted with —CH$_3$;

$R^7$ is independently at each occurrence —H or —C$_{1-3}$alkyl;

$R^8$ is —H, —F, —Cl, —C$_{1-6}$alkyl, —C$_{3-6}$cycloalkyl or —OC$_{1-4}$alkyl;

$R^9$ is —H, —F, —Cl, —CN, —C$_{1-6}$alkyl, —C$_{3-6}$cycloalkyl or —OC$_{1-4}$alkyl;

$R^{10}$ is —H or —CH$_3$; and $R^{11}$ is —H or —CH$_3$.

2. The compound of claim 1 or a pharmaceutically acceptable salt thereof wherein $R^1$ is —H or —CH$_3$; and $R^7$ is —H or —CH$_3$.

3. The compound of claim 2 having structural Formula II, III, IV or V:

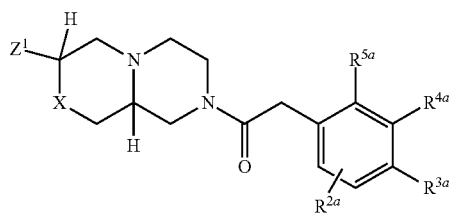

wherein one of $R^{3a}$ or $R^{4a}$ is N-tetrazolyl optionally substituted with ——CH$_3$ and the other is not N-tetrazolyl optionally substituted with ——CH$_3$;

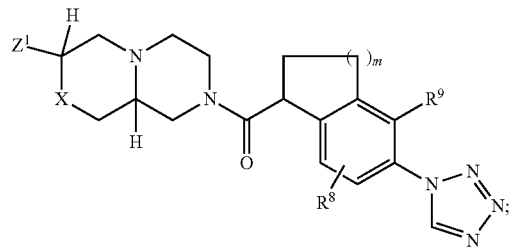

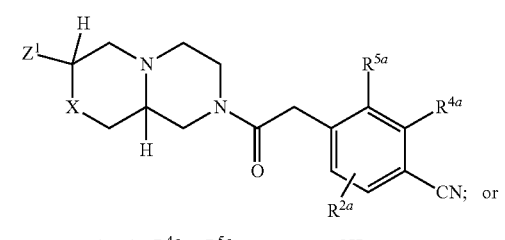

wherein $R^{4a}$ or $R^{5a}$ are not ——CH$_3$

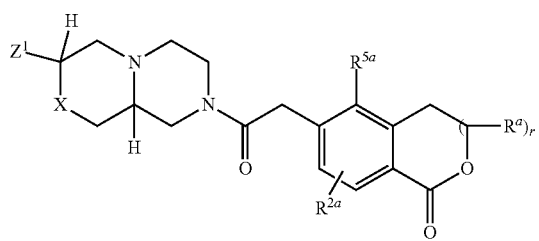

wherein r is an integer selected from 0 or 1 or a pharmaceutically acceptable salt thereof.

4. The compound of claim 1 wherein $Z^1$ is

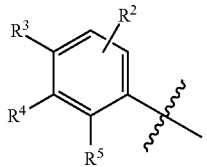

or a pharmaceutically acceptable salt thereof.

5. The compound of claim 4 wherein $R^3$ and $R^4$ are joined together with the phenyl ring to which they are attached to form a bicyclic ring system that is:

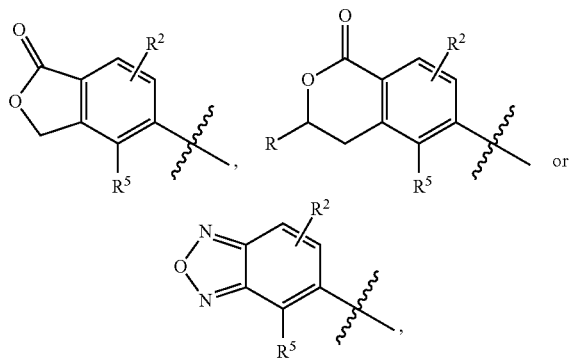

wherein R is —H or —$C_{1-4}$alkyl; or a pharmaceutically acceptable salt thereof.

6. The compound of claim 4 wherein one of $R^3$, $R^4$ or $R^5$ is —CN and the others are not —CN; or a pharmaceutically acceptable salt thereof.

7. The compound of claim 4 wherein one of $R^3$ or $R^4$ is N-tetrazolyl optionally substituted with —$CH_3$ and the other is not N-tetrazolyl optionally substituted with —$CH_3$; or a pharmaceutically acceptable salt thereof.

8. The compound of claim 1 wherein $Z^1$ is

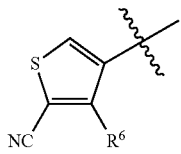

or a pharmaceutically acceptable salt thereof.

9. The compound of claim 1, wherein the compound is:
   4-methyl-5-[(3R,9aS)-8-{[4-(1H-tetrazol-1-yl)phenyl]acetyl}octahydropyrazino[2,1-c][1,4]oxazin-3-yl]-2-benzofuran-1(3H)-one;
   4-methyl-5-[(3S,9aS)-8-{[4-(1H-tetrazol-1-yl)phenyl]acetyl}octahydropyrazino[2,1-c][1,4]oxazin-3-yl]-2-benzofuran-1(3H)-one;
   3-((3R,9aS)-8-((R)-5-(1H-tetrazol-1-yl)-2,3-dihydro-1H-indene-1carbonyl)octahydropyrazino[2,1-c][1,4]oxazin-3-yl)-6-fluoro-2-methylbenzonitrile and
   3-((3S,9aS)-8-((S)-5-(1H-tetrazol-1-yl)-2,3-dihydro-1H-indene-1carbonyl)octahydropyrazino[2,1-c][1,4]oxazin-3-yl)-6-fluoro-2-methylbenzonitrile;
   2-fluoro-5-[(3S,9aS)-8-{[5-(1H-tetrazol-1-yl)-2,3-dihydro-1H-inden-1-yl]carbonyl}octahydropyrazino[2,1-c][1,4]oxazin-3-yl]benzonitrile;
   2-fluoro-5-[(3R,9aS)-8-{[5-(1H-tetrazol-1-yl)-2,3-dihydro-1H-inden-1-yl]carbonyl}octahydropyrazino[2,1-c][1,4]oxazin-3-yl]benzonitrile;
   4-{2-[(3R,9aS)-3-(3-cyano-4-fluorophenyl)hexahydropyrazino[2,1-c][1,4]oxazin-8(1H)-yl]-2-oxoethyl}-2,5-difluorobenzonitrile;
   4-{2-[(3R,9aS)-3-(3-cyano-4-fluorophenyl)hexahydropyrazino[2,1-c][1,4]oxazin-8(1H)-yl]-2-oxoethyl}-2-methoxybenzonitrile;
   5-[(3S,9aS)-8-{[4-(1H-tetrazol-1-yl)phenyl]acetyl}octahydropyrazino[2,1-c][1,4]oxazin-3-yl]-2-benzofuran-1(3H)-one;
   5-[(3R,9aS)-8-{[4-(1H-tetrazol-1-yl)phenyl]acetyl}octahydropyrazino[2,1-c][1,4]oxazin-3-yl]-2-benzofuran-1(3H)-one;
   5-fluoro-2-methoxy-4-{2-oxo-2-[(3S,9aS)-3-(1-oxo-1,3-dihydro-2-benzofuran-5-yl)hexahydropyrazino[2,1-c][1,4]oxazin-8(1H)-yl]ethyl}benzonitrile;
   5-fluoro-2-methoxy-4-{2-oxo-2-[(3R,9aS)-3-(1-oxo-1,3-dihydro-2-benzofuran-5-yl)hexahydropyrazino[2,1-c][1,4]oxazin-8 (1H)-yl]ethyl}benzonitrile;
   5-[(3S,9aS)-8-{[5-(1H-tetrazol-1-yl)-2,3-dihydro-1H-inden-1-yl]carbonyl}octahydropyrazino[2,1-c][1,4]oxazin-3-yl]-2-benzofuran-1(3H)-one;
   5-[(3R,9aS)-8-{[5-(1H-tetrazol-1-yl)-2,3-dihydro-1H-inden-1-yl]carbonyl}octahydropyrazino[2,1-c][1,4]oxazin-3-yl]-2-benzofuran-1(3H)-one;
   4-methyl-5-[(3R,9aR)-8-{[4-(1H-tetrazol-1-yl)phenyl]acetyl}octahydropyrazino[2,1-c][1,4]oxazin-3-yl]-2-benzofuran-1(3H)-one;
   4-methyl-5-[(3S,9aR)-8-{[4-(1H-tetrazol-1-yl)phenyl]acetyl}octahydropyrazino[2,1-c][1,4]oxazin-3-yl]-2-benzofuran-1(3H)-one;
   6-[(3R,9aS)-8-{[4-(1H-tetrazol-1-yl)phenyl]acetyl}octahydropyrazino[2,1-c][1,4]oxazin-3-yl]-3,4-dihydro-1H-isochromen-1-one;
   5-fluoro-2-methoxy-4-{2-[(3S,9aS)-3-(4-methyl-1-oxo-1,3-dihydro-2-benzofuran-5-yl)hexahydropyrazino[2,1-c][1,4]oxazin-8(1H)-yl]-2-oxoethyl}benzonitrile;
   5-fluoro-2-methoxy-4-{2-[(3R,9aS)-3-(4-methyl-1-oxo-1,3-dihydro-2-benzofuran-5-yl)hexahydropyrazino[2,1-c][1,4]oxazin-8(1H)-yl]-2-oxoethyl}benzonitrile;
   2-methoxy-4-[(3S,9aR)-8-{[4-(1H-tetrazol-1-yl)phenyl]acetyl}octahydropyrazino[2,1-c][1,4]oxazin-3-yl]benzonitrile;
   2-methoxy-4-[(3R,9aR)-8-{[4-(1H-tetrazol-1-yl)phenyl]acetyl}octahydropyrazino[2,1-c][1,4]oxazin-3-yl]benzonitrile;
   4-chloro-5-[(3R,9aS)-8-{[4-(1H-tetrazol-1-yl)phenyl]acetyl}octahydropyrazino[2,1-c][1,4]oxazin-3-yl]-2-benzofuran-1(3H)-one;
   4-chloro-5-[(3S,9aS)-8-{[4-(1H-tetrazol-1-yl)phenyl]acetyl}octahydropyrazino[2,1-c][1,4]oxazin-3-yl]-2-benzofuran-1(3H)-one;
   6-[(3R,9aS)-8-{[5-(1H-tetrazol-1-yl)-2,3-dihydro-1H-inden-1-yl]carbonyl}octahydropyrazino[2,1-c][1,4]oxazin-3-yl]-3,4-dihydro-1H-isochromen-1-one;
   6-fluoro-2-methyl-3-{(3S,9aS)-8-[(1-oxo-1,3-dihydro-2-benzofuran-5-yl)acetyl]octahydropyrazino[2,1-c][1,4]oxazin-3-yl}benzonitrile;
   6-fluoro-2-methyl-3-{(3R,9aS)-8-[(1-oxo-1,3-dihydro-2-benzofuran-5-yl)acetyl]octahydropyrazino[2,1-c][1,4]oxazin-3-yl}benzonitrile;
   2-fluoro-6-methoxy-3-[(3R,9aS)-8-{[4-(1H-tetrazol-1-yl)phenyl]acetyl}octahydropyrazino[2,1-c][1,4]oxazin-3-yl]benzonitrile;

6-methoxy-2-methyl-3-[(3R,9aS)-8-{[4-(1H-tetrazol-1-yl)phenyl]acetyl}octahydropyrazino[2,1-c][1,4]oxazin-3-yl]benzonitrile;
4-fluoro-2-methoxy-5-[(3R,9aS)-8-{[4-(1H-tetrazol-1-yl)phenyl]acetyl}octahydropyrazino[2,1-c][1,4]oxazin-3-yl]benzonitrile;
2-methoxy-4-{2-oxo-2-[(3S,9aR)-3-(1-oxo-3,4-dihydro-1H-isochromen-6-yl)hexahydropyrazino[2,1-c][1,4]oxazin-8(1H)-yl]ethyl}benzonitrile;
2-methoxy-4-{2-oxo-2-[(3R,9aS)-3-(1-oxo-3,4-dihydro-1H-isochromen-6-yl)hexahydropyrazino[2,1-c][1,4]oxazin-8(1H)-yl]ethyl}benzonitrile;
5-fluoro-2-methoxy-4-{2-oxo-2-[(3R,9aS)-3-(1-oxo-3,4-dihydro-1H-isochromen-6-yl)hexahydropyrazino[2,1-c][1,4]oxazin-8(1H)-yl]ethyl}benzonitrile;
5-fluoro-2-methoxy-4-{2-oxo-2-[(3S,9aR)-3-(1-oxo-3,4-dihydro-1H-isochromen-6-yl)hexahydropyrazino[2,1-c][1,4]oxazin-8(1H)-yl]ethyl}benzonitrile;
6-fluoro-2-methoxy-3-[(3R,9aS)-8-{[4-(1H-tetrazol-1-yl)phenyl]acetyl}octahydropyrazino[2,1-c][1,4]oxazin-3-yl]benzonitrile;
6-fluoro-2-methoxy-3-[(3S,9aS)-8-{[4-(1H-tetrazol-1-yl)phenyl]acetyl}octahydropyrazino[2,1-c][1,4]oxazin-3-yl]benzonitrile;
6-chloro-2-methyl-3-[(3R,9aS)-8-{[4-(1H-tetrazol-1-yl)phenyl]acetyl}octahydropyrazino[2,1-c][1,4]oxazin-3-yl)]benzonitrile;
6-chloro-2-methyl-3-[(3S,9aS)-8-{[4-(1H-tetrazol-1-yl)phenyl]acetyl}octahydropyrazino[2,1-c][1,4]oxazin-3-yl]benzonitrile;
6-chloro-2-methyl-3-[(3S,9aS)-8-{[5-(1H-tetrazol-1-yl)-2,3-dihydro-1H-inden-1-yl]carbonyl}octahydropyrazino[2,1-c][1,4]oxazin-3-yl]benzonitrile;
6-chloro-2-methyl-3-[(3R,9aS)-8-{[5-(1H-tetrazol-1-yl)-2,3-dihydro-1H-inden-1-yl]carbonyl}octahydropyrazino[2,1-c][1,4]oxazin-3-yl]benzonitrile;
2-fluoro-4-methyl-5-[(3R,9aS)-8-{[4-(1H-tetrazol-1-yl)phenyl]acetyl}octahydropyrazino[2,1-c][1,4]oxazin-3-yl]benzonitrile;
3-methyl-4-[(3R,9aS)-8-{[4-(1H-tetrazol-1-yl)phenyl]acetyl}octahydropyrazino[2,1-c][1,4]oxazin-3-yl]thiophene-2-carbonitrile;
3-methyl-4-[(3S,9aS)-8-{[4-(1H-tetrazol-1-yl)phenyl]acetyl}octahydropyrazino[2,1-c][1,4]oxazin-3-yl]thiophene-2-carbonitrile;
6-methyl-5-[(3R,9aS)-8-{[4-(1H-tetrazol-1-yl)phenyl]acetyl}octahydropyrazino[2,1-c][1,4]oxazin-3-yl]-2-benzofuran-1(3H)-one;
2-methyl-3-[(3R,9aS)-8-{[4-(1H-tetrazol-1-yl)phenyl]acetyl}octahydropyrazino[2,1-c][1,4]oxazin-3-yl]benzonitrile;
2-methyl-3-[(3S,9aS)-8-{[4-(1H-tetrazol-1-yl)phenyl]acetyl}octahydropyrazino[2,1-c][1,4]oxazin-3-yl]benzonitrile;
6-fluoro-2-methyl-3-[(3S,9aS)-8-{[5-(1H-tetrazol-1-yl)-2,3-dihydro-1H-inden-2-yl]carbonyl}octahydropyrazino[2,1-c][1,4]oxazin-3-yl]benzonitrile;
6-fluoro-2-methyl-3-[(3R,9aS)-8-{2-[4-(1H-tetrazol-1-yl)phenyl]propanoyl}octahydropyrazino[2,1-c][1,4]oxazin-3-yl]benzonitrile;
6-fluoro-2-methyl-3-[(3S,9aS)-8-{[3-(1H-tetrazol-1-yl)phenyl]acetyl}octahydropyrazino[2,1-c][1,4]oxazin-3-yl]benzonitrile;
6-fluoro-2-methyl-3-[(3R,9aS)-8-{[3-(1H-tetrazol-1-yl)phenyl]acetyl}octahydropyrazino[2,1-c][1,4]oxazin-3-yl]benzonitrile;
6-fluoro-2-methyl-3-[(3R,9aR)-8-{[4-(1H-tetrazol-1-yl)phenyl]acetyl}octahydropyrazino[2,1-c][1,4]oxazin-3-yl]benzonitrile;
6-fluoro-2-methyl-3-[(3S,9aR)-8-{[4-(1H-tetrazol-1-yl)phenyl]acetyl}octahydropyrazino[2,1-c][1,4]oxazin-3-yl]benzonitrile;
4-methyl-5-(9-{[4-(1H-tetrazol-1-yl)phenyl]acetyl}octahydro-1H-[1,4]oxazino[4,3-a][1,4]diazepin-3-yl)-2-benzofuran-1(3H)-one;
4-methyl-5-(8-{[4-(1H-tetrazol-1-yl)phenyl]acetyl}octahydro-1H-[1,4]oxazino[4,3-d][1,4]diazepin-3-yl)-2-benzofuran-1(3-H)-one;
3-[(3R,9aS)-8-{[2,6-difluoro-4-(1H-tetrazol-1-yl)phenyl]acetyl}octahydropyrazino[2,1-c][1,4]oxazin-3-yl]-6-fluoro-2-methylbenzonitrile;
3-[(3R,9aR)-8-{[2,6-difluoro-4-(1H-tetrazol-1-yl)phenyl]acetyl}octahydropyrazino[2,1-c][1,4]oxazin-3-yl]-6-fluoro-2-methylbenzonitrile;
3-[(3R,9aR)-8-{[2,5-difluoro-4-(1H-tetrazol-1-yl)phenyl]acetyl}octahydropyrazino[2,1-c][1,4]oxazin-3-yl]-6-fluoro-2-methylbenzonitrile;
3-[(3R,9aS)-8-{[2,5-difluoro-4-(1H-tetrazol-1-yl)phenyl]acetyl}octahydropyrazino[2,1-c][1,4]oxazin-3-yl]-6-fluoro-2-methylbenzonitrile;
6-fluoro-2-methyl-3-[(3R,9aR)-8-{[3-(1H-tetrazol-1-yl)phenyl]acetyl}octahydropyrazino[2,1-c][1,4]oxazin-3-yl]benzonitrile;
6-fluoro-2-methyl-3-[(3S,9aR)-8-{[3-(1H-tetrazol-1-yl)phenyl]acetyl}octahydropyrazino[2,1-c][1,4]oxazin-3-yl]benzonitrile;
6-fluoro-3-[(3S,9aR)-8-{[2-fluoro-5-(1H-tetrazol-1-yl)phenyl]acetyl}octahydropyrazino[2,1-c][1,4]oxazin-3-yl]-2-methylbenzonitrile;
6-fluoro-3-[(3R,9aR)-8-{[2-fluoro-5-(1H-tetrazol-1-yl)phenyl]acetyl}octahydropyrazino[2,1-c][1,4]oxazin-3-yl]-2-methylbenzonitrile;
6-fluoro-2-methyl-3-[(3R,9aR)-8-{[2-methyl-3-(1H-tetrazol-1-yl)phenyl]acetyl}octahydropyrazino[2,1-c][1,4]oxazin-3-yl]benzonitrile;
6-fluoro-2-methyl-3-[(3S,9aR)-8-{[2-methyl-3-(1H-tetrazol-1-yl)phenyl]acetyl}octahydropyrazino[2,1-c][1,4]oxazin-3-yl)]benzonitrile;
6-methoxy-2-methyl-3-[(3S,9aS)-8-{[5-(1H-tetrazol-1-yl)-2,3-dihydro-1H-inden-1-yl]carbonyl}octahydropyrazino[2,1-c][1,4]oxazin-3-yl]benzonitrile;
6-methoxy-2-methyl-3-[(3R,9aS)-8-{[5-(1H-tetrazol-1-yl)-2,3-dihydro-1H-inden-1-yl]carbonyl}octahydropyrazino[2,1-c][1,4]oxazin-3-yl]benzonitrile;
2-methoxy-4-[(3R,9aR)-8-{[5-(1H-tetrazol-1-yl)-2,3-dihydro-1H-inden-1-yl]carbonyl}octahydropyrazino[2,1-c][1,4]oxazin-3-yl]benzonitrile;
2-methoxy-4-[(3R,9aS)-8-{[5-(1H-tetrazol-1-yl)-2,3-dihydro-1H-inden-1-yl]carbonyl}octahydropyrazino[2,1-c][1,4]oxazin-3-yl]benzonitrile;
2-methoxy-4-[(3S,9aS)-8-{[5-(1H-tetrazol-1-yl)-2,3-dihydro-1H-inden-1-yl]carbonyl}octahydropyrazino[2,1-c][1,4]oxazin-3-yl]benzonitrile;
3-[(3R,9aS)-8-{[2-cyano-4-(1H-tetrazol-1-yl)phenyl]acetyl}octahydropyrazino[2,1-c][1,4]oxazin-3-yl]-6-fluoro-2-methylbenzonitrile;

3-[(3R,9aR)-8-{[2-cyano-4-(1H-tetrazol-1-yl)phenyl]
acetyl}octahydropyrazino[2,1-c][1,4]oxazin-3-yl]-6-
fluoro-2-methylbenzonitrile;
3-[(3R,9aR)-8-{[2-chloro-4-(1H-tetrazol-1-yl)phenyl]
acetyl}octahydropyrazino[2,1-c][1,4]oxazin-3-yl]-6-
fluoro-2-methylbenzonitrile;
3-[(3R,9aS)-8-{[2-chloro-4-(1H-tetrazol-1-yl)phenyl]
acetyl}octahydropyrazino[2,1-c][1,4]oxazin-3-yl]-6-
fluoro-2-methylbenzonitrile;
4-methyl-5-[(3S,9aS)-8-{3-[3(1H-tetrazol-1-yl)phenyl]
propanoyl}octahydropyrazino[2,1-c][1,4]oxazin-3-yl]-
2-benzofuran-1(3H)-one;
6-fluoro-2-methyl-3-[(3R,9aS)-8-{3-[3-(1H-tetrazol-1-
yl)phenyl]propanoyl}octahydropyrazino[2,1-c][1,4]
oxazin-3-yl]benzonitrile;
6-fluoro-2-methyl-3-[(3S,9aR)-8-{3-[3-(1H-tetrazol-1-
yl)phenyl]propanoyl}octahydropyrazino[2,1-c][1,4]
oxazin-3-yl]benzonitrile;
(3S,9aS)-3-(4-methyl-2,1,3-benzoxadiazol-5-yl)-8-{[4-
(1H-tetrazol-1-yl)phenyl]acetyl}octahydropyrazino[2,
1-c][1,4]oxazine;
(3R,9aS)-3-(4-methyl-2,1,3-benzoxadiazol-5-yl)-8-{[4-
(1H-tetrazol-1-yl)phenyl]acetyl}octahydropyrazino[2,
1-c][1,4]oxazine;
(3R,9aS)-3-(2,1,3-benzoxadiazol-5-yl)-8-{[4-(1H-tetra-
zol-1-yl)phenyl]acetyl}octahydropyrazino[2,1-c][1,4]
oxazine;
(3R,9aS)-3-(2,1,3-benzoxadiazol-5-yl)-8-{[5-(1H-tetra-
zol-1-yl)-2,3-dihydro-1H-inden-1-yl]
carbonyl}octahydropyrazino[2,1-c][1,4]oxazine;
5-[(3R,9aR)-8-{[2,6-difluoro-4-(1H-tetrazol-1-yl)phe-
nyl]acetyl}octahydropyrazino[2,1-c][1,4]oxazin-3-yl]-
4-methyl-2-benzofuran-1(3H)-one;
(3R,9aS)-8-{[5-(1H-tetrazol-1-yl)-2,3-dihydro-1H-in-
den-1-yl]carbonyl}-3-[3(1H-tetrazol-1-yl)phenyl]octa-
hydropyrazino[2,1-c][1,4]oxazin;
4-methyl-5-[(3S,9aS)-8-{[5-(1H-tetrazol-1-yl)-2,3-di-
hydro-1H-inden-1-yl]carbonyl}octahydropyrazino[2,
1-c][1,4]oxazin-3-yl]-2-benzofuran-1(3H)-one;
3-methyl-4-[(3R,9aS)-8-{[5-(1H-tetrazol-1-yl)-2,3-di-
hydro-1H-inden-1-yl]carbonyl}octahydropyrazino[2,
1-c][1,4]oxazin-3-yl]thiophene-2-carbonitrile;
3-methyl-4-[(3R,9aS)-8-{[5-(1H-tetrazol-1-yl)-2,3-di-
hydro-1H-inden-1-yl]carbonyl}octahydropyrazino[2,
1-c][1,4]oxazin-3-yl]thiophene-2-carbonitrile;
(3R)-3-methyl-6-[(3R,9aS)-8-{[5-(1H-tetrazol-1-yl)-2,3-
dihydro-1H-inden-1-yl]carbonyl}octahydropyrazino
[2,1-c][1,4]oxazin-3-yl]-3,4-dihydro-1H-isochromen-
1-one;
(3R)-3-methyl-6-[(3R,9aS)-8-{[5-(1H-tetrazol-1-yl)-2,3-
dihydro-1H-inden-1-yl]carbonyl}octahydropyrazino
[2,1-c][1,4]oxazin-3-yl]-3,4-dihydro-1H-isochromen-
1-one;
6-[(3R,9aS)-8-{[5-(1H-tetrazol-1-yl)-2,3-dihydro-1H-in-
den-1-yl]carbonyl}octahydropyrazino[2,1-c][1,4]ox-
azin-3-yl]-3,4-dihydro-1H-isochromen-1-one;
6-[(3R,9aS)-8-{[5-(1H-tetrazol-1-yl)-2,3-dihydro-1H-in-
den-1-yl]carbonyl}octahydropyrazino[2,1-c][1,4]ox-
azin-3-yl]-3,4-dihydro-1H-isochromen-1-one;
4-methyl-5-[(3S,9aS)-8-{[6-(1H-tetrazol-1-yl)-1,2,3,4-
tetrahydronaphthalen-1-yl]
carbonyl}octahydropyrazino[2,1-c][1,4]oxazin-3-yl]-
2-benzofuran-1(3H)-one;
4-methyl-5-[(3R,9aS)-8-{[6-(1H-tetrazol-1-yl)-1,2,3,4-
tetrahydronaphthalen-1-yl]
carbonyl}octahydropyrazino[2,1-c][1,4]oxazin-3-yl]-
2-benzofuran-1(3H)-one;

6-[(3R,9aS)-8-{[6-(1H-tetrazol-1-yl)-1,2,3,4-tetrahy-
dronaphthalen-1-yl]carbonyl}octahydropyrazino[2,1-
c][1,4]oxazin-3-yl]-3,4-dihydro-1H-isochromen-1-
one;
6-fluoro-2-methyl-3-[(3R,9aS)-8-{[6-(1H-tetrazol-1-yl)-
1,2,3,4-tetrahydronaphthalen-1-yl]
carbonyl}octahydropyrazino[2,1-c][1,4]oxazin-3-yl]
benzonitrile;
6-fluoro-2-methyl-3-[(3R,9aS)-8-{[6-(1H-tetrazol-1-yl)-
1,2,3,4-tetrahydronaphthalen-1-yl]
carbonyl}octahydropyrazino[2,1-c][1,4]oxazin-3-yl]
benzonitrile;
6-fluoro-2-methyl-3-[(3S,9aS)-8-{[6-(1H-tetrazol-1-yl)-
1,2,3,4-tetrahydronaphthalen-1-yl]
carbonyl}octahydropyrazino[2,1-c][1,4]oxazin-3-yl]
benzonitrile;
6-fluoro-2-methyl-3-[(3R,9aR)-8-{[6-(1H-tetrazol-1-yl)-
1,2,3,4-tetrahydronaphthalen-1-yl]
carbonyl}octahydropyrazino[2,1-c][1,4]oxazin-3-yl]
benzonitrile;
6-fluoro-2-methyl-3-[(3S,9aR)-8-{[6-(1H-tetrazol-1-yl)-
1,2,3,4-tetrahydronaphthalen-1-yl]
carbonyl}octahydropyrazino[2,1-c][1,4]oxazin-3-yl]
benzonitrile;
3-methyl-4-[(3R,9aS)-8-{[6-(1H-tetrazol-1-yl)-1,2,3,4-
tetrahydronaphthalen-1-yl]
carbonyl}octahydropyrazino[2,1-c][1,4]oxazin-3-yl]
thiophene-2-carbonitrile;
3-methyl-4-[(3S,9aS)-8-{[6-(1H-tetrazol-1-yl)-1,2,3,4-
tetrahydronaphthalen-1-yl]
carbonyl}octahydropyrazino[2,1-c][1,4]oxazin-3-yl]
thiophene-2-carbonitrile;
6-fluoro-2-methyl-3-[(3S,9aS)-8-{[5-(1H-tetrazol-1-yl)-
2,3-dihydro-1H-inden-1-yl]
carbonyl}octahydropyrazino[2,1-c][1,4]oxazin-3-yl]
benzonitrile;
3-((4R,9aR)-8-(2-(4-(1H-tetrazol-1-yl)phenyl)acetyl)oc-
tahydro-1H-pyrazino[1,2-a]pyrazin-3-yl)-6-fluoro-2-
methylbenzonitrile;
4-methyl-5-[(3S,9aR)-8-{[4-(1H-tetrazol-1-yl)phenyl]
acetyl}octahydro-2H-pyrazino[1,2-a]pyrazin-3-yl]-2-
benzofuran-1(3H)-one;
6-fluoro-2-methyl-3-[(3S,9aR)-8-{[4-(1H-tetrazol-1-yl)
phenyl]acetyl}octahydro-2H-pyrazino[1,2-a]pyrazin-
3-yl]benzonitrile;
3-[(3R,9aR)-8-{[2,6-difluoro-4-(1H-tetrazol-1-yl)phe-
nyl]acetyl}octahydro-2H-pyrazino[1,2-a]pyrazin-3-
yl]-6-fluoro-2-methylbenzonitrile;
3-[(3S,9aR)-8-{[2,6-difluoro-4-(1H-tetrazol-1-yl)phenyl]
acetyl}octahydro-2H-pyrazino[1,2-a]pyrazin-3-yl]-6-
fluoro-2-methylbenzonitrile;
(3R)-3-methyl-6-[(3R,9aR)-8-{[4-(1H-tetrazol-1-yl)phe-
nyl]acetyl}octahydro-2H-pyrazino[1,2-a]pyrazin-3-
yl]-3,4-dihydro-1H-isochromen-1-one; or
(3R)-6-[(3R,9aR)-8-{[2,6-difluoro-4-(1H-tetrazol-1-yl)
phenyl]acetyl}octahydro-2H-pyrazino[1,2-a]pyrazin-
3-yl]-3-methyl-3,4-dihydro-1H-isochromen-1-one.

10. A pharmaceutical composition comprised of a compound of claim 1 or a pharmaceutically acceptable salt thereof and a pharmaceutically acceptable carrier.

11. The pharmaceutical composition of claim 10 further comprised of one or more of an angiotensin converting enzyme inhibitor, an angiotensin II receptor antagonist, a neutral endopeptidase inhibitor, a dual inhibitors of angiotensin converting enzyme (ACE) and neutral endopeptidase, carbonic anhydrase inhibitor, an aldosterone antagonist, aldosterone synthase inhibitor, a renin inhibitor, an endothelin receptor antagonist, a vasodilator, a calcium channel blocker, a potassium channel activator, a diuretic, a sympatholitic, a beta-adrenergic blocking drug, an alpha adrenergic blocking drug, a central alpha adrenergic agonist, a peripheral vasodilator, an HMG-CoA reductase inhibitor, a cholesterol absorption inhibitor, niacin, niacin in combination with a prostaglandin D2 receptor 1 antagonist, a niacin receptor agonist, a niacin receptor partial agonist, an insulin sensitizing agent, an alpha glucosidase inhibitor, a dipeptidyl peptidase inhibitor, phosphodiesterase-5 inhibitor, or metformin.

12. The pharmaceutical composition of claim 10 further comprising an additional active agent selected from losartan, valsartan, candesartan, olmesartan, telmesartan, eprosartan, irbesartan, azilsartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril, amiloride, spironolactone, epleranone or triamterene, and optionally hydrochlorothiazide, or a pharmaceutically acceptable salt thereof.

\* \* \* \* \*